(12) United States Patent
Marshall et al.

(10) Patent No.: US 8,338,569 B2
(45) Date of Patent: Dec. 25, 2012

(54) FGFR EXTRACELLULAR DOMAIN ACIDIC REGION MUTEINS

(75) Inventors: Shannon Marshall, Baltimore, MD (US); Deborah H. Charych, Albany, CA (US); Ali Sadra, San Mateo, CA (US)

(73) Assignee: Five Prime Therapeutics, Inc., South San Francisco, CA (US)

( * ) Notice: Subject to any disclaimer, the term of this patent is extended or adjusted under 35 U.S.C. 154(b) by 409 days.

(21) Appl. No.: 12/535,479

(22) Filed: Aug. 4, 2009

(65) Prior Publication Data

US 2010/0087627 A1    Apr. 8, 2010

Related U.S. Application Data

(60) Provisional application No. 61/086,121, filed on Aug. 4, 2008.

(51) Int. Cl.
*C07K 14/50* (2006.01)
*C07K 14/705* (2006.01)
*C07H 21/04* (2006.01)

(52) U.S. Cl. ........... 530/351; 530/350; 424/184.1; 514/7.6; 536/23.1; 536/23.4

(58) Field of Classification Search ............... None
See application file for complete search history.

(56) References Cited

U.S. PATENT DOCUMENTS

| | | | |
|---|---|---|---|
| 5,229,501 A | 7/1993 | Keifer et al. | |
| 5,288,855 A | 2/1994 | Bergonzoni et al. | |
| 5,474,914 A | 12/1995 | Spaete | |
| 5,486,462 A | 1/1996 | Rutter et al. | |
| 5,707,632 A | 1/1998 | Williams et al. | |
| 5,750,371 A | 5/1998 | Senoo et al. | |
| 5,767,250 A | 6/1998 | Spaete | |
| 5,863,888 A | 1/1999 | Dionne et al. | |
| 6,255,454 B1 | 7/2001 | Keifer et al. | |
| 6,344,546 B1 | 2/2002 | Dionne et al. | |
| 6,350,593 B1 | 2/2002 | Williams et al. | |
| 6,355,440 B1 | 3/2002 | Williams et al. | |
| 6,384,191 B1 | 5/2002 | Williams et al. | |
| 6,517,872 B1 | 2/2003 | Yayon et al. | |
| 6,656,728 B1 | 12/2003 | Kavanaugh et al. | |
| 6,844,168 B1 | 1/2005 | Keifer et al. | |
| 7,135,311 B1 | 11/2006 | David et al. | |
| 7,297,774 B2 | 11/2007 | Ullrich et al. | |
| 7,678,890 B2 | 3/2010 | Bosch et al. | |
| 7,982,014 B2 | 7/2011 | Williams et al. | |
| 2004/0063910 A1 | 4/2004 | Kavanaugh et al. | |
| 2004/0115768 A1 | 6/2004 | Follstad | |
| 2005/0187150 A1 | 8/2005 | Mohammadi et al. | |
| 2006/0286102 A1 | 12/2006 | Jin et al. | |
| 2007/0248604 A1 | 10/2007 | Desnoyers et al. | |
| 2007/0248605 A1 | 10/2007 | Hestir et al. | |
| 2008/0171689 A1 | 7/2008 | Williams et al. | |

FOREIGN PATENT DOCUMENTS

| | | |
|---|---|---|
| EP | 0 545 343 A1 | 6/1993 |
| WO | WO 91/00916 | 1/1991 |
| WO | WO 91/11459 | 8/1991 |
| WO | WO 2004/110487 A1 | 12/2004 |
| WO | WO 2005/113596 A2 | 12/2005 |
| WO | WO 2006/081430 A2 | 8/2006 |
| WO | WO 2006/113277 A2 | 10/2006 |
| WO | WO 2007/014123 A2 | 2/2007 |
| WO | WO 2007/059574 A1 | 5/2007 |
| WO | WO 2008/065543 A2 | 6/2008 |

OTHER PUBLICATIONS

Lazar et al, 1988, Mol. Cell. Biol., vol. 8, pp. 1247-1252.*
Wells, 1990, Biochemistry 29:8509-8517.*
Marics et al, Development, 2002, vol. 129, pp. 4559-4569.*
Genbank Accession No. X76885, 1994; 2 total pages.*
Genbank Accession No. Q90330, Nov. 1, 1996; 6 total pages.*
International Preliminary Report on Patentability for PCT/US2009/052704 ; Feb. 8, 2011.
Bjornsson et al., Pharmacokinetics of Heparin. II. Studies of Time Dependence in Rats, the Journal of Pharmacology and Experimental Therapeutics, vol. 210, No. 2, Apr. 1979, pp. 243-246.
Choo et al., SPdb—a Signal Peptide Database, BMC Bioinformatics, vol. 6, No. 249, Oct. 2005, pp. 1-8.
Meijer et al., Fibroblast Growth Factor Receptor 4 Predicts Failure on Tamoxifen Therapy in Patients with Recurrent Breast Cancer, Endocrine-Related Cancer, vol. 15, 2008, pp. 101-111.
Ornitz et al., Heparin is Required for Cell-free Binding of Basic Fibroblast Growth Factor to a Soluble Receptor and for Mitogenesis in Whole Cells, Molecular and Cellular Biology, vol. 12, Jan. 1992, pp. 240-247.
Sahadevan et al., Selective Over-expression of Fibroblast Growth Factor Receptors I and 4 in Clinical Prostate Cancer, Journal of Pathology, vol. 213, Jul. 2007, pp. 82-90.
Zhang at al, Receptor Specificity of the Fibroblast Growth Factor Family: The Complete Mammalian FGF Family, The Journal of Biological Chemistry, vol. 281, No. 23, Jun. 9, 2006, pp. 15694-15700.
International Search Report and Written Opinion mailed Mar. 8, 2010, for Application No. PCT/US2009/052704, filed Aug. 4, 2009.
A. N. Plotnikov et al., "Structural basis for FGF receptor dimerization and activation" *Cell*, 98(5):641-650 (1999).
C. J. Powers et al., "Fibroblast growth factors, their receptors and signaling" *Endocrine-Related Cancer*, 7:165-197 (2000).
E. Sanchez-Heras et al., "The fibroblast growth factor receptor acid box is essential for interactions with N-cadherin and all of the major isoforms of neural cell adhesion molecules" *Journal of Biological Chemistry*, 281(46):35208-16 (2006).

(Continued)

*Primary Examiner* — Bridge E Bunner
*Assistant Examiner* — Fozia Hamud
(74) *Attorney, Agent, or Firm* — Casimir Jones, S.C.

(57) ABSTRACT

Fibroblast growth factor receptor (FGFR) extracellular domain (ECD) acidic region muteins that have been engineered to exhibit decreased tissue binding by increasing the number of acidic amino acid residues within the D1-D2 linker region are provided. Polynucleotides encoding FGFR ECD acidic region muteins are also provided. Methods of making FGFR ECD acidic region muteins, and methods of using such molecules to treat proliferative disorders, including cancers, disorders of angiogenesis, and macular degeneration, are also provided.

5 Claims, 22 Drawing Sheets

OTHER PUBLICATIONS

Akimoto et al., "Fibroblast growth factor 2 promotes microvessel formation from mouse embryonic aorta" Am. J. Physiol. Cell Physiol., vol. 284, No. 2, 2003, pp. C371-C377.

Anderson et al., "Apert syndrome mutations in fibroblast growth factor receptor 2 exhibit increased affinity for FGF ligand" Human Molecular Genetics, vol. 7, No. 9, 1998, pp. 1475-1483.

Auguste et al., "Inhibition of fibroblast growth factor/fibroblast growth factor receptor activity in glioma cells impedes tumor growth by both angiogenesis-dependent and -independent mechanisms" Cancer Research, vol. 61, Feb. 15, 2001, pp. 1717-1726.

Baker et al., "Metabolic control of recombinant protein N-glycan processing in NSO and CHO cells" Biotechnology and Bioengineering, vol. 73, No. 3, May 5, 2001, pp. 188-202.

Ballinger et al., "Semirational design of a potent, artificial agonist of fibroblast growth factor receptors" Nature Biotechnology, vol. 17, Dec. 1999, pp. 1199-1204.

Bernard et al., "Fibroblast growth factor receptors as molecular targets in thyroid carcinoma" Endocrinology, vol. 10, Nov. 24, 2004, pp. 1-26 and 6 pgs. figures.

Celli et al., "Soluble dominant-negative receptor uncovers essential roles for fibroblast growth factors in multi-organ induction and patterning" The EMBO Journal, vol. 17, No. 6, Mar. 16, 1998, pp. 1642-1655.

Chellaiah et al., "Mapping ligand binding domains in chimeric fibroblast growth factor receptor molecules" J. Biol. Chem., vol. 274, No. 49, Dec. 3, 1999, pp. 34785-34794.

Cheon et al., "High-affinity binding sites for related fibroblast growth factor ligands reside within different receptor immunoglobulin-like domains" Proc. Natl. Acad. Sci., vol. 91, Feb. 1994, pp. 989-993.

Compagni et al., "Fibroblast growth factors are required for efficient tumor angiogenesis" Cancer Research, vol. 60, Dec. 15, 2000, pp. 7163-7169.

Couglin et al., "Acidic and basic fibroblast growth factors stimulate tyrosine kinase activity in vivo" J. Biol. Chem., vol. 263, No. 2, Jan. 15, 1988, pp. 988-993.

Ezzat et al., "A soluble dominant negative fibroblast growth factor receptor 4 isoform in human MCF-7 breast cancer cells" Biochem. Biophys. Res. Comm., vol. 287, No. 1, 2001, pp. 60-65.

Feige et al., "Glycosylation of the basic fibroblast growth factor receptor" J. Biol. Chem., vol. 263, No. 28, Oct. 5, 1988, pp. 14023-14029.

Gowardhan et al., "Evaluation of the fibroblast growth factor system as a potential target for therapy in human prostate cancer" British Journal of Cancer, vol. 92, Jan. 18, 2005, pp. 320-327.

Grossman et al., "Expression of human thyrotropin in cell lines with different glycosylation patterns combined with mutagenesis of specific glycosylation sites" J. Biol. Chem., vol. 270, No. 49, Dec. 8, 1995, pp. 29378-29385.

Guillonneau et al., "Fibroblast growth factor (FGF) soluble receptor 1 acts as a natural inhibitor of FGF2 neurotrophic activity during retinal degeneration" Molecular Biology of the Cell, vol. 9, Oct. 1998, pp. 2785-2802.

Hanneken et al., "Identification of soluble forms of the fibroblast growth factor receptor in blood" Proc. Natl. Acad. Sci., vol. 91, Sep. 1994, pp. 9170-9174.

Hanneken et al., "Soluble forms of the high-affinity fibroblast growth factor receptor in human vitreous fluid" Investigative Opthalmology & Visual Science, vol. 36, No. 6, May 1995, pp. 1192-1196.

Hanneken et al., "Structural characterization of the circulating soluble FGF receptors reveals multiple isoforms generated by secretion and ectodomain shedding" FEBS Letters, vol. 489, 2001, pp. 176-181.

Harding et al., "Role of VEGF, PDGF and FGF in glioblastoma progression as determined by soluble decoy receptor expression in preclinical models" Cell Genesys, Inc., Abstract No. 3030, presented at the AACR Annual Meeting, Apr. 16-20, 2005, 1 page.

Johnson et al., "Diverse forms of a receptor for acidic and basic fibroblast growth factors" Molecular and Cellular Biology, vol. 10, No. 9, Sep. 1990, pp. 4728-4736.

Johnson et al, "The human fibroblast growth factor receptor genes: a common structural arrangement underlies the mechanisms for generating receptor forms that differ in their third immunoglobulin domain" Molecular and Cellular Biology, vol. 11, No. 9, Sep. 1991, pp. 4627-4634.

Kan et al., "Divalent cations and heparin/heparan sulfate cooperate to control assembly and activity of the fibroblast growth factor receptor complex" J. Biol. Chem., vol. 271, No. 42, Oct. 18, 1996, pp. 26143-26148.

Kaufman et al., "Characterization of ligand binding to immobilized biotinylated extracellular domains of three growth factor receptors" Anal. Biochem., vol. 211, No. 2, Jun. 1993, pp. 261-266.

Keifer et al., "Molecular cloning of a human basic fibroblast growth factor receptor cDNA and expression of a biologically active extracellular domain in a baculovirus system" Growth Factors, vol. 5, 1991, pp. 115-127.

Kleeff et al., "Adenovirus-mediated transfer of a truncated fibroblast growth factor (FGF) type I receptor blocks FGF-2 signaling in multiple pancreatic cancer cell lines" Pancreas, vol. 28, No. 1, Jan. 2004, pp. 25-30.

Kwabi-Addo et al., "The role of fibroblast growth factors and their receptors in prostate cancer" Endocrine-Related Cancer, vol. 11, No. 4, Dec. 2004, pp. 709-724.

Lee et al., "Purification and complementary DNA cloning of a receptor for basic fibroblast growth factor" Science, vol. 245, No. 4913, Jul. 7, 1989, pp. 57-60.

Levi et al., "Matrix metalloproteinase 2 releases active soluble ectodomain of fibroblast growth factor receptor 1", XP-002413740, Proc. Natl. Acad. Sci., USA, vol. 93, pp. 7069-7074, (Jul. 1996).

Li et al., "Cell transformation by fibroblast growth factors can be suppressed by truncated fibroblast growth factor receptors" Molecular and Cellular Biology, vol. 14, No. 11, Nov. 1994, pp. 7660-7669.

Liuzzo et al., "Human leukemia cell lines bind basic fibroblast growth factor (FGF) on FGF receptors and heparin sulfates: downmodulation of FGF receptors by phorbol ester" Blood, vol. 87, No. 1, Jan. 1, 1996, pp. 245-255.

Lopez et al., "A novel type I fibroblast growth factor receptor activates mitogenic signaling in the absence of detectable tyrosine phosphorylation of FRS2" J. Biol. Chem., vol. 275, No. 21, May 26, 2000, pp. 15933-15939.

Lundin et al., "Selectively desulfated heparin inhibits fibroblast growth factor-induced mitogenicity and angiogenesis" J. Biol. Chem., vol. 275, No. 32, Aug. 11, 2000, pp. 24653-24660.

Mansukhani et al., "A murine fibroblast growth factor (FGF) receptor expressed in CHO cells is activated by basic FGF and Kaposi FGF" Proc. Natl. Acad. Sci., vol. 87, Jun. 1990, pp. 4378-4382.

Ogawa et al., "Anti-tumor angiogenesis therapy using soluble receptors: enhanced inhibition of tumor growth when soluble fibroblast growth factor receptor-1 is used with soluble vascular endothelial growth factor receptor" Cancer Gene Therapy, vol. 9, Aug. 2002, pp. 633-640.

Olsen et al., "Insights into the molecular basis for fibroblast growth factor receptor autoinhibition and ligand-binding promiscuity" Proc. Natl. Acad. Sci., vol. 101, No. 4 Jan. 27, 2004, pp. 935-940.

Ornitz et al., "Heparin is required for cell-free binding of basic fibroblast growth factor to a soluble receptor and for mitogenesis in whole cells" Molecular and Cellular Biology, vol. 12, Jan. 1992, pp. 240-247.

Ornitz et al., "Receptor specificity of the fibroblast growth factor family" J. Biol. Chem., vol. 271, No. 25, Jun. 21, 1996, pp. 15292-15297.

Otto et al., "Sialylated complex-type N-glycans enhance the signaling activity of soluble intercellular adhesion molecule-1 in mouse astrocytes" J. Biol. Chem., vol. 279, No. 34, Aug. 20, 2004, pp. 35201-35209.

Pasquale et al., "Identification of a developmentally regulated protein-tyrosine kinase by using anti-phosphotyrosine antibodies to screen a cDNA expression library" Proc. Natl. Acad. Sci., vol. 86, Jul. 1989, pp. 5449-5453.

Powers et al., "Fribroblast growth factors, their receptors and signaling", XP-002165147, Endocrine-Related Cancer, 7, pp. 165-197, (2000).

Plotnikov et al., "Structural basis for FGF receptor dimerization and activation" Cell, vol. 98, Sep. 3, 1999, pp. 641-650.

Plotnikov et al., "Crystal structures of two FGF-FGFR complexes reveal the determinants of ligand-receptor specificity" Cell, vol. 101, May 12, 2000, pp. 413-424.

Powell et al., "Fibroblast growth factor receptors 1 and 2 interact differently with heparin/heparin sulfate" J. Biol. Chem., vol. 277, No. 32, Aug. 9, 2002, pp. 28554-28563.

Roghani et al., "Heparin increases the affinity of basic fibroblast growth factor for its receptor but is not required for binding" J. Biol. Chem., vol. 269, No. 6, Feb. 11, 1994, pp. 3976-3984.

Ruta et al., "A novel protein tyrosine kinase gene whose expression is modulated during endothelial cell differentiation" Oncogene, 1988, vol. 3, pp. 9-15.

Shamim et al., "Sequential roles for Fgf4, En1 and Fgf8 in specification and regionalization of the midbrain" Development, vol. 126, Feb. 1999, pp. 945-959.

Smith et al., "The asparagine-linked oligosaccharides on tissue factor pathway inhibitor terminate with $SO_4$-4GalNAc$\beta$1,4GlcNAc$\beta$1,2Man$\alpha$" J. Biol. Chem., vol. 267, No. 27, Sep. 25, 1992, pp. 19140-19146.

St. Bernard et al., "Fibroblast growth factor receptors as molecular targets in thyroid carcinoma" Endocrinology, vol. 146, No. 3, 2005, pp. 1145-1153.

Tomlinson et al., "Alternative splicing of fibroblast growth factor receptor 3 produces a secreted isoform that inhibits fibroblast growth factor-induced proliferation and is repressed in urothelial carcinoma cell lines" Cancer Research, vol. 65, No. 22, Nov. 15, 2005, pp. 10441-10449.

Trueb et al., "Characterization of FGFRL1, a novel fibroblast growth factor (FGF) receptor preferentially expressed in skeletal tissues" J. Biol. Chem., vol. 278, No. 36, Sep. 5, 2003, pp. 33857-33865.

Tucker et al., "A novel approach for inhibiting growth factor signalling in murine tooth development" Eur. J. Oral Sci., vol. 106 (suppl. 1), 1998, pp. 122-125.

Tuominen et al., "Expression and glycosylation studies of human FGF Receptor 4" Protein Expression and Purification, vol. 21, Mar. 2001, pp. 275-285.

Ueno et al., "A truncated form of fibroblast growth factor receptor 1 inhibits signal transduction by multiple types of fibroblast growth factor receptor" J. Biol. Chem., vol. 267, No. 3, Jan. 25, 1992, pp. 1470-1476.

Van Den Nieuwenhof et al., "Recombinant glycodelin carrying the same type of glycan structures as contraceptive glycodelin-A can be produced in human kidney 293 cells but not in Chinese hamster ovary cells" Eur. J. Biochem., vol. 267, Aug. 2000, pp. 4753-4762.

Wagner et al., "Suppression of fibroblast growth factor receptor signaling inhibits pancreatic cancer growth in vitro and in vivo" Gastroenterology, vol. 114, Apr. 1998, pp. 798-807.

Wang et al., "Purification and characterization of a functional soluble fibroblast growth factor receptor 1" Biochem. Biophys. Res. Comm., vol. 203, No. 3, Sep. 30, 1994, pp. 1781-1788.

Wang et al., "A natural kinase-deficient variant of fibroblast growth factor receptor 1" Biochemistry, Vo. 35, 1996, pp. 10134-10142.

Werner et al., "Differential splicing in the extracellular region of fibroblast growth factor receptor 1 generates receptor variants with different ligand-binding specificities" Molecular and Cellular Biology, vol. 12, No. 1, Jan. 1992, pp. 82-88.

Williams et al., "Activation of the FGF receptor underlies neurite outgrowth stimulated by L1, N-CAM, and N-Cadherin" Neuron, vol. 13, Sep. 1994, pp. 583-594.

Ye et al., "FGF and Shh signals control dopaminergic and serotonergic cell fate in the anterior neural plate" Cell, vol. 93, May 29, 1998, pp. 755-766.

File history for U.S. Appl. No. 13/157,712, filed Jun. 10, 2011.

PCT Notification of Transmittal of the International Search Report and the Written Opinion of the International Searching Authority, or the Declaration; International Search Report; and Written Opinion of the International Searching Authority, mailed Sep. 18, 2007, for International Application No. PCT/US2006/028597.

Patent Cooperation Treaty International Preliminary Report on Patentability, issued Jan. 22, 2008, in International Application No. PCT/US2006/028597.

Application for Entry into the European Phase with amended claims filed after receipt of European Search Report, filed Feb. 22, 2008, in European Application No. 06 800 260.9.

Amended claims filed after receipt of European Search Report, filed Mar. 17, 2008, in European Application No. 06 800 260.9.

Examination Report, mailed Jun. 10, 2008, in European Application No. 06 800 260.9.

Reply to Examination Report, filed Aug. 13, 2008, in European Application No. 06 800 260.9.

Examination Report, mailed Sep. 8, 2008, in European Application No. 06 800 260.9.

Reply to Examination Report, filed Dec. 17, 2008, in European Application No. 06 800 260.9.

Result of consultation by telephone of Dec. 17, 2008, with applicant/representative, mailed Dec. 30, 2008, in European Application No. 06 800 260.9.

Examination Report, mailed Jan. 22, 2009, in European Application No. 06 800 260.9.

Reply to Examination Report, filed Mar. 6, 2009, in European Application No. 06 800 260.9.

Reply to Examination Report, filed May 22, 2009, in European Application No. 06 800 260.9.

European Search Report, mailed Jun. 5, 2009, in European Application No. 09 075 061.3.

Examination Report, mailed Sep. 25, 2009, in European Application No. 09 075 061.3.

Reply to Examination Report, filed Feb. 25, 2010, in European Application No. 09 075 061.3.

* cited by examiner

FGFR4: D98 S99 L100 T101 S102 S103 - N104 D105 D106 E107 D108 P109 K110 S111 H112 R113 D114 P115 S116 N117 R118 H119 S120 Y121 P122 D123 Q124  (SEQ ID NO:16)

FGFR1: D99 A100 L101 P102 S103 S104 E105 D106 D107 D108 D109 D110 D111 D112 S113 S114 S115 E116 E117 K118 E119 T120 D121 N122 T123 K124 P125 N126 P127 V128  (SEQ ID NO:22)

FIG. 11B

| FGFR4 | | FGFR2 | |
|---|---|---|---|
| 98 | D | 105 | D |
| 99 | S | 106 | A |
| 100 | L | 107 | I |
| 101 | T | 108 | S |
| 102 | S | 109 | S |
| 103 | S | 110 | G |
| 104 | N | 111 | D |
| 105 | D | 112 | D |
| 106 | D | 113 | E |
| 107 | E | 114 | D |
| 108 | D | 115 | D |
| 109 | P | 116 | T |
| 110 | K | 117 | D |
| 111 | S | 118 | G |
| 112 | H | 119 | A |
| 113 | R | 120 | E |
| 114 | D | 121 | D |
| 115 | P | 122 | F |
| 116 | S | 123 | V |
| 117 | N | 124 | S |
| 118 | R | 125 | E |
| 119 | H | 126 | N |
| 120 | S | 127 | S |
| 121 | Y | 128 | N |
| 122 | P | 129 | N |
| 123 | Q | 130 | K |
| 124 | Q | 131 | R |

SEQ ID NO: 18 (FGFR4)
SEQ ID NO: 28 (FGFR2)

FIG. 11C

```
        98  99 100 101 102 103 104 105 106 107 108 109 110 111 112 113 114 115 116 117 118 119 120 121 122 123 124
FGFR4:  D   S   L   T   S   S   N   D   D   E   D   P   K   S   H   R   D   P   S   N   R   H   S   Y   P   Q   Q     SEQ ID NO: 16
       105 106 107 108 109 110 111 112 113 114 115 116 117 118 119 120 121 122 123 124 125 126 127
FGFR3:  D   A   -   P   S   S   G   D   D   D   E   D   G   E   -   -   -   D   E   A   E   D   T   G   V   D   T   G     SEQ ID NO: 33
```

FIG. 11D

FGFR2 (SEQ ID NO: 28): D A I S S G D D E D D D T D G A E D F V S E N S N N K R
                       105 106 107 108 109 110 111 112 113 114 115 116 117 118 119 120 121 122 123 124 125 126 127 128 129 130 131

FGFR1 (SEQ ID NO: 27): D A L P S S E D D D D D D D S S E E K E T D N T K P N P V
                       99 100 101 102 103 104 105 106 107 108 109 110 111 112 113 114 115 116 117 118 119 120 121 122 123 124 125 126 127 128

FIG. 11E

```
FGFR3  D A - P S S G D D E D G E D - - - - - A E D T G V D T G       SEQ ID NO:22
       105     107                 117         119             127
FGFR1  D A L P S S E D D D D D D D S S S E E K E T D N T K P N P V   SEQ ID NO:23
       99                      107             117             127
```

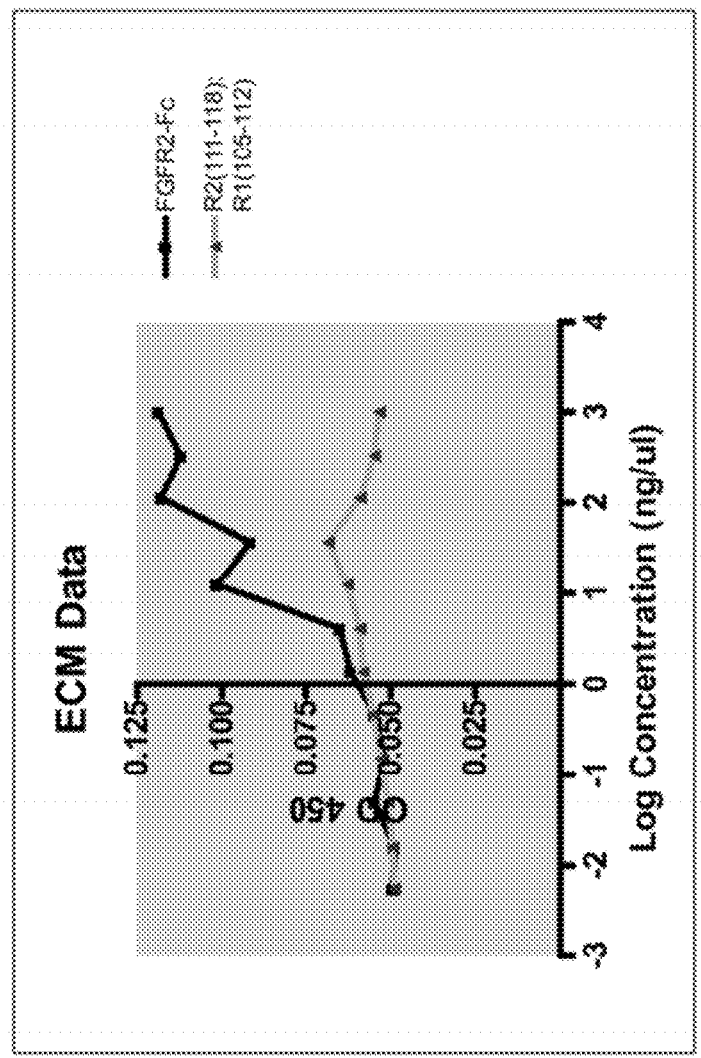

FGFR EXTRACELLULAR DOMAIN ACIDIC REGION MUTEINS

This application claims a priority benefit under 35 U.S.C. §119(e) from U.S. Provisional Application No. 61/086,121, filed Aug. 4, 2008, which is incorporated by reference herein in its entirety.

TECHNICAL FIELD

The present invention relates to fibroblast growth factor receptor (FGFR) extracellular domains (ECDs) that have been engineered to exhibit decreased tissue binding by increasing the number of acidic amino acid residues within the D1-D2 linker region. The invention further relates to polypeptide and polynucleotide sequences, vectors, host cells, compositions, and kits comprising or encoding such molecules. The invention also relates to methods of making and using FGFR ECD acidic region muteins to treat proliferative disorders, including cancer, disorders of angiogenesis, and macular degeneration.

BACKGROUND ART

Fibroblast growth factors (FGFs) and their receptors (FGFRs) are a highly conserved group of proteins with instrumental roles in angiogenesis, vasculogenesis, and wound healing, as well as in tissue patterning and limb formation in embryonic development. FGFs and FGFRs affect cell migration, proliferation, and survival, providing wide-ranging impacts on health and disease.

The FGFR family comprises four major types of receptors, FGFR1, FGFR2, FGFR3, and FGFR4. These receptors are transmembrane proteins having an extracellular domain (ECD), a transmembrane domain, and an intracytoplasmic tyrosine kinase domain. Each of the extracellular domains contains either two or three immunoglobulin (Ig) domains. When there are three Ig domains, they are referred to as D1, D2, and D3. Receptors having two Ig domains typically lack D1. An acidic motif, called the acid box, is located in the linker region between D1 and D2 in the FGFR extracellular domain. The D2 domain of FGFRs contains a heparin binding site. FGFR4 also contains a heparin binding site in D1. The acid box is believed to interact with the heparin binding site in the D2 domain. Furthermore, it has been shown that the FGFR1 and FGFR3 D1 domains are capable of interacting with the D2 and D3 domains. It has been hypothesized that the FGFR1 acid box-mediated interactions with the D2 domain, and the FGFR1 D1 domain-mediated interactions with the D2 and D3 domains play an autoinhibitory role that prevents receptor oligomerization in the absence of FGF ligand. Finally, extracellular FGFR activation by FGF ligand binding to an FGFR initiates a cascade of signaling events inside the cell, beginning with oligomerization of the receptor and activation of receptor tyrosine kinase activity.

To date, there are 22 known FGFs, each with the capacity to bind one or more FGFRs. See, e.g., Zhang et al., *J. Biol. Chem.* 281:15, 694-15,700 (2006). Several FGFs can bind to and activate each of one or more FGFRs, often with large differences in their affinities for the different FGFRs. Heparin sulfate proteoglycan ("heparin") is required for the binding of FGFs to FGFRs under certain circumstances. See, e.g., Ornitz et al., *Mol. Cell Biol.* 12:240 (1992). For example, the mitogenic response to FGF2 (also known as basic FGF (bFGF)) mediated by FGFR1 has been shown to depend on the presence of heparin. See, e.g., Ornitz et al., *Mol. Cell Biol.* 12:240 (1992).

SUMMARY

The FGFR4 extracellular domain ("ECD") binds with high affinity to FGF2 and FGF19 ligands, among others. By using the FGFR4 ECD as a 'ligand trap' to bind, for example, free FGF2 and FGF19, one may effectively treat proliferative disorders, including cancer, disorders of angiogenesis, and macular degeneration. Experiments using purified Fc fusions of the wild-type FGFR4 ECD ("FGFR4 ECD Fc fusions") showed that they exhibited poor bioavailability and a short serum half-life, which is at least partially due to excessive tissue binding, when administered to mice using intravenous (IV) methods. See FIG. 4 and Table 5. In contrast, Fc fusions of the FGFR1 ECD exhibited higher bioavailability and serum half-life. Furthermore, the FGFR4 ECD Fc fusions exhibited high levels of in vitro binding to extracellular matrix (ECM) components, whereas Fc fusions of the FGFR1, FGFR2, or FGFR3 ECD showed minimal or undetectable levels of ECM binding. See FIG. 5.

As noted above, the FGFRs typically contain an acidic motif, called an acid box, between the D1 and D2 domains. The D1 domain and the D1-D2 linker region, which contains the acid box, are more divergent than the D2 and D3 domains between FGFR4 and the other three FGFRs. Further, the FGFR1, FGFR2, and FGFR3 acid boxes all contain a greater number of acidic amino acid residues than the FGFR4 acid box. See FIGS. 11A, 11B, and 11C, respectively. Based on experiments described herein, we hypothesize that the relatively "weak" FGFR4 acid box, which contains fewer acidic amino acid residues than the FGFR1, FGFR2, and FGFR3 acid boxes, may be less effective at preventing tissue binding, and may therefore be responsible for the greater ECM binding of the FGFR4 ECD Fc fusions observed in vitro.

We have engineered FGFR4 ECDs, called FGFR4 ECD acidic region muteins, that have an increase in the total number of acidic residues within the D1-D2 linker and thus a "stronger" acid box region to reduce ECM binding and potentially reduce tissue binding in vivo and to increase the bioavailability of FGFR4 ECD fusion proteins. We have discovered that FGFR4 ECD acidic region muteins that contain an increased number of acidic residues within the D1-D2 linker exhibit decreased ECM binding. We have also discovered that certain FGFR4 ECD acidic region muteins exhibit decreased tissue binding and increased bioavailability. Thus, by increasing the total number of acidic residues within the D1-D2 linker, thus "strengthening" the FGFR4 acid box, we have engineered FGFR4 ECD acidic region muteins with improved properties, including decreased ECM binding and decreased tissue binding, which can in turn lead to increased bioavailability of FGFR4 ECD fusion proteins.

In one approach for generating "stronger" FGFR4 ECD acidic region muteins, we have replaced certain non-acidic amino acid residues with acidic amino acid residues, such that the total number of acidic residues within the FGFR4 ECD long acid box is increased relative to the wild-type FGFR4 ECD long acid box. This class of FGFR4 ECD acidic region muteins is referred to herein as "FGFR4 ECD long acid box variants." We discovered that FGFR4 ECD long acid box variants that comprise two more acidic amino acid residues than the wild-type FGFR4 ECD long acid box exhibited decreased ECM binding. See FIG. 14. FGFR4 ECD long acid box variants that contained four more acidic amino acid residues in the long acid box exhibited even further decreased ECM binding. See id.

In another approach for generating "stronger" FGFR4 ECD acidic region muteins, we have replaced all or portions of the D1-D2 linker region of FGFR4 with all or portions of the D1-D2 linker region of FGFR1, FGFR2, or FGFR3 to generate polypeptides in a class of FGFR4 ECD acidic region muteins referred to herein as "FGFR4 ECD acidic region chimeras." FGFR4 ECD acidic region chimeras include FGFR4 ECD D1-D2 linker chimeras, FGFR4 ECD exon 4 chimeras, FGFR4 ECD acid box chimeras, FGFR4 ECD long acid box chimeras, and FGFR4 ECD short acid box chimeras. We found that at least certain FGFR4 ECD D1-D2 linker chimeras, FGFR4 ECD exon 4 chimeras, and FGFR4 ECD acid box chimeras, retained the ability to bind to both FGF2 and FGF19, but showed decreased levels of ECM binding in vitro when compared to a parental FGFR4 ECD Fc fusion. See Tables 3 and 4, and FIGS. 6 and 12. Further, the FGFR4 ECD acidic region chimeras showed decreased binding to the surface of hepatocytes when compared to a parental FGFR4 ECD Fc fusion. See FIG. 7. In vitro ECM binding by an FGFR4 acidic region chimera was further reduced by introducing an N-glycan mutation either adjacent to the amino-terminus of the FGFR4 ECD D1-D2 linker or in the D2 heparin binding site. See FIG. 15.

In in vivo studies, an FGFR4 ECD acidic region mutein exhibited substantially improved bioavailability and serum half-life relative to a parental FGFR4 ECD Fc fusion. See FIG. 8. Mice injected with the FGFR4 ECD acidic region mutein showed a statistically significant reduction in tumor burden in certain tumor models when compared to a control group, showing that the FGFR4 ECD acidic region muteins possess a similar anti-tumor activity as FGFR4 ECDs administered in vivo. See FIG. 9. The FGFR4 ECD acidic region muteins may therefore be used, e.g., to treat proliferative disorders, including cancer, disorders of angiogenesis, and macular degeneration.

Both the FGFR2 ECD-Fc and FGFR3 ECD-Fc fusion proteins showed significantly lower levels of ECM binding in vitro than a parental FGFR4 ECD-Fc, however they showed slightly higher levels of ECM binding than an FGFR1 ECD-Fc fusion protein at higher protein concentrations. See FIG. 5. Although the FGFR2 and FGFR3 acid boxes contain a greater number of acidic amino acid residues than the FGFR4 acid box, they both contain fewer acidic amino acid residues than the FGFR1 acid box. See FIGS. 11D and 11E, respectively. In vitro ECM binding experiments showed that FGFR2 and FGFR3 ECD acidic region muteins in which the total number of acidic residues within the FGFR2 and FGFR3 long acid boxes was increased exhibited decreased ECM binding relative to the parental FGFR2 and FGFR3 ECDs. See FIGS. 17A and 17B, respectively.

In certain embodiments, FGFR1, FGFR2, and FGFR3 ECDs may be engineered to have a decrease in the total number of acidic residues within the D1-D2 linker, and thus a "weaker" acid box to increase tissue binding in vivo and to decrease the bioavailability of the FGFR1, FGFR2, and FGFR3 ECD fusion proteins. Such "weakened" FGFR1, FGFR2, and FGFR3 ECDs may be useful, for example, when delivered locally, to prevent toxicity and/or side effects that might occur with systemic administration.

In certain embodiments, a polypeptide comprising an FGFR4 ECD acidic region mutein is provided. In certain embodiments, an isolated polypeptide comprising an FGFR4 ECD acidic region mutein is provided. In certain embodiments, an FGFR4 ECD acidic region mutein is an FGFR4 ECD D1-D2 linker chimera. In certain embodiments, the FGFR4 ECD D1-D2 linker chimera comprises a D1-D2 linker selected from an FGFR1 D1-D2 linker, an FGFR2 D1-D2 linker, and an FGFR3 D1-D2 linker, in place of the FGFR4 D1-D2 linker. In certain embodiments, the FGFR4 ECD D1-D2 linker chimera comprises an amino acid sequence selected from SEQ ID NOs: 22, 26, 28, and 32, in place of an FGFR4 D1-D2 linker selected from SEQ ID NOs: 16 and 17. In certain embodiments, the FGFR4 ECD D1-D2 linker chimera comprises an amino acid sequence selected from SEQ ID NOs: 35 to 38.

In certain embodiments, an FGFR4 ECD acidic region mutein is an FGFR4 ECD exon 4 chimera. In certain embodiments, the FGFR4 ECD exon 4 chimera comprises an exon 4 selected from an FGFR1 exon 4, an FGFR2 exon 4, and an FGFR3 exon 4, in place of the FGFR4 exon 4. In certain embodiments, the FGFR4 ECD exon 4 chimera comprises an amino acid sequence selected from SEQ ID NOs: 23, 92, 29, and 33, in place of an FGFR4 D1-D2 linker selected from SEQ ID NOs: 18 and 19. In certain embodiments, the FGFR4 ECD exon 4 chimera comprises an amino acid sequence selected from SEQ ID NOs: 39 to 42.

In certain embodiments, an FGFR4 ECD acidic region mutein is an FGFR4 ECD acid box chimera. In certain embodiments, the FGFR4 ECD acid box chimera comprises an acid box selected from the FGFR1 acid box, the FGFR2 acid box, and the FGFR3 acid box, in place of the FGFR4 acid box. In certain embodiments, the FGFR4 ECD acid box chimera comprises an amino acid sequence selected from SEQ ID NOs: 24, 30, and 34 in place of the FGFR4 acid box having an amino acid sequence of SEQ ID NO: 20. In certain embodiments, an FGFR4 ECD acid box chimera comprises an acid box region selected from an FGFR1 acid box region, an FGFR2 acid box region, and an FGFR3 acid box region, in place of the FGFR4 acid box. In certain embodiments, the FGFR4 ECD acid box chimera comprises an amino acid sequence selected from SEQ ID NOs: 56 to 65, in place of the FGFR4 acid box having an amino acid sequence of SEQ ID NO: 20. In certain embodiments, the FGFR4 ECD acid box chimera comprises an acid box region selected from an FGFR1 acid box region, an FGFR2 acid box region, and an FGFR3 acid box region, in place of an FGFR4 acid box region. In certain embodiments, the FGFR4 ECD acid box chimera comprises an amino acid sequence selected from SEQ ID NOs: 56 to 65, in place of an FGFR4 acid box region having an amino acid sequence selected from SEQ ID NOs: 46 to 55. In certain embodiments, the FGFR4 ECD acid box chimera comprises an FGFR1 acid box region having the amino acid sequence of SEQ ID NO: 56 in place of an FGFR4 acid box region having the amino acid sequence of SEQ ID NO: 51. In certain embodiments, the FGFR4 ECD acid box chimera comprises an acid box selected from the FGFR1 acid box, the FGFR2 acid box, and the FGFR3 acid box, in place of an FGFR4 acid box region. In certain embodiments, the FGFR4 ECD acid box chimera comprises an amino acid sequence selected from SEQ ID NOs: 24, 30, and 34 in place of an FGFR4 acid box region having an amino acid sequence selected from SEQ ID NOs: 46 to 55. In certain embodiments, the FGFR4 ECD acid box chimera comprises an amino acid sequence selected from SEQ ID NOs: 43 to 45 and 157.

In certain embodiments, an FGFR4 ECD acidic region chimera is an FGFR4 ECD long acid box chimera. In certain embodiments, the FGFR4 ECD long acid box chimera comprises a long acid box selected from an FGFR1 long acid box, an FGFR2 long acid box, and an FGFR3 long acid box, in place of the FGFR4 long acid box. In certain embodiments, the FGFR4 long acid box chimera comprises an amino acid sequence selected from SEQ ID NOs: 98 to 100, in place of an FGFR4 long acid box selected from SEQ ID NOs: 96 and 97. In certain embodiments, the FGFR4 long acid box chimera comprises an amino acid sequence selected from SEQ ID NOs: 105 to 107.

In certain embodiments, an FGFR4 ECD acidic region mutein is an FGFR4 ECD short acid box chimera. In certain embodiments, the FGFR4 ECD short acid box chimera comprises a short acid box selected from an FGFR1 short acid box, an FGFR2 short acid box, and an FGFR3 short acid box, in place of the FGFR4 short acid box. In certain embodiments, the FGFR4 ECD short acid box chimera comprises an amino acid sequence selected from SEQ ID NOs: 102 to 104, in place of an FGFR4 short acid box having an amino acid sequence of SEQ ID NO: 101. In certain embodiments, the FGFR4 ECD short acid box chimera comprises an amino acid sequence selected from SEQ ID NOs: 108 to 110.

In certain embodiments, the FGFR4 ECD acidic region mutein is an FGFR4 ECD long acid box variant. In certain embodiments, the FGFR4 ECD long acid box variant comprises a variant of the FGFR4 ECD that has an increased number of acidic amino acid residues in the long acid box relative to the FGFR4 wild-type long acid box. In certain such embodiments, at least two, three, or four non-acidic residues within the long acid box of the FGFR4 ECD are each independently replaced with an acidic residue selected from Glu (E) and Asp (D). In certain such embodiments, at least one acidic residue is inserted between amino acids 103 and 104 of SEQ ID NOs: 1 and 2. In certain embodiments, two acidic residues are inserted between amino acids 103 and 104 of SEQ ID NOs; 1 and 2. In certain such embodiments, the number of acidic residues in the FGFR4 long acid box is at least seven. In certain such embodiments, FGFR4 ECD residues 104 to 114 (SEQ ID NO: 145) are replaced with FGFR1 ECD residues 106 to 117 (SEQ ID NO: 149); FGFR4 ECD residues 104 to 114 (SEQ ID NO: 145) are replaced with FGFR1 ECD residues 107 to 117 (SEQ ID NO: 150); FGFR4 ECD residues 104 to 110 (SEQ ID NO: 146) are replaced with FGFR1 ECD residues 105-113 (SEQ ID NO: 151); FGFR4 ECD residues 113 to 116 (SEQ ID NO: 147) are replaced with FGFR1 ECD residues 116-119 (SEQ ID NO: 152); or FGFR4 ECD residues 109 to 113 (SEQ ID NO: 148) are replaced with FGFR1 ECD residues 112-116 (SEQ ID NO: 153). In certain such embodiments, FGFR4 ECD residues 104 to 114 (SEQ ID NO: 145) are replaced with FGFR1 ECD residues 106 to 117 (SEQ ID NO: 149); FGFR4 ECD residues 104 to 114 (SEQ ID NO: 145) are replaced with FGFR1 ECD residues 107 to 117 (SEQ ID NO: 150); FGFR4 ECD residues 104 to 110 (SEQ ID NO: 146) are replaced with FGFR1 ECD residues 105-113 (SEQ ID NO: 151); FGFR4 ECD residues 113 to 116 (SEQ ID NO: 147) are replaced with FGFR1 ECD residues 116-119 (SEQ ID NO: 152); or FGFR4 ECD residues 109 to 113 (SEQ ID NO: 148) are replaced with FGFR1 ECD residues 112-116 (SEQ ID NO: 153).

In certain embodiments, an FGFR4 ECD fusion molecule comprising an FGFR4 ECD acidic region mutein and a fusion partner is provided. In certain embodiments, an isolated FGFR4 ECD fusion molecule comprising an FGFR4 ECD acidic region mutein and a fusion partner is provided. In certain embodiments, an FGFR4 ECD fusion molecule comprising an amino acid sequence selected from SEQ ID NOs: 35 to 45, 105 to 121, and 157 is provided. In certain embodiments, an isolated FGFR4 ECD fusion molecule comprising an amino acid sequence selected from SEQ ID NOs: 35 to 45, 105 to 121, and 157 is provided. In certain embodiments, an FGFR4 ECD fusion molecule comprising the amino acid sequence of SEQ ID NO: 35, is provided. In certain embodiments, an isolated FGFR4 ECD fusion molecule comprising the amino acid sequence of SEQ ID NO: 35, is provided. In certain embodiments, the fusion partner is selected from Fc, albumin, and polyethylene glycol. In certain embodiments, the fusion partner is Fc. In certain embodiments, an FGFR4 ECD fusion molecule comprising an amino acid sequence selected from SEQ ID NOs: 86 to 88, 124 to 140, 143, 144, and 158 is provided. In certain embodiments, an isolated FGFR4 ECD fusion molecule comprising an amino acid sequence selected from SEQ ID NOs: 86 to 88, 124 to 140, 143, 144, and 158 is provided. In certain embodiments, an FGFR4 ECD fusion molecule comprising the amino acid sequence of SEQ ID NO: 86 is provided. In certain embodiments, an isolated FGFR4 ECD fusion molecule comprising the amino acid sequence of SEQ ID NO: 86 is provided. In certain embodiments, an FGFR4 ECD fusion molecule consisting of the amino acid sequence of SEQ ID NO: 86 is provided. In certain embodiments, an isolated FGFR4 ECD fusion molecule consisting of the amino acid sequence of SEQ ID NO: 86 is provided.

In certain embodiments, a pharmaceutical composition comprising an FGFR4 ECD acidic region mutein and a pharmaceutically acceptable carrier is provided. In certain embodiments, a polynucleotide comprising a nucleic acid sequence that encodes an FGFR4 ECD acidic region mutein is provided.

In certain embodiments, a method of treating an angiogenic disorder in a patient comprising administering to the patient a pharmaceutical composition comprising an FGFR4 ECD acidic region mutein is provided. In certain embodiments, a method of treating cancer in a patient comprising administering to the patient a pharmaceutical composition comprising an FGFR4 ECD acidic region mutein is provided. In certain embodiments, the cancer is selected from colon, liver, lung, breast, and prostate cancers. In certain embodiments, a method of treating macular degeneration in a patient comprising administering to the patient a pharmaceutical composition comprising an FGFR4 ECD acidic region mutein is provided.

In certain embodiments, the FGFR4 acidic region mutein comprises at least one point mutation that inhibits glycosylation. In certain embodiments, the at least one point mutation that inhibits glycosylation is selected from N91A, N156A, N237A, N269A, N290A, and N301A. In certain embodiments, the FGFR4 acidic region mutein comprises an amino acid sequence selected from SEQ ID NOs: 120, 121, and 168.

In certain embodiments, an FGFR2 ECD acidic region mutein is provided. In certain embodiments, the FGFR2 ECD acidic region mutein is an FGFR2 ECD short acid box chimera. In certain embodiments, the FGFR2 ECD short acid box chimera comprises at least the FGFR1 short acid box in place of at least the FGFR2 short acid box. In certain such embodiments, FGFR2 ECD residues 111 to 118 (SEQ ID NO: 155) are replaced with FGFR1 ECD residues 105 to 112 (SEQ ID NO: 154). In certain embodiments, the FGFR2 ECD short acid box chimera comprises the amino acid sequence of SEQ ID NO: 122.

In certain embodiments, an FGFR3 ECD acidic region mutein is provided. In certain embodiments, the FGFR3 ECD acidic region mutein is an FGFR3 ECD short acid box chimera. In certain embodiments, the FGFR3 ECD short acid box chimera comprises at least the FGFR1 short acid box in place of at least the FGFR3 short acid box. In certain such embodiments, FGFR3 ECD residues 110 to 117 (SEQ ID NO: 156) are replaced with FGFR1 ECD residues 105 to 112 (SEQ ID NO: 154). In certain embodiments, the FGFR3 ECD short acid box chimera comprises the amino acid sequence of SEQ ID NO: 123.

BRIEF DESCRIPTION OF THE DRAWINGS

FIG. 1 shows the extracellular domain (ECD) amino acid sequence of FGFR4 with a 17 amino acid C-terminal deletion, which was fused to an Fc domain in the parental FGFR4 ECD-Fc (also referred to herein as "R4Mut4"). The amino acid sequence in FIG. 1 includes the signal peptide, which is cleaved in the mature fusion protein. The numbers refer to the amino acid position, and certain domains within the ECD are illustrated in gray above the amino acid numbers. The amino acid positions within the signal peptide are given negative values because they are cleaved in the mature fusion protein. The first amino acid residue of the mature fusion protein is designated as amino acid position 1. The linker between the first and second Ig domains (referred to herein interchangeably as the "linker domain," "linker region," "D1-D2 linker," and "D1-D2 linker region") is illustrated in a darker gray.

FIG. 2 shows a sequence alignment of the linker domains from FGFR1 and FGFR4 and the boundaries and sequence of the swapped regions in the three variants, called FGFR4ECD (ABMut1: delta17)-Fc (ABMut1), FGFR4ECD(ABMut2: delta17)-Fc (ABMut2), and FGFR4ECD(ABMut3: delta17)-Fc (ABMut3). Acidic residues within the D1-D2 linker are indicated with underlining and bold font.

FIG. 11 shows amino acid sequence alignments between (A) the FGFR4 ECD acidic region and the FGFR1 ECD acidic region, (B) the FGFR4 ECD acidic region and the FGFR2 ECD acidic region, (C) the FGFR4 ECD acidic region and the FGFR3 ECD acidic region, (D) the FGFR1 ECD acidic region and the FGFR2 ECD acidic region, and (E) the FGFR1 ECD acidic region and the FGFR3 ECD acidic region.

DETAILED DESCRIPTION OF CERTAIN EMBODIMENTS

Figure 3:
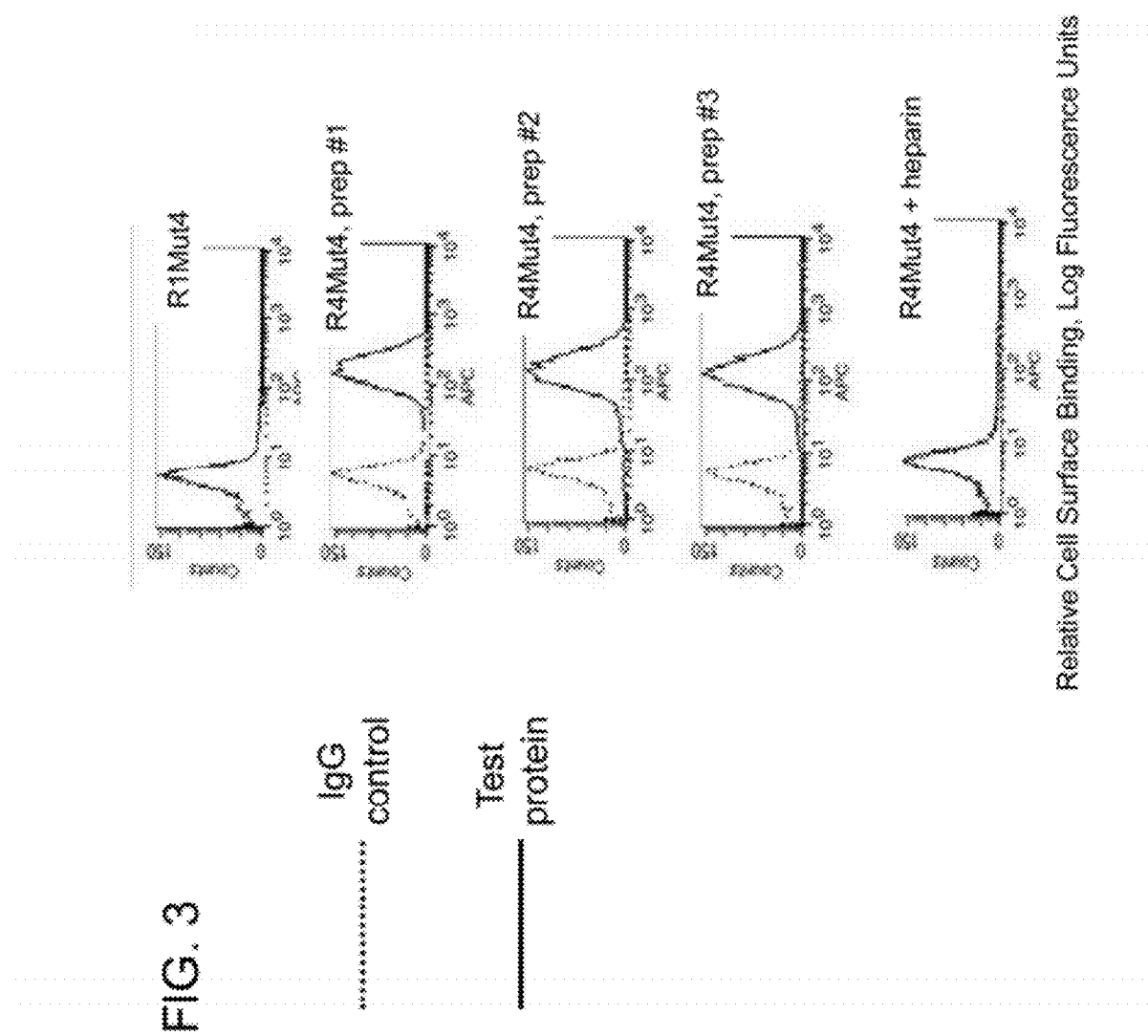
FIG. 3 shows the binding of R1Mut4, three different preparations of R4Mut4, R4Mut4 plus heparin, and an IgG control to hepatocytes, detected by flow cytometry, as described in Example 5. The number of cells (counts) is shown on the Y-axis, and the X-axis shows the relative fluorescent signal, in log units.

The section headings used herein are for organizational purposes only and are not to be construed as limiting the subject matter described.

Definitions

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular.

Certain techniques used in connection with recombinant DNA, oligonucleotide synthesis, tissue culture and transformation (e.g., electroporation, lipofection), enzymatic reactions, and purification techniques are known in the art. Many such techniques and procedures are described, e.g., in Sambrook et al. *Molecular Cloning: A Laboratory Manual* (2d ed., Cold Spring Harbor Laboratory Press, Cold Spring Harbor, N.Y. (1989)), among other places. In addition, certain techniques for chemical syntheses, chemical analyses, pharmaceutical preparation, formulation, and delivery, and treatment of patients are also known in the art.

In this application, the use of "or" means "and/or" unless stated otherwise. In the context of a multiple dependent claim, the use of "or" refers back to more than one preceding independent or dependent claim in the alternative only. Also, terms such as "element" or "component" encompass both elements and components comprising one unit and elements and components that comprise more than one subunit unless specifically stated otherwise.

As utilized in accordance with the present disclosure, the following terms, unless otherwise indicated, shall be understood to have the following meanings:

The terms "nucleic acid molecule" and "polynucleotide" may be used interchangeably, and refer to a polymer of nucleotides. Such polymers of nucleotides may contain natural and/or non-natural nucleotides, and include, but are not limited to, DNA, RNA, and PNA.

The terms "polypeptide" and "protein" are used interchangeably, and refer to a polymer of amino acid residues. Such polymers of amino acid residues may contain natural and/or non-natural amino acid residues, and include, but are not limited to, peptides, oligopeptides, dimers, trimers, and multimers of amino acid residues. The terms "polypeptide" and "protein" include natural and non-natural amino acid sequences, and both full-length proteins and fragments thereof. Those terms also include post-translationally modified polypeptides and proteins, including, for example, glycosylated, sialylated, acetylated, and/or phosphorylated polypeptides and proteins.

The terms "acidic amino acid," "acidic amino acid residue," and "acidic residue" are used interchangeably herein and refer to an amino acid residue that is negatively charged at physiological pH. Acidic amino acids include, but are not limited to, aspartic acid (Asp, D) and glutamic acid (Glu, E).

The terms "non-acidic amino acid," "non-acidic amino acid residue," and "non-acidic residue" are used interchangeably and refer to an amino acid residue that is not negatively charged at physiological pH.

The terms "FGFR extracellular domain" and "FGFR ECD" include FGFR1 ECDs, FGFR2 ECDs, FGFR3 ECDs, and FGFR4 ECDS, as defined herein.

The terms "FGFR1 extracellular domain" and "FGFR1 ECD" include native FGFR1 ECDs, FGFR1 ECD fragments, and FGFR1 ECD variants. As used herein, the term "native FGFR1 ECD" refers to an FGFR1 ECD having an amino acid sequence selected from SEQ ID NOs: 21 and 25. As used herein, the term "FGFR1 ECD fragment" refers a polypeptide having an amino acid sequence selected from SEQ ID NOs: 21 and 25, but wherein amino acid residues have been deleted from the amino-terminus and/or carboxy-terminus, wherein the fragments are capable of binding to FGF2. As used herein, the term "FGFR1 ECD variants" refers to variants of the portion of the FGFR1 polypeptide that extends into the extracellular space and variants of fragments thereof that comprise D1, D2, and D3, wherein the variants are capable of binding to FGF2. Such variants may contain amino acid additions, deletions, and substitutions, provided that the FGFR1 ECD variants remain capable of ligand binding.

In certain embodiments, an FGFR1 ECD lacks a signal peptide. In certain embodiments, an FGFR1 ECD includes at least one signal peptide, which may be selected from a native FGFR1 signal peptide and/or a heterologous signal peptide.

The terms "FGFR2 extracellular domain" and "FGFR2 ECD" include native FGFR2 ECDs, FGFR2 ECD fragments, and FGFR2 ECD variants. As used herein, the term "native FGFR2 ECD" refers to an FGFR2 ECD having an amino acid sequence of SEQ ID NO: 27. As used herein, the term "FGFR2 ECD fragment" refers a polypeptide having an amino acid sequence selected from SEQ ID NO: 27, but wherein amino acid residues have been deleted from the amino-terminus and/or carboxy-terminus, wherein the fragments are capable of binding to FGF2. A non-limiting exemplary FGFR2 ECD fragment has the amino acid sequence of SEQ ID NO: 160, which corresponds to the amino acid sequence of SEQ ID NO: 27, but with the last three carboxy-terminal amino acid residues, YLE, deleted. As used herein, the term "FGFR2 ECD variants" refers to variants of the portion of the FGFR2 polypeptide that extends into the extracellular space and variants of fragments thereof that comprise D1, D2, and D3, wherein the variants are capable of binding to FGF2. Such variants may contain amino acid additions, deletions, and substitutions, provided that the FGFR2 ECD variant remains capable of ligand binding. FGFR2 ECD variants may include amino acid substitutions within the FGFR2 ECD that inhibit N-glycosylation, referred to interchangeably herein as "FGFR2 ECD glycosylation mutants" and "FGFR2 ECD N-glycan mutants." In certain embodiments, at least one amino acid within the FGFR2 ECD is mutated to prevent glycosylation at that site in the polypeptide. Non-limiting exemplary FGFR2 ECD amino acids that may be glycosylated include N62, N1002, N207, N220, N244, N276, N297, and N310 in SEQ ID NO: 27. Non-limiting exemplary amino acid mutations in FGFR4 ECD glycosylation mutants include N62A, N102A, N207A, N220A, N244A, N276A, N297A, and N310A in SEQ ID NO: 27.

In certain embodiments, an FGFR2 ECD lacks a signal peptide. In certain embodiments, an FGFR2 ECD includes at least one signal peptide, which may be selected from a native FGFR2 signal peptide and/or a heterologous signal peptide.

The terms "FGFR3 extracellular domain" and "FGFR3 ECD" include native FGFR3 ECDs, FGFR3 ECD fragments, and FGFR3 ECD variants. As used herein, the term "native FGFR3 ECD" refers to an FGFR3 ECD having an amino acid sequence of SEQ ID NO: 31. As used herein, the term "FGFR3 ECD fragment" refers a polypeptide having an amino acid sequence selected from SEQ ID NO: 31, but wherein amino acid residues have been deleted from the amino-terminus and/or carboxy-terminus, wherein the fragments are capable of binding to FGF2. A non-limiting exemplary FGFR3 ECD fragment has the amino acid sequence of SEQ ID NO: 161, which corresponds to the amino acid sequence of SEQ ID NO: 31, but with the last three carboxy-terminal amino acid residues, YAG, deleted. As used herein, the term "FGFR3 ECD variants" refers to variants of the portion of the FGFR3 polypeptide that extends into the extracellular space and variants of fragments thereof that comprise D1, D2, and D3, wherein the variants are capable of binding to FGF2. Such variants may contain amino acid additions, deletions, and substitutions, provided that the FGFR3 ECD variant remains capable of ligand binding. FGFR3 ECD variants may include amino acid substitutions within the FGFR3 ECD that inhibit N-glycosylation, referred to interchangeably herein as "FGFR3 ECD glycosylation mutants" and "FGFR3 ECD N-glycan mutants." In certain embodiments, at least one amino acid within the FGFR3 ECD is mutated to prevent glycosylation at that site in the polypeptide. Non-limiting exemplary FGFR3 ECD amino acids that may be glycosylated include N76, N203, N240, N272, N293, and N306 in SEQ ID NO: 31. Non-limiting exemplary amino acid mutations in FGFR3 ECD glycosylation mutants include N76A, N203A, N240A, N272A, N293A, and N306A in SEQ ID NO: 31.

In certain embodiments, an FGFR3 ECD lacks a signal peptide. In certain embodiments, an FGFR3 ECD includes at least one signal peptide, which may be selected from a native FGFR3 signal peptide and/or a heterologous signal peptide.

The terms "FGFR4 extracellular domain" and "FGFR4 ECD" include native FGFR4 ECDs, FGFR4 ECD fragments, and FGFR4 ECD variants. As used herein, the term "native FGFR4 ECD" refers to an FGFR4 ECD having an amino acid sequence selected from SEQ ID NOs: 1, 2, 3, and 93. As used herein, the term "FGFR4 ECD fragment" refers a polypeptide having an amino acid sequence selected from SEQ ID NOs: 1, 2, 3, and 93, but wherein all or a portion of the sequence LEASEEVE (SEQ ID NO: 70) has been deleted from the amino terminus and/or all or a portion of the sequence LPEEDPTWTAAAPEARYTD (SEQ ID NO: 71) has been deleted from the carboxy terminus of the polypeptide, wherein the fragments are capable of binding to FGF2 and/or FGF19. Non-limiting exemplary FGFR4 ECD fragments have the amino acid sequences shown in SEQ ID NOs: 6 to 10 and 76 to 81. As used herein, the term "FGFR4 ECD variants" refers to variants of the portion of the FGFR4 polypeptide that extends into the extracellular space and variants of fragments thereof that comprise D1, D2, and D3, wherein the variants are capable of binding to FGF2 and/or FGF19. Such variants may contain amino acid additions, deletions, and substitutions, provided that the FGFR4 ECD variant remains capable of binding to FGF2 and/or FGF19 (see below for a discussion of the structure/function relationship of FGFR extracellular domains).

FGFR4 ECD variants may include amino acid substitutions within the FGFR4 ECD that inhibit N-glycosylation, referred to interchangeably herein as "FGFR4 ECD glycosylation mutants" and "FGFR4 ECD N-glycan mutants." In certain embodiments, one or more amino acids within the FGFR4 ECD are mutated to prevent glycosylation at that site in the polypeptide. Non-limiting exemplary FGFR4 ECD amino acids that may be glycosylated include N91, N156, N237, N269, N290, and N301 in SEQ ID NOs: 1 and 2. Non-limiting exemplary amino acid mutations in FGFR4 ECD glycosylation mutants include N91A, N156A, N237A, N269A, N290A, and N301A in SEQ ID NOs: 1 and 2.

In certain embodiments, an FGFR4 ECD lacks a signal peptide. In certain embodiments, an FGFR4 ECD includes at least one signal peptide, which may be selected from a native FGFR4 signal peptide and/or a heterologous signal peptide.

The terms "FGFR4 2 Ig extracellular domain" and "FGFR4 2 Ig ECD" include FGFR4 2 Ig ECDs, FGFR4 2Ig ECD fragments, and FGFR4 2Ig ECD variants. As used herein, the term "FGFR4 2 Ig ECD" refers to a polypeptide comprising the acid box and domains D2 and D3, wherein the polypeptide has an amino acid sequence selected from SEQ ID NOs: 1, 2, 3, and 93, but with at least a portion of D1 deleted. Exemplary FGFR4 2 Ig ECDs have the amino acid sequence of SEQ ID NO: 94. As used herein, the term "FGFR4 2Ig ECD fragment" refers to an FGFR4 2Ig ECD polypeptide wherein all or a portion of the sequence LPEEDPTWTAAAPEARYTD (SEQ ID NO: 71) has been deleted from the carboxy-terminus of the polypeptide. As used herein, the term "FGFR4 2Ig ECD variants" refers to variants of the FGFR4 2Ig ECDs and FGFR4 2Ig ECD fragments discussed above, wherein the variants are capable of binding to FGF2 and/or FGF19. Such variants may contain amino acid additions, deletions, and substitutions, provided that the FGFR421 g ECD variant remains capable of binding to FGF2 and/or FGF19 (see below for a discussion of the structure/function relationship of FGFR extracellular domains).

An "FGFR4 ECD D1-D2 linker chimera" refers to an FGFR4 ECD selected from native FGFR4 ECDs, FGFR4 ECD fragments, and FGFR4 ECD variants, in which the linker region between immunoglobulin-like domain I (D1) and immunoglobulin-like domain II (D2) (referred to herein interchangeably as the "linker domain," "linker region," "D1-D2 linker," and "D1-D2 linker region") has been replaced with the D1-D2 linker region from FGFR1, FGFR2, or FGFR3. The D1-D2 linker of the FGFR4 ECD has the sequence DSLTSSNDDEDPKSHRDPSNRHSYPQQ (SEQ ID NO: 16), which is amino acids 98 to 124, inclusive, of SEQ ID NO: 1; or has the sequence DSLTSSNDDEDPKSHRDL-SNRHSYPQQ (SEQ ID NO: 17), which is amino acids 98 to 124, inclusive, of SEQ ID NO: 2. The D1-D2 linker of FGFR1 has the sequence DALPSSEDDDDDDDSSSEEKETDNTK-PNPV (SEQ ID NO: 22), which is amino acids 99 to 128, inclusive, of SEQ ID NO: 21; or has the sequence DALPSSEDDDDDDDSSSEEKETDNTKPNRMPV (SEQ ID NO: 26), which is amino acids 99 to 130, inclusive, of SEQ ID NO: 25. The D1-D2 linker of FGFR2 has the sequence DAISSGDDEDDTDGAEDFVSENSNNKR (SEQ ID NO: 28), which is amino acids 105 to 131, inclusive, of SEQ ID NO: 27. The D1-D2 linker of FGFR3 has the sequence DAPSSGDDEDGEDEAEDTGVDTG (SEQ ID NO: 32), which is amino acids 105 to 127, inclusive, of SEQ ID NO: 31. Certain exemplary FGFR4 ECD D1-D2 linker chimeras include, but are not limited to, FGFR4 ECD D1-D2 linker chimeras having the amino acid sequences of SEQ ID NOs: 35 to 38.

An "FGFR4 2Ig ECD D1-D2 linker chimera" refers to an FGFR4 2Ig ECD selected from FGFR4 2 Ig ECDs, FGFR4 2Ig ECD fragments, and FGFR4 2 Ig ECD variants, in which the linker region between immunoglobulin-like domain I (D1) and immunoglobulin-like domain II (D2) (referred to herein interchangeably as the "linker domain," "linker region," "D1-D2 linker," and "D1-D2 linker region") has been replaced with the D1-D2 linker region from FGFR1, FGFR2, or FGFR3, as described above for FGFR4 ECD D1-D2 linker chimeras.

The terms "corresponding amino acid residue" and "corresponding residue" are used interchangeably herein to refer to an amino acid residue or a gap in the amino acid sequence (as indicated by "-") of a first FGFR ECD D1-D2 linker region that lines up with an amino acid residue or a gap in the amino acid sequence (as indicated by "-") of a second FGFR ECD D1-D2 linker region shown in a sequence alignment. As defined herein, the corresponding amino acid residues between FGFR4 and FGFR1 are shown in FIG. 11A. As defined herein, the corresponding amino acid residues between FGFR4 and FGFR2 are shown in FIG. 11B. As defined herein, the corresponding amino acid residues between FGFR4 and FGFR3 are shown in FIG. 11C. As defined herein, the corresponding amino acid residues between FGFR1 and FGFR2 are shown in FIG. 11D. As defined herein, the corresponding amino acid residues between FGFR1 and FGFR3 are shown in FIG. 11E. In certain embodiments, the amino acid residue of a first FGFR ECD is replaced by the corresponding amino acid residue of a second FGFR ECD. In certain such embodiments, when the corresponding amino acid of the second FGFR ECD is a gap, the amino acid residue of the first FGFR ECD is deleted. In certain such embodiments, when the amino acid residue of the first FGFR ECD is a gap, the corresponding amino acid residue of the second FGFR ECD is inserted into the first FGFR ECD.

The terms "corresponding amino acid sequence" and "corresponding sequence" are used interchangeably herein to refer to the sequence of amino acid residues within a particular region of an FGFR ECD.

An "FGFR4 ECD exon 4 chimera" refers to an FGFR4 ECD selected from native FGFR4 ECDs, FGFR4 ECD fragments, and FGFR4 ECD variants, in which the amino acid sequence encoded by exon 4 (referred to herein interchangeably as "exon 4" or "exon 4 region") has been replaced with the amino acid sequence encoded by exon 4 from FGFR1, FGFR2, or FGFR3. Exon 4 of the FGFR4 ECD encodes the sequence DSLTSSNDDEDPKSHRDLSNRHSYPQ (SEQ ID NO: 18), which is amino acids 98 to 123, inclusive, of SEQ ID NO: 1; or encodes the sequence DSLTSSNDDEDPKSHRDLSNRHSYPQ (SEQ ID NO: 19), which is amino acids 98 to 123, inclusive, of SEQ ID NO: 2. Exon 4 of FGFR1 encodes the sequence DALPSSEDDDDDDDSSSEEKETDNTKPN (SEQ ID NO: 23), which is amino acids 99 to 126, inclusive, of SEQ ID NO: 21; or encodes the sequence DALPSSEDDDDDDDSSSEEKETDNTKPNRM (SEQ ID NO: 92), which is amino acids 99 to 128, inclusive, of SEQ ID NO: 25. Exon 4 of FGFR2 encodes the sequence DAISSGDDEDDTDGAEDFVSENSNNK (SEQ ID NO: 29), which is amino acids 105 to 130, inclusive, of SEQ ID NO: 27. Exon 4 of FGFR3 encodes the sequence DAPSSGDDEDGEDEAEDTGVDT (SEQ ID NO: 33), which is amino acids 105 to 126, inclusive, of SEQ ID NO: 31. Certain exemplary FGFR4 ECD exon 4 chimeras include, but are not limited to, FGFR4 ECD exon 4 chimeras having the amino acid sequences of SEQ ID NOs: 39 to 42.

An "FGFR4 2Ig ECD exon 4 chimera" refers to an FGFR4 2Ig ECD selected from FGFR4 2Ig ECDs, FGFR4 2 Ig ECD fragments, and FGFR4 2 Ig ECD variants, in which the amino acid sequence encoded by exon 4 (referred to herein interchangeably as "exon 4" or "exon 4 region") has been replaced with the amino acid sequence encoded by exon 4 from FGFR1, FGFR2, or FGFR3, as described above for FGFR4 ECD exon 4 chimeras.

An "FGFR4 ECD acid box chimera" refers to an FGFR4 ECD selected from native FGFR4 ECDs, FGFR4 ECD fragments, and FGFR4 ECD variants, in which at least the acid box has been replaced with at least the acid box from FGFR1, FGFR2, or FGFR3. As defined herein, the acid box of FGFR4 has the sequence DDEDPKSHR (SEQ ID NO: 20). As defined herein, the acid box of FGFR1 has the sequence EDDDDDDSS SE (SEQ ID NO: 24). As defined herein, the acid box of FGFR2 has the sequence DDEDDTD (SEQ ID NO: 30). As defined herein, the acid box of FGFR3 has the sequence DDEDGE (SEQ ID NO: 34).

An "FGFR4 2Ig ECD acid box chimera" refers to an FGFR4 ECD selected from FGFR4 2Ig ECDs, FGFR4 2Ig ECD fragments, and FGFR4 2 Ig ECD variants, in which at least the acid box has been replaced with at least the acid box from FGFR1, FGFR2, or FGFR3, as described above for FGFR4 ECD acid box chimeras.

As used herein, the term "acid box region" means a region of an FGFR ECD that includes the acid box defined above, along with additional amino acids from the FGFR ECD sequence on either the amino-terminus, the carboxy-terminus, or both the amino-terminus and the carboxy-terminus of the acid box, up to and including all of the additional amino acids found in the D1-D2 linker of the FGFR ECD, as defined above. As defined herein, the term FGFR4 ECD acid box chimera includes polypeptides in which the acid box of FGFR4 is replaced with an acid box region from FGFR1, FGFR2, or FGFR3. The term FGFR4 ECD acid box chimera also includes polypeptides in which an acid box region of FGFR4 is replaced with an acid box region from FGFR1, FGFR2, or FGFR3. The term FGFR4 ECD acid box chimera also includes polypeptides in which an acid box region of FGFR4 is replaced with the acid box from FGFR1, FGFR2, or FGFR3. Certain exemplary FGFR4 ECD acid box chimeras include, but are not limited to, FGFR4 ECD acid box chimeras having the amino acid sequences of SEQ ID NOs: 43 to 45 and 157.

A "long acid box" refers to a region of an FGFR ECD that includes the acid box and certain additional amino acid residues on the amino-terminus and/or carboxy-terminus of the acid box. As defined herein, the long acid box of the FGFR4 ECD has the sequence NDDEDPKSHRDPSNR (SEQ ID NO: 96), which is amino acids 104 to 118, inclusive, of SEQ ID NO: 1; or has the sequence NDDEDPKSHRDLSNR (SEQ ID NO: 97), which is amino acids 104 to 118, inclusive, of SEQ ID NO: 2. As defined herein, the long acid box of the FGFR1 ECD has the sequence EDDDDDDDSSSEEKETD (SEQ ID NO: 98), which is amino acids 105 to 121, inclusive, of SEQ ID NOs: 21 and 25. As defined herein, the long acid box of the FGFR2 ECD has the sequence DDEDDTDGAEDFVSE (SEQ ID NO: 99), which is amino acids 111 to 125, inclusive, of SEQ ID NO: 27. As defined herein, the long acid box of the FGFR3 ECD has the sequence GDDEDGEDEAED (SEQ ID NO: 100), which is amino acids 110 to 121, inclusive, of SEQ ID NO: 31.

The term "FGFR4 ECD long acid box chimera" refers to an FGFR4 ECD selected from native FGFR4 ECDs, FGFR4 ECD fragments, and FGFR4 ECD variants, in which at least the long acid box, but not more than the D1-D2 linker region, has been replaced with at least the long acid box, but not more than the D1-D2 linker region, from FGFR1, FGFR2, or FGFR3.

The term "FGFR4 2Ig ECD long acid box chimera" refers to an FGFR4 ECD selected from native FGFR4 2Ig ECDs, FGFR4 2Ig ECD fragments, and FGFR4 2Ig ECD variants, in which at least the long acid box, but not more than the D1-D2 linker region, has been replaced with at least the long acid box, but not more than the D1-D2 linker region, from FGFR1, FGFR2, or FGFR3.

The term "short acid box" refers to a region of an FGFR ECD having a stretch of consecutive acidic amino acid residues within the acid box. As defined herein, the short acid box of the FGFR4 ECD has the sequence DDED (SEQ ID NO: 101), which is amino acids 105 to 108, inclusive, of SEQ ID NOs: 1 and 2. As defined herein, the short acid box of the FGFR1 ECD has the sequence EDDDDDDD (SEQ ID NO: 102), which is amino acids 105 to 112, inclusive, of SEQ ID NOs: 21 and 25. As defined herein, the short acid box of the FGFR2 ECD has the sequence DDEDD (SEQ ID NO: 103), which is amino acids 111 to 115, inclusive, of SEQ ID NO: 27. As defined herein, the short acid box of the FGFR3 ECD has the sequence DDED (SEQ ID NO: 104), which is amino acids 111 to 114, inclusive, of SEQ ID NO: 31.

The term "FGFR4 ECD short acid box chimera" refers to an FGFR4 ECD selected from native FGFR4 ECDs, FGFR4 ECD fragments, and FGFR4 ECD variants, in which at least the short acid box, but not more than the D1-D2 linker region, from FGFR4 has been replaced with at least the short acid box, but not more than the D1-D2 linker region, from FGFR1, FGFR2, or FGFR3.

The term "FGFR4 2Ig ECD short acid box chimera" refers to an FGFR4 ECD selected from native FGFR4 2Ig ECDs, FGFR4 2 Ig ECD fragments, and FGFR4 2 Ig ECD variants, in which at least the short acid box, but not more than the D1-D2 linker region, from FGFR4 has been replaced with at least the short acid box, but not more than the D1-D2 linker region, from FGFR1, FGFR2, or FGFR3.

The term "FGFR2 ECD short acid box chimera" refers to an FGFR2 ECD selected from native FGFR2 ECDs, FGFR2 ECD fragments, and FGFR2 ECD variants in which at least the short acid box, but not more than the D1-D2 linker region, from FGFR2 has been replaced with at least the short acid box, but not more than the D1-D2 linker region, from FGFR1. In certain embodiments of the FGFR2 ECD short acid box chimera, at least the FGFR2 acid box, but not more than the D1-D2 linker region, is replaced with the FGFR1 short acid box.

The term "FGFR3 ECD short acid box chimera" refers to an FGFR3 ECD selected from native FGFR3 ECDs, FGFR3 ECD fragments, and FGFR3 ECD variants in which at least the short acid box, but not more than the D1-D2 linker region, from FGFR3 has been replaced with at least the short acid box, but not more than the D1-D2 linker region, from FGFR1. In certain embodiments of the FGFR3 ECD short acid box chimera, at least the FGFR3 acid box, but not more than the D1-D2 linker region, is replaced with the FGFR1 short acid box.

The term "FGFR4 ECD acidic region chimera" is used herein for convenience to refer to the following five types of molecules: FGFR4 ECD D1-D2 linker chimeras, FGFR4 ECD exon 4 chimeras, FGFR4 ECD acid box chimeras, FGFR4 ECD long acid box chimeras, and FGFR4 ECD short acid box chimeras.

The term "FGFR4 2Ig ECD acidic region chimera" is used herein for convenience to refer to the following five types of molecules: FGFR4 2 Ig ECD D1-D2 linker chimeras, FGFR4 2 Ig ECD exon 4 chimeras, FGFR4 2Ig ECD acid box chimeras, FGFR4 2Ig ECD long acid box chimeras, and FGFR4 2Ig ECD short acid box chimeras.

The term "FGFR4 ECD long acid box variant" refers to variants of the FGFR4 ECD selected from native FGFR4 ECDs, FGFR4 ECD fragments, and FGFR4 ECD variants, that have increased acidity in the long acid box relative to the FGFR4 wild-type long acid box. In certain embodiments of FGFR4 ECD long acid box variants, at least two non-acidic residues within the long acid box of the FGFR4 ECD are each independently replaced with an acidic residue. In certain embodiments of FGFR4 ECD long acid box variants, at least one residue within the long acid box of the FGFR4 ECD is replaced with the corresponding amino acid residue from FGFR1, FGFR2, or FGFR3. In certain embodiments of FGFR4 ECD long acid box variants, at least one acidic residue within the long acid box of the FGFR4 ECD is replaced with a different acidic residue. In certain embodiments of FGFR4 ECD long acid box variants, one or two acidic residues are inserted between amino acids 103 and 104 of SEQ ID NOs: 1 and 2. In certain embodiments of FGFR4 ECD long acid box variants, up to three non-acidic residues are deleted from the long acid box of the FGFR4 ECD. In certain embodiments of FGFR4 ECD long acid box variants, the total number of acidic residues within the long acid box of an FGFR4 ECD acidic region variant, including any acidic residues inserted between amino acids 103 and 104 of SEQ ID NOs: 1 and 2, is at least seven.

The term "FGFR4 2Ig ECD long acid box variant" refers to variants of the FGFR4 ECD selected from native FGFR4 2 Ig ECDs, FGFR4 2Ig ECD fragments, and FGFR4 2 Ig ECD variants, that have increased acidity in the long acid box relative to the FGFR4 wild-type long acid box. In certain embodiments of FGFR4 2Ig ECD long acid box variants, at least two non-acidic residues within the long acid box of the FGFR4 2 Ig ECD are replaced with an acidic residue. In certain embodiments of FGFR4 2 Ig ECD long acid box variants, at least one residue within the long acid box of the FGFR4 2 Ig ECD is replaced with the corresponding amino acid residue from FGFR1, FGFR2, or FGFR3. In certain embodiments of FGFR4 2 Ig ECD long acid box variants, at least one acidic residue within the long acid box of the FGFR4 2 Ig ECD is replaced with a different acidic residue. In certain embodiments of FGFR4 2 Ig ECD long acid box variants, one or two acidic residues are inserted between amino acids 15 and 16 of SEQ ID NO: 94, which is an exemplary FGFR4 2 Ig ECD. In certain embodiments of FGFR4 2 Ig ECD long acid box variants, up to three non-acidic residues are deleted from the long acid box of the FGFR4 ECD. In certain embodiments of FGFR4 2Ig ECD long acid box variants, the total number of acidic residues within the long acid box of an FGFR4 2Ig ECD acidic region variant, including any acidic residues inserted between amino acids 15 and 16 of SEQ ID NO: 94, is at least seven.

An "FGFR4 ECD acidic region mutein" is an FGFR4 ECD selected from native FGFR4 ECDs, FGFR4 ECD fragments, and FGFR4 ECD variants having a greater number of acidic residues in the D1-D2 linker region than the wild-type FGFR4 ECD. The term FGFR4 ECD acidic region mutein is used herein to refer to the following types of molecules: FGFR4 ECD acidic region chimeras, including FGFR4 ECD D1-D2 linker chimeras, FGFR4 ECD exon 4 chimeras, FGFR4 ECD acid box chimeras, FGFR4 ECD long acid box chimeras, and FGFR4 ECD short acid box chimeras; and FGFR4 ECD long acid box variants.

An "FGFR4 2Ig ECD acidic region mutein" is an FGFR4 2Ig ECD selected from native FGFR4 2Ig ECDs, FGFR4 2Ig ECD fragments, and FGFR4 2Ig ECD variants having a greater number of acidic residues in the D1-D2 linker region than the wild-type FGFR4 2 Ig ECD. The term FGFR4 2Ig ECD acidic region mutein is used herein to refer to the following types of molecules: FGFR4 2 Ig ECD acidic region chimeras, including FGFR4 2Ig ECD D1-D2 linker chimeras, FGFR4 2Ig ECD exon 4 chimeras, FGFR4 2Ig ECD acid box chimeras, FGFR4 2Ig ECD long acid box chimeras, and FGFR4 2 Ig ECD short acid box chimeras; and FGFR4 2 Ig ECD long acid box variants.

An "FGFR2 ECD acidic region mutein" is an FGFR2 ECD selected from native FGFR2 ECDs, FGFR2 ECD fragments, and FGFR2 ECD variants having a greater number of acidic residues in the D1-D2 linker region than the wild-type FGFR2 ECD.

An "FGFR3 ECD acidic region mutein" is an FGFR3 ECD selected from native FGFR3 ECDs, FGFR3 ECD fragments, and FGFR3 ECD variants having a greater number of acidic residues in the D1-D2 linker region than the wild-type FGFR3 ECD.

The term "FGFR4 ECD fusion molecule" refers to a molecule comprising a polypeptide selected from an FGFR4 ECD and an FGFR4 ECD acidic region mutein, and a fusion partner. The term "FGFR4 2 Ig ECD fusion molecule" refers to a molecule comprising a polypeptide selected from an FGFR4 2Ig ECD and an FGFR4 2 Ig ECD acidic region mutein, and a fusion partner. The term "FGFR2 ECD fusion molecule" refers to a molecule comprising a polypeptide selected from an FGFR2 ECD and an FGFR2 ECD acidic region mutein, and a fusion partner. In certain embodiments, an FGFR2 ECD fusion molecule contains a "GS" linker between the FGFR2 ECD or the FGFR2 ECD acidic region mutein and the fusion partner. The term "FGFR3 ECD fusion molecule" refers to a molecule comprising a polypeptide selected from an FGFR3 ECD and an FGFR3 ECD acidic region mutein, and a fusion partner. In certain embodiments, an FGFR3 ECD fusion molecule contains a "GS" linker between the FGFR3 ECD or the FGFR3 ECD acidic region mutein and the fusion partner. The fusion partner may be linked to either the amino-terminus or the carboxy-terminus of the polypeptide. In certain embodiments, the polypeptide and the fusion partner are covalently linked. If the fusion partner is also a polypeptide ("the fusion partner polypeptide"), the polypeptide and the fusion partner polypeptide may be part of a continuous amino acid sequence. In such cases, the polypeptide and the fusion partner polypeptide may be translated as a single polypeptide from a coding sequence that encodes both the polypeptide and the fusion partner polypeptide. In certain embodiments, the polypeptide and the fusion partner are covalently linked through other means, such as, for example, a chemical linkage other than a peptide bond. Many methods of covalently linking polypeptides to other molecules (for example, fusion partners) are known in the art. One skilled in the art can select a suitable method of covalent linkage based on the particular polypeptide and fusion partner to be covalently linked.

In certain embodiments, the polypeptide and the fusion partner are noncovalently linked. In certain such embodiments, they may be linked, for example, using binding pairs. Exemplary binding pairs include, but are not limited to, biotin and avidin or streptavidin, an antibody and its antigen, etc.

Certain exemplary fusion partners include, but are not limited to, an immunoglobulin Fc domain, albumin, and polyethylene glycol. The amino acid sequences of certain exemplary Fc domains are shown in SEQ ID NOs: 72 to 74.

The term "signal peptide" refers to a sequence of amino acid residues that facilitates secretion of a polypeptide from a mammalian cell. A signal peptide is typically cleaved upon export of the polypeptide from the mammalian cell. Certain exemplary signal peptides include, but are not limited to, the signal peptides of FGFR1, FGFR2, FGFR3, and FGFR4, such as, for example, the amino acid sequences of SEQ ID NOs: 66 to 69, and 75. Certain exemplary signal peptides also include signal peptides from heterologous proteins. A "signal sequence" refers to a polynucleotide sequence that encodes a signal peptide.

A "vector" refers to a polynucleotide that is used to express a polypeptide of interest in a host cell. A vector may include one or more of the following elements: an origin of replication, one or more regulatory sequences (such as, for example, promoters and/or enhancers) that regulate the expression of the polypeptide of interest, and/or one or more selectable marker genes (such as, for example, antibiotic resistance genes and genes that can be used in colorimetric assays, e.g., β-galactosidase). One skilled in the art can select suitable vector elements for the particular host cell and application at hand.

A "host cell" refers to a cell that can be or has been a recipient of a vector or isolated polynucleotide. Host cells may be prokaryotic cells or eukaryotic cells. Exemplary eukaryotic cells include mammalian cells, such as primate or non-primate animal cells; fungal cells; plant cells; and insect cells. Certain exemplary mammalian cells include, but are not limited to, 293 and CHO cells.

The term "isolated" as used herein refers to a molecule that has been separated from at least some of the components with which it is typically found in nature. For example, a polypeptide is referred to as "isolated" when it is separated from at least some of the components of the cell in which it was produced. Where a polypeptide is secreted by a cell after expression, physically separating the supernatant containing the polypeptide from the cell that produced it is considered to be "isolating" the polypeptide. Similarly, a polynucleotide is referred to as "isolated" when it is not part of the larger polynucleotide (such as, for example, genomic DNA or mitochondrial DNA, in the case of a DNA polynucleotide) in which it is typically found in nature, or is separated from at least some of the components of the cell in which it was produced, e.g., in the case of an RNA polynucleotide. Thus, a DNA polynucleotide that is contained in a vector inside a host cell may be referred to as "isolated" so long as that polynucleotide is not found in that vector in nature.

The terms "subject" and "patient" are used interchangeably herein to refer to mammals, including, but not limited to, rodents, simians, humans, felines, canines, equines, bovines, porcines, ovines, caprines, mammalian laboratory animals, mammalian farm animals, mammalian sport animals, and mammalian pets.

The term "angiogenesis" refers to the development of new blood vessels, including capillary vessels. It can take place in healthy tissue or diseased tissue, such as, for example, cancer and macular degeneration. The term includes neovascularization, revascularization, angiopoiesis, and vasculogenesis. New blood vessel growth typically results from stimulation of endothelial cells by angiogenic factors which may be active in proliferative conditions, such as in cancer or macular degeneration. An "angiogenic factor" is one that promotes angiogenesis.

The term "angiogenic disorder" refers to a condition in which there is inappropriate development of new blood vessels.

"Treatment," as used herein, covers any administration or application of a therapeutic for disease in a mammal, including a human, and includes inhibiting the disease, arresting its development, or relieving the disease, for example, by causing regression, or restoring or repairing a lost, missing, or defective function; or stimulating an inefficient process. Treatment may achieved with surgery, radiation, and/or administration of one or more molecules, including, but not limited to, small molecules and polymers, such as polypeptides.

A "pharmaceutically acceptable carrier" refers to a non-toxic solid, semisolid, or liquid filler, diluent, encapsulating material, formulation auxiliary, or carrier conventional in the art for use with a therapeutic agent for administration to a subject. A pharmaceutically acceptable carrier is non-toxic to recipients at the dosages and concentrations employed and is compatible with other ingredients of the formulation. The pharmaceutically acceptable carrier is appropriate for the formulation employed. For example, if the therapeutic agent is to be administered orally, the carrier may be a gel capsule. If the therapeutic agent is to be administered subcutaneously, the carrier ideally is not irritable to the skin and does not cause injection site reaction.

FGFR4 Extracellular Domains

Certain exemplary FGFR4 ECDs include native FGFR4 ECDs, FGFR4 ECD fragments, and FGFR4 ECD variants. As noted above, an FGFR4 ECD fragment may have all or a portion of the sequence LEASEEVE (SEQ ID NO: 70) deleted from the amino terminus and/or all or a portion of the sequence LPEEDPTWTAAAPEARYTD (SEQ ID NO: 71) deleted from the carboxy terminus of the polypeptide. Exemplary FGFR4 ECDs include, but are not limited to, FGFR4 ECDs having amino acid sequences selected from SEQ ID NOs: 1, 2, 3, 93, 6 to 10, and 76 to 81.

One skilled in the art can create FGFR4 ECD variants that are capable of binding to FGF2 and/or FGF19 based on the extensive data available on the structure/function relationship for FGFRs.

In certain embodiments, an FGFR4 ECD is isolated.

FGFR4 ECD Acidic Region Chimeras

An FGFR4 ECD acidic region chimera is an FGFR4 ECD selected from native FGFR4 ECDs, FGFR4 ECD fragments, and FGFR4 ECD variants having a greater number of acidic residues in the D1-D2 linker region than the wild-type FGFR4 ECD. FGFR4 ECD acidic region chimeras include FGFR4 ECD D1-D2 linker chimeras, FGFR4 ECD exon 4 chimeras, FGFR4 ECD acid box chimeras, FGFR4 ECD long acid box chimeras, and FGFR4 ECD short acid box chimeras. In certain embodiments, an FGFR4 ECD acidic region chimera is isolated.

Exemplary FGFR4 ECD D1-D2 linker chimeras include, but are not limited to, FGFR4 ECDs in which the D1-D2 linker of FGFR4, DSLTSSNDDEDPK-SHRDPSNRHSYPQQ or DSLTSSNDDEDPKSHRDL-SNRHSYPQQ (SEQ ID NO: 16 or 17, respectively) has been replaced with the D1-D2 linker of FGFR 1, DALPSSED-DDDDDDSSSEEKETDNTKPNPV or DALPSSED-DDDDDDSSSEEKETDNTKPNRMPV (SEQ ID NO: 22 or 26, respectively (collectively referred to as "FGFR4 ECD R1 D1-D2 linker chimeras" and "FGFR4 ECD R1 RM D1-D2 linker chimeras," respectively), the D1-D2 linker of FGFR2, DAISSGDDEDDTDGAEDFVSENSNNKR (SEQ ID NO: 28) (collectively referred to as "FGFR4 ECD R2 D1-D2 linker chimeras"), or the D1-D2 linker of FGFR3, DAPSS-GDDEDGEDEAEDTGVDTG (SEQ ID NO: 32) (collectively referred to as "FGFR4 ECD R3 D1-D2 linker chimeras").

As discussed above for FGFR4 ECDs, FGFR4 ECD D1-D2 linker chimeras may include or lack a signal peptide. FGFR4 ECD D1-D2 linker chimeras may have all or a portion of the sequence LEASEEVE (SEQ ID NO: 70) deleted from the amino terminus and/or all or a portion of the sequence LPEEDPTWTAAAPEARYTD (SEQ ID NO: 71) deleted from the carboxy terminus of the polypeptide. Exemplary FGFR4 ECD D1-D2 linker chimeras include, but are not limited to, the FGFR4 ECD D1-D2 linker chimeras having amino acid sequences selected from SEQ ID NOs: 35 to 38. In certain embodiments, FGFR4 ECD D1-D2 linker chimeras comprise at least one FGFR4 ECD glycosylation mutation. Exemplary FGFR4 ECD D1-D2 linker chimeras comprising glycosylation mutations include, but are not limited to, the FGFR4 ECD D1-D2 linker chimera of SEQ ID NO: 35 with the N91A glycosylation mutation, the N159A glycosylation mutation, or both the N91A and N159A glycosylation mutations. In certain embodiments, an FGFR4 ECD D1-D2 linker chimera glycosylation mutants comprise an amino acid sequence selected from SEQ ID NOs: 120, 121, and 168.

Exemplary FGFR4 ECD exon 4 chimeras include, but are not limited to, FGFR4 ECDs in which the FGFR4 exon 4 amino acid sequence, DSLTSSNDDEDPK-SHRDPSNRHSYPQ or DSLTSSNDDEDPK-SHRDPSNRHSYPQ (SEQ ID NOs: 18 and 19, respectively), has been replaced with the FGFR1 exon 4 amino acid sequence, DALPSSEDDDDDDSSSEEKETDNTKPN (SEQ ID NO: 23) or DALPSSEDDDDDDSS-SEEKETDNTKPNRM (SEQ ID NO: 92) (collectively referred to as "FGFR4 ECD R1 exon 4 chimeras"), the FGFR2 exon 4 amino acid sequence, DAISSGDDEDDTD-GAEDFVSENSNNK (SEQ ID NO: 29) (collectively referred to as "FGFR4 ECD R2 exon 4 chimeras"), or the FGFR3 exon 4 amino acid sequence, DAPSSGDDEDGEDE-AEDTGVDT (SEQ ID NO: 33) (collectively referred to as "FGFR4 ECD R3 exon 4 chimeras").

As discussed above for FGFR4 ECDs, FGFR4 ECD exon 4 chimeras may include or lack a signal peptide. FGFR4 ECD exon 4 chimeras may have all or a portion of the sequence LEASEEVE (SEQ ID NO: 70) deleted from the amino terminus and/or all or a portion of the sequence LPEED-PTWTAAAPEARYTD (SEQ ID NO: 71) deleted from the carboxy terminus of the polypeptide. Exemplary FGFR4 ECD exon 4 chimeras include, but are not limited to, the FGFR4 ECD exon 4 linker chimeras having amino acid sequences selected from SEQ ID NOs: 39-42. In certain embodiments, an FGFR4 ECD exon 4 chimera comprises the amino acid sequence of SEQ ID NO: 39. In certain embodiments, FGFR4 ECD exon 4 chimeras comprise at least one FGFR4 ECD glycosylation mutation.

Exemplary FGFR4 ECD acid box chimeras include, but are not limited to, FGFR4 ECDs in which at least the FGFR4 acid box, defined herein as DDEDPKSHR (SEQ ID NO: 20) has been replaced with at least the FGFR1 acid box, defined herein as EDDDDDDDSSSE (SEQ ID NO: 24) (collectively referred to as "FGFR4 ECD R1 acid box chimeras"), at least the FGFR2 acid box, defined herein as DDEDDTD (SEQ ID NO: 30) (collectively referred to as "FGFR4 ECD R2 acid box chimeras"), or at least the FGFR3 acid box, defined herein as DDEDGE (SEQ ID NO: 34) (collectively referred to as "FGFR4 ECD R3 acid box chimeras").

In certain embodiments, additional amino acids flanking the acid box sequences noted above are also replaced in the FGFR4 ECD and/or are also inserted from the FGFR1, FGFR2, or FGFR3 ECD. Such acid boxes including additional amino acids are called "acid box regions." In certain embodiments, additional amino acids from the FGFR1, FGFR2, or FGFR3 acid box region are included up to, and including, the next acidic amino acid. Thus, for example, an FGFR4 acid box or FGFR4 acid box region (e.g., an amino acid sequence selected from SEQ ID NOs: 20 and 46 to 55) may be replaced with an FGFR1 acid box or FGFR1 acid box region having an amino acid sequence selected from EDDDDDDDSSSE (SEQ ID NO: 24), EDDDDDDDSSSEE (SEQ ID NO: 56), EDDDDDDDSSSEEKE (SEQ ID NO: 57), and EDDDDDDDSSSEEKETD (SEQ ID NO: 58). Similarly, an FGFR4 acid box or FGFR4 acid box region may replaced with an FGFR2 acid box or FGFR2 acid box region having an amino acid sequence selected from DDEDDTD (SEQ ID NO: 30), DDEDDTDGAE (SEQ ID NO: 59), DDEDDTDGAED (SEQ ID NO: 60), and DDEDDTD-GAEDFVSE (SEQ ID NO: 61). Finally, an FGFR4 acid box or FGFR4 acid box region may replaced with an FGFR3 acid box or FGFR3 acid box region having an amino acid sequence selected from DDEDGE (SEQ ID NO: 34), DDEDGED (SEQ ID NO: 62), DDEDGEDE (SEQ ID NO: 63), DDEDGEDEAE (SEQ ID NO: 64), and DDEDGEDE-AED (SEQ ID NO: 65). In certain embodiments, additional amino acids may also be replaced, up to and including all of the amino acids in the D1-D2 linker, for example, in order to retain a particular spacing or structure in the acid box region.

As non-limiting examples, an FGFR4 acid box having the amino acid sequence of SEQ ID NO: 21 or an FGFR4 acid box region having an amino acid sequence selected from SEQ ID NOs: 46 to 55 may be replaced with (1) an FGFR1 acid box having the amino acid sequence of SEQ ID NO: 24 or an FGFR1 acid box region having an amino acid sequence selected from SEQ ID NOs: 56 to 58; (2) an FGFR2 acid box having the amino acid sequence of SEQ ID NO: 30 or an FGFR2 acid box region having an amino acid sequence selected from SEQ ID NOs: 59 to 61; or (3) an FGFR3 acid box having the amino acid sequence of SEQ ID NO: 34 or an FGFR3 acid box region having an amino acid sequence selected from SEQ ID NOs: 62 to 65. In certain embodiments, the FGFR4 acid box region of SEQ ID NO: 51 is replaced with the FGFR1 acid box region of SEQ ID NO: 56.

As discussed above for FGFR4 ECDs, FGFR4 ECD acid box chimeras may include or lack a signal peptide. FGFR4 ECD acid box chimeras may have all or a portion of the sequence LEASEEVE (SEQ ID NO: 70) deleted from the amino terminus and/or all or a portion of the sequence LPEEDPTWTAAAPEARYTD (SEQ ID NO: 71) deleted from the carboxy terminus of the polypeptide. Exemplary FGFR4 ECD acid box chimeras include, but are not limited to, FGFR4 ECD acid box chimeras having amino acid sequences selected from SEQ ID NOs: 44 to 45 and 157. In certain embodiments, FGFR4 ECD acid box chimeras comprise at least one FGFR4 ECD glycosylation mutation.

Exemplary FGFR4 ECD long acid box chimeras include, but are not limited to, FGFR4 ECDs in which at least the long acid box of FGFR4, NDDEDPKSHRDPSNR or NDDED-PKSHRDLSNR (SEQ ID NO: 96 or 97, respectively), but not more than the D1-D2 linker region, has been replaced with at least the long acid box of FGFR1, EDDDDDDDSS-SEEKETD (SEQ ID NO: 98), but not more than the D1-D2 linker region (collectively referred to as "FGFR4 ECD R1 long acid box chimeras"); at least the long acid box of FGFR2, DDEDDTDGAEDFVSE (SEQ ID NO: 99), but not more than the D1-D2 linker region (collectively referred to as "FGFR4 ECD R2 long acid box chimeras"); or at least the long acid box of FGFR3, GDDEDGEDEAED (SEQ ID NO: 100), but not more than the D1-D2 linker region (collectively referred to as "FGFR4 ECD R3 long acid box chimeras").

As discussed above for FGFR4 ECDs, FGFR4 ECD long acid box chimeras may include or lack a signal peptide. FGFR4 ECD long acid box chimeras may have all or a portion of the sequence LEASEEVE (SEQ ID NO: 70) deleted from the amino terminus and/or all or a portion of the sequence LPEEDPTWTAAAPEARYTD (SEQ ID NO: 71) deleted from the carboxy terminus of the polypeptide. Exemplary FGFR4 ECD long acid box chimeras include, but are not limited to, the FGFR4 ECD long acid box chimeras having amino acid sequences selected from SEQ ID NOs: 105-107. In certain embodiments, FGFR4 ECD long acid box chimeras comprise at least one FGFR4 ECD glycosylation mutation.

Exemplary FGFR4 ECD short acid box chimeras include, but are not limited to, FGFR4 ECDs in which at least the short acid box of FGFR4, DDED (SEQ ID NO: 101), but not more than the D1-D2 linker region, has been replaced with at least the short acid box of FGFR1, EDDDDDDD (SEQ ID NO: 102), but not more than the D1-D2 linker region (collectively referred to as "FGFR4 ECD R1 short acid box chimeras"); at least the short acid box of FGFR2, DDEDD (SEQ ID NO: 103), but not more than the D1-D2 linker region (collectively referred to as "FGFR4 ECD R2 short acid box chimeras"); or at least the short acid box of FGFR3, DDED (SEQ ID NO: 104), but not more than the D1-D2 linker region (collectively referred to as "FGFR4 ECD R3 short acid box chimeras").

As discussed above for FGFR4 ECDs, FGFR4 ECD short acid box chimeras may include or lack a signal peptide. FGFR4 ECD short acid box chimeras may have all or a portion of the sequence LEASEEVE (SEQ ID NO: 70) deleted from the amino terminus and/or all or a portion of the sequence LPEEDPTWTAAAPEARYTD (SEQ ID NO: 71) deleted from the carboxy terminus of the polypeptide. Exemplary FGFR4 ECD short acid box chimeras include, but are not limited to, the FGFR4 ECD short acid box chimeras having amino acid sequences selected from SEQ ID NOs: 108-110. In certain embodiments, FGFR4 ECD short acid box chimeras comprise at least one FGFR4 ECD glycosylation mutation.

FGFR4 ECD Long Acid Box Variants

FGFR4 ECD long acid box variants include variants of the FGFR4 ECD that have an increased number of acidic amino acid residues in the long acid box relative to the FGFR4 wild-type long acid box. Exemplary FGFR4 ECD long acid variants include, but are not limited to, variants of the FGFR4 ECD in which at least two non-acidic residues within the long acid box of the FGFR4 ECD are each replaced with acidic residues; variants of the FGFR4 ECD in which at least one residue within the long acid box of the FGFR4 ECD is replaced with the corresponding amino acid residue from FGFR1, FGFR2, or FGFR3; variants of the FGFR4 ECD in which at least one acidic residue within the FGFR4 ECD long acid box is replaced with another acidic residue; variants of the FGFR4 ECD in which up to three non-acidic residues are deleted from the long acid box of the FGFR4 ECD; and variants of the FGFR4 long acid box in which the total number of acidic residues within the FGFR4 ECD long acid box, including any acidic residues inserted between amino acids 103 and 104 of SEQ ID NOs: 1 and 2, is at least seven.

As non-limiting examples of FGFR4 ECD long acid box variants, FGFR4 ECD residue N104 is replaced with the corresponding D107 residue of FGFR1; FGFR4 ECD residue P109 is replaced with the corresponding D112 residue of FGFR1; FGFR4 ECD residue R113 is replaced with the corresponding E116 residue of FGFR1; and FGFR4 ECD residue S116 is replaced with the corresponding E119 residue of FGFR1. As non-limiting examples of FGFR4 ECD long acid box variants, FGFR4 ECD residues 104 to 114, NDDEDPK-SHRD (SEQ ID NO: 145), are replaced with FGFR1 ECD residues 106 to 117, DDDDDDDSSEE (SEQ ID NO: 149); FGFR4 ECD residues 104 to 114, NDDEDPKSHRD (SEQ ID NO: 145), are replaced with FGFR1 ECD residues 107 to 117, DDDDDDSSSEE (SEQ ID NO: 150); FGFR4 ECD residues 104 to 110, NDDEDPK (SEQ ID NO: 146), are replaced with FGFR1 ECD residues 105-113, EDDDDDDDS (SEQ ID NO: 151); FGFR4 ECD residues 113 to 116, RDPS (SEQ ID NO: 147), are replaced with FGFR1 ECD residues 116-119, EEKE (SEQ ID NO: 152); and FGFR4 ECD residues 109 to 113, PKSHR (SEQ ID NO: 148), are replaced with FGFR1 ECD residues 112-116, DSSSE (SEQ ID NO: 153).

As discussed above for FGFR4 ECDs, FGFR4 ECD long acid box variants may include or lack a signal peptide. FGFR4 ECD long acid box variants may have all or a portion of the sequence LEASEEVE (SEQ ID NO: 70) deleted from the amino terminus and/or all or a portion of the sequence LPEEDPTWTAAAPEARYTD (SEQ ID NO: 71) deleted from the carboxy terminus of the polypeptide. Exemplary FGFR4 ECD long acid box muteins include, but are not limited to, the FGFR4 ECD long acid box variants having amino acid sequences selected from SEQ ID NOs: 111 to 119. In certain embodiments, FGFR4 ECD long acid box variants comprise at least one FGFR4 ECD glycosylation mutation.

FGFR2 ECD Short Acid Box Chimeras

Exemplary FGFR2 ECD short acid box chimeras include, but are not limited to, FGFR2 ECDs in which at least the FGFR2 acid box is replaced with the FGFR1 short acid box. As a non-limiting example of a short acid box chimera, FGFR2 ECD residues 111 to 118, DDEDDTDG (SEQ ID NO: 155), are replaced with FGFR1 ECD residues 105 to 112, EDDDDDDD (SEQ ID NO: 154).

As discussed above for FGFR4 ECDs, FGFR2 ECD short acid box chimeras may include or lack a signal peptide. Further, FGFR2 ECD short acid box chimeras include FGFR2 ECD short acid box chimeras in which one or more amino acid residues have been deleted from the amino-terminus and/or the carboxy-terminus of the ECD, and wherein the FGFR2 ECD short acid box chimeras are capable of binding to FGF2. Non-limiting exemplary FGFR2 ECD short acid box chimeras include, but are not limited to, FGFR2 ECD short acid box chimeras having amino acid sequences selected from SEQ ID NOs: 122 and 164.

FGFR3 ECD Short Acid Box Chimeras

Exemplary FGFR3 ECD short acid box chimeras include, but are not limited to, FGFR3 ECDs in which at least the FGFR3 acid box is replaced with the FGFR1 short acid box. As a non-limiting example of a short acid box chimera, FGFR3 ECD residues 110 to 117, GDDEDGED (SEQ ID NO: 156), are replaced with FGFR1 ECD residues 105 to 112, EDDDDDDD (SEQ ID NO: 154)

As discussed above for FGFR4 ECDs, FGFR3 ECD short acid box chimeras may include or lack a signal peptide. Further, FGFR3 ECD short acid box chimeras include FGFR3 ECD short acid box chimeras in which one or more amino acid residues have been deleted from the amino-terminus and/or the carboxy-terminus of the ECD, and wherein the FGFR3 ECD short acid box chimeras are capable of binding to FGF2. Non-limiting exemplary FGFR3 ECD short acid box chimeras include, but are not limited to, the FGFR3 ECD short acid box chimera having the amino acid sequences selected from SEQ ID NOs: 123 and 165.

FGFR ECD Fusion Molecules

FGFR ECD fusion molecules comprising an FGFR ECD and a fusion partner are provided. In certain embodiments, an FGFR ECD fusion molecule is isolated.

Fusion Partners and Conjugates

In certain embodiments, a fusion partner is selected that imparts favorable pharmacokinetics and/or pharmacodynamics on the FGFR ECD fusion molecule. For example, in certain embodiments, a fusion partner is selected that increases the half-life of the FGFR ECD fusion molecule relative to the corresponding FGFR ECD without the fusion partner. By increasing the half-life of the molecule, a lower dose and/or less-frequent dosing regimen may be required in therapeutic treatment. Further, the resulting decreased fluctuation in FGFR ECD serum levels may improve the safety and tolerability of the FGFR ECD-based therapeutics.

Many different types of fusion partners are known in the art. One skilled in the art can select a suitable fusion partner according to the intended use. Non-limiting exemplary fusion partners include polymers, polypeptides, lipophilic moieties, and succinyl groups. Exemplary polypeptide fusion partners include serum albumin and an antibody Fc domain. Exemplary polymer fusion partners include, but are not limited to, polyethylene glycol, including polyethylene glycols having branched and/or linear chains.

Oligomerization Domain Fusion Partners

In various embodiments, oligomerization offers certain functional advantages to a fusion protein, including, but not limited to, multivalency, increased binding strength, and the combined function of different domains. Accordingly, in certain embodiments, a fusion partner comprises an oligomerization domain, for example, a dimerization domain. Exemplary oligomerization domains include, but are not limited to, coiled-coil domains, including alpha-helical coiled-coil domains; collagen domains; collagen-like domains, and certain immunoglobulin domains. Certain exemplary coiled-coil polypeptide fusion partners include the tetranectin coiled-coil domain; the coiled-coil domain of cartilage oligomeric matrix protein; angiopoietin coiled-coil domains; and leucine zipper domains. Certain exemplary collagen or collagen-like oligomerization domains include, but are not limited to, those found in collagens, mannose binding lectin, lung surfactant proteins A and D, adiponectin, ficolin, conglutinin, macrophage scavenger receptor, and emilin.

Antibody Fc Immunoglobulin Domain Fusion Partners

Many Fc domains that could be used as fusion partners are known in the art. One skilled in the art can select an appropriate Fc domain fusion partner according to the intended use. In certain embodiments, a fusion partner is an Fc immunoglobulin domain. An Fc fusion partner may be a wild-type Fc found in a naturally occurring antibody, a variant thereof, or a fragment thereof. Non-limiting exemplary Fc fusion partners include Fcs comprising a hinge and the CH2 and CH3 constant domains of a human IgG, for example, human IgG1, IgG2, IgG3, or IgG4. Certain additional Fc fusion partners include, but are not limited to, human IgA and IgM. In certain embodiments, an Fc fusion partner comprises a C237S mutation. In certain embodiments, an Fc fusion partner comprises a hinge, CH2, and CH3 domains of human IgG2 with a P331S mutation, as described in U.S. Pat. No. 6,900,292. Certain exemplary Fc domain fusion partners are shown in SEQ ID NOs: 72 to 74, 170, and 171.

Certain exemplary FGFR4 ECD fusion molecules comprising an FGFR4 ECD include, but are not limited to, polypeptides having the amino acid sequences of SEQ ID NOs: 5 and 11 to 15. Certain exemplary FGFR4 ECD fusion molecules comprising an FGFR4 ECD acidic region chimera include, but are not limited to, polypeptides having the amino acid sequences of SEQ ID NOs: 86 to 88 and 158. In certain embodiments, an FGFR4 ECD fusion molecule comprises the amino acid sequence of SEQ ID NO: 86. In certain embodiments, an FGFR4 ECD fusion molecule consists of the amino acid sequence of SEQ ID NO: 86.

Albumin Fusion Partners and Albumin-Binding Molecule Fusion Partners

In certain embodiments, a fusion partner is an albumin. Certain exemplary albumins include, but are not limited to, human serum album (HSA) and fragments of HSA that are capable of increasing the serum half-life and/or bioavailability of the polypeptide to which they are fused. In certain embodiments, a fusion partner is an albumin-binding molecule, such as, for example, a peptide that binds albumin or a molecule that conjugates with a lipid or other molecule that binds albumin. In certain embodiments, a fusion molecule comprising HSA is prepared as described, e.g., in U.S. Pat. No. 6,686,179.

Polymer Fusion Partners

In certain embodiments, a fusion partner is a polymer, for example, polyethylene glycol (PEG). PEG may comprise branched and/or linear chains. In certain embodiments, a fusion partner comprises a chemically-derivatized polypeptide having at least one PEG moiety attached. Pegylation of a polypeptide may be carried out by any method known in the art. One skilled in the art can select an appropriate method of pegylating a particular polypeptide, taking into consideration the intended use of the polypeptide. Certain exemplary PEG attachment methods include, for example, EP 0 401 384; Malik et al., *Exp. Hematol.*, 20:1028-1035 (1992); Francis, *Focus on Growth Factors*, 3:4-10 (1992); EP 0 154 316; EP 0

401 384; WO 92/16221; and WO 95/34326. As non-limiting examples, pegylation may be performed via an acylation reaction or an alkylation reaction, resulting in attachment of one or more PEG moieties via acyl or alkyl groups. In certain embodiments, PEG moieties are attached to a polypeptide through the α- or ε-amino group of one or more amino acids, although any other points of attachment known in the art are also contemplated.

Pegylation by acylation typically involves reacting an activated ester derivative of a PEG moiety with a polypeptide. A non-limiting exemplary activated PEG ester is PEG esterified to N-hydroxysuccinimide (NHS). As used herein, acylation is contemplated to include, without limitation, the following types of linkages between a polypeptide and PEG: amide, carbamate, and urethane. See, e.g., Chamow, *Bioconjugate Chem.*, 5:133-140 (1994). Pegylation by alkylation typically involves reacting a terminal aldehyde derivative of a PEG moiety with a polypeptide in the presence of a reducing agent. Non-limiting exemplary reactive PEG aldehydes include PEG propionaldehyde, which is water stable, and mono C1-C10 alkoxy or aryloxy derivatives thereof. See, e.g., U.S. Pat. No. 5,252,714.

In certain embodiments, a pegylation reaction results in poly-pegylated polypeptides. In certain embodiments, a pegylation reaction results in mono-, di-, and/or tri-pegylated polypeptides. One skilled in the art can select appropriate pegylation chemistry and reaction conditions to achieve the desired level of pegylation. Further, desired pegylated species may be separated from a mixture containing other pegylated species and/or unreacted starting materials using various purification techniques known in the art, including among others, dialysis, salting-out, ultrafiltration, ion-exchange chromatography, gel filtration chromatography, and electrophoresis.

Exemplary Attachment of Fusion Partners

The fusion partner may be attached, either covalently or non-covalently, to the amino-terminus or the carboxy-terminus of the FGFR ECD. The attachment may also occur at a location within the FGFR ECD other than the amino-terminus or the carboxy-terminus, for example, through an amino acid side chain (such as, for example, the side chain of cysteine, lysine, histidine, serine, or threonine).

In either covalent or non-covalent attachment embodiments, a linker may be included between the fusion partner and the FGFR ECD. Such linkers may be comprised of amino acids and/or chemical moieties. One skilled in the art can select a suitable linker depending on the attachment method used, the intended use of the FGFR ECD fusion molecule, and the desired spacing between the FGFR ECD and the fusion partner.

Exemplary methods of covalently attaching a fusion partner to an FGFR ECD include, but are not limited to, translation of the fusion partner and the FGFR ECD as a single amino acid sequence and chemical attachment of the fusion partner to the FGFR ECD. When the fusion partner and the FGFR ECD are translated as single amino acid sequence, additional amino acids may be included between the fusion partner and the FGFR ECD as a linker. In certain embodiments, the linker is glycine-serine ("GS"). In certain embodiments, the linker is selected based on the polynucleotide sequence that encodes it, to facilitate cloning the fusion partner and/or FGFR ECD into a single expression construct (for example, a polynucleotide containing a particular restriction site may be placed between the polynucleotide encoding the fusion partner and the polynucleotide encoding the FGFR ECD, wherein the polynucleotide containing the restriction site encodes a short amino acid linker sequence).

When the fusion partner and the FGFR ECD are covalently coupled by chemical means, linkers of various sizes can typically be included during the coupling reaction. One skilled in the art can select a suitable method of covalently attaching a fusion partner to an FGFR ECD depending, for example, on the identity of the fusion partner and the particular use intended for the FGFR ECD fusion molecule. One skilled in the art can also select a suitable linker type and length, if one is desired.

Exemplary methods of non-covalently attaching a fusion partner to an FGFR ECD include, but are not limited to, attachment through a binding pair. Exemplary binding pairs include, but are not limited to, biotin and avidin or streptavidin, an antibody and its antigen, etc. Again, one skilled in the art can select a suitable method of non-covalently attaching a fusion partner to an FGFR ECD depending, for example, on the identity of the fusion partner and the particular use intended for the FGFR ECD fusion molecule. The selected non-covalent attachment method should be suitable for the conditions under which the FGFR ECD fusion molecule will be used, taking into account, for example, the pH, salt concentrations, and temperature.

Nucleic Acid Molecules Encoding the Polypeptides of the Invention

Nucleic acid molecules comprising polynucleotides that encode the polypeptides of the invention are provided. Nucleic acid molecules comprising polynucleotides that encode FGFR ECD fusion molecules in which the FGFR ECD and the fusion partner are translated as a single polypeptide, are also provided. Such nucleic acid molecules can be constructed by one skilled in the art using recombinant DNA techniques conventional in the art.

In certain embodiments, a polynucleotide encoding a polypeptide of the invention comprises a nucleotide sequence that encodes a signal peptide, which, when translated, will be fused to the amino-terminus of the FGFR polypeptide of the invention. As discussed above, the signal peptide may be the native signal peptide, the signal peptide of FGFR1, FGFR2, FGFR3, or FGFR4, or may be another heterologous signal peptide. The amino acid sequences for certain exemplary FGFR signal peptides are shown, e.g., in SEQ ID NOs: 66 to 69 and 75. Certain exemplary signal peptides are known in the art, and are described, e.g., in the online Signal Peptide Database maintained by the Department of Biochemistry, National University of Singapore (see also Choo et al., *BMC Bioinformatics*, 6: 249(2005)); and in PCT Publication No. WO 2006/081430.

In certain embodiments, the nucleic acid molecule comprising the polynucleotide encoding the gene of interest is an expression vector that is suitable for expression in a selected host cell.

Expression and Production of the Proteins of the Invention

Vectors

Vectors comprising polynucleotides that encode the polypeptides of the invention are provided. Such vectors include, but are not limited to, DNA vectors, phage vectors, viral vectors, retroviral vectors, etc. One skilled in the art can select a suitable vector depending on the polypeptide to be expressed and the host cell chosen for expression.

In certain embodiments, a vector is selected that is optimized for expression of polypeptides in CHO-S or CHO-S-derived cells. Exemplary such vectors are described, e.g., in Running Deer et al., *Biotechnol. Prog.* 20:880-889 (2004).

In certain embodiments, a vector is chosen for in vivo expression of the polypeptides of the invention in animals, including humans. In certain such embodiments, expression of the polypeptide is under the control of a promoter that functions in a tissue-specific manner. For example, liver-specific promoters are described, e.g., in PCT Publication No. WO 2006/076288.

Host Cells

The polypeptides of the invention can be expressed, in various embodiments, in prokaryotic cells, such as bacterial cells; or eukaryotic cells, such as fungal cells, plant cells, insect cells, and mammalian cells. Such expression may be carried out, for example, according to procedures known in the art. Certain exemplary eukaryotic cells that can be used to express polypeptides include, but are not limited to, Cos cells, including Cos 7 cells; 293 cells, including 293-6E and 293-T cells; CHO cells, including CHO-S and DG44 cells; and NS0 cells. One skilled in the art can select a suitable host cell depending on the polypeptide to be expressed, the desired use of that polypeptide, and the scale of the production (e.g., a small amount for laboratory use, or a larger amount for pharmaceutical use). In certain embodiments, a particular eukaryotic host cell is selected based on its ability to make certain desired post-translational modifications of the polypeptide of the invention. For example, in certain embodiments, CHO cells produce FGFR4 ECD acidic region muteins and/or FGFR4 ECD fusion molecules that have a higher level of glycosylation and/or sialylation than the same polypeptide produced in 293 cells.

Introduction of a nucleic acid into a desired host cell can be accomplished by any method known in the art, including, but not limited to, calcium phosphate transfection, DEAE-dextran mediated transfection, cationic lipid-mediated transfection, electroporation, transduction, infection, etc. Certain exemplary methods are described, e.g., in Sambrook et al., *Molecular Cloning, A Laboratory Manual*, 3$^{rd}$ ed. Cold Spring Harbor Laboratory Press (2001). Nucleic acids may be transiently or stably transfected in the desired host cells, according to methods known in the art.

In certain embodiments, a polypeptide can be produced in vivo in an animal that has been engineered or transfected with a nucleic acid molecule encoding the polypeptide, according to methods known in the art.

Purification of FGFR ECD Polypeptides

The polypeptides of the invention can be purified by various methods known in the art. Such methods include, but are not limited to, the use of affinity matrices, ion exchange chromatography, and/or hydrophobic interaction chromatography. Suitable affinity ligands include any ligands of the FGFR ECD or of the fusion partner, or antibodies thereto. For example, a Protein A, Protein G, Protein A/G, or an antibody affinity column may be used to bind to an Fc fusion partner to purify a polypeptide of the invention. Antibodies to the polypeptides of the invention may also be used to purify the polypeptides of the invention. Hydrophobic interactive chromatography, for example, a butyl or phenyl column, may also suitable for purifying certain polypeptides. Many methods of purifying polypeptides are known in the art. One skilled in the art can select a suitable method depending on the identity of the polypeptide or molecule to be purified and on the scale of the purification (i.e., the quantity of polypeptide or molecule produced).

Therapeutic Compositions

Routes of Administration and Carriers

In various embodiments, the polypeptides of the invention can be administered in vivo by various routes known in the art, including, but not limited to, intravenous, intra-arterial, subcutaneous, parenteral, intranasal, intramuscular, intracardiac, intraventricular, intratracheal, buccal, rectal, intraperitoneal, intradermal, topical, transdermal, and intrathecal, or otherwise by implantation or inhalation. The subject compositions can be formulated into preparations in solid, semi-solid, liquid, or gaseous forms; including, but not limited to, tablets, capsules, powders, granules, ointments, solutions, suppositories, enemas, injections, inhalants, and aerosols. Nucleic acid molecules encoding the polypeptides of the invention can be coated onto gold microparticles and delivered intradermally by a particle bombardment device, or "gene gun," as described in the literature (see, e.g., Tang et al., *Nature* 356:152-154 (1992)). One skilled in the art can select the appropriate formulation and route of administration according to the intended application.

In various embodiments, compositions comprising the polypeptides of the invention are provided in formulation with pharmaceutically acceptable carriers, a wide variety of which are known in the art (see, e.g., Gennaro, *Remington: The Science and Practice of Pharmacy with Facts and Comparisons: Drugfacts Plus*, 20th ed. (2003); Ansel et al., *Pharmaceutical Dosage Forms and Drug Delivery Systems*, 7$^{th}$ ed., Lippencott Williams and Wilkins (2004); Kibbe et al., *Handbook of Pharmaceutical Excipients*, 3$^{rd}$ ed., Pharmaceutical Press (2000)). Various pharmaceutically acceptable carriers, which include vehicles, adjuvants, carriers, and diluents, are available to the public. Moreover, various pharmaceutically acceptable auxiliary substances, such as pH adjusting and buffering agents, tonicity adjusting agents, stabilizers, wetting agents and the like, are also available to the public. Certain non-limiting exemplary carriers include saline, buffered saline, dextrose, water, glycerol, ethanol, and combinations thereof. One skilled in the art can select a suitable carrier according to the intended use.

In various embodiments, compositions comprising polypeptides of the invention can be formulated for injection by dissolving, suspending, or emulsifying them in an aqueous or nonaqueous solvent, such as vegetable or other oils, synthetic aliphatic acid glycerides, esters of higher aliphatic acids, or propylene glycol; and if desired, with conventional additives such as solubilizers, isotonic agents, suspending agents, emulsifying agents, stabilizers and preservatives. In various embodiments, the compositions may be formulated for inhalation, for example, using pressurized acceptable propellants such as dichlorodifluoromethane, propane, nitrogen, and the like. The compositions may also be formulated, in various embodiments, into sustained release microcapsules, such as with biodegradable or non-biodegradable polymers. A non-limiting exemplary biodegradable formulation includes poly lactic acid-glycolic acid polymer. A non-limiting exemplary non-biodegradable formulation includes a polyglycerin fatty acid ester. Certain methods of making such formulations are described, for example, in EP 1 125 584 A1. One skilled in the art can select a suitable formulation depending on the intended route of administration, using techniques and components known in the art.

Pharmaceutical packs and kits comprising one or more containers, each containing one or more doses of the polypeptides of the invention are also provided. In certain embodiments, a unit dosage is provided wherein the unit dosage contains a predetermined amount of a composition comprising a polypeptide of the invention, with or without one or more additional agents. In certain embodiments, such a unit dosage is supplied in single-use prefilled syringe for injection. In various embodiments, the composition contained in the unit dosage may comprise saline, sucrose, or the like; a buffer, such as phosphate, or the like; and/or be formulated within a stable and effective pH range. Alternatively, in certain embodiments, the composition may be provided as a lyophilized powder that can be reconstituted upon addition of an appropriate liquid, for example, sterile water. In certain embodiments, the composition comprises one or more substances that inhibit protein aggregation, including, but not limited to, sucrose and arginine. In certain embodiments, a composition of the invention comprises heparin and/or a proteoglycan.

Pharmaceutical compositions are administered in an amount effective for treatment and/or prophylaxis of the specific indication. The effective amount is typically dependent on the weight of the subject being treated, his or her physical or health condition, the extensiveness of the condition to be treated, and/or the age of the subject being treated. In general, the polypeptides of the invention are to be administered in an amount in the range of about 50 ug/kg body weight to about 30 mg/kg body weight per dose. Optionally, the polypeptides of the invention can be administered in an amount in the range of about 100 ug/kg body weight to about 20 mg/kg body weight per dose. Further optionally, the polypeptides of the invention can be administered in an amount in the range of about 0.5 mg/kg body weight to about 20 mg/kg body weight per dose.

The compositions comprising the polypeptides of the invention can be administered as needed to subjects. Determination of the frequency of administration can be made by persons skilled in the art, such as an attending physician based on considerations of the condition being treated, age of the subject being treated, severity of the condition being treated, general state of health of the subject being treated and the like. In certain embodiments, an effective dose of the polypeptide of the invention is administered to a subject one or more times. In various embodiments, an effective dose of the polypeptide of the invention is administered to the subject at least twice a month, once a week, twice a week, or three times a week. In various embodiments, an effective dose of the polypeptide of the invention is administered to the subject for at least a week, at least a month, at least three months, at least six months, or at least a year.

Combination Therapy

Polypeptides of the invention may be administered alone or with other modes of treatment. They may be provided before, substantially contemporaneous with, or after other modes of treatment, for example, surgery, chemotherapy, radiation therapy, or the administration of a biologic, such as a therapeutic antibody.

Methods of Treating Diseases Using FGFR ECD Polypeptides

Results from the experiments described herein show that FGFR4 ECD acidic region muteins retain FGFR4's ability to bind FGF2 and/or FGF19. See, e.g., Example 8, including Tables 3 and 4. Thus, those chimeras can be used in a variety of treatment methods in a similar manner to native FGFR4 ECD (see, e.g., U.S. Publication No. US 2008/0171689).

For example, polypeptides of the invention may be used as ligand traps in vivo to treat diseases associated with one or more ligands of the FGFR family, such as FGF2 and/or FGF19. The FGFR ECD polypeptide ligand traps may be used, for example, to treat a range of cancers and/or angiogenic disorders. In certain embodiments, the FGFR ECD polypeptide ligand traps comprise a fusion partner such as an Fc, albumin, or polyethylene glycol (discussed above).

In certain embodiments, FGFR4 ECD acidic region muteins may be used to treat colon cancer. Expression of both FGFR4 and FGF19 has been detected in primary colon tumors and several colon tumor cell lines (see, e.g., Desnoyers, Oncogene, 27:85-97 (2008); U.S. Patent Application No. 20070248604). Administration of a monoclonal antibody to FGF19 significantly reduced tumor growth in two human colon cancer cell line xenograft models (HCT116 and Colo201; see Desnoyers). Experiments herein demonstrate that the FGFR4 ECD acidic region chimera ABMut1 reduced tumor growth in an HCT116 xenograft model. Reduced tumor growth was also seen in a Colo201 model following administration of ABMut1 (data not shown). Thus, in certain embodiments, the FGFR4 ECD acidic region muteins of the invention may be administered, e.g., as described above, to patients who have colon cancer. In certain embodiments, the FGFR4 ECD acidic region muteins may be administered to colon cancer patients along with at least one other therapeutic regimen and/or agent.

FGFR4 and FGF19 expression have also been detected in liver and lung tumors (see, e.g., Desnoyers, Oncogene, 27:85-97 (2008); U.S. Patent Publication No. 2007/0248604). A monoclonal antibody against FGF19 reduced tumor burden in an FGF19-transgenic mouse hepatocellular carcinoma model (see Desnoyers). FGFR4 expression has also been implicated in breast cancer (see, e.g., U.S. Pat. No. 7,297, 774). High FGFR4 mRNA levels in estrogen receptor-positive breast carcinomas correlated with poor clinical benefit in patients on tamoxifen as a first-line treatment (Meijer et al., Endocr. Relat. Cancer., 15(1):101-11 (2008)). Thus, FGFR4 ECD acidic region muteins may also be used to treat liver cancers, breast cancers, including infiltrating ductal carcinoma and adenocarcinoma, and lung carcinomas, including small cell lung carcinomas and non-small cell lung carcinomas.

FGFR1 and FGFR4 overexpression have also been detected in prostate cancer, with a greater frequency of high levels of protein expression in grade 5 cancers than in grades 1-3 (Sahadevan et al., J. Pathol., 213(1):82-90 (2007)). Suppression of FGFR4 by RNA interference blocked prostate cancer cell proliferation in vitro (see id.). FGFR4 ECD acidic region muteins may therefore also be used to treat prostate cancers.

FGFR ligands, such as FGF2, are known stimulators of angiogenesis. Thus, FGFR ECD polypeptides may be administered to patients with angiogenic disorders such as cancer and/or macular degeneration in order to inhibit angiogenesis. Additional cancers that may be treated with the FGFR ECD polypeptides of the invention include, for example, sarcomas and carcinomas including, but not limited to fibrosarcomas, myxosarcomas, liposarcomas, chondrosarcomas, osteogenic sarcomas, chordomas, angiosarcomas, endotheliosarcomas, lymphangiosarcomas, lymphangioendotheliosarcomas, synoviomas, mesotheliomas, Ewing's tumors, leiomyosarcomas, rhabdomyosarcomas, gastic cancers, pancreatic cancers, ovarian cancers, prostate cancers, squamous cell carcinomas, basal cell carcinomas, adenocarcinomas, sweat gland carcinomas, sebaceous gland carcinomas, papillary carcinomas, papillary adenocarcinomas, cystadenocarcinomas, medullary carcinomas, bronchogenic carcinomas, renal cell carcinomas, hepatomas, liver metastases, bile duct carcinomas, choriocarcinomas, seminomas, embryonal carcinomas, thyroid carcinomas such as anaplastic thyroid cancers, Wilms' tumors, cervical cancers, testicular tumors, bladder carcinomas, epithelial carcinomas, gliomas, astrocytomas, medulloblastomas, craniopharyngiomas, ependymomas, pinealomas, hemangioblastomas, acoustic neuromas, oligodendrogliomas, meningiomas, melanomas, neuroblastomas, glioblastomas, and retinoblastomas. Also among the cancers within the scope of the invention are hematologic malignancies; prostate cancer; bladder cancer; pancreatic cancer; ovarian cancer; salivary cancer; pituitary cancer; renal cell carcinoma; melanoma; glioblastoma; and retinoblastoma.

Tumors comprising dysproliferative changes, such as hyperplasias, metaplasias, and dysplasias, may be treated, modulated, or prevented with FGFR ECD polypeptides as well, such as those found in epithelial tissues, including the cervix, esophagus, and lung, for example. Hyperplasia is a form of controlled cell proliferation involving an increase in cell number in a tissue or organ, without significant alteration in structure or function. By way of example, endometrial hyperplasia often precedes endometrial cancer. Metaplasia is a form of controlled cell growth in which one type of adult or fully differentiated cell substitutes for another type of adult cell. Metaplasia can occur in epithelial or connective tissue cells. Atypical metaplasia involves a somewhat disorderly metaplastic epithelium. Dysplasia is frequently a forerunner of cancer, and is found mainly in the epithelia; it is a disorderly form of non-neoplastic cell growth, involving losses in individual cell uniformity and in the cell's architectural orientation. Dysplasia characteristically occurs where there exists chronic irritation or inflammation and is often found in the cervix, respiratory passages, oral cavity, and gall bladder. Other examples of benign tumors which can be treated, modulated, or prevented in accordance with the present invention include arteriovenous (AV) malformations, particularly in intracranial sites and myoleomas.

Since FGFs contribute to normal bone formation and are expressed locally in the bone stromal environment, they may play a role in seeding, growth, and survival of bone metastases. FGFs have been implicated in bone formation, affecting osteoprogenitor cell replication, osteoblast differentiation, and apoptosis. Thus, agents that block FGF/FGFR interactions, including FGFR ECD polypeptides, can be used to treat bone metastases in cancers such as prostate cancer and breast cancer. Such agents will not only inhibit local osteoblastic conversion events, but also inhibit initial seeding, growth, and survival of the cancer bone metastases.

EXAMPLES

The examples discussed below are intended to be purely exemplary of the invention and should not be considered to limit the invention in any way. The examples are not intended to represent that the experiments below are all or the only experiments performed. Efforts have been made to ensure accuracy with respect to numbers used (for example, amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Construction of Certain FGFR4 ECD-Fc Fusion Molecules

The cloning, expression and purification of the R1Mut4 fusion protein used in these examples has been previously described (WO 2007/014123). The cloning of the parental FGFR4 ECD-Fc fusion protein used in these examples has also been described (WO 2007/014123, called "R4Mut4"). For transient expression in 293-6E cells, R4Mut4 was cloned into and expressed from vector pTT5 (Biotechnology Research Institute, Montreal, Canada). Chimeras of the R4Mut4 fusion protein were constructed using PCR and conventional mutagenesis techniques. The R4Mut4 chimeras were originally cloned into the mammalian expression vector pcDNA3.1 (Invitrogen) for transient expression in 293-6E cells.

Figure 1:
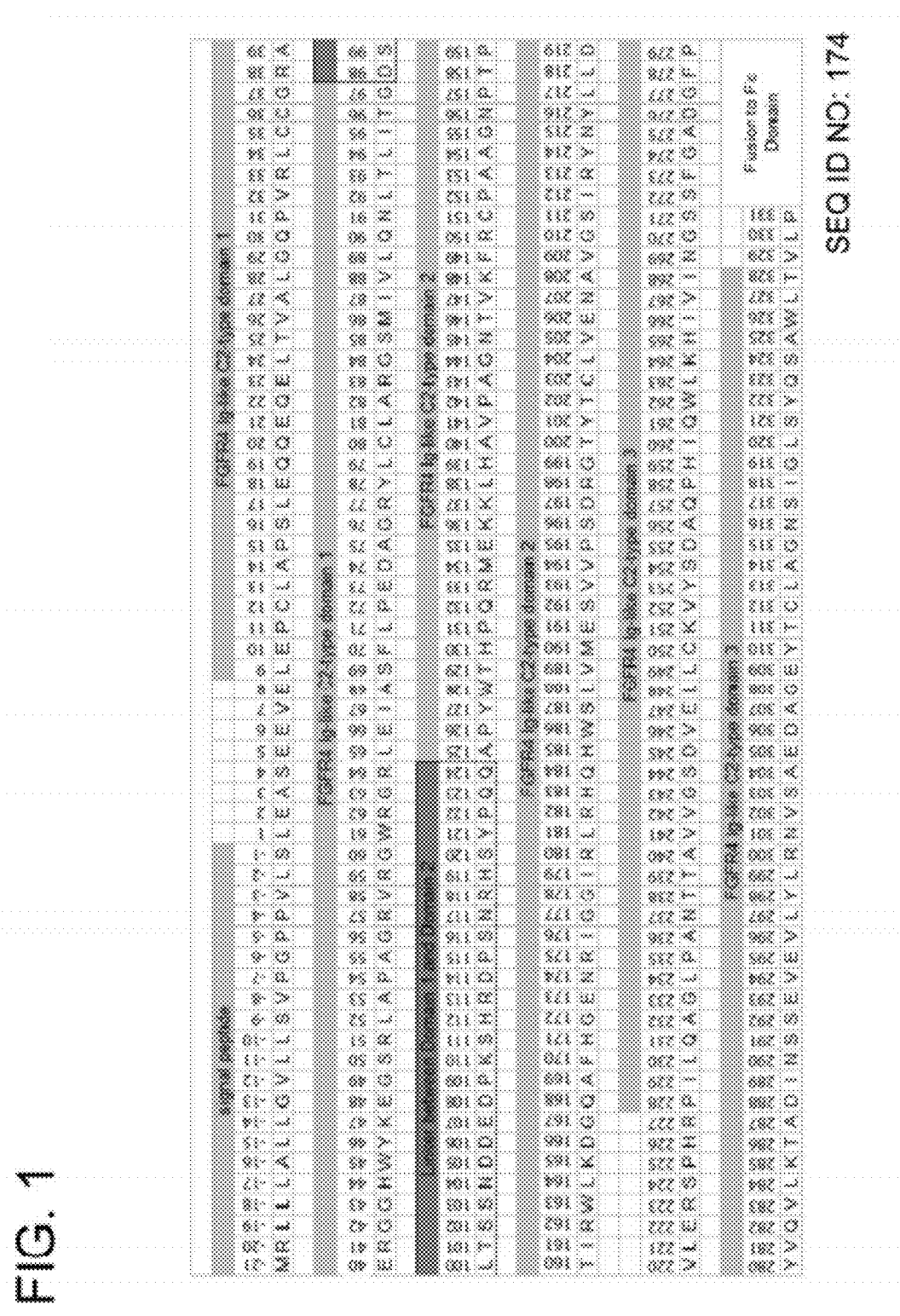
Figure 2:
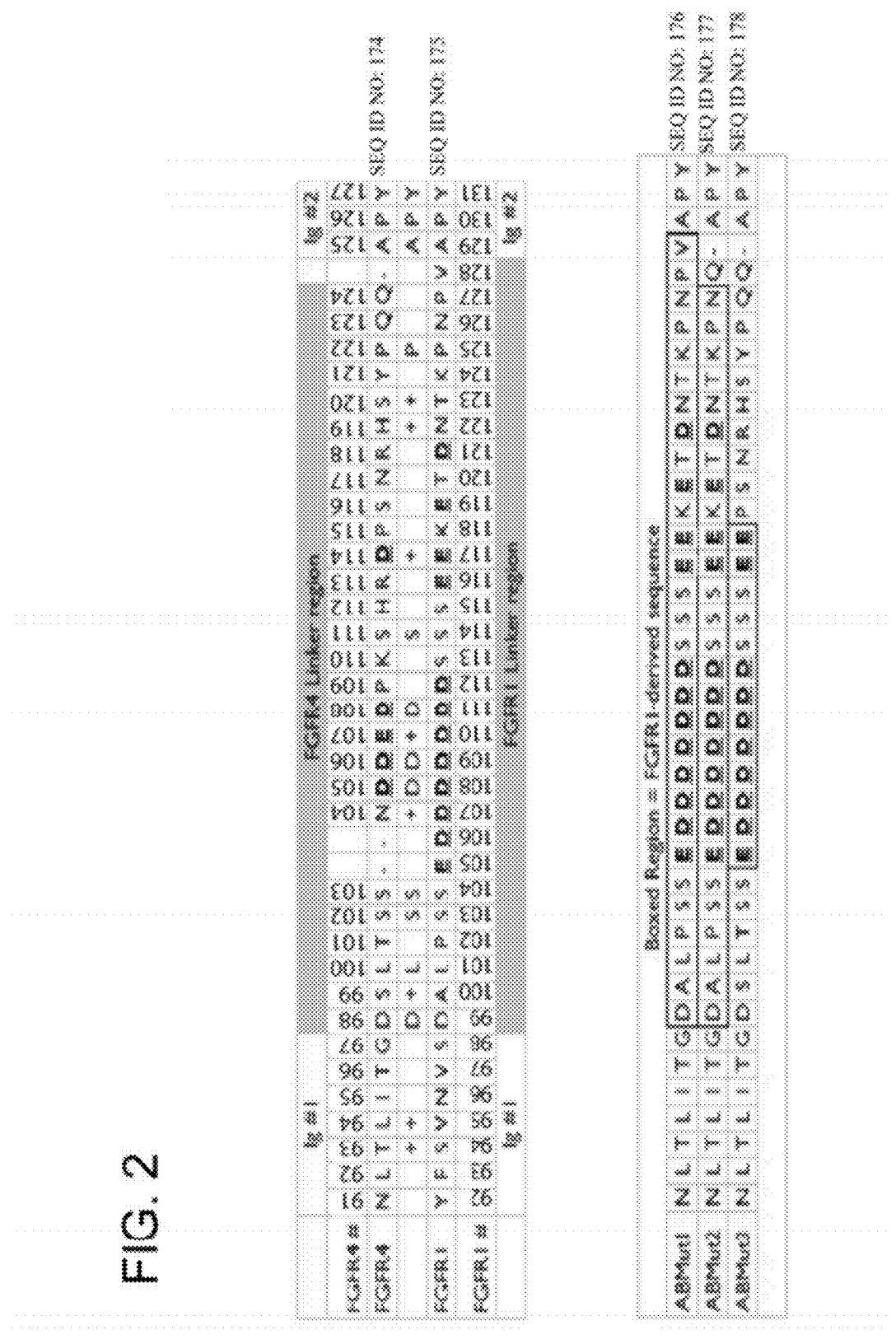

The primary sequence and domain structure of the FGFR4 moiety in the parental R4Mut4 construct is shown in FIG. 1. The stretch of amino acids between the first and second immunoglobulin (Ig) domains (amino acids 98 to 124) is denoted interchangeably herein as the "linker domain" "linker region," "D1-D2 linker," and "D1-D2 linker region" (see FIG. 1). Within the linker domain is a smaller region called the "acid box" ("AB") found within the FGFR family. Three chimeras of the parental R4Mut4 were constructed, in which regions within the R4Mut4 linker domain were replaced with the corresponding sequences from the FGFR1 linker domain. FIG. 2 shows a sequence alignment of the linker domains from FGFR1 and FGFR4 and the boundaries and sequence of the swapped regions in the three variants, called ABMut1, ABMut2, and ABMut3 (see Table 1), that were constructed. Table 1 lists the various FGFR-Fc fusion proteins used in these examples with names and brief descriptions.

TABLE 1

FGFR-Fc Fusion Proteins

| Protein Name | SEQ ID # | Brief Description | Short name |
|---|---|---|---|
| FGFR4ECD(delta17)-Fc | 14 | Parental FGFR4ECD-Fc, which has a 17 amino acid carboxy-terminal deletion from the FGFR4 ECD. | R4Mut4 |
| FGFR4ECD(ABMut1: delta17)-Fc | 86 | The D1-D2 linker from FGFR1 is swapped into R4Mut4. | ABMut1 |
| FGFR4ECD(ABMut2: delta17)-Fc | 87 | Exon 4 from FGFR1 is swapped into R4Mut4. | ABMut2 |
| FGFR4ECD(ABMut3: delta17)-Fc | 158 | An acid box region from FGFR1 is swapped into R4Mut4. | ABMut3 |
| FGFR4ECD(2Ig + Linker)-GS linker-Fc | 89 | The first Ig domain of R4Mut4 is deleted, but the D1-D2 linker is retained with a GS linker. | R4(2Ig + L) |
| FGFR4ECD(2Ig − Linker)-GS linker-Fc | 90 | Both the first Ig domain and the D1-D2 linker are deleted from R4Mut4 with a GS linker. | R4(2Ig − L) |
| FGFR1ECD(delta14)-Fc | 91 | FGFR1 ECD-Fc fusion protein with 14 amino acid C-terminal deletion. | R1Mut4 |

TABLE 1-continued

FGFR-Fc Fusion Proteins

| Protein Name | SEQ ID # | Brief Description | Short name |
|---|---|---|---|
| FGFR1ECD-Fc | N/A | Commercially-available FGFR1 ECD-Fc fusion protein | R1Fc |
| FGFR2ECD-Fc | N/A | Commercially-available FGFR2 ECD-Fc fusion protein | R2Fc |
| FGFR3ECD-FC | N/A | Commercially-available FGFR3 ECD-Fc fusion protein | R3Fc |
| FGFR4ECD-Fc | N/A | Commercially-available FGFR4 ECD-Fc fusion protein | R4Fc |
| FGFR4ECD(R4Mut4(N104D): delta17)-Fc | 130 | R4Mut4 with N104D point mutation. | R4Mut4(N104D) |
| FGFR4ECD(R4Mut4(P109D): delta17)-Fc | 131 | R4Mut4 with P109D point mutation. | R4Mut4(P109D) |
| FGFR4ECD(R4Mut4(R113E): delta17)-Fc | 132 | R4Mut4 with R113E point mutation. | R4Mut4(R113E) |
| FGFR4ECD(R4Mut4(S116E): delta17)-Fc | 133 | R4Mut4 with S116E point mutation. | R4Mut4(S116E) |
| FGFR4ECD(R4Mut4(104-114): FGFR1(106-117): delta 17)-Fc | 134 | Residues 106 to 117 from FGFR1 swapped into R4Mut4. | R4(104-114): R1(106-117) |
| FGFR4ECD(R4Mut4(104-114): FGFR1(107-117): delta 17)-Fc | 135 | Residues 107 to 117 from FGFR1 swapped into R4Mut4. | R4(104-114): R1(107-117) |
| FGFR4ECD(R4Mut4(104-110): FGFR1(105-113): delta 17)-Fc | 136 | Residues 105 to 113 from FGFR1 swapped into R4Mut4. | R4(104-110): R1(105-113) |
| FGFR4ECD(R4Mut4(113-116): FGFR1(116-119): delta 17)-Fc | 137 | Residues 116 to 119 from FGFR1 swapped into R4Mut4. | R4(113-116): R1(116-119) |
| FGFR4ECD(R4Mut4(109-113): FGFR1(112-116): delta 17)-Fc | 138 | Residues 112 to 116 from FGFR1 swapped into R4Mut4. | R4(109-113): R1(112-116) |
| FGFR4ECD(ABMut1(N91A): delta 17)-Fc | 139 | ABMut1 with N91A point mutation. | ABMut1(N91A) |
| FGFR4ECD(ABMut1(N159A): delta 17)-Fc | 140 | ABMut1 with N159A point mutation. | ABMut1(N159A) |
| FGFR4ECD(R4Mut4(D1-D2): FGFR2(D1-D2): delta 17)-Fc | 143 | D1-D2 linker from FGFR2 swapped into R4Mut4. | R4(D1-D2): R2(D1-D2) |
| FGFR4ECD(R4Mut4(D1-D2): FGFR3(D1-D2): delta 17)-Fc | 144 | D1-D2 linker from FGFR3 swapped into R4Mut4. | R4(D1-D2): R3(D1-D2) |
| FGFR2ECD(delta3)-GS linker-Fc | 162 | Parental FGFR2ECD-Fc, which has a 3 amino acid carboxy-terminal deletion from the FGFR2 ECD and a GS linker. | FGFR2-Fc |
| FGFR3ECD(delta3)-GS linker-Fc | 163 | Parental FGFR3ECD-Fc, which has a 3 amino acid carboxy-terminal deletion from the FGFR3 ECD and a GS linker. | FGFR3-Fc |
| FGFR2ECD(FGFR2(111-118): FGFR1(105-112): delta3)-GS linker-Fc | 166 | Residues 105-112 from FGFR1 swapped into FGFR2-Fc. | R2(111-118): R1(105-112) |
| FGFR3ECD(FGFR3(110-117): FGFR1(105-112): delta3)-GS linker-Fc | 167 | Residues 105-112 from FGFR1 swapped into FGFR3-Fc. | R3(110-117): R1(105-112) |

CHO-S host cells can give higher yields and/or different glycosylation patterns for recombinant proteins when compared to 293-6E host cells. For expression of the fusion proteins in CHO-S host cells, we used the pTT5 and pDEF38 (ICOS Corporation, Bothell, Wash.) vectors. R4Mut4 and the FGFR4 ECD-Fc acidic region muteins were subcloned into the pTT5 and pDEF38 vectors using PCR and conventional subcloning techniques.

DG44 (Invitrogen, Carlsbad, Calif.) is a derivative cell line of the CHO-S cell line that we have found can give higher yields of recombinant proteins. For expression of the fusion proteins in DG44 host cells, we used the vector pDEF38.

Example 2

Transient Expression of Fusion Proteins in 293-6E and CHO-S Host Cells

In certain Examples herein, fusion protein was transiently expressed in 293-6E cells. The R4Mut4/pTT5 expression vector described in Example 1 was designed to provide transient expression in 293-6E host cells. The 293-6E host cells used for expression were previously adapted to serum-free suspension culture in Free-Style medium (Invitrogen). The cells were transfected with the expression vector while in logarithmic growth phase (log phase growth) at a cell density of between $9 \times 10^5$/ml and $1.2 \times 10^6$/ml.

In order to transfect 500 ml of 293-6E cell suspension, a transfection mixture was made by mixing 500 micrograms (ug) of the expression vector DNA in 25 ml of sterile phosphate buffered saline (PBS) with 1 mg of polyethylenimine (from a 1 mg/ml solution in sterile water) in 25 ml of sterile PBS. This transfection mixture was incubated for 15 min at room temperature. Following incubation, the transfection mixture was added to the 293-6E cells in log phase growth for transfection. The cells and the transfection mixture were then incubated at 37° C. in 5% $CO_2$ for 24 hours. Following incubation, Trypton-N1 (Organotechnie S. A., La Courneuve, France; 20% solution in sterile FreeStyle medium) was added to a final concentration of 0.5% (v/v). The mixture was maintained at 37° C. and 5% $CO_2$ for about 6-8 days until the cells reached a density of about $3-4 \times 10^6$ cells/ml and showed a viability of >80%. To harvest the fusion protein from the cell culture medium, cells were pelleted at 400×g for 15 min at 4° C. and the supernatant was decanted. The supernatant was cleared of cell debris by centrifugation at 3,315×g for 15 min at 4° C. The cleared supernatant containing fusion protein was then submitted for purification.

To provide small batches (1-2 mg) of R4Mut4 for in vivo study in a short period of time, transient production from suspension CHO-S host cells was carried out using the plasmid construct R4Mut4/pDEF38. Briefly, suspension CHO-S cells (Invitrogen) were cultured in Freestyle CHO expression medium supplemented with L-Glutamine (Invitrogen). The day before transfection, the CHO-S cells were seeded into a shaker flask at a density of about $5 \times 10^5$/ml, which then reached a density of about $1 \times 10^6$/ml on the day of transfection. In order to transfect 125 ml of cell suspension, 156.25 ug of the expression vector DNA was mixed with 2.5 ml of OptiPro serum free medium. 156.25 ul of FreestyleMax transfection reagent (Invitrogen) was separately mixed with 2.5 ml of OptiPro serum free medium. The transfection mixture was made by combining the DNA/OptiPro medium mixture and the FreestyleMax/Optipro medium mixture for 10 min at room temperature. Following incubation, the transfection mixture was added to the CHO-S cells. The cells and the transfection mixture were then incubated at 37° C. in 5% $CO_2$ for 6 days. Following incubation, the cell density was about $3.3-3.7 \times 10^6$/ml with a viability of about 82-88%. The supernatant from the culture was separated from the cells by centrifugation and collected for purification. Using this method, 1 mg of R4Mut4 can be produced from 400 ml of transiently transfected cell culture in about 1 week.

When indicated below, the R4Mut4 variants ABMut1, ABMut2, and ABMut3 were similarly produced by transient expression in CHO-S cells using the pDEF38 expression vectors described in Example 1.

Example 3

Purification of Expressed Proteins

FGFR ECD-Fc fusion proteins expressed from recombinant host cells were purified from the cell culture supernatant using a first purification step of Protein-A affinity chromatography, followed by a second purification step of butyl hydrophobic interaction chromatography. For the Protein-A affinity chromatography step, the components of the media were separated on a Mabselect Protein-A Sepharose column (GE Healthcare Bio-Sciences, Piscataway, N.J.), which will bind to the Fc region of the fusion molecule. The column was equilibrated with ten column volumes of a sterile buffer of 10 mM Tris, 100 mM NaCl, pH 8.0; then the cell culture supernatant was applied to the column. The column was washed with eight column volumes of sterile 10 mM Tris, 100 mM NaCl buffer, pH 8.0. The bound material, including R4Mut4, was then eluted at a rate of 10 ml/min with a one step elution using seven column volumes of elution buffer (100 mM glycine, 100 mM NaCl, pH 2.7). Ten ml fractions were collected in tubes containing one ml 1 M Tris pH 8.0 (Ambion, Austin, Tex.) to neutralize the eluate. Fractions comprising R4Mut4 were identified by gel electrophoresis and pooled.

For the second purification step of butyl hydrophobic interaction chromatography, pooled Protein-A column eluates were further purification on a butyl Sepharose column using a GE Healthcare Akta Purifier 100 (GE Healthcare Bio-Sciences, Piscataway, N.J.). The column was first equilibrated with five column volumes of sterile 10 mM Tris, 1 M ammonium sulfate, pH 8.0. A half volume of 3 M ammonium sulfate was then added to the eluate, which was then applied to the equilibrated butyl Sepharose column. The column was washed with four column volumes of the equilibration buffer and the bound material was eluted at a rate of five ml/min with a linear gradient starting at 50% equilibration buffer/50% elution buffer (10 mM Tris pH 8.0) and ending at 90% elution buffer/10% equilibration buffer over a total volume of 20 column volumes. Finally, an additional two column volumes of 100% elution buffer was used. Fourteen ml fractions were collected. R4Mut4 was eluted with approximately 40-60% elution buffer. The fractions containing the bulk of the R4Mut4 were identified by gel electrophoresis and pooled.

After purification, endotoxin levels were checked by the limulus amoebocyte lysate (LAL) assay (Cambrex, Walkersville, Md.). Endotoxin levels were confirmed to be less than or equal to 1 endotoxin unit (EU) per mg of R4Mut4.

Example 4

Stable Production in DG44 Cells

The expression vector R4Mut4/pDEF38, described in Example 1, was used to transfect DG44 host cells for stable production of R4Mut4. The untransfected DHFR-negative CHO cell line, DG44, was cultured in CHO-CD serum free medium (Irvine Scientific, Irvine, Calif.) supplemented with 8 mM L-Glutamine, 1× Hypoxanthine/Thymidine (HT; Invitrogen), and 18 ml/L of Pluronic-68 (Invitrogen). About 50 ug of R4Mut4/pDEF38 plasmid DNA was linearized by digestion with restriction enzyme PvuI, then precipitated by addition of ethanol, briefly air-dried, and then resuspended in 400 ul of sterile, distilled water. The DG44 cells were seeded into a shaker flask at a density of about $4 \times 10^5$/ml the day before transfection, and reached a density of about $0.8 \times 10^6$/ml on the day of transfection. The cells were harvested by centrifugation and about $1 \times 10^7$ cells were used per transfection.

For transfection, each cell pellet was resuspended in 0.1 ml of Nucleofector V solution and transferred to an Amaxa Nucleofector cuvette (Amaxa, Cologne, Germany). About 5 ug of the resuspended linearized plasmid DNA was added and mixed with the suspended DG44 cells in the cuvette. Cells were then electroporated with an Amaxa Nucleofector Device II using program U-024. Electroporated cells were cultured in CHO-CD medium for two days and then transferred into selective medium (CHO-CD serum free medium supplemented with 8 mM L-Glutamine and 18 ml/L Pluronic-68). The selective medium was changed once every week. After about 12 days, 1 ug/ml R3 Long IGF I growth factor (Sigma, St. Louis, Mo.) was added to the medium and the culture was continued for another week until confluent. The supernatants from pools of stably transfected cell lines were assayed by a sandwich R4Mut4 ELISA to determine the product titer. This transfection method generated an expression level of about 30 ug/ml of R4Mut4 from the pools of stably transfected cells.

Example 5

Binding to Hepatocytes In Vitro

Preliminary experiments demonstrated that R4Mut4 had antitumor properties in a xenograft model yet exhibited a very fast initial serum concentration decline when injected into the tail vein of the mouse. (Data not shown.) Follow-up experiments demonstrated that, unlike the FGFR1 ECD fusion protein R1Mut4, R4Mut4 bound in a concentration-dependent manner to the extracellular matrix Matrigel in vitro. See, e.g., FIG. 6 and Example 9. To ascertain whether the R4Mut4 was binding to liver in vivo, further in vitro binding experiments were conducted to determine whether R4Mut4 and R1Mut4 bound to hepatocytes and also to determine the heparin-sensitivity of that binding.

R4Mut4 and R1Mut4 were expressed and purified from CHO-S cells as described in Examples 2 and 3. For this experiment, three different batches of R4Mut4 were tested; each had been expressed and purified independently. Human IgG1 control protein was obtained from Caltag (now part of Invitrogen).

Hepatocytes were isolated from adult rats. Rats were anesthetized with isoflurane and the animals were kept as close to 37° C. as possible with a heating element. A midline incision was made and the organs were removed from the cavity to access the portal vein. The portal vein was cannulated with a butterfly catheter secured with a bulldog clamp. The pump was started at 8 ml/min with Hanks Balanced Salt Solution without $Ca^{2+}$ or $Mg^{2+}$, with 10 mM Hepes, 0.5 mM EGTA, 50 ug/ml gentamicin, pH 7.38. The inferior vena cava (IVC) was then cut about 2 cm below the liver and an exit point was created by cutting the heart. The flow was adjusted to 40 ml/min and once clear signs of perfusion were observed, the IVC was clamped between the liver and the posterior cut of the IVC. After 4 minutes, Liver Digest Media (Invitrogen) was added to the perfusion line. Both solutions were perfused together for 30 seconds, and then the Hanks Balanced Salt Solution was stopped. The flow rate of the Liver Digest Media was then decreased to 20 ml/min and the perfusion continued for approximately 10 minutes. The liver was excised and small slits in the capsule of each lobe were made. The liver was placed on sterile gauze affixed to the top of a beaker and gently rolled around while continuously rinsing the hepatocytes into the beaker using Liver Digest Media.

The media containing the hepatocytes was poured into 50 ml conical tubes and centrifuged for approximately 2 minutes at 400 rpm. The media was aspirated off and 25 ml of Culture Media (Williams Medium E (Sigma), 100 IU/ml of penicillin (Cellgro), 100 ug/ml of streptomycin (Cellgro), 1×ITS (Insulin, Transferrin and Sodium Selenite, from Sigma) and 10% FBS (Cellgro)) was added to half of the tubes and the cells were resuspended. The resuspended cells were then decanted into the remaining tubes and the volume of Culture Media was brought to 50 ml in each tube. The tubes were centrifuged again as above and the decanting step was repeated. The cells were then resuspended in ice-cold staining buffer ($Ca^{2+}$ and $Mg^{2+}$ free PBS (Invitrogen) supplemented with 1% bovine serum albumin (BSA; w/v) and 0.1% $NaN_3$ (w/v), both from Sigma) at a concentration of 500,000 cells per ml. The hepatocytes were then incubated with 5 ug/ml of R1Mut4, R4Mut4, or control human IgG1 for 30 minutes. In samples where heparin was present, the R1Mut4, R4Mut4, or control human IgG1 was pre-incubated with a 10-fold molar excess of sodium heparin (from porcine intestinal mucosa, Catalog #086K2231, Sigma) before mixing with the hepatocytes.

Following incubation with the fusion proteins or control IgG1, with or without heparin, the cells were washed in staining buffer and incubated with 5 ug/ml biotinylated goat anti-human Fc (Becton Dickinson) on ice for 30 min. The cells were then washed in staining buffer and incubated with 1 ug/ml streptavidin-APC conjugate (Becton Dickinson) on ice for 30 min. The cells were again washed with staining buffer and then stained with 0.5 ug/ml propidium iodide (Sigma). Non-viable cells that had absorbed the propidium iodide were gated out such that only viable cells were included in the flow cytometry analysis. The viable cells were quantitated for APC fluorescence. As shown in FIG. 3, R4Mut4 showed 10-fold more binding to rat hepatocytes than either control IgG1 or R1Mut4 in that experiment. In addition, all three batches of R4Mut4 bound the rat hepatocytes with similar affinity, indicating that the high affinity of R4Mut4 for rat hepatocytes was not due to unusual expression or purification conditions. Finally, the addition of heparin prevented R4Mut4 binding to hepatocytes in that experiment.

Example 6

Heparin Increases the Cmax of R4Mut4 in Plasma In Vivo

The experiment discussed in Example 5 demonstrated that R4Mut4 bound to hepatocytes and that heparin could interfere with that binding. To test whether heparin could increase in the amount of R4Mut4 present in the serum in vivo, R4Mut4 was administered to mice with and without exogenous heparin, and the amount of R4Mut4 in the serum was analyzed by ELISA at different time points following injection. The R4Mut4 injected in the experiment was expressed and purified from CHO-S cells as described in Examples 2 and 3.

Thirty male Balb/C mice (Jackson Laboratories, Bar Harbor, Me.) were weighed and sorted into two groups of 15 mice each based on a random distribution of body weight. Mice in the first group were given an intravenous injection (via tail vein) of 3 mg/kg R4Mut4 in a total volume of 0.5 ml PBS (Cellgro, Herndon, Va.). Mice in the second group were given an intravenous injection (via tail vein) of 3 mg/kg R4Mut4 that had been premixed with 5 mg/kg sodium heparin (from porcine intestinal mucosa, Sigma) for 30 minutes-2 hours before IV dosing.

Blood from the mice was collected at 6 different time points after IV administration, at approximately 2 minutes, 2 hours, 8 hours, 1 day, 4 days, and 6 days. Blood was collected from each mouse only twice, the first by a retro-orbital bleed and the second terminally by cardiac puncture. The 15 mice from each IV group were further divided into three subgroups of 5 mice. The first subgroup was used to collect blood at 2 minutes and 2 hours. The second subgroup was used to collect blood at 24 hours and 4 days. The third subgroup was used to collect blood at 8 hours and 6 days.

The retro-orbital bleeds were collected through heparin-coated capillary tubes (Fisher Scientific, Pittsburgh, Pa.) into $K_2$-EDTA coated tubes (BD Biosciences; San Jose, Calif.), placed on wet ice for approximately 30 minutes and then spun at 10,621×g (10,000 rpm) in a microfuge for 8 minutes. The second, terminal bleed, was collected through uncoated syringes into $K_2$-EDTA coated tubes (BD Biosciences) and then processed as above. Following centrifugation, the plasma was removed and frozen at −80° C. until analyzed by ELISA.

For detection of R4Mut4 in plasma samples, a direct ELISA for FGF2 binding activity was used. Briefly, Maxisorp 96-well plates (Nunc, Rochester, N.Y.) were coated with recombinant human FGF2 (PeproTech, Rocky Hill, N.J.) in PBS (Mediatech, Herndon, Va.) at 1 ug/ml overnight at 4° C. The plates were then blocked with blocking buffer (1% BSA (Sigma) in PBS) for 2-3 hours at room temperature. The plates were washed 6 times with wash buffer (0.05% Tween-20 (v/v; Sigma) in PBS). Various dilutions of the test samples and R4Mut4 standards were made with a constant final concentration of 5% plasma in each sample. 100 ul of test sample was added to each well and then incubated for approximately 90 minutes at room temperature. The plates were washed 6 times with wash buffer, and then a peroxidase-conjugated AffiPure goat anti-human IgG-Fc antibody (Jackson ImmunoResearch Laboratories, West Grove, Pa.) diluted at 1:60,000 in assay diluent (1% BSA and 0.05% Tween-20 in PBS) was added to each well and incubated for approximately 1 hour at room temperature. The plates were washed 6 times with wash buffer. 100 ul per well of TMB substrate (Pierce Biotechnology, Chicago, Ill.) was then added and incubated for 10 minutes. The reactions were quenched with 50 ul stop solution (2 N $H_2SO_4$). The absorbance at 450 nm was then read on a SPECTRAmax PLUS microplate reader (Molecular Devices, Sunnyvale, Calif.).

Figure 4:
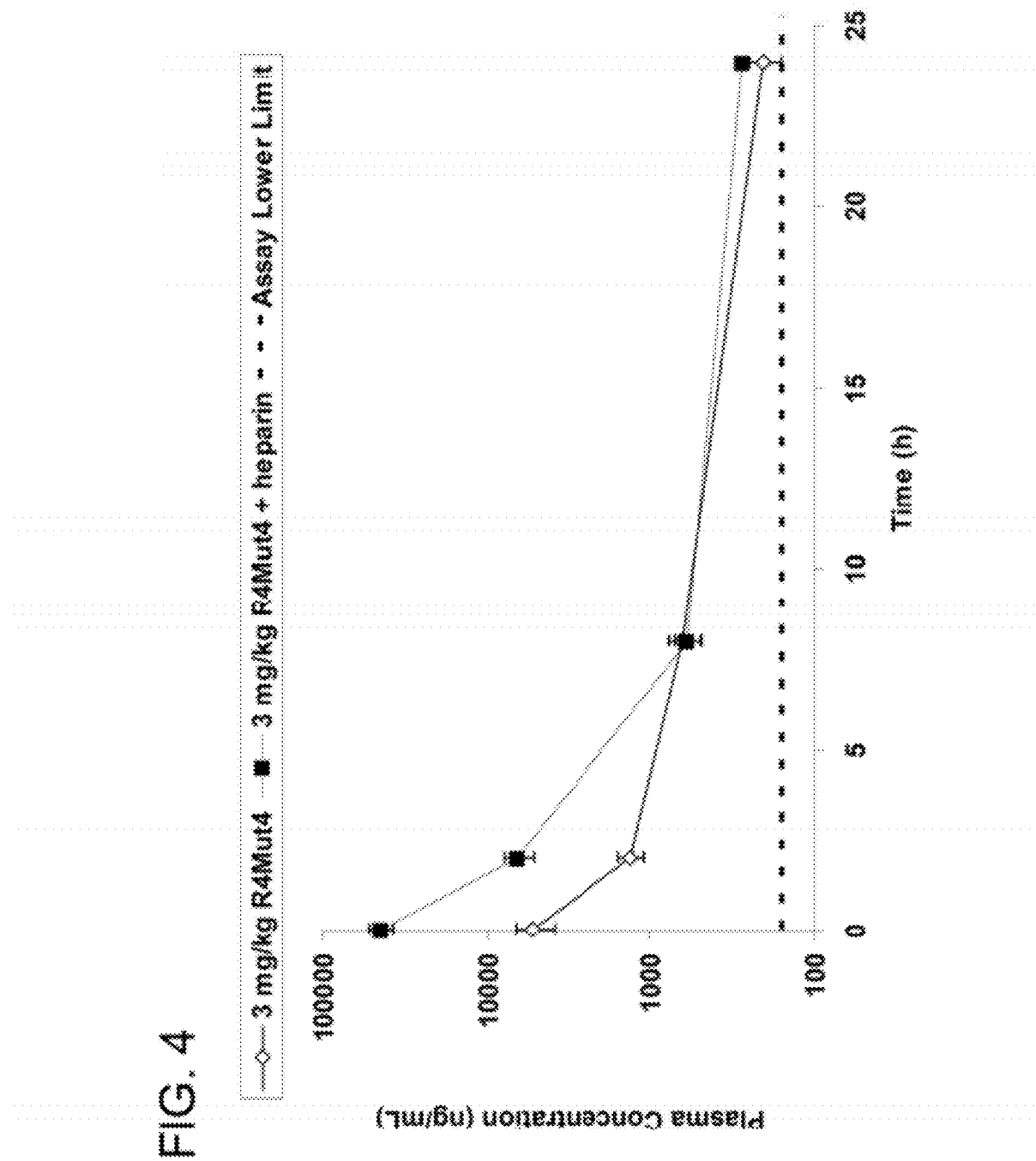
FIG. 4 is a graphical representation of the plasma concentration (ng/ml) in mice of R4Mut4, administered with and without heparin, as described in Example 6. The plasma concentration is shown on the Y-axis, and was determined using an FGF2-binding ELISA. The X-axis shows the time following administration. The dashed line represents the lower limit of reproducible R4Mut4 detectability in the ELISA (approximately 156 ng/ml). Each data point represents the average from 5 animals, with the error bars representing the standard error of the mean.

Results for all six time points from that experiment are shown in Table 2 and the first 4 time points are shown graphically in FIG. 4.

TABLE 2

R4Mut4 Serum Levels

| Time point | Average R4Mut4 serum plasma concentration +/− standard deviation (ng/ml) | |
|---|---|---|
| | No Heparin | With Heparin |
| 2 minutes | 5247 +/− 1367 | 44404 +/− 7362 |
| 2 hours | 1329 +/− 236 | 6516 +/− 1293 |
| 8 hours | 628 +/− 138 | 592 +/− 109 |
| 1 day | 204 +/− 45 | 273 +/− 27 |
| 4 day | Below limit of detection (156 ng/ml) | Below limit of detection (156 ng/ml) |
| 6 day | Below limit of detection (156 ng/ml) | Below limit of detection (156 ng/ml) |

Those results demonstrate that co-administration of heparin with R4Mut4 increased the maximum R4Mut4 concentration in the plasma ($C_{max}$) by approximately 9-fold over R4Mut4 administered alone at the 2 min time point and approximately 7-fold at the 2 hour time point in that experiment. The two curves merge at the 8 hour time point. These data show that heparin increases the amount of R4Mut4 that is free in the serum but that the protection was lost by 8 hours in that experiment. Previous reports have shown that heparin has a short half-life in vivo (~45-60 minutes; see Bjornsson and Levy, J. Pharmacol. Exp. Ther. (1979) 210:243-246) and this may play a role in the duration of the protective effect of heparin in that experiment.

Example 7

FGFR ECD-Fc Binding to Extracellular Matrix Components In Vitro

In vitro binding studies were conducted to characterize the ability of each of the four FGFR ECD-Fc fusion proteins to bind to extracellular matrix components (ECM). For this study, wild-type FGFR1 ECD-Fc, FGFR2 ECD-Fc, FGFR3 ECD-Fc and FGFR4 ECD-Fc fusion proteins were purchased from R&D Systems (Minneapolis, Minn.).

Figure 5:
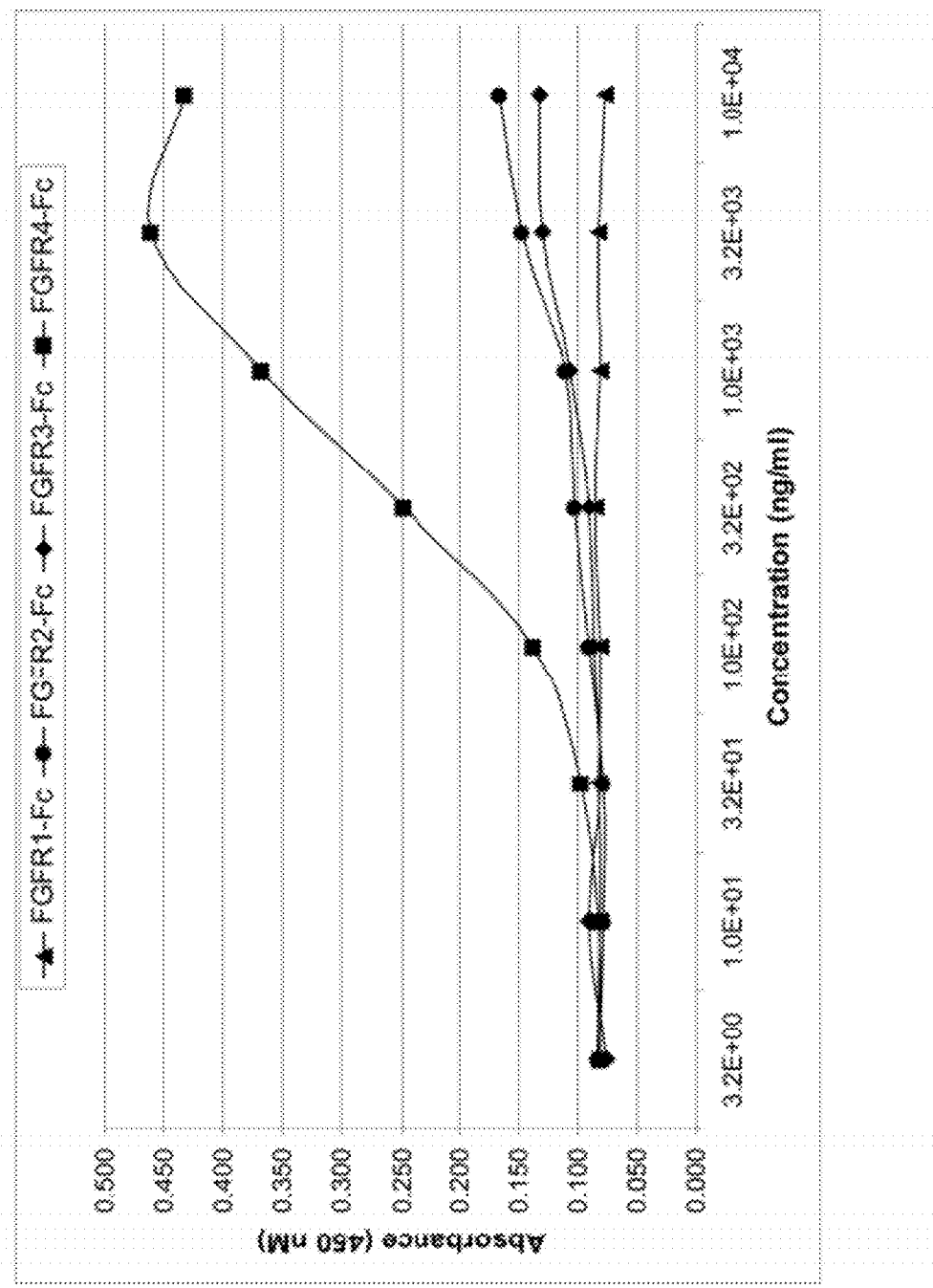
FIG. 5 shows the binding of commercially-available FGFR1 ECD-Fc, FGFR2 ECD-Fc, FGFR3 ECD-Fc, and FGFR4 ECD-Fc to Matrigel plates, as described in Example 7. The X-axis shows the concentration of the Fc fusion proteins and the Y-axis shows the absorbance at 450 nm following incubation of the bound Fc fusion protein with OPD substrate. All binding reactions were carried out in triplicate and the data points represent the average values obtained.

96-well Matrigel plates (Becton-Dickinson) were blocked with a 1% (w/v) solution of BSA (Sigma). The FGFR ECD-Fc fusion proteins were serially diluted, transferred to the Matrigel plates, and allowed to bind for 1 hour at room temperature. Unbound fusion proteins were removed by washing three times with PBS (EMD Biosciences; La Jolla, Calif.) and 0.5% Tween (v/v; Sigma). Bound fusion proteins were detected using a peroxidase-conjugated anti-human Fc antibody (Bethel Laboratories, Montgomery, Tex.) and OPD (o-phenylenediamine dihydrochloride) substrate (Sigma), according to the manufacturer's instructions. FGFR4 ECD-Fc bound tightly to the Matrigel plates with an $EC_{50}$ of approximately 300 ng/mL in that experiment. See FIG. 5. FGFR1 ECD-Fc, FGFR2 ECD-Fc, and FGFR3 ECD-Fc all showed significantly weaker binding to the Matrigel plates than the FGFR4 ECD-Fc, with half-maximal binding not observed in that experiment even at concentrations of 10,000 ng/ml. See FIG. 5.

Example 8

FGFR4 ECD Acidic Region Chimera-Fc Fusion Proteins Bind to FGF2 and FGF19

In order to reduce tissue binding and improve the pharmacokinetic profile, three FGFR4 ECD acidic region chimeras were fused to Fc, expressed in 293-6E cells, and purified. In addition, two FGFR4 2Ig ECD-Fc fusion proteins in which D1 or D1+the acid box region were deleted, were constructed, expressed, and purified.

The FGF2 and FGF19 ligand binding affinity and kinetics of the parental R4Mut4 and the five different FGFR4 ECD-Fc fusion proteins (collectively "the R4 proteins") were determined using Biacore® X surface plasmon resonance (SPR) technology (Uppsala, Sweden). FGF2 was selected because it is broadly expressed in adult tissue and has been implicated in cancer progression and angiogenesis. FGF19 was selected because, in the absence of other protein cofactors, it binds specifically to FGFR4. Briefly, Protein-A was covalently linked to a CM5 chip, according to manufacturer's instructions. The R4 proteins were produced in 293-6E host cells as described in Example 2, purified as described in Example 3, and then bound to the chip by interaction of the Fc domain with Protein-A. The R4 proteins were captured onto flow channels 2-4, while channel 1 served as a reference. FGF2 was purchased from Peprotech (Rocky Hill, N.J.) and FGF19 was purchased from R&D Systems. Each FGF ligand was injected at 5 concentrations (100 nM, 25 nM, 6.25 nM, 1.56 nM, and 0 nM) for 2 minutes and dissociation was monitored for 4 minutes. 50 uM Heparin was included in the running buffer. The association constant, dissociation constant, affinity, and binding capacity of each of the R4 proteins for FGF2 and FGF19 was calculated using the Biacore T100 Evaluation software package using the 1:1 binding model.

The results of that experiment are shown in Tables 3 and 4.

TABLE 3

FGF2 Ligand Binding

| Protein Name | $k_a$ (1/M · ms) | $k_d$ (1/s) · 1000 | $K_D$ (nM) | $R_{max}$ (RU) |
|---|---|---|---|---|
| R4Mut4 (experiment 1) | 59 | 0.23 | 3.90 | 46 |
| R4Mut4 (experiment 2) | 45 | 0.27 | 5.88 | 53 |
| ABMut1 | 160 | 0.27 | 1.70 | 56 |
| ABMut2 | 114 | 0.26 | 2.26 | 57 |
| ABMut3 | 242 | 0.35 | 1.44 | 58 |
| R4(2Ig + L) | 313 | 0.79 | 2.54 | 62 |
| R4(2Ig − L) | 306 | 0.73 | 2.40 | 51 |

TABLE 4

FGF19 Ligand Binding

| Protein Name | $k_a$ (1/M · ms) | $k_d$ (1/s) · 1000 | $K_D$ (nM) | $R_{max}$ (RU) |
|---|---|---|---|---|
| R4Mut4 (experiment 1) | 176 | 0.63 | 3.60 | 55 |
| R4Mut4 (experiment 2) | 184 | 0.61 | 3.32 | 50 |
| ABMut1 | 213 | 0.68 | 3.18 | 45 |
| ABMut2 | 250 | 0.64 | 2.58 | 44 |
| ABMut3 | 211 | 0.74 | 3.50 | 40 |
| R4(2Ig + L) | 80 | 2.76 | 34.31 | 26 |
| R4(2Ig − L) | 118 | 2.14 | 18.15 | 18 |

As shown in Tables 3 and 4, the three chimeras ABMut1, ABMut2, and ABMut3, had an affinity equal to or greater than the parental R4Mut4 for both FGF2 and FGF19 in that experiment, as measured by the equilibrium dissociation constant ($K_D$).

In addition, FGFR4 ECD-Fc fusion proteins in which D1 was deleted, in either the presence (R4(2Ig+L)) or absence (R4(2Ig−L)) of the D1-D2 linker region, bound FGF2 with an affinity equal to or greater than the parental R4Mut4 in that experiment, as measured by the equilibrium dissociation constant ($K_D$). Deletion of D1 reduced binding to FGF19 by approximately ten-fold in the presence of the D1-D2 linker region (R4(2Ig+L)), and by approximately five-fold in the absence of the D1-D2 linker region (R4(2Ig−L)) in that experiment.

Those results show that all of the R4 proteins tested retained the ability to bind to FGF2 and/or FGF19, although the D1 deletion proteins exhibited weaker binding to FGF19 than the parental or the acidic region chimeras in that experiment.

Example 9

FGFR4 ECD Acidic Region Chimera-Fc Fusion Protein Binding to Extracellular Matrix (ECM) Components In Vitro In vitro binding studies were conducted to characterize the ability of the FGFR4 ECD acidic region chimeras to bind to ECM. FGFR4-Fc acidic region chimera-Fc fusion proteins were expressed in 293-6E cells, as described in Example 2, and all were purified as described in Example 3. The parental R4Mut4 was expressed in CHO cells as described in Example 2 and also purified as described in Example 3.

Figure 6:
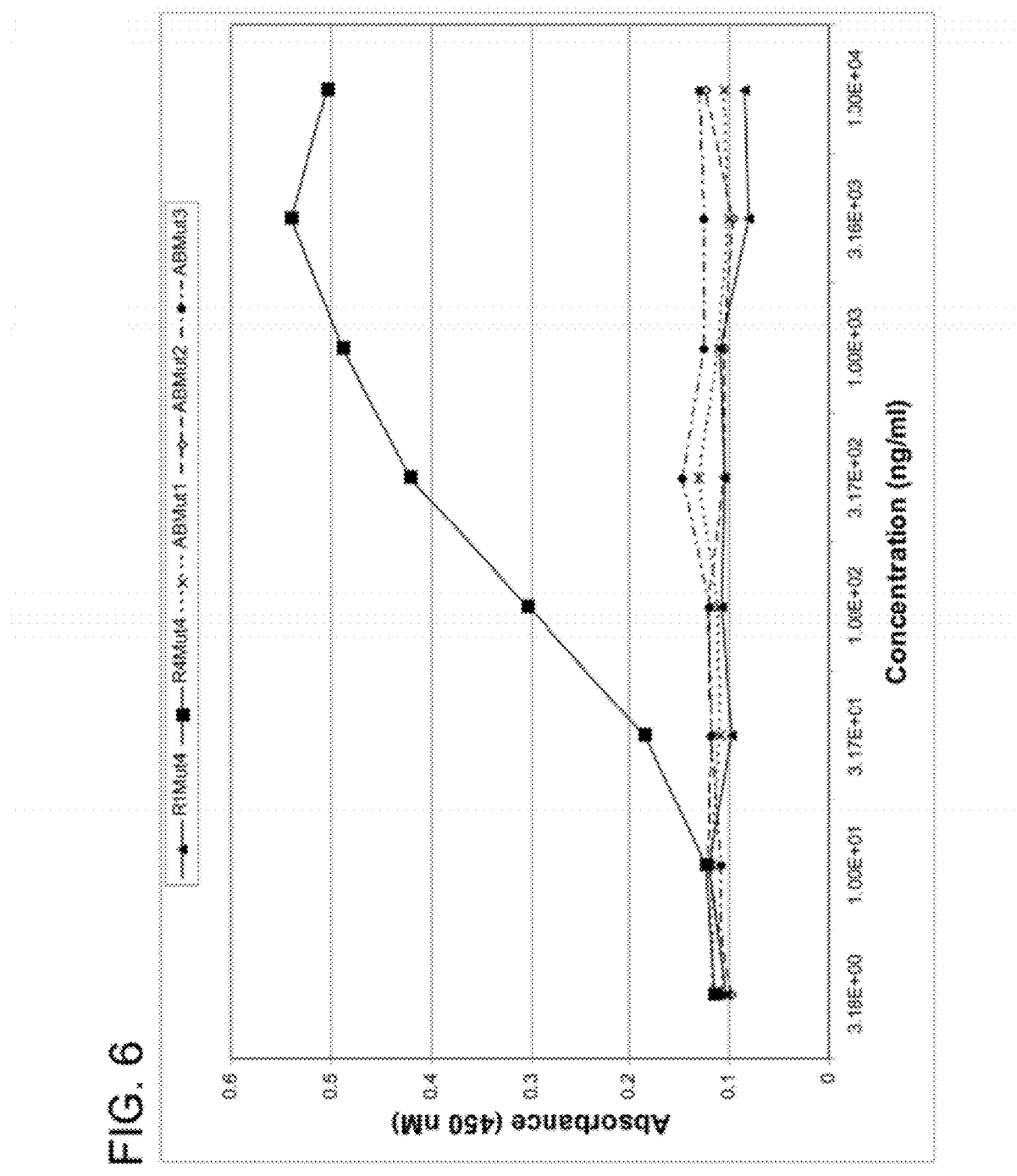
FIG. 6 shows the binding of R1Mut4, R4Mut4, and FGFR4 ECD acidic region chimeras ABMut1, ABMut2, and ABMut3 to Matrigel plates, as described in Example 9. The X-axis shows the concentration of the Fc fusion proteins and the Y-axis shows the absorbance at 450 nm following incubation of the bound Fc fusion protein with OPD substrate. All binding reactions were carried out in triplicate and the data points represent the average value obtained.

Binding experiments were performed as described in Example 7, and a graphical representation of the results is shown in FIG. 6. In this experiment, the parental R4Mut4 bound to Matrigel plates with an $EC_{50}$ of approximately 100 ng/ml. All three FGFR ECD acidic region chimera-Fc fusion proteins showed minimal binding to Matrigel plates up to a concentration of 10,000 ng/ml in that experiment. Therefore, the substitution of the FGFR1 D1-D2 linker, FGFR1 exon 4, or FGFR1 acid box region for the corresponding region of the FGFR4 ECD abrogated the in vitro extracellular matrix binding of the FGFR4 ECD in that experiment.

Example 10

FGFR4 ECD Acidic Region Chimera-Fc Fusion Protein Binding to Hepatocytes In Vitro FGFR4 ECD acidic region chimera-Fc fusion proteins ABMut1, ABMut2 and ABMut3 were tested for their ability to bind hepatocytes. The fusion proteins were expressed in 293-6E cells, as described in Example 2, and purified as described in Example 3. The R1Mut4 and R4Mut4 proteins were expressed in CHO-S cells, as described in Example 2, and purified as described in Example 3. Human IgG1 control protein was obtained from Caltag.

Figure 7:
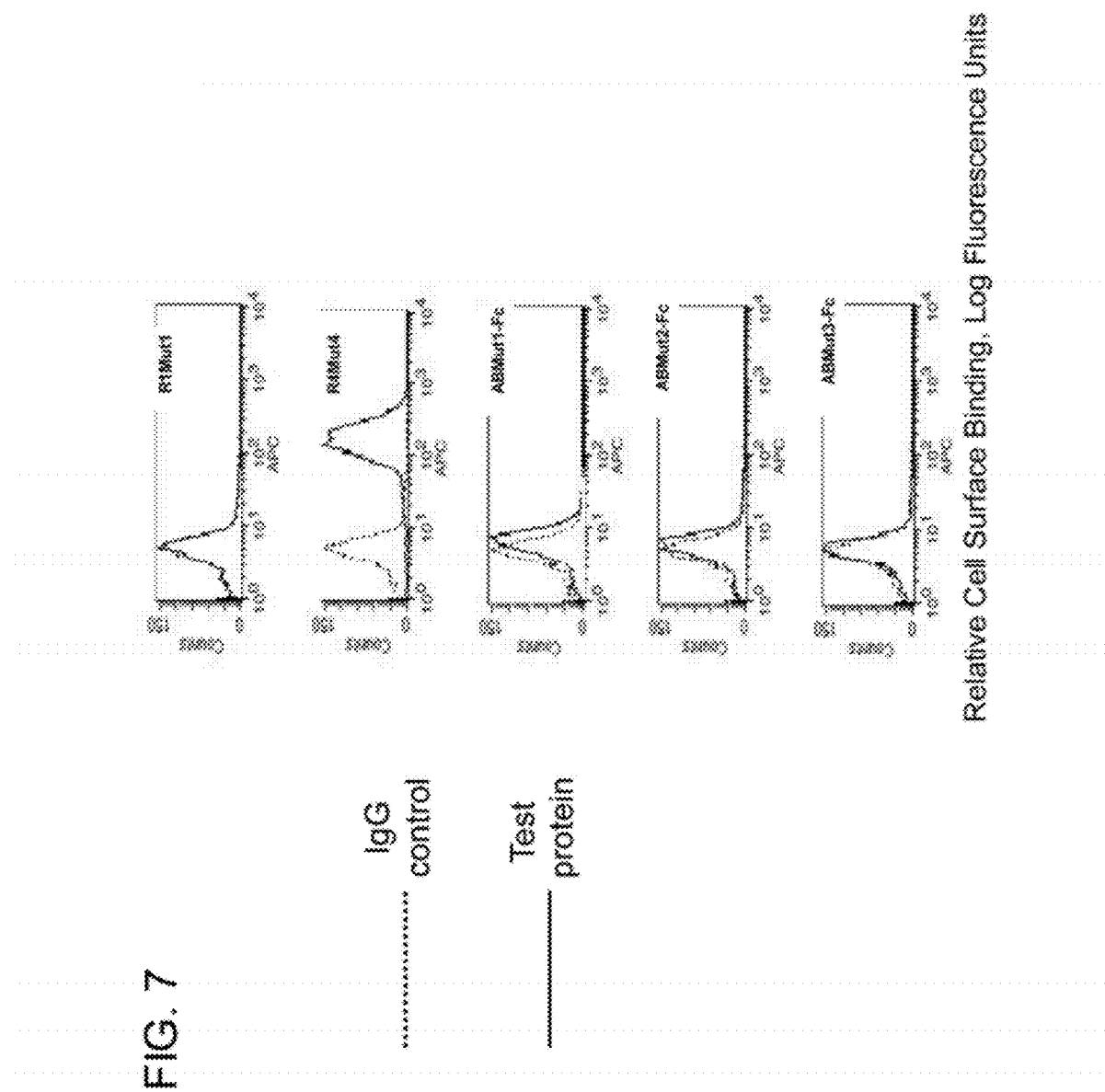
FIG. 7 shows the binding of R1Mut4, R4Mut4, FGFR4 ECD acidic region chimeras ABMut1, ABMut2, and ABMut3, and an IgG control, to hepatocytes detected by flow cytometry, as described in Example 10. The number of cells (counts) is shown on the Y-axis, and the X-axis shows the relative fluorescent signal, in log units.

The hepatocyte binding experiments were performed as described in Example 5 and a graphical representation of the results is shown in FIG. 7. In that experiment, all three FGFR4 ECD acidic region chimera-Fc fusion proteins showed hepatocyte binding that was equivalent to R1Mut4, and was greatly reduced compared to the parental R4Mut4.

Example 11

Pharmacokinetics of an FGFR4 ECD Acidic Region Chimera-Fc Fusion Protein in Mice The pharmacokinetic properties of ABMut1 were compared to the parental R4Mut4 in vivo. Both proteins were expressed in CHO-S cells as described in Example 2 and purified as described in Example 3.

Forty female Balb/C mice (Charles River Laboratories, Wilmington, Mass.) were weighed and sorted into two groups of 20 mice based on a random distribution of body weight. Mice in the first group received R4Mut4 and mice in the second group received ABMut1. Each mouse received 5 mg protein per kilogram body weight via intravenous injection through the tail vein in a total volume of 0.2 ml PBS (Cellgro).

Blood plasma was collected at 9 different time points following IV administration, at approximately 2 minutes, 30 minutes, 2 hours, 7 hours, 1 day, 2 days, 3 days, 5 days, and 7 days. Blood was collected from each mouse two or three times, the first one or two collections by a retro-orbital bleed and the last terminally by cardiac puncture. The 20 mice from each treatment group were further divided into four subgroups of 5 mice. Each group was bled at the times shown in Table 5.

TABLE 5

Sample Collection Times and Methods

| | Time points of blood collection (following IV administration) | |
|---|---|---|
| Group (n = 5) | Retro-orbital bleed | Terminal cardiac puncture |
| Group 1 | 2 and 5 minutes | 7 days |
| Group 2 | 30 minutes | 7 hours |
| Group 3 | 2 hours | 24 hours |
| Group 4 | 2 days | 3 days |

Figure 8:
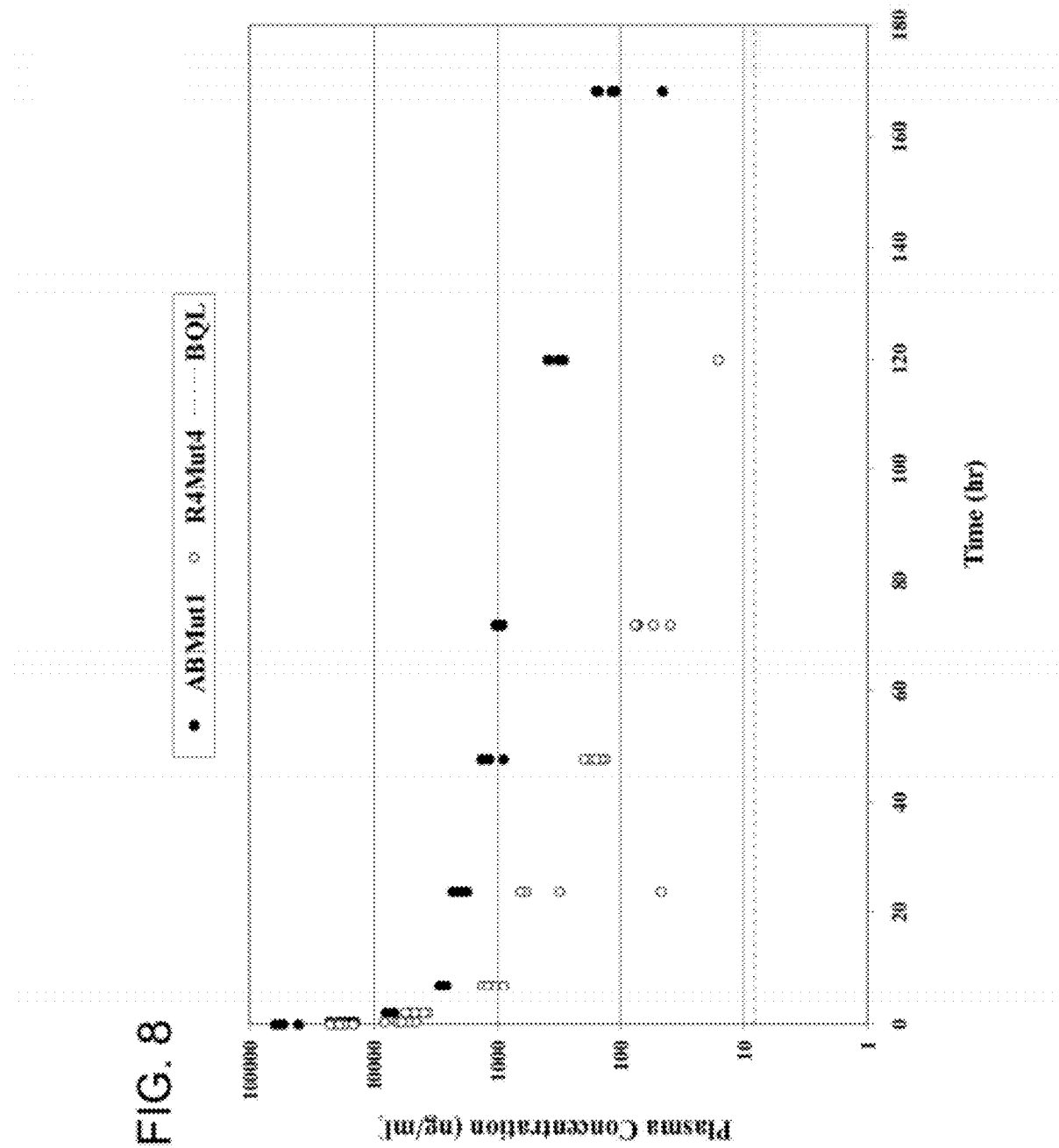
FIG. 8 is a graphical representation of the plasma concentrations (ng/ml) of R4Mut4 and ABMut1 following their administration to mice, as described in Example 11. The plasma concentrations are shown on the Y-axis, and were determined using an FGF2-binding ELISA. The X-axis shows the time following administration. The dashed line represents the lower limit of reproducible R4Mut4 detectability in the ELISA (approximately 8 ng/ml). Data from five animals for each time point are included in the figure.

Plasma serum was collected and the R4Mut4 and ABMut1 protein levels determined by a direct FGF2 binding ELISA as described in Example 7. The results are shown in FIG. 8 and certain pharmacokinetic parameters are given in Table 6. The results show that the replacement of the DL-D2 linker of the FGFR4 ECD with the FGFR1 D1-D2 linker increased the half-life ($t_{1/2}$) of the administered protein by 126%, increased the maximum observed plasma concentration ($C_{max}$) by 183%, and increased the clearance time (CL) by 302%. The improved pharmacokinetic profile of ABMut1 shows that it is present in the blood, at a therapeutic concentration, longer than the parental R4Mut4 molecule.

TABLE 6

Pharmacokinetic Parameters of R4Mut4 and ABMut1

| Protein | $t_{1/2}$ (in hours) | $C_{max}$ (in ug/ml) | CL (in ml/hr/kg) |
|---|---|---|---|
| R4Mut4 | 15.7 | 18.7 | 23.6 |
| ABMut1 | 35.5 | 52.9 | 94.8 |
| Change (%) | 126% | 183% | 302% |

Example 12

Activity in HCT116sc Cancer Xenograft Model

The anti-cancer activities of the parental R4Mut4 and ABMut1 were tested in a xenograft colon cancer model using human colon carcinoma HCT116sc cells. The HCT116sc cell line is a sub-line of the HCT116 colon carcinoma cell line (ATCC, Manassas, Va.) isolated from a subcutaneous HCT116 tumor and selected for more consistent in vivo growth using standard cell culture and xenograft techniques. To prepare the HCT116sc cells for the xenograft experiment, the cells were cultured for five passages in RPMI 1640 media supplemented with 10% FBS (vol/vol), 2 mM L-Glutamine, 100 IU/ml of penicillin and 100 ug/ml of streptomycin (all from Cellgro) at 37° C. in a humidified atmosphere with 5% $CO_2$. Semi-confluent cells (~80%) were re-suspended in PBS without calcium and magnesium (Cellgro) at a concentration of $1 \times 10^8$ cells per ml. Matrigel basement membrane matrix (BD Biosciences) was added to 50% (vol/vol) to give a final concentration of $5 \times 10^7$ cells per ml and the mixture stored on ice until implantation into mice.

For the xenograft experiments, sixty CB17 SCID mice (Charles River Laboratories) were used. On day 1, the body weight of each mouse was measured. The mice were randomly distributed into 6 groups of 10 mice based on their body weight. Once assigned to a treatment group, the mice were shaved on the right hind flank and then inoculated subcutaneously with $5 \times 10^6$ (100 ul) of the HCT116sc cells prepared as described above.

On the next day, animals were dosed with the test articles according to the dosing scheme shown in Table 7. R4Mut4 and ABMut1 were expressed in CHO-S cells and purified as described in Examples 2 and 3, respectively.

TABLE 7

HCT116sc Xenograft Dosing Groups

| Group | Number of Animals | Test Article and Dose (mg test article per weight mouse) | Dosing Route and Schedule |
|---|---|---|---|
| 1 | 10 | Vehicle | Intravenous, 2×/week |
| 2 | 10 | R4Mut4, 20 mg/kg | Intraperitoneal, daily |
| 3 | 10 | R4Mut4, 10 mg/kg | Intravenous, 2×/week |
| 4 | 10 | R4Mut4, 20 mg/kg | Intravenous, 2×/week |
| 5 | 10 | ABMut1, 10 mg/kg | Intravenous, 2×/week |
| 6 | 10 | ABMut1, 20 mg/kg | Intravenous, 2×/week |

Tumor sizes were measured in each mouse on days 7, 14, and 21 following the day of tumor cell inoculation. The length and width of each tumor was measured using calipers and the tumor size calculated according to the formula:

Tumor size $(mm^3)$=width$^2$(mm)×length (mm)×($\pi$/6)

Figure 9:
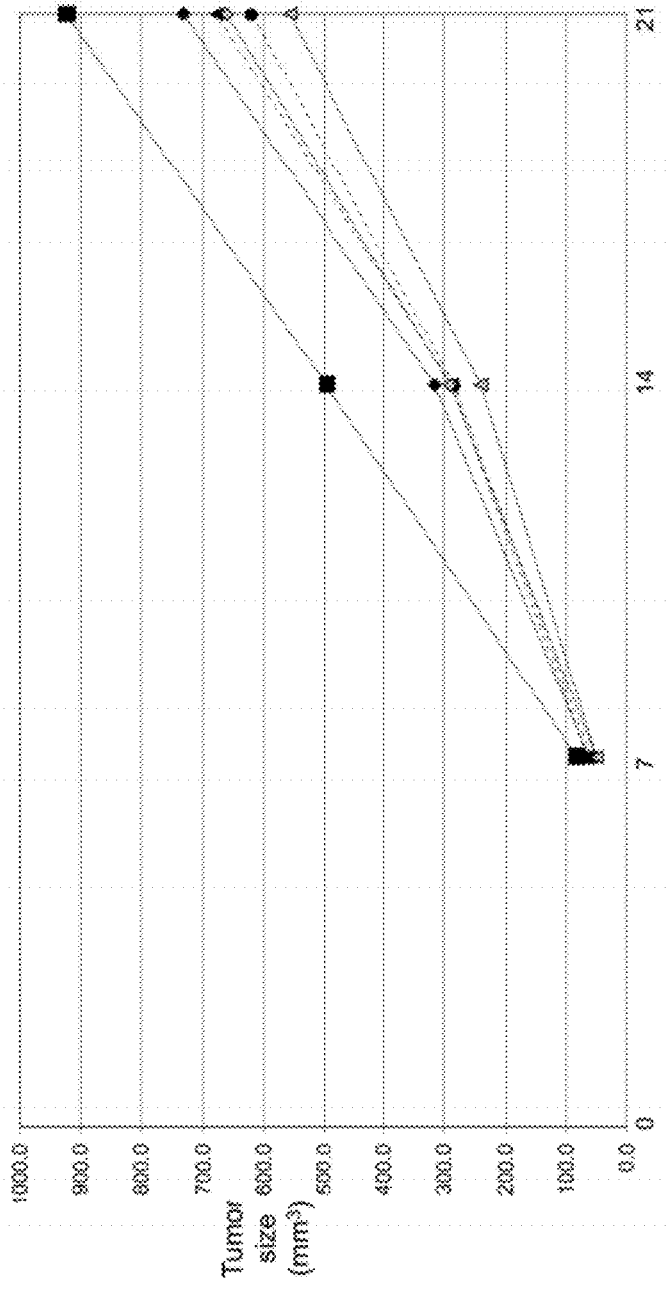
FIG. 9 shows the results of the xenograft experiment described in Example 12. Mice were inoculated with tumor cells, and tumor growth was measured after administration of R4Mut4, ABMut1, or vehicle alone. The tumor size is shown on the Y-axis, and the number of days following tumor inoculation is shown on the X-axis. The dosing schedule for each treatment group is shown in Table 9, and the p-values of each treatment group at days 14 and 21 are shown in Table 10.
Figure 10:
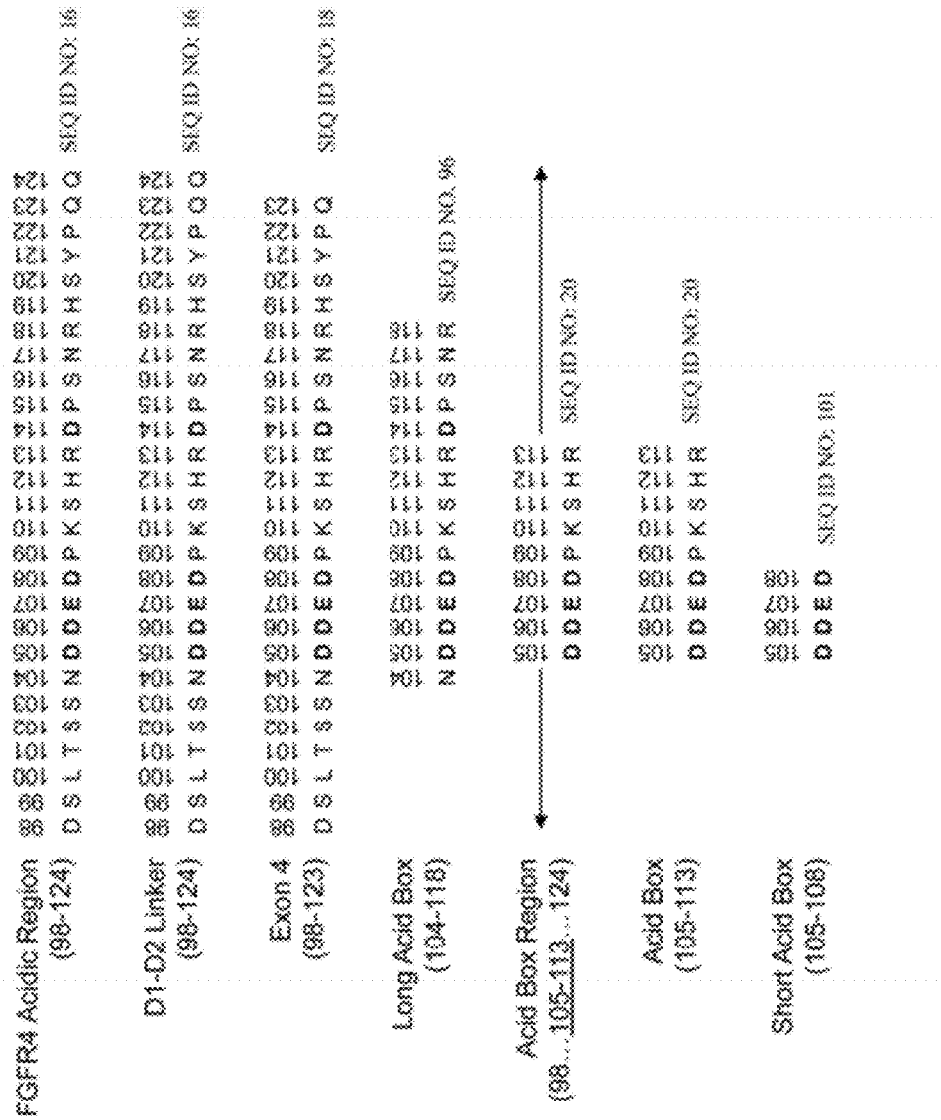
FIG. 10 shows the amino acid sequence of the FGFR4 ECD acidic region, along with the locations of certain regions within the FGFR4 ECD acidic region, as defined herein.

FIG. 9 shows the results of that experiment. All groups of mice that received R4Mut4 or ABMut1 showed a diminution of tumor growth compared to vehicle-treated animals. Table 8 shows the average percent inhibition of tumor growth for each treatment group at days 14 and 21 compared to the vehicle treated group, and the corresponding p-values. P-values were calculated using an ANOVA analysis followed by the Bonferonni t-test. See, e.g., *Mathematical Statistics and Data Analysis*, 1988, Wadsworth & Brooks, Pacific Grove, Calif. This analysis demonstrated that ABMut1 reduced tumor growth to a similar or greater extent than the parental R4Mut4 in that experiment.

TABLE 8

HCT116sc Xenograft Results

| Group | Day 14: Percent inhibition; p-value | Day 21: Percent inhibition; p-value |
|---|---|---|
| R4Mut4, 20 mg/kg, IP | 43%, p-value = 0.003 | 33%, p-value = 0.014 |
| R4Mut4, 10 mg/kg, IV | 42%; p-value = 0.003 | 27%; p-value = 0.068 |
| R4Mut4, 20 mg/kg, IV | 37%; p-value = 0.011 | 21%; p-value = 0.083 |
| ABMut1, 10 mg/kg, IV | 42%; p-value = 0.003 | 29%; p-value = 0.015 |
| ABMut1, 20 mg/kg, IV | 52%; p-value = 0.002 | 40%; p-value = 0.003 |

Example 13

Increasing the Concentration of an FGFR4 ECD Acidic Region Chimera Leads to Detectable ECM Binding In Vitro As described in Example 9 and shown in FIG. 6, early in vitro binding experiments showed minimal binding of three FGFR4 ECD acidic region chimera-Fc fusion proteins (ABMut1, ABMut1, and ABMut3) to ECM components when up to 10,000 ng/ml of purified protein was incubated with Matrigel plates. Experiments were carried out to determine whether higher concentrations (up to 1 mg/ml) of the ABMut1 fusion protein could exhibit increased levels of ECM binding in the same in vitro ECM binding assay.

Figure 12:
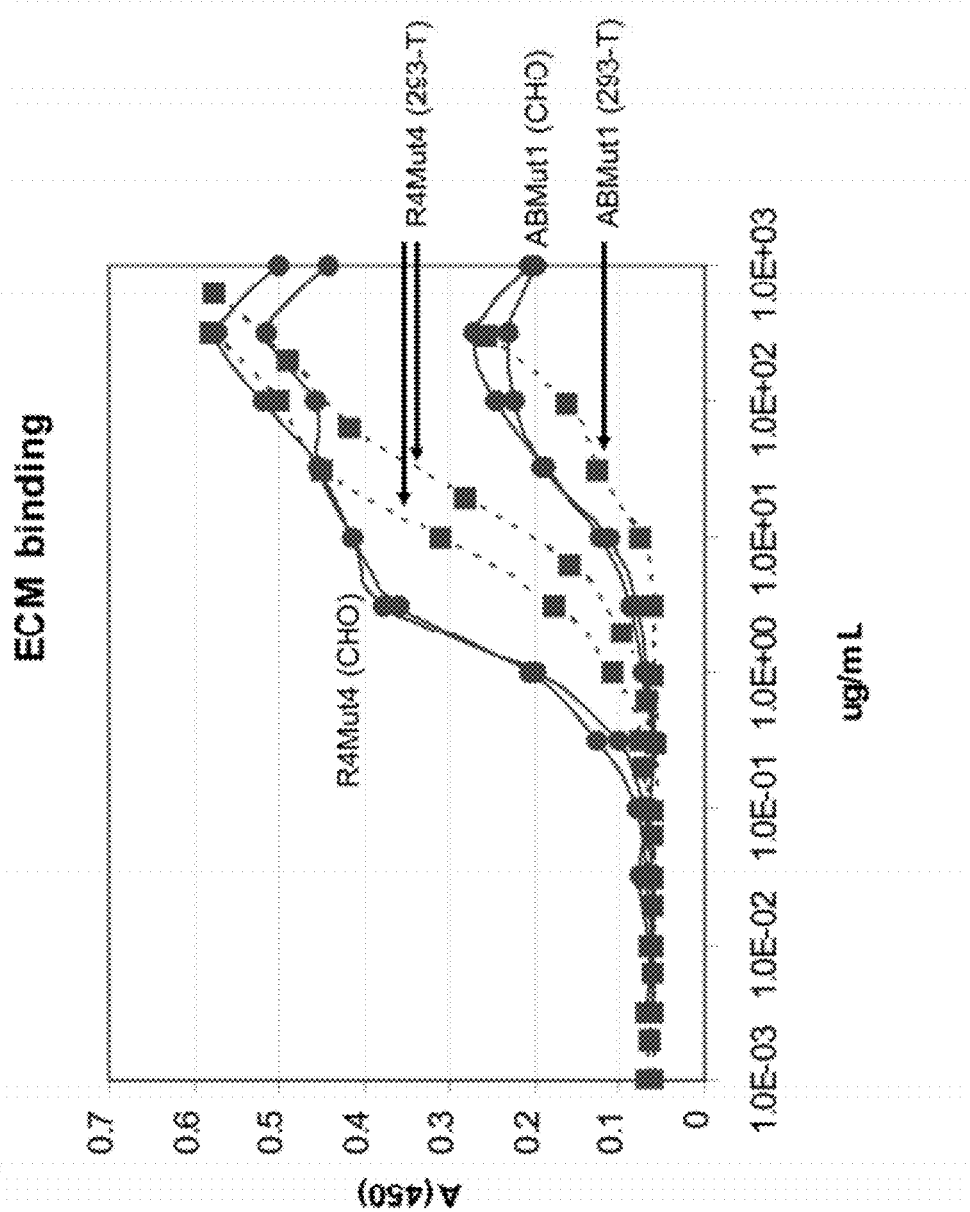
FIG. 12 shows the binding of high concentrations of R4Mut4 and ABMut1 fusion proteins expressed in CHO or 293-T cells to Matrigel plates, as described in Example 13. The X-axis shows the concentration of the Fc fusion proteins and the Y-axis shows the absorbance at 450 nm following incubation of the bound Fc fusion protein with OPD substrate.

In these experiments, the R1Mut4, R4Mut4, and ABMut1 fusion proteins were used. The R1Mut4 fusion protein served as a negative control for ECM binding (data not shown), and the R4Mut4 fusion protein served as a positive control for ECM binding. All three fusion proteins were expressed in CHO cells as described in Example 2 and purified as described in Example 3. The R4Mut4 and ABMut1 fusion proteins were also transiently expressed in 293-T cells. For transient expression in 293-T cells, $0.5$-$0.65 \times 10^6$ cells were plated in each well of a 6-well plate (with or without polylysine coating) in 2 ml DMEM supplemented with 10% FBS. A Fugene™ (Roche) stock was made by combining 93.5 ul Optimem with 6.5 ul Fugene™, followed by a 5 min incubation. A DNA stock was made by combining 1.3 ug DNA with Optimem to a final volume of 100 ul. The Fugene™ stock (100 ul) was added to the DNA stock (100 ul), and the combined solution (200 ul) was added to one well of the 6-well plate. The solution was gently swirled and allowed to incubate with the cells for 30 min at room temperature. The cells were incubated in a humidified incubator with 5% $CO_2$. After 40 hours, the medium was removed, the cells were washed, and 1.5 ml Optimem was added to each well. Forty-nine hours after the medium was changed, the supernatant was collected, spun at 1,400 rpm for 10 min, and transferred to a fresh tube. The fusion proteins were purified from the culture medium as described in Example 3, except that only the first purification step of Protein-A affinity chromatography was used. Protein levels were determined using AlphaScreen (hu IgG AlphaLISA; Perkin-Elmer #AL205C). ECM binding experiments were carried out as described in Example 7, except that up to 1 mg/ml of each FGFR ECD-Fc fusion protein was used in the in vitro ECM binding assay. A graphical representation of the results is shown in FIG. 12. As shown in FIG. 12, detectable levels of ECM binding were observed for the ABMut1 fusion protein at higher concentrations, although ECM binding by the ABMut1 fusion protein was still much lower than that of the R4Mut4 fusion protein.

Example 14

Replacement of Certain Individual Non-Acidic Residues in the FGFR4 ECD Long Acid Box with the Corresponding Acidic Residues from FGFR1 is not Sufficient to Inhibit ECM Binding In Vitro Experiments were carried out to determine whether the replacement of individual non-acidic residues in the FGFR4 ECD long acid box with the corresponding acidic residues from FGFR1 could inhibit ECM binding in vitro. This experiment used four FGFR4 ECD long acid box variants in which a single non-acidic residue from the FGFR4 ECD of R4Mut4 was replaced with the corresponding acidic residue from FGFR1. Conventional cloning and site-directed mutagenesis methods were employed to generate clones in the pTT5 vector encoding the R4Mut4(N104D), R4Mut4(P109D), R4Mut4(R113E), and R4Mut4(S116E) fusion proteins. The R4Mut4(N104D), R4Mut4(P109D), R4Mut4(R113E), and R4Mut4(S116E) long acid box variants correspond to SEQ ID NOs: 130, 131, 132, and 133, respectively. The R4Mut4 (N104D), R4Mut4(P109D), R4Mut4(R113E), and R4Mut4 (S116E) variants each contained a single amino acid change at amino acids 104, 109, 113, and 116, respectively, in SEQ ID NOs: 1 and 2. In vitro ECM binding of the four FGFR4 ECD long acid box variants with single amino acid substitutions was compared to the R1Mut4, R4Mut4, and ABMut1 fusion proteins.

Figure 13:
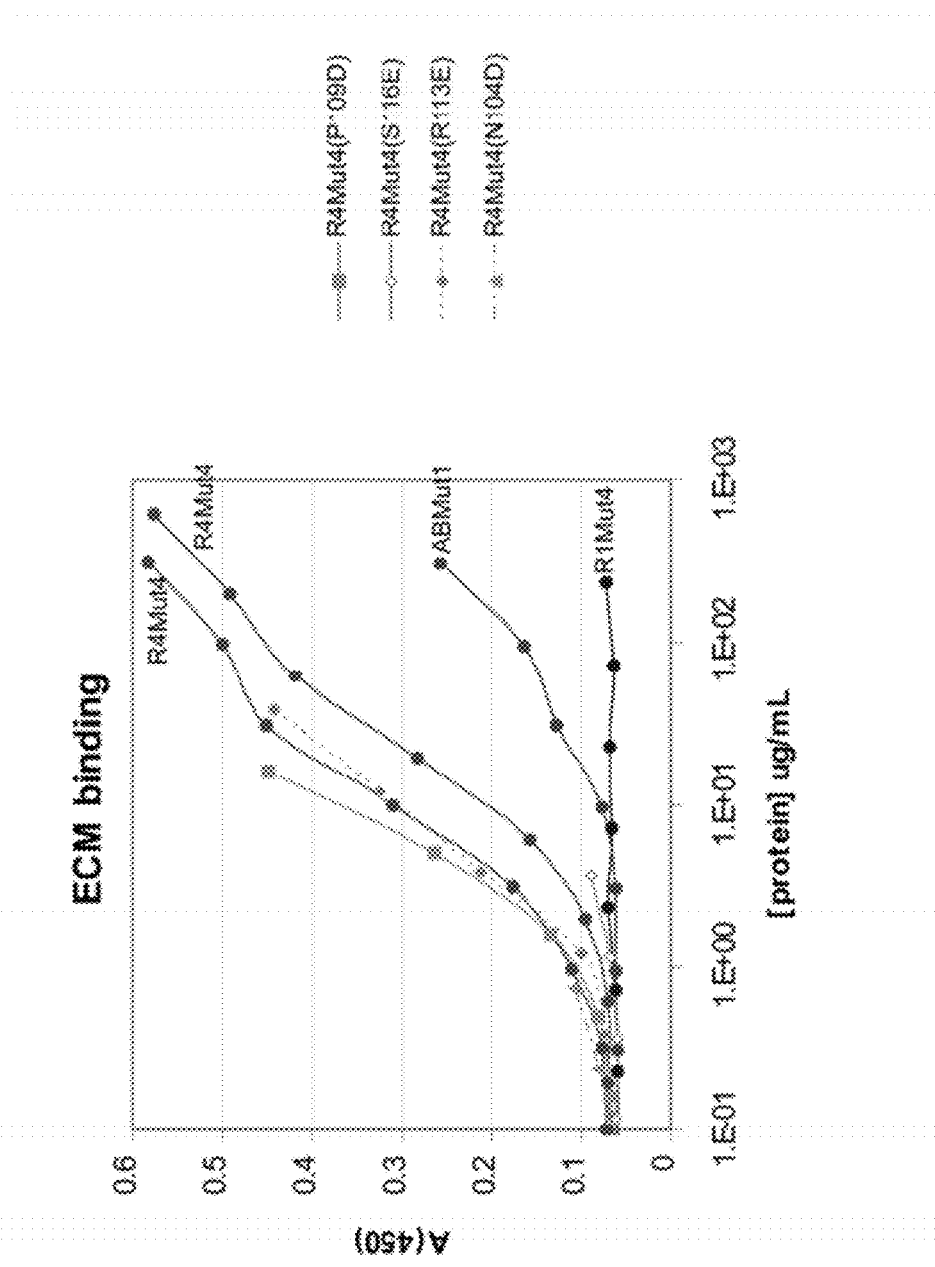
FIG. 13 shows the binding of R1Mut4, R4Mut4, ABMut1, R4Mut4(N104D), R4Mut4(P109D), R4Mut4(R113E), and R4Mut4(S116E) fusion proteins to Matrigel plates, as described in Example 14. The X-axis shows the concentration of the Fc fusion proteins and the Y-axis shows the absorbance at 450 nm following incubation of the bound Fc fusion protein with OPD substrate.

All of the fusion proteins, including R1Mut4, R4Mut4, ABMut1, R4Mut4(N104D), R4Mut4(P109D), R4Mut4 (R113E), and R4Mut4(S116E) were transiently expressed in 293-T cells and purified as described in Example 1. Protein levels were determined using AlphaScreen (hu IgG AlphaLISA; Perkin-Elmer #AL205C). The concentrations of purified R4Mut4(N104D) and R4Mut4(S116E) were too low to reliably determine ECM binding. The concentrations of the purified R4Mut4(P109D) and R4Mut4(R113E) fusion proteins were lower than the concentrations of the purified R1Mut4, R4Mut4, and ABMut1 fusion proteins, and did not permit an analysis of their ECM binding at the highest concentrations. ECM binding experiments were carried out as described in Example 7, except that higher protein levels were used for most of the fusion proteins tested in the in vitro ECM binding assay. A graphical representation of the results is shown in FIG. 13. As shown in FIG. 13, the R4Mut4 variants with single amino acid substitutions that were expressed at sufficient levels to determine ECM binding (i.e., the R4Mut4 (P109D) and R4Mut4(R113E)) did not exhibit decreased ECM binding relative to R4Mut4.

Example 15

FGFR4 ECD Long Acid Box Variants that Contain at Least Two Additional Acidic Residues Exhibit Decreased ECM Binding Experiments described in Example 14 showed that increasing the total number of acidic amino acid residues in the long acid box of an FGFR4 ECD acidic region mutein by one was not sufficient to inhibit ECM binding in vitro. Thus, experiments were carried out to determine whether a further increase in the number of acidic amino acid residues in the long acid box of an FGFR4 ECD acidic region mutein, including any acidic amino acid residues inserted between amino acids 103 and 104 of SEQ ID NOs: 1 and 2, could inhibit ECM binding in vitro.

Five FGFR4 ECD long acid box variant fusion molecules, called R4(104-114):R1(106-117), R4(104-114):R1(107-117), R4(104-110):R1(105-113), R4(113-116):R1(116-119), and R4(109-113):R1(112-116), corresponding to SEQ. ID. NOs: 134, 135, 136, 137, and 138, respectively, were used in these experiments. In the R4(104-114):R1(106-117) FGFR4 ECD long acid box variant, amino acids 106 to 117 of the FGFR1 ECD replace amino acids 104 to 114 of the FGFR4 ECD. In the R4(104-114):R1(107-117) FGFR4 ECD long acid box variant, amino acids 107 to 117 of the FGFR1 ECD replace amino acids 104 to 114 of the FGFR4 ECD. In the R4(104-110):R1(105-113) FGFR4 ECD long acid box variant, amino acids 105 to 113 of the FGFR1 ECD replace amino acids 104 to 110 of the FGFR4 ECD. In the R4(113-116):R1(116-119) FGFR4 ECD long acid box variant, amino acids 116 to 119 of the FGFR1 ECD replace amino acids 113 to 116 of the FGFR4 ECD. In the R4(109-113):R1(112-116) FGFR4 ECD long acid box variant, amino acids 112 to 116 of the FGFR1 ECD replace amino acids 109 to 113 of the FGFR4 ECD. Conventional cloning and site-directed mutagenesis were employed to generate clones in the pTT5 vector encoding the R4(104-114):R1(106-117), R4(104-114):R1(107-117), R4(104-110):R1(105-113), R4(113-116):R1(116-119), and R4(109-113):R1(112-116) fusion proteins using the R4Mut4 parental clone as a template. In vitro ECM binding of the four FGFR4 ECD long acid box variants was compared to the R1Mut4, R4Mut4, and ABMut1 fusion proteins.

Figure 14:
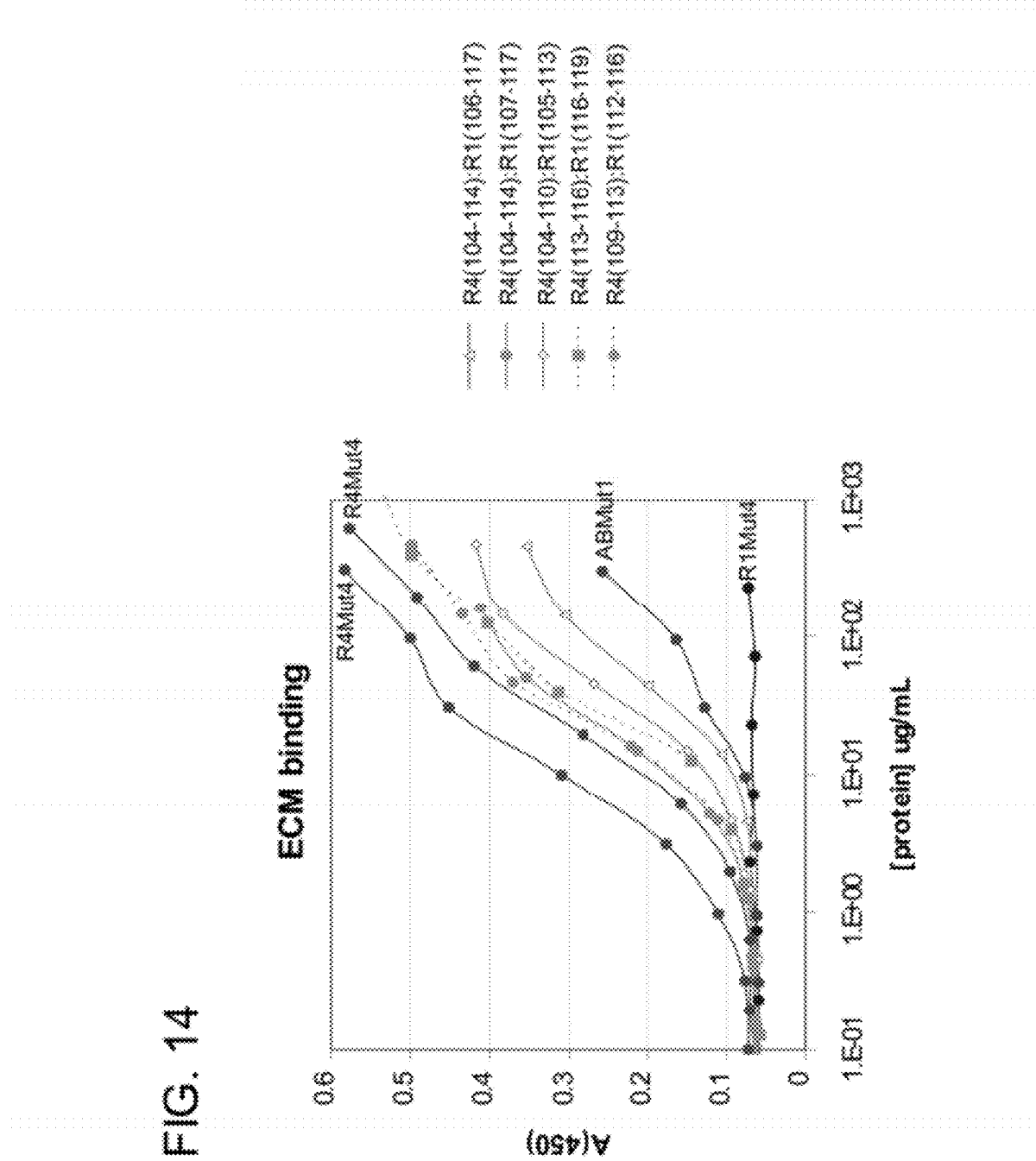
FIG. 14 shows the binding of R1Mut4, R4Mut4, ABMut1, R4(104-114):R1(106-117), R4(104-114):R1(107-117), R4(104-110):R1(105-113), R4(113-116):R1(116-119), and R4(109-113):R1(112-116) fusion proteins to Matrigel plates, as described in Example 15. The X-axis shows the concentration of the Fc fusion proteins and the Y-axis shows the absorbance at 450 nm following incubation of the bound Fc fusion protein with OPD substrate.

All of the fusion proteins, including R1Mut4, R4Mut4, ABMut1, R4(104-114):R1(106-117), R4(104-114):R1(107-117), R4(104-110):R1(105-113), R4(113-116):R1(116-119), and R4(109-113):R1(112-116) were transiently expressed in 293-T cells and purified as described in Example 11. Protein levels were determined using AlphaScreen (hu IgG AlphaLISA; Perkin-Elmer #AL205C). ECM binding experiments were carried out as described in Example 7, except that up to 1 mg/ml of the FGFR ECD-Fc fusion proteins were used in the in vitro ECM binding assay. A graphical representation of the results is shown in FIG. 14. As shown in FIG. 14, at least the R4(104-114):R1(106-117) and R4(104-110):R1(105-113) FGFR4 ECD long acid box variants exhibited ECM binding levels that were intermediate between the R4Mut4 and ABMut1 fusion proteins.

Example 16

FGFR4 ECD Acidic Region Chimeras Lacking Individual N-Glycan Sites Exhibit Decreased ECM Binding The FGFR4 ECD contains five N-glycan sites as determined by mass spectrometry. (Data not shown.) The FGFR4 ECD N-glycan sites at amino acids N91 and N156 of SEQ. ID. NOs: 1 and 2 are located adjacent to the amino-terminus of the FGFR4 D1-D2 linker and in the D2 heparin binding domain, respectively. In the ABMut1 FGFR4 ECD D1-D2 linker chimera of SEQ ID NO: 25, those N-glycan sites are located at amino acids N91 and N159. Experiments were carried out to determine whether the introduction of either the N91A or the N159A N-glycan mutation could further reduce the in vitro ECM binding of the ABMut1 fusion protein. Conventional cloning and site-directed mutagenesis methods were employed to generate clones in the pTT5 vector encoding the ABMut1 fusion protein with the N91A or the N159A N-glycan mutation, referred to herein as ABMut1(N91A) and ABMut1(N159A), respectively. ABMut1(N91A) and ABMut1(N159A) fusion proteins correspond to SEQ ID NOs: 139 and 140, respectively.

The R4Mut4, ABMut1, ABMut1(N91A), and ABMut1 (N159A) fusion proteins were used in these experiments. All four fusion proteins were transiently expressed in CHO-S cells. Briefly, a 500 ml culture of CHO-S cells (Invitrogen) was established by inoculating $0.5 \times 10^6$ cells/ml in fresh 37° C. Freestyle CHO medium containing 8 mM L-Glutamine (Invitrogen). The cells were grown in a 2 l plastic flask and were derived from a seed strain that was continuously maintained up to passage 20. The following day, the cells were counted and diluted, if necessary, to $1 \times 10^6$ cells/ml in 37° C. Freestyle CHO medium (Invitrogen) with a cell viability greater than 95%. The cells were transfected by transferring 10 ml of 37° C. OptiPRO SFM medium containing 8 mM L-Glutamine (dilution media) into two 50 ml tubes. To the first tube (A), 625 ul of FreestyleMax transfection reagent (Invitrogen) were added. To the second tube (B), 625 ug of DNA were added. Both tubes were gently mixed by inverting, and the contents of tube A were immediately added to tube B, followed by gentle mixing by inversion. The mixture was incubated at room temperature for between 10 to 20 min, and was then delivered drop-wise into the 500 ml cell culture in the 2 l culture flask while slowly swirling the flask. The culture was then transferred to an incubator at 37° C., 5% $CO_2$, 125 rpm. After six days, the cell viability was greater than 80%, and the culture supernatant was collected into a centrifuge bottle. The supernatant was centrifuged at 1,000×g for 10 min, transferred to a new centrifuge bottle, and centrifuged at 4,000×g for 10 min. The supernatant was collected into a new bottle and filtered through a 0.2 um filter. The supernatant was stored at 37° C. prior to the purification step. The fusion proteins were purified from the culture supernatant as described in Example 3, except that Q Sepharose anion exchange chromatography was used as the second purification step. Protein-A eluates were applied to a Q Sepharose HP column (GE Healthcare 17-1014-01) equilibrated with five column volumes of sterile buffer (10 mM Tris, 50 mM NaCl, pH 8.0). The column was washed with five column volumes of the same buffer and the bound material was eluted at a rate of five ml/min with a linear gradient of 15 column volumes of elution buffer (10 mM Tris, 2 M NaCl, pH 8.0), followed by five column volumes with 100% elution buffer. Fourteen ml fractions were collected and the fractions comprising the FGFR ECD-Fc were identified by gel electrophoresis and pooled. FGFR ECD-Fc fusion proteins eluted with approximately 10-25% elution buffer.

Figure 15:
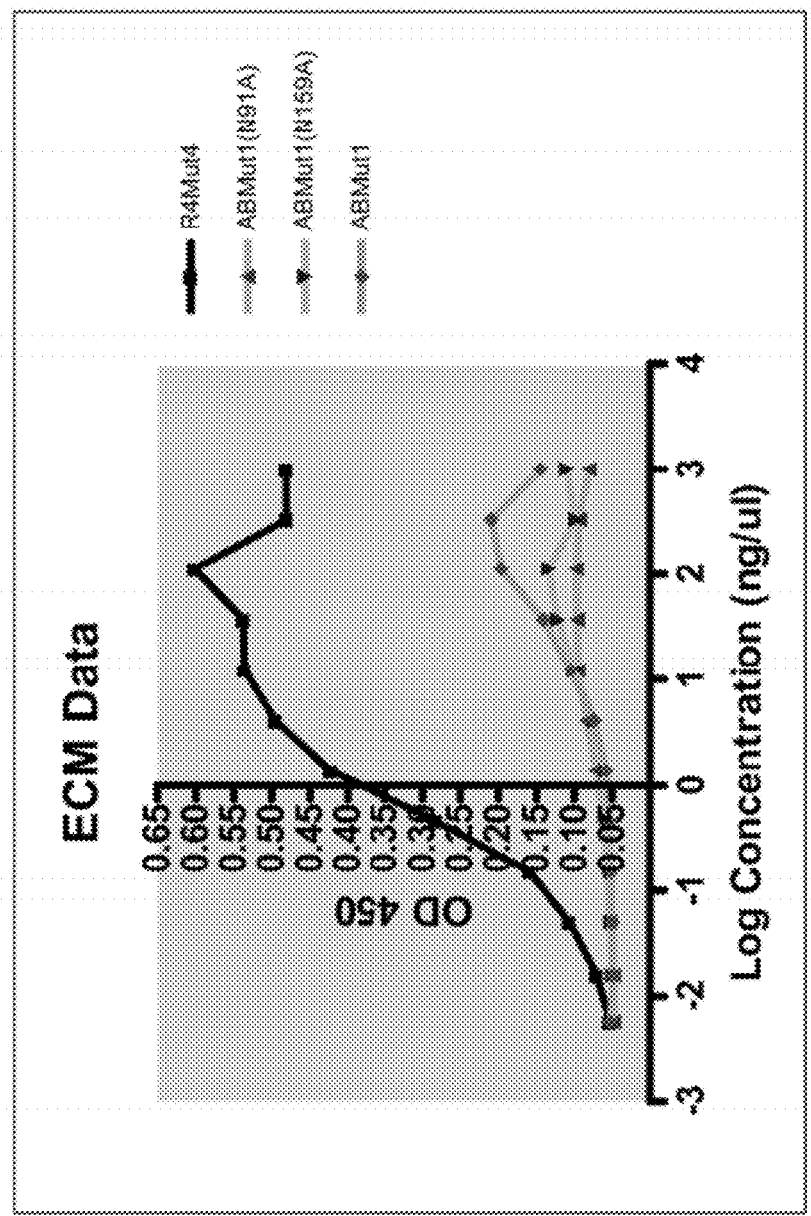
FIG. 15 shows the binding of R4Mut4, ABMut1, ABMut1 (N91A), and ABMut1(N159A) fusion proteins to Matrigel plates, as described in Example 16. The X-axis shows the concentration of the Fc fusion proteins and the Y-axis shows the absorbance at 450 nm following incubation of the bound Fc fusion protein with OPD substrate.

Protein levels were determined based on absorbance measurements at 280 nm. ECM binding experiments were carried out as described in Example 7, except that up to 1 mg/ml of the fusion proteins was used in the in vitro ECM binding assay. A graphical representation of the results is shown in FIG. 15. As shown in FIG. 15, the ABMut1 fusion protein with either the N91A or the N159A N-glycan mutation exhibited a further decrease in in vitro ECM binding, which would also predict a further increase in both $C_{max}$ and bioavailability.

An FGF2 competition ELISA assay was carried out to determine whether the ABMut1(N91A) and ABMut1 (N159A) fusion proteins could inhibit the binding of FGF2 or FGF19 to surface-bound FGFR4 ECD-Fc (R4Mut4). In these assays, ABMut1 was the reference standard, and ABMut1 (N91A) and ABMut1(N159A) were the test samples. Purified ABMut1, ABMut1(N91A), and ABMut1(N159A) were serially diluted in sample diluent (PBS containing 1% BSA (fraction V; Sigma #A3059), 0.05% Tween-20, 200 ng/ml FGF2 (PreproTech #100-18B) or 50 ng/ml FGF19 (PeproTech #100-32), and 20 ug/ml heparin (Sigma #H3149)) to concentrations ranging from 1.5 ng/ml to 90,000 ng/ml. The protein mixtures were incubated for 60 min. A 96-well plate was incubated with 100 ul of 5 ug/ml R4Mut4 overnight at 4° C., washed three times, blocked in blocking buffer (PBS containing 1% BSA) for between one and two hours at room temperature, and washed three times. The protein mixtures (100 ul) were then transferred to the wells of the 96-well plate and incubated for one hour at room temperature with shaking.

In this assay, FGF2 or FGF19 that was not bound to the test samples or the reference standard during the initial incubation step would be free to bind to the surface-bound R4Mut4. The wells were washed three times using a plate washer, followed by detection using biotinylated anti-FGF2 antibody (R&D Systems #BAM233) or biotinylated anti-FGF19 antibody (R&D Systems #BAF969) with the VECTASTAIN ABC Kit (Vector Laboratories #PK-4000). Biotinylated anti-FGF2 antibody or biotinylated anti-FGF19 was diluted to 1 ug/ml in assay diluent (PBS containing 1% BSA and 0.05% Tween-20), and 100 ul was added to each well, followed by a one hour incubation at room temperature with shaking. The ABC solution was reconstituted by mixing three drops of solution A with three drops of solution B in 15 ml PBS, and the solution was allowed to stand for 30 min at room temperature. The plates were washed six times using a plate washer and 100 ul of the freshly reconstituted ABC solution were added to each well, followed by a 45 min to one hour incubation at room temperature. TMB substrate (100 ul) was added to each well, followed by incubation for 6 to 8 min at room temperature in the dark with gentle shaking. One hundred microliters of stop solution were added to each well, and the plates were mixed by tapping. The plate optical density (OD) was read at 450 nm with 570 nm subtraction.

The OD values were then plotted versus the protein concentration on a log scale to generate standard curves. The OD value for each well was directly proportional to the amount of bound FGF2 or FGF19, and was inversely proportional to the amount of active FGFR4 ECD-Fc fusion protein in the test solution. The concentration profiles for the test samples and the reference standards were fit using a 4-parameter logistic. The relative binding activity (% bioactivity) of each test sample was calculated by dividing the $IC_{50}$ value for the standard reference by the $IC_{50}$ value for the test sample, which was then multiplied by 100%. The relative FGF2 binding activities of ABMut1(N91A) and ABMut1(N159A) in this assay were 44% and 42%, respectively. The relative FGF19 binding activities of ABMut1(N91A) and ABMut1 (N159A) in this assay were 51% and 56%, respectively.

Example 17

FGFR4 ECD D1-D2 Linker Chimeras with the FGFR2 or FGFR3 D1-D2 Linker Exhibit Decreased ECM Binding In Vitro Experiments were carried out to determine whether FGFR4 ECD D1-D2 linker chimeras in which the FGFR4 D1-D2 linker was replaced with either the FGFR2 D1-D2 linker ("R4(D1-D2):R2(D1-D2)") or the FGFR3 D1-D2 linker ("R4(D1-D2):R3(D1-D2)") exhibited decreased binding to ECM components in vitro. Both the FGFR2 D1-D2 linker and the FGFR3 D1-D2 linker contain more acidic residues than the FGFR4 D1-D2 linker. Conventional cloning techniques were employed to generate clones in the pTT5 vector encoding the R4(D1-D2):R2(D1-D2) and R4(D1-D2):R3(D1-D2) fusion proteins. R4(D1-D2):R2(D1-D2) and R4(D1-D2):R3(D1-D2) correspond to SEQ ID NOs: 143 and 144, respectively.

Figure 16:
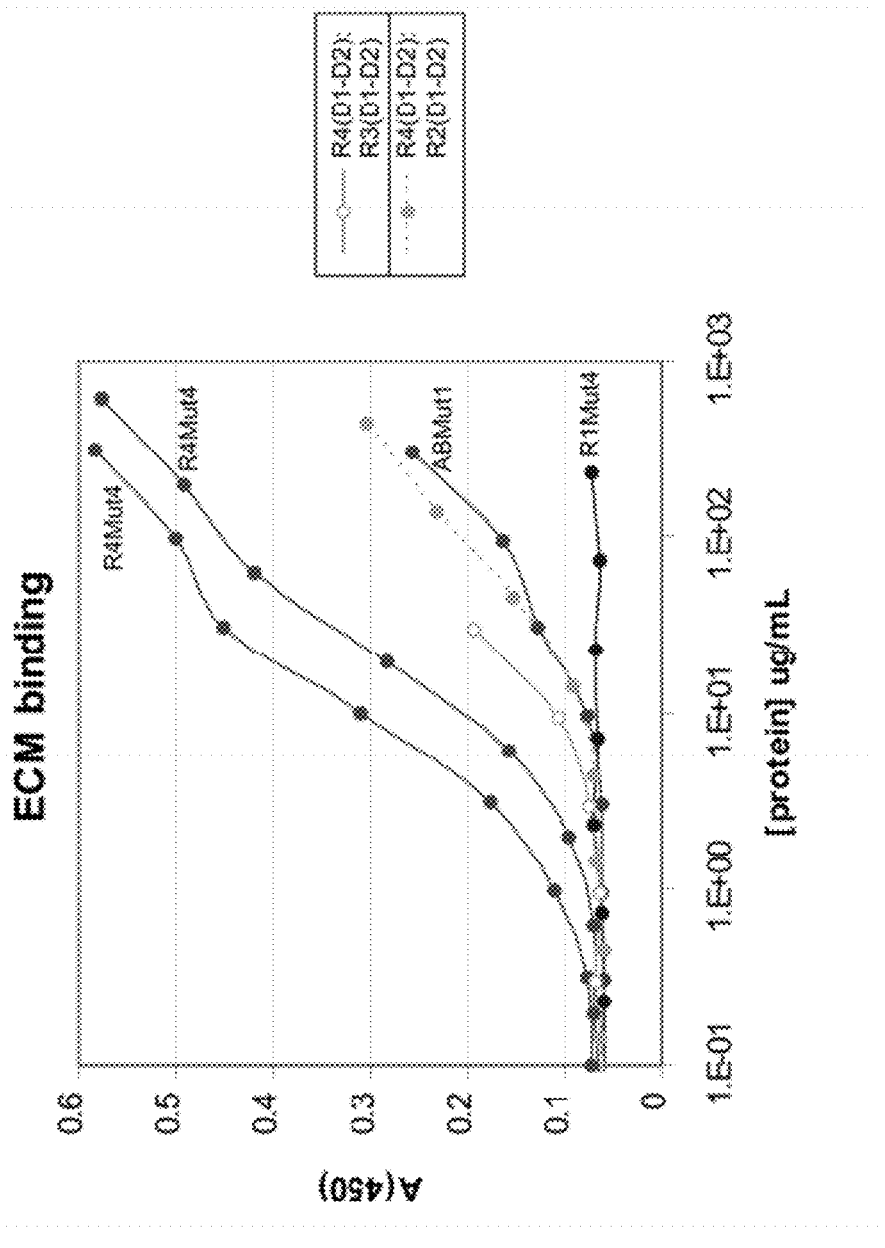
FIG. 16 shows the binding of the R1Mut4, R4Mut4, ABMut1, R4(D1-D2):R2(D1-D2), and R4(D1-D2):R3(D1-D2) fusion proteins to Matrigel plates, as described in Example 17. The X-axis shows the concentration of the Fc fusion proteins and the Y-axis shows the absorbance at 450 nm following incubation of the bound Fc fusion protein with OPD substrate.

The R1Mut4, R4Mut4, ABMut1, R4(D1-D2):R2(D1-D2), and R4(D1-D2):R3(D1-D2) fusion proteins were used in these experiments. All of the fusion proteins were expressed in 293-T cells as described in Example 11. Protein levels were determined using AlphaScreen (hu IgG AlphaLISA; Perkin-Elmer #AL205C). The concentration of the purified R4(D1-D2):R3(D1-D2) fusion protein was lower than the concentrations of the purified R1Mut4, R4Mut4, ABMut1, and R4(D1-D2):R2(D1-D2) fusion proteins, and did not permit an analysis of its ECM binding at higher concentrations. ECM binding experiments were carried out as described in Example 7, except that up to nearly 1 mg/ml of the FGFR ECD-Fc fusion proteins were used in the in vitro ECM binding assay. A graphical representation of the results is shown in FIG. 16. As shown in FIG. 16, both the R4(D1-D2):R2(D1-D2) and R4(D1-D2):R3(D1-D2) fusion proteins exhibited ECM binding levels similar to that of the ABMut1 fusion protein.

Example 18

FGFR2 and FGFR3 Short Acid Box Chimeras with the FGFR1 Short Acid Box Exhibit Decreased ECM Binding In Vitro Experiments were carried out to determine whether an increase in the total number of acidic residues within the long acid box of FGFR2 and FGFR3 could further decrease their ECM binding in vitro. FGFR2 and FGFR3 short acid box chimeras were generated in which the amino acid residues of the short acid box of FGFR1 replaced the corresponding amino acid residues within the FGFR2 and FGFR3 long acid box, referred to as R2(111-118):R1(105-112) and R3(110-117):R1(105-112), respectively. Conventional cloning techniques were employed to generate clones in the pTT5 vector encoding the R2(111-118):R1(105-112) and R3(110-117):R1(105-112) fusion proteins. R2(111-118):R1(105-112) and R3(110-117):R1(105-112) correspond to SEQ ID NOs: 166 and 167, respectively.

Figure 17B:
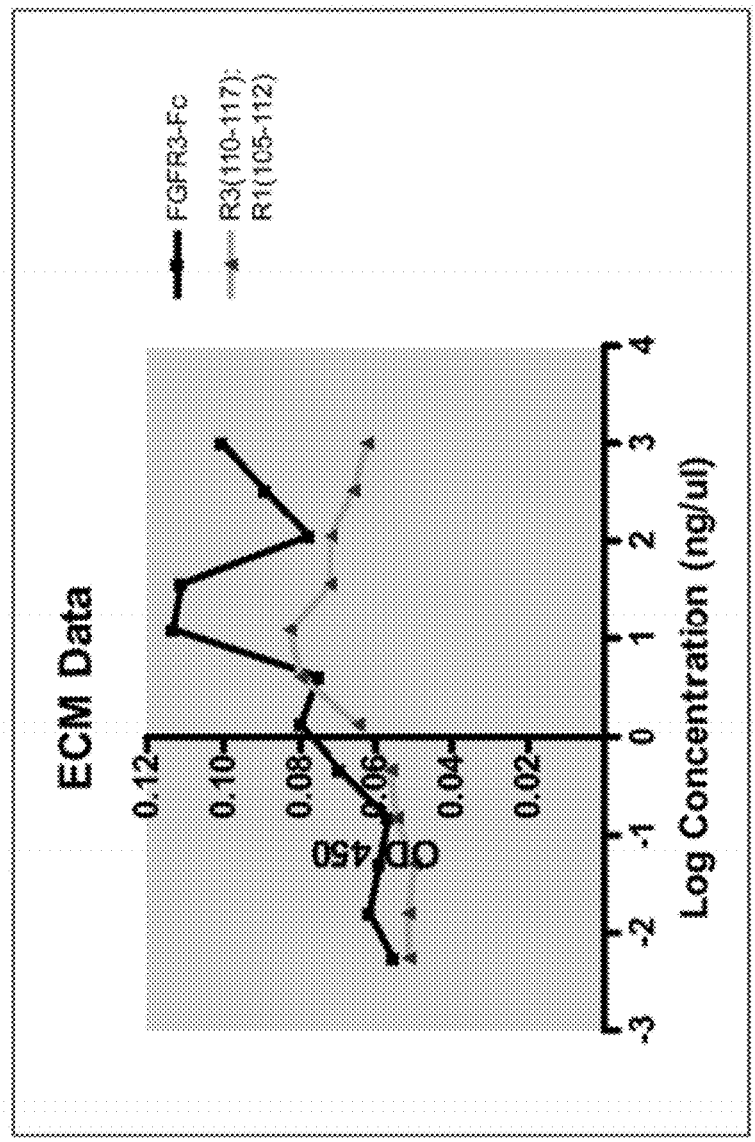
FIGS. 17A and B show the binding of FGFR2 ECD-Fc, FGFR3 ECD-Fc, R2(111-118):R1(105-112), and R3(110-117):R1(105-112) fusion proteins to Matrigel plates, as described in Example 18. The X-axis shows the concentration of the Fc fusion proteins and the Y-axis shows the absorbance at 450 nm following incubation of the bound Fc fusion protein with OPD substrate.

The FGFR2 ECD-Fc, FGFR3 ECD-Fc, R2(111-118):R1(105-112), and R3(110-117):R1(105-112) fusion proteins were used in these experiments. The FGFR2 ECD-Fc, FGFR3 ECD-Fc fusion proteins, R2(111-118):R1(105-112), and R3(110-117):R1(105-112) fusion proteins were transiently expressed in CHO-S cells and purified as described in Example 16. Protein levels were determined using absorbance measurements at 280 nm. ECM binding experiments were carried out as described in Example 7, except that up to 1 mg/ml of each fusion protein was used in the in vitro ECM binding assays. Graphical representations of the results are shown in FIGS. 17A-B. As shown in FIG. 17A and FIG. 17B, the R2(111-118):R1(105-112) and R3(110-117):R1(105-112) fusion proteins exhibited slightly less ECM binding in vitro relative to the FGFR2 ECD-Fc and FGFR3 ECD-Fc fusion proteins, respectively.

INDUSTRIAL APPLICABILITY

The FGFR ECD acidic region muteins and the FGFR ECD fusion molecules described herein are useful in treating proliferative diseases and diseases involving angiogenesis, including cancer and macular degeneration. They can be used to diagnose, prevent, and treat these diseases.

TABLE OF SEQUENCES

Table 11 provides certain sequences discussed herein. All FGFR sequences are shown without the signal peptide unless otherwise indicated.

TABLE 11

Sequences and Descriptions

| SEQ. ID. NO. | Description | Sequence |
|---|---|---|
| 1 | FGFR4 ECD | LEASEEVELE PCLAPSLEQQ EQELTVALGQ PVRLCCGRAE RGGHWYKEGS RLAPAGRVRG WRGRLEIASF LPEDAGRYLC LARGSNIVLQ NLTLITGDSL TSSNDDEDPK SHRDPSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL PEEDPTWTAA APEARYTD |
| 2 | FGFR4 ECD P115L | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSNDDEDPK SHRDLSNRHS YPQQAPYWTH PQRNEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL PEEDPTWTAA APEARYTD |
| 3 | FGFR4 ECD D276V | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSNDDEDPK SHRDPSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGAVGFPY |

TABLE 11-continued

Sequences and Descriptions

| SEQ. ID. NO. | Description | Sequence |
|---|---|---|
| | | VQVLKTADIN SSEVEVLYLR NVSAEDAGEY TCLAGNSIGL SYQSAWLTVL PEEDPTWTAA APEARYTD |
| 93 | FGFR4 ECD T158A | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSNDDEDPK SHRDPSNRHS YPQQAPYWTH PQRMEKKLHA VPAGNTVKFR CPAAGNPAPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL PEEDPTWTAA APEARYTD |
| 4 | FGFR 4ECD + linker + Fc | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSNDDEDPK SHRDPSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGEPY VQVLKTADIN SSEVEVLYLR NVSAEDAGEY TCLAGNSIGL SYQSAWLTVL PEEDPTWTAA APEARYTDGS EPKSSDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSR DELTKNQVSL TCLVKGFYPS DIAVEWESNG QPENNYKTTP PVLDSDGSFF LYSKLTVDKS RWQQGNVFSC SVMHEALHNH YTQKSLSLSP GK |
| 5 | FGFR4 ECD + Fc | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSNDDEDPK SHRDPSNRHS YPQQAPYWTH PQRMEKKLHA VPAGNTVKFR CPAAGNPTPT IRWLKDGQAF EGENRIGGIR LRHQHWSLVN ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL PEEDPTWTAA APEARYTDEP KSSDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSRDE LTKNQVSLTC LVKGFYPSDI AVEWESNGQP ENNYKTTPPV LDSDGSFFLY SKLTVDKSRW QQGNVFSCSV MHEALHNHYT QKSLSLSPGK |
| 6 | FGFR4 ECD Δ5 | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSNDDEDPK SHRDPSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPERPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL PEEDPTWTAA APE |
| 7 | FGFR4 ECD Δ10 | LEASEEVELE PCLAPSLEQQ EQELTVALGQ PVRLCCGRAE RGGHWYKEGS RLAPAGRVRG WRGRLEIASF LPEDAGRYLC LARGSNIVLQ NLTLITGDSL TSSNDDEDPK SHRDPSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL PEEDPTW |
| 8 | FGFR4 ECD Δ15 | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSNDDEDPK SHRDPSNRHS YPQQAPYWTH PQRMEKKLHA VPAGNTVKFR CPAAGNPTPT IRWLKDGQAF HGENRIGGIR LRHQHWSLVN ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL PEE |

TABLE 11-continued

Sequences and Descriptions

| SEQ. ID. NO. | Description | Sequence |
|---|---|---|
| 9 | FGFR4 ECD Δ17 | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSNDDEDPK SHRDPSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL P |
| 10 | FGFR4 ECD Δ18 | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSNDDEDPK SHRDPSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL |
| 11 | FGFR4 ECD Δ5 + Fc | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSNDDEDPK SHRDPSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVINGS SFGADGFPYV QVLKTADINS SEVEVLYLRN VSAEDAGEYT CLAGNSIGLS YQSAWLTVLP EEDPTWTAAA PEEPKSSDKT HTCPPCPAPE LLGGPSVFLF PPKPKDTLMI SRTPEVTCVV VDVSHEDPEV KFNWYVDGVE VHNAKTKPRE EQYNSTYRVV SVLTVLHQDW LNGKEYKCKV SNKALPAPIE KTISKAKGQP REPQVYTLPP SRDELTKNQV SLTCLVKGFY PSDIAVEWES NGQPENNYKT TPPVLDSDGS FFLYSKLTVD KSRWQQGNVF SCSVMHEALH NHYTQKSLSL SPGK |
| 12 | FGFR4 ECD Δ10 + Fc | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSNDDEDPK SHRDPSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL PEEDPTWTEP KSSDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSRDE LTKNQVSLTC LVKGFYPSDI AVEWESNGQP ENNYKTTPPV LDSDGSFFLY SKLTVDKSRW QQGNVFSCSV MHEALHNHYT QKSLSLSPGK |
| 13 | FGFR4 ECD Δ15 + Fc | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSNDDEDPK SHRDPSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL PEEEPKSSDK THTCPPCPAP ELLGGPSVFL FPPKPKDTLM ISRTPEVTCV VVDVSHEDPE VKFNWYVDGV EVHNAKTKPR EEQYNSTYRV VSVLTVLHQD WLNGKEYKCK VSNKALPAPI EKTISKAKGQ PREPQVYTLP PSRDELTKNQ VSLTCLVKGF YPSDIAVEWE SNGQPENNYK TTPPVLDSDG SFFLYSKLTV DKSRWQQGNV FSCSVMHEAL HNHYTQKSLS LSPGK |
| 14 | FGFR4 ECD Δ17 + Fc (also called FGFR4ECD (delta17)-Fc and R4Mut4) | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSNDDEDPK SHRDPSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY |

TABLE 11-continued

Sequences and Descriptions

| SEQ. ID. NO. | Description | Sequence |
|---|---|---|
| | | VQVLKTADIN SSEVEVLYLR NVSAEDAGEY TCLAGNSIGL SYQSAWLTVL PEPKSSDKTH TCPPCPAPEL LGGPSVFLFP PKPKDTLMIS RTPEVTCVVV DVSHEDPEVK FNWYVDGVEV HNAKTKPREE QYNSTYRVVS VLTVLHQDWL NGKEYKCKVS NKALPAPIEK TISKAKGQPR EPQVYTLPPS RDELTKNQVS LTCLVKGFYP SDIAVEWESN GQPENNYKTT PPVLDSDGSF FLYSKLTVDK SRWQQGNVFS CSVMHEALHN HYTQKSLSLS PGK |
| 15 | FGFR4 ECD Δ18 + Fc | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSNDDEDPK SHRDPSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL EPKSSDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSR DELTKNQVSL TCLVKGFYPS DIAVEWESNG QPENNYKTTP PVLDSDGSFF LYSKLTVDKS RWQQGNVFSC SVMHEALHNH YTQKSLSLSP GK |
| 16 | FGFR4 D1-D2 linker | DSLTSSNDDED PKSHRDPSNR HSYPQQ |
| 17 | FGFR4 P115L D1-D2 linker | DSLTSSNDDED PKSHRDLSNR HSYPQQ |
| 18 | FGFR4 exon 4 | DSLTSSNDDE DPKSHRDPSN RHSYPQ |
| 19 | FGFR4 P115L exon 4 | DSLTSSNDDE DPKSHRDLSN RHSYPQ |
| 20 | FGFR4 acid box | DDEDPKSHR |
| 21 | FGFR1 ECD | RPSPTLPEQ AQPWGAPVEV ESFLVHPGDL LQLRCRLRDD VQSINWLRDG VQLAESNRTR ITGEEVEVQD SVPADSGLYA CVTSSPSGSD TTYFSVNVSD ALPSSEDDDD DDDSSSEEKE TDNTKPNPVA PYWTSPEKME KKLHAVPAAK TVKFKCPSSG TPNPTLRWLK NGKEFKPDHR IGGYKVRYAT WSIIMDSVVP SDKGNYTCIV ENEYGSINHT YQLDVVERSP HRPILQAGLP ANKTVALGSN VEFMCKVYSD PQPHIQWLKH IEVNGSKIGP DNLPYVQILK TAGVNTTDKE NEVLHLRNVS FEDAGEYTCL AGNSIGLSHH SAWLTVLEAL EERPAVMTSP LYLE |
| 22 | FGFR1 D1-D2 linker | DALPSSEDDDD DDDSSSEEKE TDNTKPNPV |
| 23 | FGFR1 exon 4 | DALPSSEDDD DDDDSSSEEK ETDNTKPN |
| 24 | FGFR1 acid box | EDDDDDDDSS SE |
| 25 | FGFR1 RM ECD | RPSPTLPEQ AQPWGAPVEV ESFLVHPGDL LQLRCRLRDD VQSINWLRDG VQLAESNRTR ITGEEVEVQD SVPADSGLYA CVTSSPSGSD TTYFSVNVSD ALPSSEDDDD DDDSSSEEKE TDNTKPNRMP VAPYWTSPEK MEKKLHAVPA AKTVKFKCPS SGTPNPTLRW LKNGKEFKPD HRIGGYKVRY ATWSIIMDSV VPSDKGNYTC IVENEYGSIN HTYQLDVVER SPHRPILQAG LPANKTVALG SNVEFMCKVY SDPQPHIQWL KHIEVNGSKI GPDNLPYVQI LKTAGVNTTD KEMEVLHLRN VSFEDAGEYT CLAGNSIGLS HHSAWLTVLE ALEERPAVMT SPLYLE |
| 26 | FGFR1 RM D1-D2 linker | DALPSSEDDDD DDDSSSEEKE TDNTKPNRMP V |
| 92 | FGFR1 RM exon 4 | DALPSSEDDD DDDDSSSEEK ETDNTKPNRM |
| 27 | FGFR2 ECD | RPSFSLVED TTLEPEEPPT KYQISQPEVY VAAPGESLEV RCLLKDAAVI SWTKDGVHLG PNNRTVLIGE YLQIKGATPR DSGLYACTAS RTVDSETWYF MVNVTDAISS GDDEDDTDGA EDFVSENSNN KRAPYWTNTE KMEKRLHAVP AANTVKFRCP AGGNPMPTMR WLKNGKEFKQ EHRIGGYKVR NQHWSLIMES VVPSDKGNYT CVVENEYGSI NHTYHLDVVE RSPHRPILQA GLPANASTVV GGDVEFVCKV YSDAQPHIQW IKHVEKNGSK |

TABLE 11-continued

Sequences and Descriptions

| SEQ. ID. NO. | Description | Sequence |
|---|---|---|
| | | YGPDGLPYLK VLKAAGVNTT DKEIEVLYIR NVTFEDAGEY TCLAGNSIGI SFHSAWLTVL PAPGREKEIT ASPDYLE |
| 28 | FGFR2 D1-D2 linker | DAISSGDDED DTDGAEDFVS ENSNNKR |
| 29 | FGFR2 exon 4 | DAISSGDDED DTDGAEDFVS ENSNNK |
| 30 | FGFR2 acid box | DDEDDTD |
| 31 | FGFR3 ECD | ESLGTEQR VVGRAAEVPG PEPGQQEQLV FGSGDAVELS CPPPGGGPMG PTVWVKDGTG LVPSERVLVG PQRLQVLNAS HEDSGAYSCR QRLTQRVLCH FSVRVTDAPS SGDDEDGEDE AEDTGVDTGA PYWTRPERMD KKLLAVPAAN TVRFRCPAAG NPTPSISWLK NGREFRGEHR IGGIKLRHQQ WSLVMESVVP SDRGNYTCVV ENKFGSIRQT YTLDVLERSP HRPILQAGLP ANQTAVLGSD VEFHCKVYSD AQPHIQWLKH VEVNGSKVGP DGTPYVTVLK TAGANTTDKE LEVLSLHNVT FEDAGEYTCL AGNSIGFSHH SAWLVVLPAE EELVEADEAG SVYAG |
| 32 | FGFR3 D1-D2 linker | DAPSSGDDEDG EDEAEDTGVD TG |
| 33 | FGFR3 exon 4 | DAPSSGDDED GEDEAEDTGV DT |
| 34 | FGFR3 acid box | DDEDGE |
| 35 | FGFR4 ECD Δ17 R1 D1-D2 linker chimera | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDAL PSSEDDDDDD DSSSEEKETD NTKPNPVAPY WTHPQRMEKK LHAVPAGNTV KFRCPAAGNP TPTIRWLKDG QAFHGENRIG GIRLRHQHWS LVMESVVPSD RGTYTCLVEN AVGSIRYNYL LDVLERSPHR PILQAGLPAN TTAVVGSDVE LLCKVYSDAQ PHIQWLKHIV INGSSFGADG FPYVQVLKTA DINSSEVEVL YLRNVSAEDA GEYTCLAGNS IGLSYQSAWL TVLP |
| 36 | FGFR4 ECD Δ17 R1 RM D1-D2 linker chimera | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLTTGDAL PSSEDDDDDD DSSSEEKETD NTKPNRMPVA PYWTHPQRNE KKLHAVPAGN TV KFRCPAAGNP TPTIRWLKDG QAFEGENRIG GIRLRHQHWS LVMESVVPSD RGTYTCLVEN AVGSIRYNYL LDVLERSPHR PILQAGLPAN TTAVVGSDVE LLCKVYSDAQ PHIQWLKHIV INGSSFGADG FPYVQVLKTA DINSSEVEVL YLRNVSAEDA GEYTCLAGNS IGLSYQSAWL TVLP |
| 37 | FGFR4 ECD Δ17 R2 D1-D2 linker chimera | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDAI SSGDDEDDTD GAEDFVSENS NNKRAPYWTH PQRMEKKLHA VPAGNTVKFR CPAAGNPTPT IRWLKDGQAF HGENRIGGIR LRHQHWSLVN ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL P |
| 38 | FGFR4 ECD Δ17 R3 D1-D2 linker chimera | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDAP SSGDDEDGED EAEDTGVDTG APYWTHPQRM EKKLHAVPAG NTVKFRCPAA GNPTPTIRWL KDGQAFHGEN RIGGIRLRHQ HWSLVMESVV PSDRGTYTCL VENAVGSIRY NYLLDVLERS PHRPILQAGL PANTTAVVGS DVELLCKVYS DAQPHIQWLK HIVINGSSFG ADGFPYVQVL KTADINSSEV EVLYLRNVSA EDAGEYTCLA GNSIGLSYQS AWLTVLP |
| 39 | FGFR4 ECD Δ17 R1 exon 4 chimera | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDAL PSSEDDDDDD DSSSEEKETD NTKPNQAPYW THPQRMEKKL HAVPAGNTVK FR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL P |

TABLE 11-continued

Sequences and Descriptions

| SEQ. ID. NO. | Description | Sequence |
|---|---|---|
| 40 | FGFR4 ECD Δ17 R1 RM exon 4 chimera | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDAL PSSEDDDDDD DSSSEEKETD NTKPNRMQAPYW THPQRMEKKL HAVPAGNTVK FR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL P |
| 41 | FGFR4 ECD Δ17 R2 exon 4 chimera | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDAISSGDDED DTDGAEDFVS ENSNNKQAPYWTH PQRNEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL P |
| 42 | FGFR4 ECD Δ17 R3 exon 4 chimera | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDAPSSGDDED GEDEAEDTGV DTQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL P |
| 43 | FGFR4 ECD Δ17 R1 acid box chimera | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSNEDDDDDDSS SEDPSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL P |
| 44 | FGFR 4ECD Δ17 R2 acid box chimera | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSNDDEDDT DDPSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHEPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL P |
| 45 | FGFR4 ECD Δ17 R3 acid box chimera | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSNDDEDGE DPSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL P |
| 46 | FGFR4 acid box region 1 | DDEDPKSHRD |
| 47 | FGFR4 acid box region 2 | DDEDPKSHRD P |
| 48 | FGFR4 acid box region 3 | DDEDPKSHRD PS |
| 49 | FGFR4 acid box region 4 | DDEDPKSHRD PSN |
| 50 | FGFR4 acid box region 5 | DDEDPKSHRD PSNR |
| 51 | FGFR4 acid box region 6 | NDDEDPKSHR D |
| 52 | FGFR4 acid box region 7 | NDDEDPKSHR DP |
| 53 | FGFR4 acid box region 8 | NDDEDPKSHR DPS |

TABLE 11-continued

Sequences and Descriptions

| SEQ. ID. NO. | Description | Sequence |
|---|---|---|
| 54 | FGFR4 acid box region 9 | NDDEDPKSHR DPSN |
| 55 | FGFR4 acid box region 10 | NDDEDPKSHR DPSNR |
| 56 | FGFR1 acid box region 1 | EDDDDDDDSS SEE |
| 57 | FGFR1 acid box region 2 | EDDDDDDDSS SEEKE |
| 58 | FGFR1 acid box region 3 | EDDDDDDDSS SEEKETD |
| 59 | FGFR2 acid box region 1 | DDEDDTDGAE |
| 60 | FGFR2 acid box region 2 | DDEDDTDGAED |
| 61 | FGFR2 acid box region 3 | DDEDDTDGAEDFVSE |
| 62 | FGFR3 acid box region 1 | DDEDGED |
| 63 | FGFR3 acid box region 2 | DDEDGEDE |
| 64 | FGFR3 acid box region 3 | DDEDGEDEAE |
| 65 | FGFR3 acid box region 4 | DDEDGEDEAED |
| 66 | FGFR1 signal peptide | MWSWKCLLFWAVLVTATLCTA |
| 67 | FGFR2 signal peptide | MVSWGRFICLVVVTMATLSLA |
| 68 | FGFR3 signal peptide | MGAPACALALCVAVAIVAGASS |
| 69 | FGFR4 signal peptide | MRLLLALLGI LLSVPGPPVL S |
| 70 | FGFR4 N-terminal sequence | LEASEEVE |
| 71 | FGFR4 C-terminal sequence | LPEEDPTWTAA APEARYTD |
| 72 | Fc C237S | EPKSSDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSRD ELTKNQVSLT CLVKGFYPSD IAVEWESNGQ PENNYKTTPP VLDSDGSFFL YSKLTVDKSR WQQGNVFSCS VMHEALHNHYTQKSLSLSPGK |
| 73 | Fc | ERKCCVECPP CPAPPVAGPS VFLFPPKPKD TLMISRTPEV TCVVVDVSHE DPEVQFNWYV DGVEVHNAKT KPREEQFNST FRVVSVLTVV HQDWLNGKEY KCKVSNKGLP APIEKTISKT KGQPREPQVY TLPPSREEMT KNQVSLTCLV KGFYPSDIAV EWESNGQPEN NYKTTPPMLD SDGSFFLYSK LTVDKSRWQQ GNVFSCSVMH EALHNHYTQK SLSLSPGK |
| 74 | Fc | ESKYGPPCPS CPAPEFLGGP SVFLFPPKPK DTLMISRTPE VTCVVVDVSQ EDPEVQFNWY VDGVEVHNAK TKPREEQFNS TYRVVSVLTV LHQDWLNGKE YKCKVSNKGL PSSIEKTISK AKGQPREPQV YTLPPSQEEM TKNQVSLTCL VKGFYPSDIA VEWESNGQPE NNYKTTPPVL DSDGSFFLYS RLTVDKSRWQ EGNVFSCSVM HEALHNHYTQ KSLSLSLGK |
| 75 | FGFR4 V101 signal peptide | MRLLLALLGI LLSVPGPPVL S |
| 76 | FGFR4 ECD NΔ2 | ASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSNDDEDPK SHRDPSNRHS YPQQAPYWTH PQRMEKKLHA VPAGNTVKFR CPAAGNPTPT IRWLKDGQAF HGENRIGGIR LRHQWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL PEEDPTWTAA APEARYTD |
| 77 | FGFR4 ECD NΔ3 | SEEVELE PCLAPSLEQQ EQELTVALGQ PVRLCCGRAE RGGHWYKEGS RLAPAGRVRG WRGRLEIASF LPEDAGRYLC |

TABLE 11-continued

Sequences and Descriptions

| SEQ. ID. NO. | Description | Sequence |
|---|---|---|
| | | LARGSMIVLQ NLTLITGDSL TSSNDDEDPK SHRDPSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL PEEDPTWTAA APEARYTD |
| 78 | FGFR4 ECD NΔ5 | EVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSNDDEDPK SHRDPSNRHS YPQQAPYWTH PQRMEKKLHA VPAGNTVKFR CPAAGNPTPT IRWLKDGQAF HGENRIGGIR LRHQHWSLVN ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL PEEDPTWTAA APEARYTD |
| 79 | FGFR4 ECD NΔ7 | ELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSNDDEDPK SHRDPSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL PEEDPTWTAA APEARYTD |
| 80 | FGFR4 ECD NΔ8 | LE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSNDDEDPK SHRDPSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL PEEDPTWTAA APEARYTD |
| 81 | FGFR4 ECD NΔ8 Δ17 | LE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSNDDEDPK SHRDPSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL P |
| 82 | FGFR4 ECD w/ signal peptide | MRLLLALLGI LLSVPGPPVL SLEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSNDDEDPK SHRDPSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL PEEDPTWTAA APEARYTD |
| 83 | FGFR1 RM ECD w/ signal peptide | MWSWKCLLFW AVLVTATLCT ARPSPTLPEQ AQPWGAPVEV ESFLVHPGDL LQLRCRLRDD VQSINWLRDG VQLAESNRTR ITGEEVEVQD SVPADSGLYA CVTSSPSGSD TTYFSVNVSD ALPSSEDDDD DDDSSSEEKE TDNTKPNRMP VAPYWTSPEK MEKKLHAVPA AKTVKFKCPS SGTPNPTLRW LKNGKEFKPD HRIGGYKVRY ATWSIIMDSV VPSDKGNYTC IVENEYGSIN HTYQLDVVER SPHRPILQAG LPANKTVALG SNVEFMCKVY SDPQPHIQWL KHIEVNGSKI GPDNLPYVQI LKTAGVNTTD KEMEVLHLRN VSFEDAGEYT CLAGNSIGLS HHSAWLTVLE ALEERPAVMT SPLYLE |
| 84 | FGFR2 ECD w/ signal peptide | MVSWGRFICL VVVTMATLSL ARPSFSLVED TTLEPEEPPT KYQISQPEVY VAAPGESLEV RCLLKDAAVI SWTKDGVHLG PNNRTVLIGE YLQIKGATPR DSGLYACTAS RTVDSETWYF MVNVTDAISS GDDEDDTDGA EDFVSENSNN KRAPYWTNTE KMEKRLHAVP AANTVKFRCP AGGNPMPTMR WLKNGKEFKQ |

TABLE 11-continued

Sequences and Descriptions

| SEQ. ID. NO. | Description | Sequence |
|---|---|---|
| | | EHRIGGYKVR NQHWSLIMES VVPSDKGNYT CVVENEYGSI NHTYHLDVVE RSPHRPILQA GLPANASTVV GGDVEFVCKV YSDAQPHIQW IKHVEKNGSK YGPDGLPYLK VLKAAGVNTT DKEIEVLYIR NVTFEDAGEY TCLAGNSIGI SFHSAWLTVL PAPGREKEIT ASPDYLE |
| 85 | FGFR3 ECD w/ signal peptide | MGAPACALAL CVAVAIVAGA SSESLGTEQR VVGRAAEVPG PEPGQQEQLV FGSGDAVELS CPPPGGGPMG PTVWVKDGTG LVPSERVLVG PQRLQVLNAS HEDSGAYSCR QRLTQRVLCH FSVRVTDAPS SGDDEDGEDE AEDTGVDTGA PYWTRPERMD KKLLAVPAAN TVRFRCPAAG NPTPSISWLK NGREFRGEHR IGGIKLRHQQ WSLVMESVVP SDRGNYTCVV ENKFGSIRQT YTLDVLERSP HRPILQAGLP ANQTAVLGSD VEFHCKVYSD AQPHIQWLKH VEVNGSKVGP DGTPYVTVLK TAGANTTDKE LEVLSLHNVT FEDAGEYTCL AGNSIGFSHH SAWLVVLPAE FELVEADEAG SVYAG |
| 86 | FGFR4 ECD Δ17 R1 D1-D2 linker chimera + Fc (also called FGFR4ECD (ABMut1: delta 17)-Fc and ABMut1) | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDAL PSSEDDDDDD DSSSEEKETD NTKPNPVAPY WTHPQRMEKK LHAVPAGNTV KFRCPAAGNP TPTIRWLKDG QAFHGENRIG GIRLRHQHWS LVMESVVPSD RGTYTCLVEN AVGSIRYNYL LDVLERSPHR PILQAGLPAN TTAVVGSDVE LLCKVYSDAQ PHIQWLKHIV INGSSFGADG FPYVQVLKTA DINSSEVEVL YLRNVSAEDA GEYTCLAGNS IGLSYQSAWL TVLPEPKSSD KTH TCPPCPAPEL LGGPSVFLFP PKPKDTLMIS RTPEVTCVVV DVSHEDPEVK FNWYVDGVEV HNAKTKPREE QYNSTYRVVS VLTVLHQDWL NGKEYKCKVS NKALPAPIEK TISKAKGQPR EPQVYTLPPS RDELTKNQVS LTCLVKGFYP SDIAVEWESN GQPENNYKTT PPVLDSDGSF FLYSKLTVDK SRWQQGNVFS CSVMHEALHN HYTQKSLSLS PGK |
| 87 | FGFR4 ECD Δ17 R1 exon 4 chimera + Fc (also called FGFR4ECD (ABMut2: delta17)-Fc and ABMut2) | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDAL PSSEDDDDDD DSSSEEKETD NTKPNQAPYW THPQRMEKKL HAVPAGNTVK FR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL PEPKSSD KTH TCPPCPAPEL LGGPSVFLFP PKPKDTLMIS RTPEVTCVVV DVSHEDPEVK FNWYVDGVEV HNAKTKPREE QYNSTYRVVS VLTVLHQDWL NGKEYKCKVS NKALPAPIEK TISKAKGQPR EPQVYTLPPS RDELTKNQVS LTCLVKGFYP SDIAVEWESN GQPENNYKTT PPVLDSDGSF FLYSKLTVDK SRWQQGNVFS CSVMHEALHN HYTQKSLSLS PGK |
| 88 | FGFR4 ECD Δ17 R1 acid box chimera + Fc | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSNEDDDDDDSS SEDPSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL PEPKSSD KTH TCPPCPAPEL LGGPSVFLFP PKPKDTLMIS RTPEVTCVVV DVSHEDPEVK FNWYVDGVEV HNAKTKPREE QYNSTYRVVS VLTVLHQDWL NGKEYKCKVS NKALPAPIEK TISKAKGQPR EPQVYTLPPS RDELTKNQVS LTCLVKGFYP SDIAVEWESN GQPENNYKTT PPVLDSDGSF FLYSKLTVDK SRWQQGNVFS CSVMHEALHN HYTQKSLSLS PGK |
| 89 | FGFR4 ECD 21g + D1-D2 linker + GS linker + Fc (also called FGFR4ECD(21g + Linker)-Fc and R4(21g + L)) | LEASEEVELED SLTSSNDDED PKSHRDPSNR HSYPQQAPYW THPQRMEKKL HAVPAGNTVK FRCPAAGNPT PTIRWLKDGQ AFHGENRIGG IRLRHQHWSL VMESVVPSDR GTYTCLVENA VGSIRYNYLL DVLERSPHRP ILQAGLPANT TAVVGSDVEL LCKVYSDAQP HIQWLKHIVI NGSSFGADGF PYVQVLKTAD INSSEVEVLY LRNVSAEDAG EYTCLAGNSI GLSYQSAWLT VLPEEDPTWT AAAPEARYTD GSEPKSSDKT HTCPPCPAPE LLGGPSVFLF PPKPKDTLMI SRTPEVTCVV VDVSHEDPEV KFNWYVDGVE VHNAKTKPRE EQYNSTYRVV SVLTVLHQDW LNGKEYKCKV SNKALPAPIE KTISKAKGQP REPQVYTLPP |

TABLE 11-continued

Sequences and Descriptions

| SEQ. ID. NO. | Description | Sequence |
|---|---|---|
|  |  | SRDELTKNQV SLTCLVKGFY PSDIAVEWES NGQPENNYKT TPPVLDSDGS FFLYSKLTVD KSRWQQGNVF SCSVMHEALH NHYTQKSLSL SPGK |
| 90 | FGFR4 ECD 21g - D1-D2 linker + GS linker + Fc (also called FGFR4ECD(21g - Linker)-Fc and R4(21g - L)) | LEASEEVELEA PYWTHPQRNE KKLHAVPAGN TVKFRCPAAG NPTPTIRWLK DGQAFHGENR IGGIRLRHQH WSLVNESVVP SDRGTYTCLV ENAVGSIRYN YLLDVLERSP HRPILQAGLP ANTTAVVGSD VELLCKVYSD AQPHIQWLKH IVINGSSFGA DGFPYVQVLK TADINSSEVE VLYLRNVSAE DAGEYTCLAG NSIGLSYQSA WLTVLPEEDP TWTAAAPEAR YTDGSEPKSS DKTHTCPPCP APELLGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSRDELTK NQVSLTCLVK GFYPSDIAVE WESNGQPENN YKTTPPVLDS DGSFFLYSKL TVDKSRWQQG NVFSCSVMHE ALHNHYTQKS LSLSPGK |
| 91 | FGFR1 ECD Δ14 + Fc (also called FGFR1ECD(delta14)-Fc and R1 Mut4) | RPSPTLPEQA QPWGAPVEVE SFLVHPGDLL QLRCRLRDDV QSINWLRDGV QLAESNRTRI TGEEVEVQDS VPADSGLYAC VTSSPSGSDT TYFSVNVSDA LPSSEDDDDD DDSSSEEKET DNTKPNPVAP YWTSPEKMEK KLHAVPAAKT VKFKCPSSGT PNPTLRWLKN GKEFKPDHRI GGYKVRYATW SIIMDSVVPS DKGNYTCIVE NEYGSINHTY QLDVVERSPH RPILQAGLPA NKTVALGSNV EFMCKVYSDP QPHIQWLKHI EVNGSKIGPD NLPYVQILKT AGVNTTDKEM EVLHLRNVSF EDAGEYTCLA GNSIGLSHHS AWLTVLEALE PKSSDKTHTC PPCPAPELLG GPSVFLFPPK PKDTLMISRT PEVTCVVVDV SHEDPEVKFN WYVDGVEVHN AKTKPREEQY NSTYRVVSVL TVLHQDWLNG KEYKCKVSNK ALPAPIEKTI SKAKGQPREP QVYTLPPSRD ELTKNQVSLT CLVKGFYPSD IAVEWESNGQ PENNYKTTPP VLDSDGSFFL YSKLTVDKSR WQQGNVFSCS VMHEALHNHY TQKSLSLSPG K |
| 94 | FGFR4 ECD 21g + D1-D2 linker | LEASEEVELED SLTSSNDDED PKSHRDPSNR HSYPQQAPYW THPQRMEKKL HAVPAGNTVK FRCPAAGNPT PTIRWLKDGQ AFHGENRIGG IRLRHQHWSL VMESVVPSDR GTYTCLVENA VGSIRYNYLL DVLERSPHRP ILQAGLPANT TAVVGSDVEL LCKVYSDAQP HIQWLKHIVI NGSSFGADGF PYVQVLKTAD INSSEVEVLY LRNVSAEDAG EYTCLAGNSI GLSYQSAWLT VLPEEDPTWT AAAPEARYTD |
| 95 | FGFR4 ECD 21g - D1-D2 linker | LEASEEVELEA PYWTHPQRME KKLHAVPAGN TVKFRCPAAG NPTPTIRWLK DGQAFHGENR IGGIRLRHQH WSLVNESVVP SDRGTYTCLV ENAVGSIRYN YLLDVLERSP HRPILQAGLP ANTTAVVGSD VELLCKVYSD AQPHIQWLKH IVINGSSFGA DGFPYVQVLK TADINSEEVE VLYLRNVSAE DAGEYTCLAG NSIGLSYQSA WLTVLPEEDP TWTAAAPEAR YTD |
| 96 | FGFR4 long acid box | NDDEDPKSHR DPSNR |
| 97 | FGFR4 P115L long acid box | NDDEDPKSHR DLSNR |
| 98 | FGFR1 long acid box | EDDDDDDDSS SEEKETD |
| 99 | FGFR2 long acid box | DDEDDTDGAE DFVSE |
| 100 | FGFR3 long acid box | GDDEDGEDEA ED |
| 101 | FGFR4 short acid box | DDED |
| 102 | FGFR1 short acid box | EDDDDDDD |
| 103 | FGFR2 short acid box | DDEDD |
| 104 | FGFR3 short acid box | DDED |
| 105 | FCFR4 ECD Δ17 R1 long acid box chimera | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSS EDDDDDDDSSSEEKETD HS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL P |

TABLE 11-continued

Sequences and Descriptions

| SEQ. ID. NO. | Description | Sequence |
|---|---|---|
| 106 | FGFR4 ECD Δ17 R2 long acid box chimera | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSS DDEDDTDGAEDFVSE HS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL P |
| 107 | FGFR4 ECD Δ17 R3 long acid box chimera | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSS GDDEDGEDEAED HS YPQQAPYWTH PQRMEKKLHA VPAGNTVKFR CPAAGNPTPT IRWLKDGQAF HGENRIGGIR LRHQHWSLVN ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL P |
| 108 | FGFR4 ECD Δ17 R1 short acid box chimera | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSN EDDDDDDD PK SHRDPSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHEPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL P |
| 109 | FGFR4 ECD Δ17 R2 short acid box chimera | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TEEN DDEDD PK SHRDPSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL P |
| 110 | FGFR4 ECD Δ17 R3 short acid box chimera | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TEEN DDED PK SHRDPSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL P |
| 111 | FGFR4 ECD Δ17 N104D | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSDDDEDPK SHRDPSNRHS YPQQAPYWTH PQRMEKKLHA VPAGNTVKFR CPAAGNPTPT IRWLKDGQAF HGENRIGGIR LRHQHWSLVM ESVVPEDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVEAEDAGEY TCLAGNSIGL SYQSAWLTVL P |
| 112 | FGFR4 ECD Δ17 P109 | LEAEEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSNDDEDDK SHRDPSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL P |
| 113 | FGFR4 ECD Δ17 R113E | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSNDDEDPK SHEDPSNRHS YPQQAPYWTH PQRMEKKLHA VPAGNTVKFR CPAAGNPTPT |

TABLE 11-continued

Sequences and Descriptions

| SEQ. ID. NO. | Description | Sequence |
|---|---|---|
| | | IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGEPY VQVLKTADIN SSEVEVLYLR NVSAEDAGEY TCLAGNSIGL SYQSAWLTVL P |
| 114 | FGFR4 ECD Δ17 S116E | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSNDDEDPK SHRDPENRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL P |
| 115 | FGFR4 ECD Δ17 R4(104-114):R1(106-117) | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TEE DDDDDDDSSSEE PSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL P |
| 116 | FGFR4 ECD Δ17 R4(104-114):R1(107-117) | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSS DDDDDDSSSEE PSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL P |
| 117 | FGFR4 ECD Δ17 R4(104-110):R1(105-113) | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSS EDDDDDDDS SHRDPSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL P |
| 118 | FGFR4 ECD Δ17 R4(113-116):R1(116-119) | LEASEEVELE PCLAPSLEQQ EQELTVALGQ PVRLCCGRAE RGGHWYKEGS RLAPAGRVRG WRGELFIASE LPEDAGRYLC LARGSMIVLQ NLTLITGDSL TSSNDDEDPK SH EEKE NRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL P |
| 119 | FGFR4 ECD Δ17 R4(109-113):R1(112-116) | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSNDDED DSSSE DPSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL P |
| 120 | FGFR4 ECD Δ17 R1 D1-D2 linker chimera (N91A) | LEASEEVELE PCLAPSLEQQ EQELTVALGQ PVRLCCGRAE RGGHWYKEGS RLAPAGRVRG WRGRLEIASE LPEDAGRYLC LARGSMIVLQ ALTLITGDAL PSSEDDDDDD DSSSEEKETD NTKPNPVAPY WTHPQRMEKK LHAVPAGNTV KFRCPAAGNP TPTIRWLKDG QAFHGENRIG GIRLRHQHWS LVMESVVPSD RGTYTCLVEN AVGSIRYNYL LDVLERSPHR PILQAGLPAN TTAVVGSDVE LLCKVYSDAQ PHIQWLKHIV INGSSFGADG FPYVQVLKTA DINSSEVEVL YLRNVSAEDA GEYTCLAGNS IGLSYQSAWL TVLP |

TABLE 11-continued

Sequences and Descriptions

| SEQ. ID. NO. | Description | Sequence |
|---|---|---|
| 121 | FGFR4 ECD Δ17 R1 D1-D2 linker chimera (N159A) | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDAL PSSEDDDDDD DSSSEEKETD NTKPNPVAPY WTHPQRMEKK LHAVPAGNTV KFRCPAAGAP TPTIRWLKDG QAFHGENRIG GIRLRHQHWS LVMESVVPSD RGTYTCLVEN AVOSIRYNYL LDVLERSPHR PILQAGLPAN TTAVVGSDVE LLCKVYSDAQ PHIQWLKHIV INGSSFGADG FPYVQVLKTA DINSSEVEVL YLRNVSAEDA GEYTCLAGNS IGLSYQSAWL TVLP |
| 122 | FGFR2 ECD R2(111-118):R1(105-112) | RPSFSLVED TTLEPEEPPT KYQISQPEVY VAAPGESLEV RCLLKDAAVI SWTKDGVHLG PNNRTVLIGE YLQIKGATPR DSGLYACTAS RTVDSETWYF MVNVTDAISS G EDDDDDDD A EDFVSENSNN KRAPYWTNTE KMEKRLHAVP AANTVKFRCP AGGNPMPTMR WLKNGKEFKQ EHRIGGYKVR NQHWSLIMES VVPSDKGNYT CVVENEYGSI NHTYHLDVVE RSPHRPILQA GLPANASTVV GGDVEFVCKV YSDAQPHIQW IKHVEKNGSK YGPDGLPYLK VLKAAGVNTT DKEIEVLYIR NVTFEDAGEY TCLAGNSIGI SFHSAWLTVL PAPGREKEIT ASPDYLE |
| 123 | FGFR3 ECD R3(110-117):R1(105-112) | ESLGTEQR VVGRAAEVPG PEPGQQEQLV FGSGDAVELS CPPPGGGPMG PTVWVKDGTG LVPSERVLVG PQRLQVLNAS HEDSGAYSCR QRLTQRVLCH ESVRVTDAPS S EDDDDDDD E AEDTGVDTGA PYWTRPERMD KKLLAVPAAN TVRFRCPAAG NPTPSISWLK NGREFRGEHR IGGIKLRHQQ WSLVMESVVP SDRGNYTCVV ENKFGSIRQT YTLDVLERSP HRPILQAGLP ANQTAVLGSD VEFHCKVYSD AQPHIQWLKH VEVNGSKVGP DGTPYVTVLK TAGANTTDKE LEVLSLHNVT FEDAGEYTCL AGNSIGFSHH SAWLVVLPAE EELVEADEAG SVYAG |
| 124 | FGFR4 ECD Δ17 R1 long acid box chimera-Fc | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSS EDDDDDDDSSSEEKETD HS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL P EPKSSDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSRD ELTKNQVSLT CLVKGFYPSD IAVEWESNGQ PENNYKTTPP VLDSDGSFFL YSKLTVDKSR WQQGNVFSCS VMHEALHNHYTQKSLSLSPGK |
| 125 | FGFR4 ECD Δ17 R2 long acid box chimera-Fc | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSS DDEDDTDGAEDFVSE HS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL P EPKSSDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSRD ELTKNQVSLT CLVKGFYPSD IAVEWESNGQ PENNYKTTPP VLDSDGSFFL YSKLTVDKSR WQQGNVFSCS VMHEALHNHYTQKSLSLSPGK |
| 126 | FGFR4 ECD Δ17 R3 long acid box chimera-Fc | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSS GDDEDGEDEAED HS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL P EPKSSDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN |

TABLE 11-continued

Sequences and Descriptions

| SEQ. ID. NO. | Description | Sequence |
|---|---|---|
| | | GKEYKCKVSN KALPAPIEKT ISKAKGQPRE PQVYTLPPSRD ELTKNQVSLT CLVYGFYPSD IAVEWESNGQ PENNYKTTPP VLDSDGSFFL YSKLTVDKSR WQQGNVFSCS VMHEALHNHYTQKSLSLSPGK |
| 127 | FGFR4 ECD Δ17 R1 short acid box chimera-Fc | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSN EDDDDDDD PK SHRDPSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL P |
| 128 | FGFR4 ECD Δ17 R2 short acid box chimera-Fc | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSN DDEDD PK SHRDPSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL P EPKSSDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSRD ELTKNQVSLT CLVKGFYPSD IAVEWESNGQ PENNYKTTPP VLDSDGSFFL YSKLTVDKSR WQQGNVFSCS VMHEALHNHYTQKSLSLSPGK |
| 129 | FGFR4 ECD Δ17 R3 short acid box chimera-Fc | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSN DDED PK SHRDPSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL P EPKSSDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSRD ELTKNQVSLT CLVKGFYPSD IAVEWESNGQ PENNYKTTPP VLDSDGSFFL YSKLTVDKSR WQQGNVFSCS VMHEALHNHYTQKSLSLSPGK |
| 130 | FGFR4 ECD Δ17 N104D + Fc (also called FGFR4ECD(R4Mut4 (N104D):delta17)-Fc and R4Mut4(N104D)) | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSDDDEDPK SHRDPSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING ESEGADGFPY VQVLKTADIN SSEVEVLYLR NVSAEDAGEY TCLAGNSIGL SYQSAWLTVL P EPKSSDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSRD ELTKNQVSLT CLVKGFYPSD IAVEWESNGQ PENNYKTTPP VLDSDGSFFL YSKLTVDKSR WQQGNVFSCS VMHEALHNHYTQKSLSLSPGK |
| 131 | FGFR4 ECD Δ17 P109D + Fc (also called FGFR4ECD(R4Mut4(P 109D):delta17)-Fc and R4Mut4(P109D)) | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSNDDEDDK SHRDPSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL P EPKSSDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSRD |

TABLE 11-continued

Sequences and Descriptions

| SEQ. ID. NO. | Description | Sequence |
|---|---|---|
| | | ELTKNQVSLT CLVKGFYPSD IAVEWESNGQ PENNYKTTPP VLDSDGSFFL YSKLTVDKSR WQQGNVFSCS VMHEALHNHYTQKSLSLSPGK |
| 132 | FGFR4 ECD Δ17 R113E + Fc (also called FGFR4ECD(R4Mut4(R 113E): delta17)-Fc and R4Mut4(R113E)) | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSNDDEDPK SHEDPSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL P EPKSSDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSRD ELTKNQVSLT CLVKGFYPSD IAVEWESNGQ PENNYKTTPP VLDSDGSFFL YSKLTVDKSR WQQGNVFSCS VMHEALHNHYTQKSLSLSPGK |
| 133 | FGFR4 ECD Δ17 S116E + Fc (also called FGFR4ECD(R4Mut4(S 116E): delta17)-Fc and R4Mut4(S116E)) | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSNDDEDPK SHRDPENRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL P EPKSSDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSRD ELTKNQVSLT CLVKGFYPSD IAVEWESNGQ PENNYKTTPP VLDSDGSFFL YSKLTVDKSR WQQGNVFSCS VMHEALHNHYTQKSLSLSPGK |
| 134 | FGFR4 ECD Δ17 R4(104-114):R1(106-117) + Fc (also called FGFR4ECD(R4Mut4(104-114):FGFR1(106-117): delta 17)-Fc and R4(104-114):R1(106-117)) | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSS DDDDDDSSSEE PSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL P EPKSSDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSRD ELTKNQVSLT CLVKGFYPSD IAVEWESNGQ PENNYKTTPP VLDSDGSFFL YSKLTVDKSR WQQGNXTFSCS VMHEALHNHYTQKSLSLSPGK |
| 135 | FGFR4 ECD Δ17 R4(104-114):R1(107-117) + Fc (also called FGFR4ECD(R4Mut4(104-114):FCFRI(107-117): delta 17)-Fc and R4(104-114):R1(107-117)) | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSS DDDDDDSSEE PSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL P EPKSSDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSRD ELTKNQVSLT CLVKGFYPSD IAVEWESNGQ PENNYKTTPP VLDSDGSFFL YSKLTVDKSR WQQGNVFSCS VMHEALHNHYTQKSLSLSPGK |
| 136 | FGFR4 ECD Δ17 R4(104 - 110):R1(105-113) + Fc (also called FGFR4ECD(R4Mut4(104-110):FGFR1(105-113): delta 17)-Fc and | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSS EDDDDDDS SHRDPSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING |

TABLE 11-continued

Sequences and Descriptions

| SEQ. ID. NO. | Description | Sequence |
|---|---|---|
| | R4(104-110):R1(105-113)) | SSFGADGFPY VQVLKTADIN SSEVEVLYLR NVSAEDAGEY TCLAGNSIGL SYQSAWLTVL P EPKSSDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSRD ELTKNQVSLT CLVKGFYPSD IAVEWESNGQ PENNYKTTPP VLDSDGSFFL YSKLTVDKSR WQQGNVFSCS VMHEALHNHYTQKSLSLSPGK |
| 137 | FGFR4 ECD Δ17 R4(113-116):R1(116-119) + Fc (also called FGFR4ECD(R4Mut4(113-116):FGFR1(116-119):delta17)-Fc and R4(113-116):R1(116-119)) | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSNDDEDPK SH EEKE NRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL P EPKSSDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSRD ELTKNQVSLT CLVKGFYPSD IAVEWESNGQ PENNYKTTPP VLDSDGSFFL YSKLTVDKSR WQQGNVFSCS VMHEALHNHYTQKSLSLSPGK |
| 138 | FGFR4 ECD Δ17 R4(109-113):R1(112-116) + Fc (also called FGFR4ECD(R4Mut4(109-113):FGFR1(112-116): delta 17)-Fc and R4(109-113):R1(112-116)) | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSNDDED DSSSE DPSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL P EPKSSDKTHT CPPCPAPELL GGPSVFLFPP KPKDTLNISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSRD ELTKNQVSLT CLVKGFYPSD IAVEWESNGQ PENNYKTTPP VLDSDGSFFL YSKLTVDKSR WQQGNVFSCS VMHEALHNHYTQKSLSLSPGK |
| 139 | FGFR4 ECD Δ17 R1 D1-D2 linker chimera (N91A) + Fc (also called FGFR4ECD(ABMut1 (N91A): delta 17)-Fc and ABMut1(N91A)) | LEASEEVELE PCLAPSLEQQ EQELTVALGQ PVRLCCGRAE RGGHWYKEGS RLAPAGRVRG WRGRLEIASF LPEDAGRYLC LARGSMIVLQ ALTLITGDAL PSSEDDDDDD DSSSEEKETD NTKPNPVAPY WTHPQRMEKK LHAVPAGNTV KFRCPAAGNP TPTIRWLKDG QAFHGENRIG GIRLRHQHWS LVMESVVPSD RGTYTCLVEN AVGSIRYNYL LDVLERSPHR PILQAGLPAN TTAVVGSDVE LLCKVYSDAQ PHIQWLKHIV INGSSFGADG FPYVQVLKTA DINSSEVEVL YLRNVSAEDA GEYTCLAGNS IGLSYQSAWL TVLP EPKSSDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSRD ELTKNQVSLT CLVKGFYPSD IAVEWESNGQ PENNYKTTPP VLDSDGSFFL YSKLTVDKSR WQQGNVFSCS VMHEALHNHYTQKSLSLSPGK |
| 140 | FCFR4 ECD Δ17 R1 D1-D2 linker chimera (N159A) + Fc (also called FCFR4ECD(ABMut1 (N159A): delta 17)-Fc and ABMut1(N159A)) | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDAL PSSEDDDDDD DSSSEEKETD NTKPNPVAPY WTHPQRMEKK LHAVPAGNTV KFRCPAAGAP TPTIRWLKDG QAFHGENRIG GIRLRHQHWS LVMESVVPSD RGTYTCLVEN AVGSIRYNYL LDVLERSPHR PILQAGLPAN TTAVVGSDVE LLCKVYSDAQ PHIQWLKHIV INGSSFGADG FPYVQVLKTA DINSSEVEVL YLRNVSAEDA GEYTCLAGNS IGLSYQSAWL TVL EPKSSDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSRD ELTKNQVSLT CLVKGFYPSD IAVEWESNGQ PENNYKTTPP VLDSDGSFFL YSKLTVDKSR WQQGNVFSCS VMHEALHNHYTQKSLSLSPGK |
| 141 | FGFR2 ECD R2(111-118):R1(105-112) + Fc | RPSFSLVED TTLEPEEPPT KYQISQPEVY VAAPGESLEV RCLLKDAAVI SWTKDGVHLG PNNRTVLIGE YLQIKGATPR |

TABLE 11-continued

Sequences and Descriptions

| SEQ. ID. NO. | Description | Sequence |
|---|---|---|
| | | DSGLYACTAS RTVDSETWYF MVNVTDAISS G EDDDDDDD A EDFVSENSNN KRAPYWTNTE KMEKRLHAVP AANTVKFRCP AGGNPMPTMR WLKNGKEFKQ EHRIGGYKVR NQHWSLIMES VVPSDKGNYT CVVENEYGSI NHTYHLDVVE RSPHRPILQA GLPANASTVV GGDVEFCKV YSDAQPHIQW IKHVEKNGSK YGPDGLPYLK VLKAAGVNTT DKEIEVLYIR NVTFEDAGEY TCLAGNSIGI SFHSAWLTVL PAPGREKEIT ASPDYLE EPKSSDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSRD ELTKNQVSLT CLVKGFYPSD IAVEWESNGQ PENNYKTTPP VLDSDGSFFL YSKLTVDKSR WQQGNVFSCS VMHEALHNHYTQKSLSLSPGK |
| 142 | FGFR3 ECD R3(110-117):R1(105-112) + Fc | ESLGTEQR VVGRAAEVPG PEPGQQEQLV FGSGDAVELS CPPPGGGPMG PTVWVKDGTG LVPSERVLVG PQRLQVLNAS HEDSGAYSCR QRLTQRVLCH FSVRVTDAPS S EDDDDDDD E AEDTGVDTGA PYWTRPERMD KKLLAVPAAN TVRFRCPAAG NPTPSISWLK NGREFRGEHR IGGIKLRHQQ WSLVMESVVP SDRGNYTCVV ENKFGSIRQT YTLDVLERSP HRPILQAGLP ANQTAVLGSD VEFHCKVYSD AQPHIQWLKH VEVNGSKVGP DGTPYVTVLK TAGANTTDKE LEVLSLHNVT FEDAGEYTCL AGNSIGFSHH SAWLVVLPAE EELVEADEAG SVYAG EPKSSDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSRD ELTKNQVSLT CLVKGFYPSD IAVEWESNGQ PENNYKTTPP VLDSDGSFFL YSKLTVDKSR WQQGNVFSCS VMHEALHNHYTQKSLSLSPGK |
| 143 | FGFR4 ECD Δ17 R2 D1-D2 linker chimera + Fc (also called FGFR4ECD(R4Mut4 (D1-D2):FGFR2(D1-D2): delta 17)-Fc and R4(D1-D2):R2(D1-D2)) | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDAI SSGDDEDDTD GAEDFVSENS NNKRAPYWTH PQRMEKKLHA VPAGNTVKFR CPAAGNPTPT IRWLKDGQAF HGENRIGGIR LRHQHWSLVM ESVVPSDRGT YTCLVENAVG SIRYNLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL P EPKSSDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSRD ELTKNQVSLT CLVKGFYPSD IAVEWESNGQ PENNYKTTPP VLDSDGSFFL YSKLTVDKSR WQQGNVFSCS VMHEALHNHYTQKSLSLSPGK |
| 144 | FGFR4 ECD Δ17 R3 D1-D2 linker chimera + Fc (also called FGFR4ECD(R4Mut4 (D1-D2):FGFR3(D1-D2): delta 17)-Fc and R4(D1-D2):R3(D1-D2)) | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDAP SSGDDEDGED AEDTGVDTGA PYWTHPQRM EKKLHAVPAG NTVKFRCPAA GNPTPTIRWL KDGQAFHGEN RIGGIRLRHQ HWSLVMESVV PSDRGTYTCL VENAVGSIRY NYLLDVLERS PHRPILQAGL PANTTAVVGS DVELLCKVYS DAQPHIQWLK HIVINGSSFG ADGFPYVQVL KTADINSSEV EVLYLRNVSA EDAGEYTCLA GNSIGLSYQS AWLTVLP EPKSSDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSRD ELTKNQVSLT CLVKGFYPSD IAVEWESNGQ PENNYKTTPP VLDSDGSFFL YSKLTVDKSR WQQGNVFSCS VMHEALHNHYTQKSLSLSPGK |
| 145 | R4(104-114) | NDDEDPKSHR D |
| 146 | R4(104-110) | NDDEDPK |
| 147 | R4(113-116) | RDPS |
| 148 | R4(109-113) | PKSHR |
| 149 | R1(106-117) | DDDDDDDSSS EE |
| 150 | R1(107-117) | DDDDDDSSSE E |
| 151 | R1(105-113) | EDDDDDDDS |

TABLE 11-continued

Sequences and Descriptions

| SEQ. ID. NO. | Description | Sequence |
|---|---|---|
| 152 | R1(116-119) | EEKE |
| 153 | R1(112-116) | DSSSE |
| 154 | R1(105-112) | EDDDDDDD |
| 155 | R2(111-118) | DDEDDTDG |
| 156 | R3(110-117) | GDDEDGED |
| 157 | FGFR4 ECD Δ17 R4(104-114):R1(105-117) acid box chimera | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSS EDDDDDDDSSSEE PSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL P |
| 158 | FCFR4 ECD Δ17 R4(104-114):R1(105-117) acid box chimera + Fc (also called FCF4ECD(ABMut3:delta17)-Fc or ABMut3) | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSS EDDDDDDDSSSEE PSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL P EPKSSDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSRD ELTKNQVSLT CLVKGFYPSD IAVEWESNGQ PENNYKTTPP VLDSDGSFFL YSKLTVDKSR WQQGNVFSCS VMHEALHNHYTQKSLSLSPGK |
| 159 | R1(105-117) | EDDDDDDDSS SEE |
| 160 | FGFR2 ECD Δ3 | RPSFSLVED TTLEPEEPPT KYQISQPEVY VAAPGESLEV RCLLKDAAVI SWTKDGVHLG PNNRTVLIGE YLQIKGATPR DSGLYACTAS RTVDSETWYF MVNVTDAISS GDDEDDTGA EDFVSENSNN KRAPYWTNTE KMEKRLHAVP AANTVKFRCP AGGNPMPTMR WLKNGKEFKQ EHRIGGYKVR NQHWSLIMES VVPSDKGNYT CVVENEYGSI NHTYHLDVVE RSPHRPILQA GLPANASTVV GGDVEFVCKV YSDAQPHIQW IKHVEKNGSK YGPDGLPYLK VLKAAGVNTT DKEIEVLYIR NVTFEDAGEY TCLAGNSIGI SFHSAWLTVL PAPGREKEIT ASPD |
| 161 | FGFR3 ECD Δ3 | ESLGTEQR VVGRAAEVPG PEPGQQEQLV FGSGDAVELS CPPPGGGPMG PTVWVKDGTG LVPSERVLVG PQRLQVLNAS HEDSGAYSCR QRLTQRVLCH FSVRVTDAPS SGDDEDGEDE AEDTGVDTGA PYWTRPERMD KKLLAVPAAN TVRFRCPAAG NPTPSISWLK NGREFRGEHR IGGIKLRHQQ WSLVMESVVP SDRGNYTCVV ENKFGSIRQT YTLDVLERSP HRPILQAGLP ANQTAVLGSD VEFHCKVYSD AQPHIQWLKH VEVNGSKVGP DGTPYVTVLK TAGANTTDKE LEVLSLHNVT FEDAGEYTCL AGNSIGFSHH SAWLVVLPAE ELVEADEAG SV |
| 162 | FGFR2 ECD Δ3 + GS linker + Fc (also called FGFR2ECD(delta3)-GS linker-Fc and FGFR2-Fc) | RPSFSLVED TTLEPEEPPT KYQISQPEVY VAAPGESLEV RCLLKDAAVI SWTKDGVHLG PNNRTVLIGE YLQIKGATPR DSGLYACTAS RTVDSETWYF MVNVTDAISS GDDEDDTGA EDFVSENSNN KRAPYWTNTE KMEKRLHAVP AANTVKFRCP AGGNPMPTMR WLKNGKEFKQ EHRIGGYKVR NQHWSLIMES VVPSDKGNYT CVVENEYGSI NHTYHLDVVE RSPHRPILQA GLPANASTVV GGDVEFVCKV YSDAQPHIQW IKHVEKNGSK YGPDGLPYLK VLKAAGVNTT DKEIEVLYIR NVTFEDAGEY TCLAGNSIGI SFHSAWLTVL PAPGREKEIT ASPD GS EPKSSDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSRD ELTKNQVSLT CLVKGFYPSD IAVEWESNGQ PENNYKTTPP VLDSDGSFFL YSKLTVDKSR WQQGNVFSCS VMHEALHNHYTQKSLSLSPGK |

TABLE 11-continued

Sequences and Descriptions

| SEQ. ID. NO. | Description | Sequence |
|---|---|---|
| 163 | FGFR3 ECD Δ3 + GS linker + Fc (also called FGFR3ECD(delta3)-GS linker-Fc and FGFR3-Fc) | ESLGTEQR VVGRAAEVPG PEPGQQEQLV FGSGDAVELS CPPPGGGPMG PTVWVKDGTG LVPSERVLVG PQRLQVLNAS HEDSGAYSCR QRLTQRVLCH FSVRVTDAPS SGDDEDGEDE AEDTGVDTGA PYWTRPERMD KKLLAVPAAN TVRFRCPAAG NPTPSISWLK NGREFRGEHR IGGIKLRHQQ WSLVMESVVP SDRGNYTCVV ENKFGSIRQT YTLDVLERSP HRPILQAGLP ANQTAVLGSD VEFHCKVYSD AQPHIQWLKH VEVNGSKVGP DGTPYVTVLK TAGANTTDKE LEVLSLHNVT FEDAGEYTCL AGNSIGFSHH SAWLVVLPAE EELVEADEAG SV GS EPKSSDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSRD ELTKNQVSLT CLVKGFYPSD IAVEWESNGQ PENNYKTTPP VLDSDGSFFL YSKLTVDKSR WQQGNVFSCS VMHEALHNHYTQKSLSLSPGK |
| 164 | FGFR2 ECD Δ3 R2(111-118):R1(105-112) | RPSFSLVED TTLEPEEPPT KYQISQPEVY VAAPGESLEV RCLLKDAAVI SWTKDGVHLG PNNRTVLIGE YLQIKGATPR DSGLYACTAS RTVDSETWYF MVNVTDAISS G EDDDDDDD A EDFVSENSNN KRAPYWTNTE KMEKRLHAVP AANTVKFRCP AGGNPMPTMR WLKNGKEFKQ EHRIGGYKVR NQHWSLIMES VVPSDKGNYT CVVENEYGSI NHTYHLDVVE RSPHRPILQA GLPANASTVV GGDVEFVCKV YSDAQPHIQW IKHVEKNGSK YGPDGLPYLK VLKAAGVNTT DKEIEVLYIR NVTFEDAGEY TCLAGNSIGI SFHSAWLTVL PAPGREKEIT ASPD |
| 165 | FGFR3 ECD Δ3 R3(110-117):R1(105-112) | ESLGTEQR VVGRAAEVPG PEPGQQEQLV FGSGDAVELS CPPPGGGPMG PTVWVKDGTG LVPSERVLVG PQRLQVLNAS HEDSGAYSCR QRLTQRVLCH FSVRVTDAPS S EDDDDDDD E AEDTGVDTGA PYWTRPERMD KKLLAVPAAN TVRFRCPAAG NPTPSISWLK NGREFRGEHR IGGIKLRHQQ WSLVMESVVP SDRGNYTCVV ENKFGSIRQT YTLDVLERSP HRPILQAGLP ANQTAVLGSD VEFHCKVYSD AQPHIQWLKH VEVNGSKVGP DGTPYVTVLK TAGANTTDKE LEVLSLHNVT FEDAGEYTCL AGNSIGFSHH SAWLVVLPAE EELVEADEAG SV |
| 166 | FGFR2 ECD Δ3 R2(111-118):R1(105-112) + GS linker + Fc (also called FGFR2ECD(FGFR2(111-118):FCFR1(105-112): delta3)-GS linker-Fc and R2(111-118):R1(105-112)) | RPSFSLVED TTLEPEEPPT KYQISQPEVY VAAPGESLEV RCLLKDAAVI SWTKDGVHLG PNNRTVLIGE YLQIKGATPR DSGLYACTAS RTVDSETWYF MVNVTDAISS G EDDDDDDD A EDFVSENSNN KRAPYWTNTE KMEKRLHAVP AANTVKFRCP AGGNPMPTMR WLKNGKEFKQ EHRIGGYKVR NQHWSLIMES VVPSDKGNYT CVVENEYGSI NHTYHLDVVE RSPHRPILQA GLPANASTVV GGDVEFVCKV YSDAQPHIQW IKHVEKNGSK YGPDGLPYLK VLKAAGVNTT DKEIEVLYIR NVTFEDAGEY TCLAGNSIGI SFHSAWLTVL PAPGREKEIT ASPD GS EPKSSDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSRD ELTKNQVSLT CLVKGFYPSD IAVEWESNGQ PENNYKTTPP VLDSDGSFFL YSKLTVDKSR WQQGNVFSCS VMHEALHNHYTQKSLSLSPGK |
| 167 | FGFR3 ECD Δ3 R3(110-117):R1(105-112)GSlinker + Fc (also called FGFR3ECD(FGFR3(110-117):FCFR1(105-112): delta3)-GS linker-Fc and R3(110-117):R1(105-112)) | ESLGTEQR VVGRAAEVPG PEPGQQEQLV FGSGDAVELS CPPPGGGPMG PTVWVKDGTG LVPSERVLVG PQRLQVLNAS HEDSGAYSCR QRLTQRVLCH FSVRVTDAPS S EDDDDDDD E AEDTGVDTGA PYWTRPERMD KKLLAVPAAN TVRFRCPAAG NPTPSISWLK NGREFRGEHR IGGIKLRHQQ WSLVMESVVP SDRGNYTCVV ENKFGSIRQT YTLDVLERSP HRPILQAGLP ANQTAVLGSD VEFHCKVYSD AQPHIQWLKH VEVNGSKVGP DGTPYVTVLK TAGANTTDKE LEVLSLHNVT FEDAGEYTCL AGNSIGFSHH SAWLVVLPAE EELVEADEAG SV GS EPKSSDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSRD ELTKNQVSLT CLVKGFYPSD IAVEWESNGQ PENNYKTTPP VLDSDGSFFL YSKLTVDKSR WQQGNVFSCS VMHEALHNHYTQKSLSLSPGK |
| 168 | FGFR4 ECD Δ17 R1 D1-D2 linker chimera (N91A, N159) | LEASEEVELE PCLAPSLEQQ EQELTVALGQ PVRLCCGRAE RGGHWYKEGS RLAPAGRVRG WRGRLEIASF LPEDAGRYLC LARGSMIVLQ ALTLITGDAL PSSEDDDDDD DSSSEEKETD NTKPNPVAPY WTHPQRMEKK LHAVPAGNTV KFRCPAAGAP TPTIRWLKDG QAFHGENRIG GIRLRHQHWS LVMESVVPSD |

TABLE 11-continued

Sequences and Descriptions

| SEQ. ID. NO. | Description | Sequence |
|---|---|---|
| | | RGTYTCLVEN AVGSIRYNYL LDVLERSPHR PILQAGLPAN
TTAVVGSDVE LLCKVYSDAQ PHIQWLKHIV INGSSFGADG
FPYVQVLKTA DINSSEVEVL YLRNVSAEDA GEYTCLAGNS
IGLSYQSAWL TVLP |
| 169 | FGFR4 ECD Δ17 R1 D1-D2 linker chimera (N91A, N159) + Fc | LEASEEVELE PCLAPSLEQQ EQELTVALGQ PVRLCCGRAE
RGGHWYKEGS RLAPAGRVRG WRGRLEIASF LPEDAGRYLC
LARGSMIVLQ ALTLITGDAL PSSEDDDDDD DSSSEEKETD
NTKPNPVAPY WTHPQRMEKK LHAVPAGNTV KFRCPAAGAP
TPTIRWLKDG QAFHGENRIG GIRLRHQHWS LVMESVVPSD
RGTYTCLVEN AVGSIRYNYL LDVLERSPHR PILQAGLPAN
TTAVVGSDVE LLCKVYSDAQ PHIQWLKHIV INGSSFGADG
FPYVQVLKTA DINSSEVEVL YLRNVSAEDA GEYTCLAGNS
IGLSYQSAWL TVLP EPKSSDKTHT CPPCPAPELL
GGPSVFLFPP KPKDTLMISR TPEVTCVVVD VSHEDPEVKF
NWYVDGVEVH NAKTKPREEQ YNSTYRVVSV LTVLHQDWLN
GKEYKCKVSN KALPAPIEKT ISKAKGQPRE PQVYTLPPSRD
ELTKNQVSLT CLVKGFYPSD IAVEWESNGQ PENNYKTTPP
VLDSDGSFFL YSKLTVDKSR WQQGNVFSCS
VMHEALHNHYTQKSLSLSPGK |
| 170 | Fc | ESKYGPPCPP CPAPEFLGGP SVFLFPPKPK DTLMISRTPE
VTCVVVDVSQ EDPEVQFNWY VDGVEVHNAK TKPREEQFNS
TYRVVSVLTV LHQDWLNGKE YKCKVSNKGL PSSIEKTISK
AKGQPREPQV YTLPPSQEEM TKNQVSLTCL VKGFYPSDIA
VEWESNGQPE NNYKTTPPVL DSDGSFFLYS RLTVDKSRWQ
EGNVFSCSVM HEALHNHYTQ KSLSLSLGK |
| 171 | Fc | ERKSSVECPP CPAPPVAGPS VFLFPPKPKD TLMISRTPEV
TCVVVDVSHE DPEVQFNWYV DGVEVHNAKT KPREEQFNST
FRVVSVLTVV HQDWLNGKEY KCKVSNKGLP APIEKTISKT
KGQPREPQVY TLPPSREEMT KNQVSLTCLV KGFYPSDIAV
EWESNGQPEN NYKTTPPMLD SDGSFFLYSK LTVDKSRWQQ
GNVFSCSVMH EALHNHYTQK SLSLSPGK |
| 172 | FGFR1 ECD Δ14 | RPSPTLPEQ AQPWGAPVEV ESFLVHPGDL LQLRCRLRDD
VQSINWLRDG VQLAESNRTR ITGEEVEVQD SVPADSGLYA
CVTSSPSGSD TTYFSVNVSD ALPSSEDDDD DDDSSSEEKE
TDNTKPNPVA PYWTSPEKME KKLHAVPAAK TVKFKCPSSG
TPNPTLRWLK NGKEFKPDHR IGGYKVRYAT WSIIMDSVVP
SDKGNYTCIV ENEYGSINHT YQLDVVERSP HRPILQAGLP
ANKTVALGSN VEFMCKVYSD PQPHIQWLKH IEVNGSKIGP
DNLPYVQILK TAGVNTTDKE MEVLHLRNVS FEDAGEYTCL
AGNSIGLSHH SAWLTVLEAL |
| 173 | FGFR1 ECD w/ signal peptide | MWSWKCLLFW AVLVTATLCT A RPSPTLPEQ AQPWGAPVEV
ESFLVHPGDL LQLRCRLRDD VQSINWLRDG VQLAESNRTR
ITGEEVEVQD SVPADSGLYA CVTSSPSGSD TTYFSVNVSD
ALPSSEDDDD DDDSSSEEKE TDNTKPNPVA PYWTSPEKME
KKLHAVPAAK TVKFKCPSSG TPNPTLRWLK NGKEFKPDHR
IGGYKVRYAT WSIIMDSVVP SDKGNYTCIV ENEYGSINHT
YQLDVVERSP HRPILQAGLP ANKTVALGSN VEFMCKVYSD
PQPHIQWLKH IEVNGSKIGP DNLPYVQILK TAGVNTTDKE
MEVLHLRNVS FEDAGEYTCL AGNSIGLSHH SAWLTVLEAL
EERPAVMTSP LYLE |

The invention claimed is:

1. An FGFR4 ECD fusion molecule comprising a polypeptide and a fusion partner, wherein the polypeptide comprises the amino acid sequence of SEQ ID NO:35.

2. The FGFR4 ECD fusion molecule of claim 1, wherein the fusion partner is an Fc.

3. The FGFR4 ECD fusion molecule of claim 2, wherein the FGFR4 ECD fusion molecule has the amino acid sequence of SEQ ID NO:86.

4. A polynucleotide comprising a nucleic acid sequence that encodes the polypeptide of claim 1.

5. A polynucleotide comprising a nucleic acid sequence that encodes the FGFR4 ECD fusion molecule of claim 3.

* * * * *

SEQUENCE LISTING

<160> NUMBER OF SEQ ID NOS: 174

<210> SEQ ID NO 1
<211> LENGTH: 348
<212> TYPE: PRT
<213> ORGANISM: Artificial Sequence
<220> FEATURE:
<223> OTHER INFORMATION: Synthetic sequence

<400> SEQUENCE: 1

| Leu | Glu | Ala | Ser | Glu | Glu | Val | Glu | Leu | Glu | Pro | Cys | Leu | Ala | Pro | Ser |
|---|---|---|---|---|---|---|---|---|---|---|---|---|---|---|---|
| 1 | | | | 5 | | | | | 10 | | | | | 15 | |

| Leu | Glu | Gln | Gln | Glu | Gln | Glu | Leu | Thr | Val | Ala | Leu | Gly | Gln | Pro | Val |
|---|---|---|---|---|---|---|---|---|---|---|---|---|---|---|---|
| | | | 20 | | | | | 25 | | | | | 30 | | |

| Arg | Leu | Cys | Cys | Gly | Arg | Ala | Glu | Arg | Gly | Gly | His | Trp | Tyr | Lys | Glu |
|---|---|---|---|---|---|---|---|---|---|---|---|---|---|---|---|
| | | 35 | | | | | 40 | | | | | 45 | | | |

| Gly | Ser | Arg | Leu | Ala | Pro | Ala | Gly | Arg | Val | Arg | Gly | Trp | Arg | Gly | Arg |
|---|---|---|---|---|---|---|---|---|---|---|---|---|---|---|---|
| | 50 | | | | | 55 | | | | | 60 | | | | |

| Leu | Glu | Ile | Ala | Ser | Phe | Leu | Pro | Glu | Asp | Ala | Gly | Tyr | Leu | Cys |
|---|---|---|---|---|---|---|---|---|---|---|---|---|---|---|
| 65 | | | | | 70 | | | | | 75 | | | | 80 |

| Leu | Ala | Arg | Gly | Ser | Met | Ile | Val | Leu | Gln | Asn | Leu | Thr | Leu | Ile | Thr |
|---|---|---|---|---|---|---|---|---|---|---|---|---|---|---|---|
| | | | | 85 | | | | | 90 | | | | | 95 | |

| Gly | Asp | Ser | Leu | Thr | Ser | Ser | Asn | Asp | Glu | Asp | Pro | Lys | Ser | His |
|---|---|---|---|---|---|---|---|---|---|---|---|---|---|---|
| | | | 100 | | | | | 105 | | | | | 110 | |

| Arg | Asp | Pro | Ser | Asn | Arg | His | Ser | Tyr | Pro | Gln | Gln | Ala | Pro | Tyr | Trp |
|---|---|---|---|---|---|---|---|---|---|---|---|---|---|---|---|
| | | | 115 | | | | | 120 | | | | | 125 | | |

| Thr | His | Pro | Gln | Arg | Met | Glu | Lys | Lys | Leu | His | Ala | Val | Pro | Ala | Gly |
|---|---|---|---|---|---|---|---|---|---|---|---|---|---|---|---|
| | 130 | | | | | 135 | | | | | 140 | | | | |

| Asn | Thr | Val | Lys | Phe | Arg | Cys | Pro | Ala | Ala | Gly | Asn | Pro | Thr | Pro | Thr |
|---|---|---|---|---|---|---|---|---|---|---|---|---|---|---|---|
| 145 | | | | | 150 | | | | | 155 | | | | | 160 |

| Ile | Arg | Trp | Leu | Lys | Asp | Gly | Gln | Ala | Phe | His | Gly | Glu | Asn | Arg | Ile |
|---|---|---|---|---|---|---|---|---|---|---|---|---|---|---|---|
| | | | | 165 | | | | | 170 | | | | | 175 | |

| Gly | Gly | Ile | Arg | Leu | Arg | His | Gln | His | Trp | Ser | Leu | Val | Met | Glu | Ser |
|---|---|---|---|---|---|---|---|---|---|---|---|---|---|---|---|
| | | | 180 | | | | | 185 | | | | | 190 | | |

| Val | Val | Pro | Ser | Asp | Arg | Gly | Thr | Tyr | Thr | Cys | Leu | Val | Glu | Asn | Ala |
|---|---|---|---|---|---|---|---|---|---|---|---|---|---|---|---|
| | | 195 | | | | | 200 | | | | | 205 | | | |

| Val | Gly | Ser | Ile | Arg | Tyr | Asn | Tyr | Leu | Leu | Asp | Val | Leu | Glu | Arg | Ser |
|---|---|---|---|---|---|---|---|---|---|---|---|---|---|---|---|
| | 210 | | | | | 215 | | | | | 220 | | | | |

| Pro | His | Arg | Pro | Ile | Leu | Gln | Ala | Gly | Leu | Pro | Ala | Asn | Thr | Thr | Ala |
|---|---|---|---|---|---|---|---|---|---|---|---|---|---|---|---|
| 225 | | | | | 230 | | | | | 235 | | | | | 240 |

| Val | Val | Gly | Ser | Asp | Val | Glu | Leu | Leu | Cys | Lys | Val | Tyr | Ser | Asp | Ala |
|---|---|---|---|---|---|---|---|---|---|---|---|---|---|---|---|
| | | | | 245 | | | | | 250 | | | | | 255 | |

| Gln | Pro | His | Ile | Gln | Trp | Leu | Lys | His | Ile | Val | Ile | Asn | Gly | Ser | Ser |
|---|---|---|---|---|---|---|---|---|---|---|---|---|---|---|---|
| | | | 260 | | | | | 265 | | | | | 270 | | |

| Phe | Gly | Ala | Asp | Gly | Phe | Pro | Tyr | Val | Gln | Val | Leu | Lys | Thr | Ala | Asp |
|---|---|---|---|---|---|---|---|---|---|---|---|---|---|---|---|
| | | 275 | | | | | 280 | | | | | 285 | | | |

| Ile | Asn | Ser | Ser | Glu | Val | Glu | Val | Leu | Tyr | Leu | Arg | Asn | Val | Ser | Ala |
|---|---|---|---|---|---|---|---|---|---|---|---|---|---|---|---|
| | 290 | | | | | 295 | | | | | 300 | | | | |

| Glu | Asp | Ala | Gly | Glu | Tyr | Thr | Cys | Leu | Ala | Gly | Asn | Ser | Ile | Gly | Leu |
|---|---|---|---|---|---|---|---|---|---|---|---|---|---|---|---|
| 305 | | | | | 310 | | | | | 315 | | | | | 320 |

| Ser | Tyr | Gln | Ser | Ala | Trp | Leu | Thr | Val | Leu | Pro | Glu | Glu | Asp | Pro | Thr |
|---|---|---|---|---|---|---|---|---|---|---|---|---|---|---|---|
| | | | | 325 | | | | | 330 | | | | | 335 | |

| Trp | Thr | Ala | Ala | Ala | Pro | Glu | Ala | Arg | Tyr | Thr | Asp |
|---|---|---|---|---|---|---|---|---|---|---|---|
| | | | 340 | | | | | 345 | | | |

<210> SEQ ID NO 2
<211> LENGTH: 348
<212> TYPE: PRT
<213> ORGANISM: Artificial Sequence
<220> FEATURE:
<223> OTHER INFORMATION: Synthetic sequence

<400> SEQUENCE: 2

Leu Glu Ala Ser Glu Glu Val Glu Leu Glu Pro Cys Leu Ala Pro Ser

```
                   1               5                  10                  15
Leu Glu Gln Gln Glu Gln Glu Leu Thr Val Ala Leu Gly Gln Pro Val
                  20                  25                  30

Arg Leu Cys Cys Gly Arg Ala Glu Arg Gly Gly His Trp Tyr Lys Glu
                  35                  40                  45

Gly Ser Arg Leu Ala Pro Ala Gly Arg Val Arg Gly Trp Arg Gly Arg
                  50                  55                  60

Leu Glu Ile Ala Ser Phe Leu Pro Glu Asp Ala Gly Arg Tyr Leu Cys
 65                  70                  75                  80

Leu Ala Arg Gly Ser Met Ile Val Leu Gln Asn Leu Thr Leu Ile Thr
                  85                  90                  95

Gly Asp Ser Leu Thr Ser Ser Asn Asp Asp Glu Asp Pro Lys Ser His
                 100                 105                 110

Arg Asp Leu Ser Asn Arg His Ser Tyr Pro Gln Gln Ala Pro Tyr Trp
                 115                 120                 125

Thr His Pro Gln Arg Met Glu Lys Lys Leu His Ala Val Pro Ala Gly
                 130                 135                 140

Asn Thr Val Lys Phe Arg Cys Pro Ala Ala Gly Asn Pro Thr Pro Thr
145                 150                 155                 160

Ile Arg Trp Leu Lys Asp Gly Gln Ala Phe His Gly Glu Asn Arg Ile
                 165                 170                 175

Gly Gly Ile Arg Leu Arg His Gln His Trp Ser Leu Val Met Glu Ser
                 180                 185                 190

Val Val Pro Ser Asp Arg Gly Thr Tyr Thr Cys Leu Val Glu Asn Ala
                 195                 200                 205

Val Gly Ser Ile Arg Tyr Asn Tyr Leu Leu Asp Val Leu Glu Arg Ser
                 210                 215                 220

Pro His Arg Pro Ile Leu Gln Ala Gly Leu Pro Ala Asn Thr Thr Ala
225                 230                 235                 240

Val Val Gly Ser Asp Val Glu Leu Leu Cys Lys Val Tyr Ser Asp Ala
                 245                 250                 255

Gln Pro His Ile Gln Trp Leu Lys His Ile Val Ile Asn Gly Ser Ser
                 260                 265                 270

Phe Gly Ala Asp Gly Phe Pro Tyr Val Gln Val Leu Lys Thr Ala Asp
                 275                 280                 285

Ile Asn Ser Ser Glu Val Glu Val Leu Tyr Leu Arg Asn Val Ser Ala
                 290                 295                 300

Glu Asp Ala Gly Glu Tyr Thr Cys Leu Ala Gly Asn Ser Ile Gly Leu
305                 310                 315                 320

Ser Tyr Gln Ser Ala Trp Leu Thr Val Leu Pro Glu Glu Asp Pro Thr
                 325                 330                 335

Trp Thr Ala Ala Ala Pro Glu Ala Arg Tyr Thr Asp
                 340                 345

<210> SEQ ID NO 3
<211> LENGTH: 348
<212> TYPE: PRT
<213> ORGANISM: Artificial Sequence
<220> FEATURE:
<223> OTHER INFORMATION: Synthetic sequence

<400> SEQUENCE: 3

Leu Glu Ala Ser Glu Glu Val Glu Leu Glu Pro Cys Leu Ala Pro Ser
 1               5                  10                  15

Leu Glu Gln Gln Glu Gln Glu Leu Thr Val Ala Leu Gly Gln Pro Val
                  20                  25                  30
```

```
Arg Leu Cys Cys Gly Arg Ala Glu Arg Gly Gly His Trp Tyr Lys Glu
            35                  40                  45

Gly Ser Arg Leu Ala Pro Ala Gly Arg Val Arg Gly Trp Arg Gly Arg
 50                  55                  60

Leu Glu Ile Ala Ser Phe Leu Pro Glu Asp Ala Gly Arg Tyr Leu Cys
 65                  70                  75                  80

Leu Ala Arg Gly Ser Met Ile Val Leu Gln Asn Leu Thr Leu Ile Thr
                85                  90                  95

Gly Asp Ser Leu Thr Ser Ser Asn Asp Asp Glu Asp Pro Lys Ser His
               100                 105                 110

Arg Asp Pro Ser Asn Arg His Ser Tyr Pro Gln Gln Ala Pro Tyr Trp
               115                 120                 125

Thr His Pro Gln Arg Met Glu Lys Lys Leu His Ala Val Pro Ala Gly
       130                 135                 140

Asn Thr Val Lys Phe Arg Cys Pro Ala Ala Gly Asn Pro Thr Pro Thr
145                 150                 155                 160

Ile Arg Trp Leu Lys Asp Gly Gln Ala Phe His Gly Glu Asn Arg Ile
               165                 170                 175

Gly Gly Ile Arg Leu Arg His Gln His Trp Ser Leu Val Met Glu Ser
           180                 185                 190

Val Val Pro Ser Asp Arg Gly Thr Tyr Thr Cys Leu Val Glu Asn Ala
           195                 200                 205

Val Gly Ser Ile Arg Tyr Asn Tyr Leu Leu Asp Val Leu Glu Arg Ser
       210                 215                 220

Pro His Arg Pro Ile Leu Gln Ala Gly Leu Pro Ala Asn Thr Thr Ala
225                 230                 235                 240

Val Val Gly Ser Asp Val Glu Leu Leu Cys Lys Val Tyr Ser Asp Ala
               245                 250                 255

Gln Pro His Ile Gln Trp Leu Lys His Ile Val Ile Asn Gly Ser Ser
               260                 265                 270

Phe Gly Ala Val Gly Phe Pro Tyr Val Gln Val Leu Lys Thr Ala Asp
           275                 280                 285

Ile Asn Ser Ser Glu Val Glu Val Leu Tyr Leu Arg Asn Val Ser Ala
           290                 295                 300

Glu Asp Ala Gly Glu Tyr Thr Cys Leu Ala Gly Asn Ser Ile Gly Leu
305                 310                 315                 320

Ser Tyr Gln Ser Ala Trp Leu Thr Val Leu Pro Glu Glu Asp Pro Thr
               325                 330                 335

Trp Thr Ala Ala Ala Pro Glu Ala Arg Tyr Thr Asp
               340                 345

<210> SEQ ID NO 4
<211> LENGTH: 582
<212> TYPE: PRT
<213> ORGANISM: Artificial Sequence
<220> FEATURE:
<223> OTHER INFORMATION: Synthetic sequence

<400> SEQUENCE: 4

Leu Glu Ala Ser Glu Glu Val Glu Leu Glu Pro Cys Leu Ala Pro Ser
1               5                  10                  15

Leu Glu Gln Gln Glu Gln Glu Leu Thr Val Ala Leu Gly Gln Pro Val
                20                  25                  30

Arg Leu Cys Cys Gly Arg Ala Glu Arg Gly Gly His Trp Tyr Lys Glu
            35                  40                  45
```

```
Gly Ser Arg Leu Ala Pro Ala Gly Arg Val Arg Gly Trp Arg Gly Arg
     50                  55                  60

Leu Glu Ile Ala Ser Phe Leu Pro Glu Asp Ala Gly Arg Tyr Leu Cys
 65                  70                  75                  80

Leu Ala Arg Gly Ser Met Ile Val Leu Gln Asn Leu Thr Leu Ile Thr
                 85                  90                  95

Gly Asp Ser Leu Thr Ser Ser Asn Asp Glu Asp Pro Lys Ser His
                100                 105                 110

Arg Asp Pro Ser Asn Arg His Ser Tyr Pro Gln Gln Ala Pro Tyr Trp
             115                 120                 125

Thr His Pro Gln Arg Met Glu Lys Lys Leu His Ala Val Pro Ala Gly
         130                 135                 140

Asn Thr Val Lys Phe Arg Cys Pro Ala Ala Gly Asn Pro Thr Pro Thr
145                 150                 155                 160

Ile Arg Trp Leu Lys Asp Gly Gln Ala Phe His Gly Glu Asn Arg Ile
                165                 170                 175

Gly Gly Ile Arg Leu Arg His Gln His Trp Ser Leu Val Met Glu Ser
                180                 185                 190

Val Val Pro Ser Asp Arg Gly Thr Tyr Thr Cys Leu Val Glu Asn Ala
            195                 200                 205

Val Gly Ser Ile Arg Tyr Asn Tyr Leu Leu Asp Val Leu Glu Arg Ser
210                 215                 220

Pro His Arg Pro Ile Leu Gln Ala Gly Leu Pro Ala Asn Thr Thr Ala
225                 230                 235                 240

Val Val Gly Ser Asp Val Glu Leu Leu Cys Lys Val Tyr Ser Asp Ala
                245                 250                 255

Gln Pro His Ile Gln Trp Leu Lys His Ile Val Ile Asn Gly Ser Ser
            260                 265                 270

Phe Gly Ala Asp Gly Phe Pro Tyr Val Gln Val Leu Lys Thr Ala Asp
            275                 280                 285

Ile Asn Ser Ser Glu Val Glu Val Leu Tyr Leu Arg Asn Val Ser Ala
            290                 295                 300

Glu Asp Ala Gly Glu Tyr Thr Cys Leu Ala Gly Asn Ser Ile Gly Leu
305                 310                 315                 320

Ser Tyr Gln Ser Ala Trp Leu Thr Val Leu Pro Glu Glu Asp Pro Thr
                325                 330                 335

Trp Thr Ala Ala Ala Pro Glu Ala Arg Tyr Thr Asp Gly Ser Glu Pro
            340                 345                 350

Lys Ser Ser Asp Lys Thr His Thr Cys Pro Pro Cys Pro Ala Pro Glu
            355                 360                 365

Leu Leu Gly Gly Pro Ser Val Phe Leu Phe Pro Pro Lys Pro Lys Asp
    370                 375                 380

Thr Leu Met Ile Ser Arg Thr Pro Glu Val Thr Cys Val Val Val Asp
385                 390                 395                 400

Val Ser His Glu Asp Pro Glu Val Lys Phe Asn Trp Tyr Val Asp Gly
                405                 410                 415

Val Glu Val His Asn Ala Lys Thr Lys Pro Arg Glu Glu Gln Tyr Asn
            420                 425                 430

Ser Thr Tyr Arg Val Val Ser Val Leu Thr Val Leu His Gln Asp Trp
            435                 440                 445

Leu Asn Gly Lys Glu Tyr Lys Cys Lys Val Ser Asn Lys Ala Leu Pro
    450                 455                 460

Ala Pro Ile Glu Lys Thr Ile Ser Lys Ala Lys Gly Gln Pro Arg Glu
465                 470                 475                 480
```

```
Pro Gln Val Tyr Thr Leu Pro Pro Ser Arg Asp Glu Leu Thr Lys Asn
                485                 490                 495

Gln Val Ser Leu Thr Cys Leu Val Lys Gly Phe Tyr Pro Ser Asp Ile
            500                 505                 510

Ala Val Glu Trp Glu Ser Asn Gly Gln Pro Glu Asn Asn Tyr Lys Thr
        515                 520                 525

Thr Pro Pro Val Leu Asp Ser Asp Gly Ser Phe Phe Leu Tyr Ser Lys
    530                 535                 540

Leu Thr Val Asp Lys Ser Arg Trp Gln Gln Gly Asn Val Phe Ser Cys
545                 550                 555                 560

Ser Val Met His Glu Ala Leu His Asn His Tyr Thr Gln Lys Ser Leu
                565                 570                 575

Ser Leu Ser Pro Gly Lys
            580

<210> SEQ ID NO 5
<211> LENGTH: 580
<212> TYPE: PRT
<213> ORGANISM: Artificial Sequence
<220> FEATURE:
<223> OTHER INFORMATION: Synthetic sequence

<400> SEQUENCE: 5

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
            20                  25                  30

Arg Leu Cys Cys Gly Arg Ala Glu Arg Gly Gly His Trp Tyr Lys Glu
        35                  40                  45

Gly Ser Arg Leu Ala Pro Ala Gly Arg Val Arg Gly Trp Arg Gly Arg
    50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ser Leu Thr Ser Ser Asn Asp Asp Glu Asp Pro Lys Ser His
            100                 105                 110

Arg Asp Pro Ser Asn Arg His Ser Tyr Pro Gln Gln Ala Pro Tyr Trp
        115                 120                 125

Thr His Pro Gln Arg Met Glu Lys Lys Leu His Ala Val Pro Ala Gly
    130                 135                 140

Asn Thr Val Lys Phe Arg Cys Pro Ala Ala Gly Asn Pro Thr Pro Thr
145                 150                 155                 160

Ile Arg Trp Leu Lys Asp Gly Gln Ala Phe His Gly Glu Asn Arg Ile
                165                 170                 175

Gly Gly Ile Arg Leu Arg His Gln His Trp Ser Leu Val Met Glu Ser
            180                 185                 190

Val Val Pro Ser Asp Arg Gly Thr Tyr Thr Cys Leu Val Glu Asn Ala
        195                 200                 205

Val Gly Ser Ile Arg Tyr Asn Tyr Leu Leu Asp Val Leu Glu Arg Ser
    210                 215                 220

Pro His Arg Pro Ile Leu Gln Ala Gly Leu Pro Ala Asn Thr Thr Ala
225                 230                 235                 240

Val Val Gly Ser Asp Val Glu Leu Leu Cys Lys Val Tyr Ser Asp Ala
                245                 250                 255
```

```
Gln Pro His Ile Gln Trp Leu Lys His Ile Val Ile Asn Gly Ser Ser
                260                 265                 270

Phe Gly Ala Asp Gly Phe Pro Tyr Val Gln Val Leu Lys Thr Ala Asp
            275                 280                 285

Ile Asn Ser Ser Glu Val Glu Val Leu Tyr Leu Arg Asn Val Ser Ala
        290                 295                 300

Glu Asp Ala Gly Glu Tyr Thr Cys Leu Ala Gly Asn Ser Ile Gly Leu
305                 310                 315                 320

Ser Tyr Gln Ser Ala Trp Leu Thr Val Leu Pro Glu Glu Asp Pro Thr
                325                 330                 335

Trp Thr Ala Ala Ala Pro Glu Ala Arg Tyr Thr Asp Glu Pro Lys Ser
            340                 345                 350

Ser Asp Lys Thr His Thr Cys Pro Pro Cys Pro Ala Pro Glu Leu Leu
        355                 360                 365

Gly Gly Pro Ser Val Phe Leu Phe Pro Pro Lys Pro Lys Asp Thr Leu
370                 375                 380

Met Ile Ser Arg Thr Pro Glu Val Thr Cys Val Val Val Asp Val Ser
385                 390                 395                 400

His Glu Asp Pro Glu Val Lys Phe Asn Trp Tyr Val Asp Gly Val Glu
                405                 410                 415

Val His Asn Ala Lys Thr Lys Pro Arg Glu Glu Gln Tyr Asn Ser Thr
            420                 425                 430

Tyr Arg Val Val Ser Val Leu Thr Val Leu His Gln Asp Trp Leu Asn
        435                 440                 445

Gly Lys Glu Tyr Lys Cys Lys Val Ser Asn Lys Ala Leu Pro Ala Pro
450                 455                 460

Ile Glu Lys Thr Ile Ser Lys Ala Lys Gly Gln Pro Arg Glu Pro Gln
465                 470                 475                 480

Val Tyr Thr Leu Pro Pro Ser Arg Asp Glu Leu Thr Lys Asn Gln Val
                485                 490                 495

Ser Leu Thr Cys Leu Val Lys Gly Phe Tyr Pro Ser Asp Ile Ala Val
            500                 505                 510

Glu Trp Glu Ser Asn Gly Gln Pro Glu Asn Asn Tyr Lys Thr Thr Pro
        515                 520                 525

Pro Val Leu Asp Ser Asp Gly Ser Phe Phe Leu Tyr Ser Lys Leu Thr
530                 535                 540

Val Asp Lys Ser Arg Trp Gln Gln Gly Asn Val Phe Ser Cys Ser Val
545                 550                 555                 560

Met His Glu Ala Leu His Asn His Tyr Thr Gln Lys Ser Leu Ser Leu
                565                 570                 575

Ser Pro Gly Lys
            580

<210> SEQ ID NO 6
<211> LENGTH: 343
<212> TYPE: PRT
<213> ORGANISM: Artificial Sequence
<220> FEATURE:
<223> OTHER INFORMATION: Synthetic sequence

<400> SEQUENCE: 6

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
            20                  25                  30

Arg Leu Cys Cys Gly Arg Ala Glu Arg Gly Gly His Trp Tyr Lys Glu
```

```
            35                  40                  45
Gly Ser Arg Leu Ala Pro Ala Gly Arg Val Arg Gly Trp Arg Gly Arg
 50                  55                  60

Leu Glu Ile Ala Ser Phe Leu Pro Glu Asp Ala Gly Arg Tyr Leu Cys
 65                  70                  75                  80

Leu Ala Arg Gly Ser Met Ile Val Leu Gln Asn Leu Thr Leu Ile Thr
                 85                  90                  95

Gly Asp Ser Leu Thr Ser Ser Asn Asp Asp Glu Asp Pro Lys Ser His
                100                 105                 110

Arg Asp Pro Ser Asn Arg His Ser Tyr Pro Gln Gln Ala Pro Tyr Trp
            115                 120                 125

Thr His Pro Gln Arg Met Glu Lys Lys Leu His Ala Val Pro Ala Gly
            130                 135                 140

Asn Thr Val Lys Phe Arg Cys Pro Ala Ala Gly Asn Pro Thr Pro Thr
145                 150                 155                 160

Ile Arg Trp Leu Lys Asp Gly Gln Ala Phe His Gly Glu Asn Arg Ile
                165                 170                 175

Gly Gly Ile Arg Leu Arg His Gln His Trp Ser Leu Val Met Glu Ser
            180                 185                 190

Val Val Pro Ser Asp Arg Gly Thr Tyr Thr Cys Leu Val Glu Asn Ala
            195                 200                 205

Val Gly Ser Ile Arg Tyr Asn Tyr Leu Leu Asp Val Leu Glu Arg Ser
        210                 215                 220

Pro His Arg Pro Ile Leu Gln Ala Gly Leu Pro Ala Asn Thr Thr Ala
225                 230                 235                 240

Val Val Gly Ser Asp Val Glu Leu Leu Cys Lys Val Tyr Ser Asp Ala
                245                 250                 255

Gln Pro His Ile Gln Trp Leu Lys His Ile Val Ile Asn Gly Ser Ser
            260                 265                 270

Phe Gly Ala Asp Gly Phe Pro Tyr Val Gln Val Leu Lys Thr Ala Asp
        275                 280                 285

Ile Asn Ser Ser Glu Val Glu Val Leu Tyr Leu Arg Asn Val Ser Ala
290                 295                 300

Glu Asp Ala Gly Glu Tyr Thr Cys Leu Ala Gly Asn Ser Ile Gly Leu
305                 310                 315                 320

Ser Tyr Gln Ser Ala Trp Leu Thr Val Leu Pro Glu Glu Asp Pro Thr
                325                 330                 335

Trp Thr Ala Ala Ala Pro Glu
            340

<210> SEQ ID NO 7
<211> LENGTH: 337
<212> TYPE: PRT
<213> ORGANISM: Artificial Sequence
<220> FEATURE:
<223> OTHER INFORMATION: Synthetic sequence

<400> SEQUENCE: 7

Leu Glu Ala Ser Glu Glu Val Glu Leu Glu Pro Cys Leu Ala Pro Ser
 1               5                  10                  15

Leu Glu Gln Gln Glu Gln Glu Leu Thr Val Ala Leu Gly Gln Pro Val
                20                  25                  30

Arg Leu Cys Cys Gly Arg Ala Glu Arg Gly Gly His Trp Tyr Lys Glu
            35                  40                  45

Gly Ser Arg Leu Ala Pro Ala Gly Arg Val Arg Gly Trp Arg Gly Arg
 50                  55                  60
```

```
Leu Glu Ile Ala Ser Phe Leu Pro Glu Asp Ala Gly Arg Tyr Leu Cys
 65                  70                  75                  80

Leu Ala Arg Gly Ser Met Ile Val Leu Gln Asn Leu Thr Leu Ile Thr
                 85                  90                  95

Gly Asp Ser Leu Thr Ser Ser Asn Asp Asp Glu Asp Pro Lys Ser His
                100                 105                 110

Arg Asp Pro Ser Asn Arg His Ser Tyr Pro Gln Gln Ala Pro Tyr Trp
            115                 120                 125

Thr His Pro Gln Arg Met Glu Lys Lys Leu His Ala Val Pro Ala Gly
        130                 135                 140

Asn Thr Val Lys Phe Arg Cys Pro Ala Ala Gly Asn Pro Thr Pro Thr
145                 150                 155                 160

Ile Arg Trp Leu Lys Asp Gly Gln Ala Phe His Gly Glu Asn Arg Ile
                165                 170                 175

Gly Gly Ile Arg Leu Arg His Gln His Trp Ser Leu Val Met Glu Ser
            180                 185                 190

Val Val Pro Ser Asp Arg Gly Thr Tyr Thr Cys Leu Val Glu Asn Ala
        195                 200                 205

Val Gly Ser Ile Arg Tyr Asn Tyr Leu Leu Asp Val Leu Glu Arg Ser
210                 215                 220

Pro His Arg Pro Ile Leu Gln Ala Gly Leu Pro Ala Asn Thr Thr Ala
225                 230                 235                 240

Val Val Gly Ser Asp Val Glu Leu Leu Cys Lys Val Tyr Ser Asp Ala
                245                 250                 255

Gln Pro His Ile Gln Trp Leu Lys His Ile Val Ile Asn Gly Ser Ser
            260                 265                 270

Phe Gly Ala Asp Gly Phe Pro Tyr Val Gln Val Leu Lys Thr Ala Asp
        275                 280                 285

Ile Asn Ser Ser Glu Val Glu Val Leu Tyr Leu Arg Asn Val Ser Ala
290                 295                 300

Glu Asp Ala Gly Glu Tyr Thr Cys Leu Ala Gly Asn Ser Ile Gly Leu
305                 310                 315                 320

Ser Tyr Gln Ser Ala Trp Leu Thr Val Leu Pro Glu Glu Asp Pro Thr
                325                 330                 335

Trp
```

<210> SEQ ID NO 8
<211> LENGTH: 333
<212> TYPE: PRT
<213> ORGANISM: Artificial Sequence
<220> FEATURE:
<223> OTHER INFORMATION: Synthetic sequence

<400> SEQUENCE: 8

```
Leu Glu Ala Ser Glu Glu Val Glu Leu Glu Pro Cys Leu Ala Pro Ser
 1               5                  10                  15

Leu Glu Gln Gln Glu Gln Glu Leu Thr Val Ala Leu Gly Gln Pro Val
                20                  25                  30

Arg Leu Cys Cys Gly Arg Ala Glu Arg Gly Gly His Trp Tyr Lys Glu
            35                  40                  45

Gly Ser Arg Leu Ala Pro Ala Gly Arg Val Arg Gly Trp Arg Gly Arg
        50                  55                  60

Leu Glu Ile Ala Ser Phe Leu Pro Glu Asp Ala Gly Arg Tyr Leu Cys
 65                  70                  75                  80

Leu Ala Arg Gly Ser Met Ile Val Leu Gln Asn Leu Thr Leu Ile Thr
```

```
                      85                  90                  95
Gly Asp Ser Leu Thr Ser Ser Asn Asp Glu Asp Pro Lys Ser His
                100                 105                 110

Arg Asp Pro Ser Asn Arg His Ser Tyr Pro Gln Gln Ala Pro Tyr Trp
            115                 120                 125

Thr His Pro Gln Arg Met Glu Lys Lys Leu His Ala Val Pro Ala Gly
        130                 135                 140

Asn Thr Val Lys Phe Arg Cys Pro Ala Ala Gly Asn Pro Thr Pro Thr
145                 150                 155                 160

Ile Arg Trp Leu Lys Asp Gly Gln Ala Phe His Gly Glu Asn Arg Ile
                165                 170                 175

Gly Gly Ile Arg Leu Arg His Gln His Trp Ser Leu Val Met Glu Ser
            180                 185                 190

Val Val Pro Ser Asp Arg Gly Thr Tyr Thr Cys Leu Val Glu Asn Ala
        195                 200                 205

Val Gly Ser Ile Arg Tyr Asn Tyr Leu Leu Asp Val Leu Glu Arg Ser
210                 215                 220

Pro His Arg Pro Ile Leu Gln Ala Gly Leu Pro Ala Asn Thr Thr Ala
225                 230                 235                 240

Val Val Gly Ser Asp Val Glu Leu Leu Cys Lys Val Tyr Ser Asp Ala
            245                 250                 255

Gln Pro His Ile Gln Trp Leu Lys His Ile Val Ile Asn Gly Ser Ser
        260                 265                 270

Phe Gly Ala Asp Gly Phe Pro Tyr Val Gln Val Leu Lys Thr Ala Asp
    275                 280                 285

Ile Asn Ser Ser Glu Val Glu Val Leu Tyr Leu Arg Asn Val Ser Ala
290                 295                 300

Glu Asp Ala Gly Glu Tyr Thr Cys Leu Ala Gly Asn Ser Ile Gly Leu
305                 310                 315                 320

Ser Tyr Gln Ser Ala Trp Leu Thr Val Leu Pro Glu Glu
                325                 330

<210> SEQ ID NO 9
<211> LENGTH: 331
<212> TYPE: PRT
<213> ORGANISM: Artificial Sequence
<220> FEATURE:
<223> OTHER INFORMATION: Synthetic sequence

<400> SEQUENCE: 9

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
            20                  25                  30

Arg Leu Cys Cys Gly Arg Ala Glu Arg Gly Gly His Trp Tyr Lys Glu
        35                  40                  45

Gly Ser Arg Leu Ala Pro Ala Gly Arg Val Arg Gly Trp Arg Gly Arg
    50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ser Leu Thr Ser Ser Asn Asp Asp Glu Asp Pro Lys Ser His
            100                 105                 110

Arg Asp Pro Ser Asn Arg His Ser Tyr Pro Gln Gln Ala Pro Tyr Trp
        115                 120                 125
```

```
Thr His Pro Gln Arg Met Glu Lys Lys Leu His Ala Val Pro Ala Gly
        130                 135                 140

Asn Thr Val Lys Phe Arg Cys Pro Ala Ala Gly Asn Pro Thr Pro Thr
145                 150                 155                 160

Ile Arg Trp Leu Lys Asp Gly Gln Ala Phe His Gly Glu Asn Arg Ile
                165                 170                 175

Gly Gly Ile Arg Leu Arg His Gln His Trp Ser Leu Val Met Glu Ser
                180                 185                 190

Val Val Pro Ser Asp Arg Gly Thr Tyr Thr Cys Leu Val Glu Asn Ala
                195                 200                 205

Val Gly Ser Ile Arg Tyr Asn Tyr Leu Leu Asp Val Leu Glu Arg Ser
        210                 215                 220

Pro His Arg Pro Ile Leu Gln Ala Gly Leu Pro Ala Asn Thr Thr Ala
225                 230                 235                 240

Val Val Gly Ser Asp Val Glu Leu Leu Cys Lys Val Tyr Ser Asp Ala
                245                 250                 255

Gln Pro His Ile Gln Trp Leu Lys His Ile Val Ile Asn Gly Ser Ser
                260                 265                 270

Phe Gly Ala Asp Gly Phe Pro Tyr Val Gln Val Leu Lys Thr Ala Asp
                275                 280                 285

Ile Asn Ser Ser Glu Val Glu Val Leu Tyr Leu Arg Asn Val Ser Ala
        290                 295                 300

Glu Asp Ala Gly Glu Tyr Thr Cys Leu Ala Gly Asn Ser Ile Gly Leu
305                 310                 315                 320

Ser Tyr Gln Ser Ala Trp Leu Thr Val Leu Pro
                325                 330

<210> SEQ ID NO 10
<211> LENGTH: 330
<212> TYPE: PRT
<213> ORGANISM: Artificial Sequence
<220> FEATURE:
<223> OTHER INFORMATION: Synthetic sequence

<400> SEQUENCE: 10

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
                20                  25                  30

Arg Leu Cys Cys Gly Arg Ala Glu Arg Gly Gly His Trp Tyr Lys Glu
                35                  40                  45

Gly Ser Arg Leu Ala Pro Ala Gly Arg Val Arg Gly Trp Arg Gly Arg
        50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ser Leu Thr Ser Ser Asn Asp Asp Glu Asp Pro Lys Ser His
                100                 105                 110

Arg Asp Pro Ser Asn Arg His Ser Tyr Pro Gln Gln Ala Pro Tyr Trp
                115                 120                 125

Thr His Pro Gln Arg Met Glu Lys Lys Leu His Ala Val Pro Ala Gly
        130                 135                 140

Asn Thr Val Lys Phe Arg Cys Pro Ala Ala Gly Asn Pro Thr Pro Thr
145                 150                 155                 160
```

```
Ile Arg Trp Leu Lys Asp Gly Gln Ala Phe His Gly Glu Asn Arg Ile
            165                 170                 175

Gly Gly Ile Arg Leu Arg His Gln His Trp Ser Leu Val Met Glu Ser
            180                 185                 190

Val Val Pro Ser Asp Arg Gly Thr Tyr Thr Cys Leu Val Glu Asn Ala
            195                 200                 205

Val Gly Ser Ile Arg Tyr Asn Tyr Leu Leu Asp Val Leu Glu Arg Ser
            210                 215                 220

Pro His Arg Pro Ile Leu Gln Ala Gly Leu Pro Ala Asn Thr Thr Ala
225                 230                 235                 240

Val Val Gly Ser Asp Val Glu Leu Leu Cys Lys Val Tyr Ser Asp Ala
            245                 250                 255

Gln Pro His Ile Gln Trp Leu Lys His Ile Val Ile Asn Gly Ser Ser
            260                 265                 270

Phe Gly Ala Asp Gly Phe Pro Tyr Val Gln Val Leu Lys Thr Ala Asp
            275                 280                 285

Ile Asn Ser Ser Glu Val Glu Val Leu Tyr Leu Arg Asn Val Ser Ala
            290                 295                 300

Glu Asp Ala Gly Glu Tyr Thr Cys Leu Ala Gly Asn Ser Ile Gly Leu
305                 310                 315                 320

Ser Tyr Gln Ser Ala Trp Leu Thr Val Leu
            325                 330

<210> SEQ ID NO 11
<211> LENGTH: 575
<212> TYPE: PRT
<213> ORGANISM: Artificial Sequence
<220> FEATURE:
<223> OTHER INFORMATION: Synthetic sequence

<400> SEQUENCE: 11

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
            20                  25                  30

Arg Leu Cys Cys Gly Arg Ala Glu Arg Gly Gly His Trp Tyr Lys Glu
            35                  40                  45

Gly Ser Arg Leu Ala Pro Ala Gly Arg Val Arg Gly Trp Arg Gly Arg
            50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
            85                  90                  95

Gly Asp Ser Leu Thr Ser Ser Asn Asp Asp Glu Asp Pro Lys Ser His
            100                 105                 110

Arg Asp Pro Ser Asn Arg His Ser Tyr Pro Gln Gln Ala Pro Tyr Trp
            115                 120                 125

Thr His Pro Gln Arg Met Glu Lys Lys Leu His Ala Val Pro Ala Gly
            130                 135                 140

Asn Thr Val Lys Phe Arg Cys Pro Ala Ala Gly Asn Pro Thr Pro Thr
145                 150                 155                 160

Ile Arg Trp Leu Lys Asp Gly Gln Ala Phe His Gly Glu Asn Arg Ile
            165                 170                 175

Gly Gly Ile Arg Leu Arg His Gln His Trp Ser Leu Val Met Glu Ser
            180                 185                 190

Val Val Pro Ser Asp Arg Gly Thr Tyr Thr Cys Leu Val Glu Asn Ala
```

```
            195                 200                 205
Val Gly Ser Ile Arg Tyr Asn Tyr Leu Leu Asp Val Leu Glu Arg Ser
210                 215                 220

Pro His Arg Pro Ile Leu Gln Ala Gly Leu Pro Ala Asn Thr Thr Ala
225                 230                 235                 240

Val Val Gly Ser Asp Val Glu Leu Leu Cys Lys Val Tyr Ser Asp Ala
                245                 250                 255

Gln Pro His Ile Gln Trp Leu Lys His Ile Val Ile Asn Gly Ser Ser
                260                 265                 270

Phe Gly Ala Asp Gly Phe Pro Tyr Val Gln Val Leu Lys Thr Ala Asp
                275                 280                 285

Ile Asn Ser Ser Glu Val Glu Val Leu Tyr Leu Arg Asn Val Ser Ala
            290                 295                 300

Glu Asp Ala Gly Glu Tyr Thr Cys Leu Ala Gly Asn Ser Ile Gly Leu
305                 310                 315                 320

Ser Tyr Gln Ser Ala Trp Leu Thr Val Leu Pro Glu Glu Asp Pro Thr
                325                 330                 335

Trp Thr Ala Ala Ala Pro Glu Glu Pro Lys Ser Ser Asp Lys Thr His
                340                 345                 350

Thr Cys Pro Pro Cys Pro Ala Pro Glu Leu Leu Gly Gly Pro Ser Val
            355                 360                 365

Phe Leu Phe Pro Pro Lys Pro Lys Asp Thr Leu Met Ile Ser Arg Thr
370                 375                 380

Pro Glu Val Thr Cys Val Val Val Asp Val Ser His Glu Asp Pro Glu
385                 390                 395                 400

Val Lys Phe Asn Trp Tyr Val Asp Gly Val Glu Val His Asn Ala Lys
                405                 410                 415

Thr Lys Pro Arg Glu Glu Gln Tyr Asn Ser Thr Tyr Arg Val Val Ser
                420                 425                 430

Val Leu Thr Val Leu His Gln Asp Trp Leu Asn Gly Lys Glu Tyr Lys
            435                 440                 445

Cys Lys Val Ser Asn Lys Ala Leu Pro Ala Pro Ile Glu Lys Thr Ile
450                 455                 460

Ser Lys Ala Lys Gly Gln Pro Arg Glu Pro Gln Val Tyr Thr Leu Pro
465                 470                 475                 480

Pro Ser Arg Asp Glu Leu Thr Lys Asn Gln Val Ser Leu Thr Cys Leu
                485                 490                 495

Val Lys Gly Phe Tyr Pro Ser Asp Ile Ala Val Glu Trp Glu Ser Asn
                500                 505                 510

Gly Gln Pro Glu Asn Asn Tyr Lys Thr Thr Pro Pro Val Leu Asp Ser
            515                 520                 525

Asp Gly Ser Phe Phe Leu Tyr Ser Lys Leu Thr Val Asp Lys Ser Arg
530                 535                 540

Trp Gln Gln Gly Asn Val Phe Ser Cys Ser Val Met His Glu Ala Leu
545                 550                 555                 560

His Asn His Tyr Thr Gln Lys Ser Leu Ser Leu Ser Pro Gly Lys
                565                 570                 575

<210> SEQ ID NO 12
<211> LENGTH: 570
<212> TYPE: PRT
<213> ORGANISM: Artificial Sequence
<220> FEATURE:
<223> OTHER INFORMATION: Synthetic sequence

<400> SEQUENCE: 12
```

```
Leu Glu Ala Ser Glu Glu Val Glu Leu Glu Pro Cys Leu Ala Pro Ser
1               5                   10                  15

Leu Glu Gln Gln Glu Gln Leu Thr Val Ala Leu Gly Gln Pro Val
            20                  25                  30

Arg Leu Cys Cys Gly Arg Ala Glu Arg Gly Gly His Trp Tyr Lys Glu
            35                  40                  45

Gly Ser Arg Leu Ala Pro Ala Gly Arg Val Arg Gly Trp Arg Gly Arg
        50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ser Leu Thr Ser Ser Asn Asp Asp Glu Asp Pro Lys Ser His
            100                 105                 110

Arg Asp Pro Ser Asn Arg His Ser Tyr Pro Gln Gln Ala Pro Tyr Trp
            115                 120                 125

Thr His Pro Gln Arg Met Glu Lys Lys Leu His Ala Val Pro Ala Gly
        130                 135                 140

Asn Thr Val Lys Phe Arg Cys Pro Ala Ala Gly Asn Pro Thr Pro Thr
145                 150                 155                 160

Ile Arg Trp Leu Lys Asp Gly Gln Ala Phe His Gly Glu Asn Arg Ile
                165                 170                 175

Gly Gly Ile Arg Leu Arg His Gln His Trp Ser Leu Val Met Glu Ser
            180                 185                 190

Val Val Pro Ser Asp Arg Gly Thr Tyr Thr Cys Leu Val Glu Asn Ala
        195                 200                 205

Val Gly Ser Ile Arg Tyr Asn Tyr Leu Leu Asp Val Leu Glu Arg Ser
        210                 215                 220

Pro His Arg Pro Ile Leu Gln Ala Gly Leu Pro Ala Asn Thr Thr Ala
225                 230                 235                 240

Val Val Gly Ser Asp Val Glu Leu Leu Cys Lys Val Tyr Ser Asp Ala
            245                 250                 255

Gln Pro His Ile Gln Trp Leu Lys His Ile Val Ile Asn Gly Ser Ser
            260                 265                 270

Phe Gly Ala Asp Gly Phe Pro Tyr Val Gln Val Leu Lys Thr Ala Asp
        275                 280                 285

Ile Asn Ser Ser Glu Val Glu Val Leu Tyr Leu Arg Asn Val Ser Ala
        290                 295                 300

Glu Asp Ala Gly Glu Tyr Thr Cys Leu Ala Gly Asn Ser Ile Gly Leu
305                 310                 315                 320

Ser Tyr Gln Ser Ala Trp Leu Thr Val Leu Pro Glu Glu Asp Pro Thr
            325                 330                 335

Trp Thr Glu Pro Lys Ser Ser Asp Lys Thr His Thr Cys Pro Pro Cys
            340                 345                 350

Pro Ala Pro Glu Leu Leu Gly Gly Pro Ser Val Phe Leu Phe Pro Pro
        355                 360                 365

Lys Pro Lys Asp Thr Leu Met Ile Ser Arg Thr Pro Glu Val Thr Cys
    370                 375                 380

Val Val Val Asp Val Ser His Glu Asp Pro Glu Val Lys Phe Asn Trp
385                 390                 395                 400

Tyr Val Asp Gly Val Glu Val His Asn Ala Lys Thr Lys Pro Arg Glu
                405                 410                 415

Glu Gln Tyr Asn Ser Thr Tyr Arg Val Val Ser Val Leu Thr Val Leu
```

```
                         420                 425                 430
His Gln Asp Trp Leu Asn Gly Lys Glu Tyr Lys Cys Lys Val Ser Asn
            435                 440                 445
Lys Ala Leu Pro Ala Pro Ile Glu Lys Thr Ile Ser Lys Ala Lys Gly
        450                 455                 460
Gln Pro Arg Glu Pro Gln Val Tyr Thr Leu Pro Pro Ser Arg Asp Glu
465                 470                 475                 480
Leu Thr Lys Asn Gln Val Ser Leu Thr Cys Leu Val Lys Gly Phe Tyr
                485                 490                 495
Pro Ser Asp Ile Ala Val Glu Trp Glu Ser Asn Gly Gln Pro Glu Asn
            500                 505                 510
Asn Tyr Lys Thr Thr Pro Pro Val Leu Asp Ser Asp Gly Ser Phe Phe
        515                 520                 525
Leu Tyr Ser Lys Leu Thr Val Asp Lys Ser Arg Trp Gln Gln Gly Asn
530                 535                 540
Val Phe Ser Cys Ser Val Met His Glu Ala Leu His Asn His Tyr Thr
545                 550                 555                 560
Gln Lys Ser Leu Ser Leu Ser Pro Gly Lys
                565                 570

<210> SEQ ID NO 13
<211> LENGTH: 565
<212> TYPE: PRT
<213> ORGANISM: Artificial Sequence
<220> FEATURE:
<223> OTHER INFORMATION: Synthetic sequence

<400> SEQUENCE: 13

Leu Glu Ala Ser Glu Glu Val Glu Leu Glu Pro Cys Leu Ala Pro Ser
1               5                   10                  15
Leu Glu Gln Gln Glu Gln Glu Leu Thr Val Ala Leu Gly Gln Pro Val
            20                  25                  30
Arg Leu Cys Cys Gly Arg Ala Glu Arg Gly Gly His Trp Tyr Lys Glu
        35                  40                  45
Gly Ser Arg Leu Ala Pro Ala Gly Arg Val Arg Gly Trp Arg Gly Arg
    50                  55                  60
Leu Glu Ile Ala Ser Phe Leu Pro Glu Asp Ala Gly Arg Tyr Leu Cys
65                  70                  75                  80
Leu Ala Arg Gly Ser Met Ile Val Leu Gln Asn Leu Thr Leu Ile Thr
                85                  90                  95
Gly Asp Ser Leu Thr Ser Ser Asn Asp Asp Glu Asp Pro Lys Ser His
            100                 105                 110
Arg Asp Pro Ser Asn Arg His Ser Tyr Pro Gln Gln Ala Pro Tyr Trp
        115                 120                 125
Thr His Pro Gln Arg Met Glu Lys Lys Leu His Ala Val Pro Ala Gly
    130                 135                 140
Asn Thr Val Lys Phe Arg Cys Pro Ala Ala Gly Asn Pro Thr Pro Thr
145                 150                 155                 160
Ile Arg Trp Leu Lys Asp Gly Gln Ala Phe His Gly Glu Asn Arg Ile
                165                 170                 175
Gly Gly Ile Arg Leu Arg His Gln His Trp Ser Leu Val Met Glu Ser
            180                 185                 190
Val Val Pro Ser Asp Arg Gly Thr Tyr Thr Cys Leu Val Glu Asn Ala
        195                 200                 205
Val Gly Ser Ile Arg Tyr Asn Tyr Leu Leu Asp Val Leu Glu Arg Ser
    210                 215                 220
```

```
Pro His Arg Pro Ile Leu Gln Ala Gly Leu Pro Ala Asn Thr Thr Ala
225                 230                 235                 240
Val Val Gly Ser Asp Val Glu Leu Leu Cys Lys Val Tyr Ser Asp Ala
                245                 250                 255
Gln Pro His Ile Gln Trp Leu Lys His Ile Val Ile Asn Gly Ser Ser
            260                 265                 270
Phe Gly Ala Asp Gly Phe Pro Tyr Val Gln Val Leu Lys Thr Ala Asp
        275                 280                 285
Ile Asn Ser Ser Glu Val Glu Val Leu Tyr Leu Arg Asn Val Ser Ala
    290                 295                 300
Glu Asp Ala Gly Glu Tyr Thr Cys Leu Ala Gly Asn Ser Ile Gly Leu
305                 310                 315                 320
Ser Tyr Gln Ser Ala Trp Leu Thr Val Leu Pro Glu Glu Pro Lys
                325                 330                 335
Ser Ser Asp Lys Thr His Thr Cys Pro Pro Cys Pro Ala Pro Glu Leu
                340                 345                 350
Leu Gly Gly Pro Ser Val Phe Leu Phe Pro Pro Lys Pro Lys Asp Thr
                355                 360                 365
Leu Met Ile Ser Arg Thr Pro Glu Val Thr Cys Val Val Val Asp Val
370                 375                 380
Ser His Glu Asp Pro Glu Val Lys Phe Asn Trp Tyr Val Asp Gly Val
385                 390                 395                 400
Glu Val His Asn Ala Lys Thr Lys Pro Arg Glu Glu Gln Tyr Asn Ser
                405                 410                 415
Thr Tyr Arg Val Val Ser Val Leu Thr Val Leu His Gln Asp Trp Leu
                420                 425                 430
Asn Gly Lys Glu Tyr Lys Cys Lys Val Ser Asn Lys Ala Leu Pro Ala
            435                 440                 445
Pro Ile Glu Lys Thr Ile Ser Lys Ala Lys Gly Gln Pro Arg Glu Pro
        450                 455                 460
Gln Val Tyr Thr Leu Pro Pro Ser Arg Asp Glu Leu Thr Lys Asn Gln
465                 470                 475                 480
Val Ser Leu Thr Cys Leu Val Lys Gly Phe Tyr Pro Ser Asp Ile Ala
                485                 490                 495
Val Glu Trp Glu Ser Asn Gly Gln Pro Glu Asn Asn Tyr Lys Thr Thr
                500                 505                 510
Pro Pro Val Leu Asp Ser Asp Gly Ser Phe Phe Leu Tyr Ser Lys Leu
            515                 520                 525
Thr Val Asp Lys Ser Arg Trp Gln Gln Gly Asn Val Phe Ser Cys Ser
        530                 535                 540
Val Met His Glu Ala Leu His Asn His Tyr Thr Gln Lys Ser Leu Ser
545                 550                 555                 560
Leu Ser Pro Gly Lys
                565

<210> SEQ ID NO 14
<211> LENGTH: 563
<212> TYPE: PRT
<213> ORGANISM: Artificial Sequence
<220> FEATURE:
<223> OTHER INFORMATION: Synthetic sequence

<400> SEQUENCE: 14

Leu Glu Ala Ser Glu Glu Val Glu Leu Glu Pro Cys Leu Ala Pro Ser
1               5                   10                  15
```

```
Leu Glu Gln Gln Glu Gln Glu Leu Thr Val Ala Leu Gly Gln Pro Val
                 20                  25                  30

Arg Leu Cys Cys Gly Arg Ala Glu Arg Gly Gly His Trp Tyr Lys Glu
         35                  40                  45

Gly Ser Arg Leu Ala Pro Ala Gly Arg Val Arg Gly Trp Arg Gly Arg
 50                  55                  60

Leu Glu Ile Ala Ser Phe Leu Pro Glu Asp Ala Gly Arg Tyr Leu Cys
 65                  70                  75                  80

Leu Ala Arg Gly Ser Met Ile Val Leu Gln Asn Leu Thr Leu Ile Thr
                 85                  90                  95

Gly Asp Ser Leu Thr Ser Ser Asn Asp Asp Glu Asp Pro Lys Ser His
                100                 105                 110

Arg Asp Pro Ser Asn Arg His Ser Tyr Pro Gln Gln Ala Pro Tyr Trp
                115                 120                 125

Thr His Pro Gln Arg Met Glu Lys Lys Leu His Ala Val Pro Ala Gly
                130                 135                 140

Asn Thr Val Lys Phe Arg Cys Pro Ala Ala Gly Asn Pro Thr Pro Thr
145                 150                 155                 160

Ile Arg Trp Leu Lys Asp Gly Gln Ala Phe His Gly Glu Asn Arg Ile
                165                 170                 175

Gly Gly Ile Arg Leu Arg His Gln His Trp Ser Leu Val Met Glu Ser
                180                 185                 190

Val Val Pro Ser Asp Arg Gly Thr Tyr Thr Cys Leu Val Glu Asn Ala
                195                 200                 205

Val Gly Ser Ile Arg Tyr Asn Tyr Leu Leu Asp Val Leu Glu Arg Ser
210                 215                 220

Pro His Arg Pro Ile Leu Gln Ala Gly Leu Pro Ala Asn Thr Thr Ala
225                 230                 235                 240

Val Val Gly Ser Asp Val Glu Leu Leu Cys Lys Val Tyr Ser Asp Ala
                245                 250                 255

Gln Pro His Ile Gln Trp Leu Lys His Ile Val Ile Asn Gly Ser Ser
                260                 265                 270

Phe Gly Ala Asp Gly Phe Pro Tyr Val Gln Val Leu Lys Thr Ala Asp
                275                 280                 285

Ile Asn Ser Ser Glu Val Glu Val Leu Tyr Leu Arg Asn Val Ser Ala
290                 295                 300

Glu Asp Ala Gly Glu Tyr Thr Cys Leu Ala Gly Asn Ser Ile Gly Leu
305                 310                 315                 320

Ser Tyr Gln Ser Ala Trp Leu Thr Val Leu Pro Glu Pro Lys Ser Ser
                325                 330                 335

Asp Lys Thr His Thr Cys Pro Pro Cys Pro Ala Pro Glu Leu Leu Gly
                340                 345                 350

Gly Pro Ser Val Phe Leu Phe Pro Pro Lys Pro Lys Asp Thr Leu Met
                355                 360                 365

Ile Ser Arg Thr Pro Glu Val Thr Cys Val Val Val Asp Val Ser His
                370                 375                 380

Glu Asp Pro Glu Val Lys Phe Asn Trp Tyr Val Asp Gly Val Glu Val
385                 390                 395                 400

His Asn Ala Lys Thr Lys Pro Arg Glu Glu Gln Tyr Asn Ser Thr Tyr
                405                 410                 415

Arg Val Val Ser Val Leu Thr Val Leu His Gln Asp Trp Leu Asn Gly
                420                 425                 430

Lys Glu Tyr Lys Cys Lys Val Ser Asn Lys Ala Leu Pro Ala Pro Ile
                435                 440                 445
```

```
Glu Lys Thr Ile Ser Lys Ala Lys Gly Gln Pro Arg Glu Pro Gln Val
    450                 455                 460

Tyr Thr Leu Pro Pro Ser Arg Asp Glu Leu Thr Lys Asn Gln Val Ser
465                 470                 475                 480

Leu Thr Cys Leu Val Lys Gly Phe Tyr Pro Ser Asp Ile Ala Val Glu
                485                 490                 495

Trp Glu Ser Asn Gly Gln Pro Glu Asn Asn Tyr Lys Thr Thr Pro Pro
                500                 505                 510

Val Leu Asp Ser Asp Gly Ser Phe Phe Leu Tyr Ser Lys Leu Thr Val
                515                 520                 525

Asp Lys Ser Arg Trp Gln Gln Gly Asn Val Phe Ser Cys Ser Val Met
530                 535                 540

His Glu Ala Leu His Asn His Tyr Thr Gln Lys Ser Leu Ser Leu Ser
545                 550                 555                 560

Pro Gly Lys

<210> SEQ ID NO 15
<211> LENGTH: 562
<212> TYPE: PRT
<213> ORGANISM: Artificial Sequence
<220> FEATURE:
<223> OTHER INFORMATION: Synthetic sequence

<400> SEQUENCE: 15

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
                20                  25                  30

Arg Leu Cys Cys Gly Arg Ala Glu Arg Gly Gly His Trp Tyr Lys Glu
                35                  40                  45

Gly Ser Arg Leu Ala Pro Ala Gly Arg Val Arg Gly Trp Arg Gly Arg
    50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ser Leu Thr Ser Ser Asn Asp Asp Glu Asp Pro Lys Ser His
                100                 105                 110

Arg Asp Pro Ser Asn Arg His Ser Tyr Pro Gln Gln Ala Pro Tyr Trp
                115                 120                 125

Thr His Pro Gln Arg Met Glu Lys Lys Leu His Ala Val Pro Ala Gly
    130                 135                 140

Asn Thr Val Lys Phe Arg Cys Pro Ala Ala Gly Asn Pro Thr Pro Thr
145                 150                 155                 160

Ile Arg Trp Leu Lys Asp Gly Gln Ala Phe His Gly Glu Asn Arg Ile
                165                 170                 175

Gly Gly Ile Arg Leu Arg His Gln His Trp Ser Leu Val Met Glu Ser
                180                 185                 190

Val Val Pro Ser Asp Arg Gly Thr Tyr Thr Cys Leu Val Glu Asn Ala
                195                 200                 205

Val Gly Ser Ile Arg Tyr Asn Tyr Leu Leu Asp Val Leu Glu Arg Ser
    210                 215                 220

Pro His Arg Pro Ile Leu Gln Ala Gly Leu Pro Ala Asn Thr Thr Ala
225                 230                 235                 240

Val Val Gly Ser Asp Val Glu Leu Leu Cys Lys Val Tyr Ser Asp Ala
```

```
                    245                 250                 255
Gln Pro His Ile Gln Trp Leu Lys His Ile Val Ile Asn Gly Ser Ser
                260                 265                 270

Phe Gly Ala Asp Gly Phe Pro Tyr Val Gln Val Leu Lys Thr Ala Asp
            275                 280                 285

Ile Asn Ser Ser Glu Val Glu Val Leu Tyr Leu Arg Asn Val Ser Ala
        290                 295                 300

Glu Asp Ala Gly Glu Tyr Thr Cys Leu Ala Gly Asn Ser Ile Gly Leu
305                 310                 315                 320

Ser Tyr Gln Ser Ala Trp Leu Thr Val Leu Glu Pro Lys Ser Ser Asp
                325                 330                 335

Lys Thr His Thr Cys Pro Pro Cys Pro Ala Pro Glu Leu Leu Gly Gly
                340                 345                 350

Pro Ser Val Phe Leu Phe Pro Lys Pro Lys Asp Thr Leu Met Ile
            355                 360                 365

Ser Arg Thr Pro Glu Val Thr Cys Val Val Val Asp Val Ser His Glu
        370                 375                 380

Asp Pro Glu Val Lys Phe Asn Trp Tyr Val Asp Gly Val Glu Val His
385                 390                 395                 400

Asn Ala Lys Thr Lys Pro Arg Glu Glu Gln Tyr Asn Ser Thr Tyr Arg
                405                 410                 415

Val Val Ser Val Leu Thr Val Leu His Gln Asp Trp Leu Asn Gly Lys
            420                 425                 430

Glu Tyr Lys Cys Lys Val Ser Asn Lys Ala Leu Pro Ala Pro Ile Glu
        435                 440                 445

Lys Thr Ile Ser Lys Ala Lys Gly Gln Pro Arg Glu Pro Gln Val Tyr
                450                 455                 460

Thr Leu Pro Pro Ser Arg Asp Glu Leu Thr Lys Asn Gln Val Ser Leu
465                 470                 475                 480

Thr Cys Leu Val Lys Gly Phe Tyr Pro Ser Asp Ile Ala Val Glu Trp
                485                 490                 495

Glu Ser Asn Gly Gln Pro Glu Asn Asn Tyr Lys Thr Thr Pro Pro Val
            500                 505                 510

Leu Asp Ser Asp Gly Ser Phe Phe Leu Tyr Ser Lys Leu Thr Val Asp
        515                 520                 525

Lys Ser Arg Trp Gln Gln Gly Asn Val Phe Ser Cys Ser Val Met His
                530                 535                 540

Glu Ala Leu His Asn His Tyr Thr Gln Lys Ser Leu Ser Leu Ser Pro
545                 550                 555                 560

Gly Lys

<210> SEQ ID NO 16
<211> LENGTH: 27
<212> TYPE: PRT
<213> ORGANISM: Artificial Sequence
<220> FEATURE:
<223> OTHER INFORMATION: Synthetic sequence

<400> SEQUENCE: 16

Asp Ser Leu Thr Ser Ser Asn Asp Asp Glu Asp Pro Lys Ser His Arg
1               5                   10                  15

Asp Pro Ser Asn Arg His Ser Tyr Pro Gln Gln
            20                  25

<210> SEQ ID NO 17
<211> LENGTH: 27
```

```
<212> TYPE: PRT
<213> ORGANISM: Artificial Sequence
<220> FEATURE:
<223> OTHER INFORMATION: Synthetic sequence

<400> SEQUENCE: 17

Asp Ser Leu Thr Ser Ser Asn Asp Asp Glu Asp Pro Lys Ser His Arg
1               5                   10                  15

Asp Leu Ser Asn Arg His Ser Tyr Pro Gln Gln
            20                  25

<210> SEQ ID NO 18
<211> LENGTH: 26
<212> TYPE: PRT
<213> ORGANISM: Artificial Sequence
<220> FEATURE:
<223> OTHER INFORMATION: Synthetic sequence

<400> SEQUENCE: 18

Asp Ser Leu Thr Ser Ser Asn Asp Asp Glu Asp Pro Lys Ser His Arg
1               5                   10                  15

Asp Pro Ser Asn Arg His Ser Tyr Pro Gln
            20                  25

<210> SEQ ID NO 19
<211> LENGTH: 26
<212> TYPE: PRT
<213> ORGANISM: Artificial Sequence
<220> FEATURE:
<223> OTHER INFORMATION: Synthetic sequence

<400> SEQUENCE: 19

Asp Ser Leu Thr Ser Ser Asn Asp Asp Glu Asp Pro Lys Ser His Arg
1               5                   10                  15

Asp Leu Ser Asn Arg His Ser Tyr Pro Gln
            20                  25

<210> SEQ ID NO 20
<211> LENGTH: 9
<212> TYPE: PRT
<213> ORGANISM: Artificial Sequence
<220> FEATURE:
<223> OTHER INFORMATION: Synthetic sequence

<400> SEQUENCE: 20

Asp Asp Glu Asp Pro Lys Ser His Arg
1               5

<210> SEQ ID NO 21
<211> LENGTH: 353
<212> TYPE: PRT
<213> ORGANISM: Artificial Sequence
<220> FEATURE:
<223> OTHER INFORMATION: Synthetic sequence

<400> SEQUENCE: 21

Arg Pro Ser Pro Thr Leu Pro Glu Gln Ala Gln Pro Trp Gly Ala Pro
1               5                   10                  15

Val Glu Val Glu Ser Phe Leu Val His Pro Gly Asp Leu Leu Gln Leu
            20                  25                  30

Arg Cys Arg Leu Arg Asp Asp Val Gln Ser Ile Asn Trp Leu Arg Asp
                35                  40                  45

Gly Val Gln Leu Ala Glu Ser Asn Arg Thr Arg Ile Thr Gly Glu Glu
        50                  55                  60
```

Val Glu Val Gln Asp Ser Val Pro Ala Asp Ser Gly Leu Tyr Ala Cys
65                  70                  75                  80

Val Thr Ser Ser Pro Ser Gly Ser Asp Thr Thr Tyr Phe Ser Val Asn
                85                  90                  95

Val Ser Asp Ala Leu Pro Ser Ser Glu Asp Asp Asp Asp Asp Asp Asp
                100                 105                 110

Ser Ser Ser Glu Glu Lys Glu Thr Asp Asn Thr Lys Pro Asn Pro Val
        115                 120                 125

Ala Pro Tyr Trp Thr Ser Pro Glu Lys Met Glu Lys Lys Leu His Ala
        130                 135                 140

Val Pro Ala Ala Lys Thr Val Lys Phe Lys Cys Pro Ser Ser Gly Thr
145                 150                 155                 160

Pro Asn Pro Thr Leu Arg Trp Leu Lys Asn Gly Lys Glu Phe Lys Pro
                165                 170                 175

Asp His Arg Ile Gly Gly Tyr Lys Val Arg Tyr Ala Thr Trp Ser Ile
                180                 185                 190

Ile Met Asp Ser Val Val Pro Ser Asp Lys Gly Asn Tyr Thr Cys Ile
                195                 200                 205

Val Glu Asn Glu Tyr Gly Ser Ile Asn His Thr Tyr Gln Leu Asp Val
210                 215                 220

Val Glu Arg Ser Pro His Arg Pro Ile Leu Gln Ala Gly Leu Pro Ala
225                 230                 235                 240

Asn Lys Thr Val Ala Leu Gly Ser Asn Val Glu Phe Met Cys Lys Val
                245                 250                 255

Tyr Ser Asp Pro Gln Pro His Ile Gln Trp Leu Lys His Ile Glu Val
                260                 265                 270

Asn Gly Ser Lys Ile Gly Pro Asp Asn Leu Pro Tyr Val Gln Ile Leu
                275                 280                 285

Lys Thr Ala Gly Val Asn Thr Thr Asp Lys Glu Met Glu Val Leu His
        290                 295                 300

Leu Arg Asn Val Ser Phe Glu Asp Ala Gly Glu Tyr Thr Cys Leu Ala
305                 310                 315                 320

Gly Asn Ser Ile Gly Leu Ser His His Ser Ala Trp Leu Thr Val Leu
                325                 330                 335

Glu Ala Leu Glu Glu Arg Pro Ala Val Met Thr Ser Pro Leu Tyr Leu
                340                 345                 350

Glu

<210> SEQ ID NO 22
<211> LENGTH: 30
<212> TYPE: PRT
<213> ORGANISM: Artificial Sequence
<220> FEATURE:
<223> OTHER INFORMATION: Synthetic sequence

<400> SEQUENCE: 22

Asp Ala Leu Pro Ser Ser Glu Asp Asp Asp Asp Asp Asp Asp Ser Ser
1               5                   10                  15

Ser Glu Glu Lys Glu Thr Asp Asn Thr Lys Pro Asn Pro Val
            20                  25                  30

<210> SEQ ID NO 23
<211> LENGTH: 28
<212> TYPE: PRT
<213> ORGANISM: Artificial Sequence
<220> FEATURE:
<223> OTHER INFORMATION: Synthetic sequence

<400> SEQUENCE: 23

Asp Ala Leu Pro Ser Ser Glu Asp Asp Asp Asp Asp Ser Ser
1               5                   10                  15

Ser Glu Glu Lys Glu Thr Asp Asn Thr Lys Pro Asn
            20                  25

<210> SEQ ID NO 24
<211> LENGTH: 12
<212> TYPE: PRT
<213> ORGANISM: Artificial Sequence
<220> FEATURE:
<223> OTHER INFORMATION: Synthetic sequence

<400> SEQUENCE: 24

Glu Asp Asp Asp Asp Asp Asp Ser Ser Ser Glu
1               5                   10

<210> SEQ ID NO 25
<211> LENGTH: 355
<212> TYPE: PRT
<213> ORGANISM: Artificial Sequence
<220> FEATURE:
<223> OTHER INFORMATION: Synthetic sequence

<400> SEQUENCE: 25

Arg Pro Ser Pro Thr Leu Pro Glu Gln Ala Gln Pro Trp Gly Ala Pro
1               5                   10                  15

Val Glu Val Glu Ser Phe Leu Val His Pro Gly Asp Leu Leu Gln Leu
            20                  25                  30

Arg Cys Arg Leu Arg Asp Asp Val Gln Ser Ile Asn Trp Leu Arg Asp
        35                  40                  45

Gly Val Gln Leu Ala Glu Ser Asn Arg Thr Arg Ile Thr Gly Glu Glu
    50                  55                  60

Val Glu Val Gln Asp Ser Val Pro Ala Asp Ser Gly Leu Tyr Ala Cys
65                  70                  75                  80

Val Thr Ser Ser Pro Ser Gly Ser Asp Thr Thr Tyr Phe Ser Val Asn
                85                  90                  95

Val Ser Asp Ala Leu Pro Ser Ser Glu Asp Asp Asp Asp Asp Asp Asp
            100                 105                 110

Ser Ser Glu Glu Lys Glu Thr Asp Asn Thr Lys Pro Asn Arg Met
        115                 120                 125

Pro Val Ala Pro Tyr Trp Thr Ser Pro Glu Lys Met Glu Lys Lys Leu
    130                 135                 140

His Ala Val Pro Ala Ala Lys Thr Val Lys Phe Lys Cys Pro Ser Ser
145                 150                 155                 160

Gly Thr Pro Asn Pro Thr Leu Arg Trp Leu Lys Asn Gly Lys Glu Phe
                165                 170                 175

Lys Pro Asp His Arg Ile Gly Gly Tyr Lys Val Arg Tyr Ala Thr Trp
            180                 185                 190

Ser Ile Ile Met Asp Ser Val Val Pro Ser Asp Lys Gly Asn Tyr Thr
        195                 200                 205

Cys Ile Val Glu Asn Glu Tyr Gly Ser Ile Asn His Thr Tyr Gln Leu
    210                 215                 220

Asp Val Val Glu Arg Ser Pro His Arg Pro Ile Leu Gln Ala Gly Leu
225                 230                 235                 240

Pro Ala Asn Lys Thr Val Ala Leu Gly Ser Asn Val Glu Phe Met Cys
                245                 250                 255

Lys Val Tyr Ser Asp Pro Gln Pro His Ile Gln Trp Leu Lys His Ile

```
                      260                 265                 270
Glu Val Asn Gly Ser Lys Ile Gly Pro Asp Asn Leu Pro Tyr Val Gln
            275                 280                 285
Ile Leu Lys Thr Ala Gly Val Asn Thr Thr Asp Lys Glu Met Glu Val
            290                 295                 300
Leu His Leu Arg Asn Val Ser Phe Glu Asp Ala Gly Glu Tyr Thr Cys
305                 310                 315                 320
Leu Ala Gly Asn Ser Ile Gly Leu Ser His His Ser Ala Trp Leu Thr
                325                 330                 335
Val Leu Glu Ala Leu Glu Glu Arg Pro Ala Val Met Thr Ser Pro Leu
            340                 345                 350
Tyr Leu Glu
        355

<210> SEQ ID NO 26
<211> LENGTH: 32
<212> TYPE: PRT
<213> ORGANISM: Artificial Sequence
<220> FEATURE:
<223> OTHER INFORMATION: Synthetic sequence

<400> SEQUENCE: 26

Asp Ala Leu Pro Ser Ser Glu Asp Asp Asp Asp Asp Asp Ser Ser
1               5                   10                  15

Ser Glu Glu Lys Glu Thr Asp Asn Thr Lys Pro Asn Arg Met Pro Val
            20                  25                  30

<210> SEQ ID NO 27
<211> LENGTH: 356
<212> TYPE: PRT
<213> ORGANISM: Artificial Sequence
<220> FEATURE:
<223> OTHER INFORMATION: Synthetic sequence

<400> SEQUENCE: 27

Arg Pro Ser Phe Ser Leu Val Glu Asp Thr Thr Leu Glu Pro Glu Glu
1               5                   10                  15

Pro Pro Thr Lys Tyr Gln Ile Ser Gln Pro Glu Val Tyr Val Ala Ala
            20                  25                  30

Pro Gly Glu Ser Leu Glu Val Arg Cys Leu Leu Lys Asp Ala Ala Val
            35                  40                  45

Ile Ser Trp Thr Lys Asp Gly Val His Leu Gly Pro Asn Asn Arg Thr
        50                  55                  60

Val Leu Ile Gly Glu Tyr Leu Gln Ile Lys Gly Ala Thr Pro Arg Asp
65                  70                  75                  80

Ser Gly Leu Tyr Ala Cys Thr Ala Ser Arg Thr Val Asp Ser Glu Thr
                85                  90                  95

Trp Tyr Phe Met Val Asn Val Thr Asp Ala Ile Ser Ser Gly Asp Asp
            100                 105                 110

Glu Asp Asp Thr Asp Gly Ala Glu Asp Phe Val Ser Glu Asn Ser Asn
            115                 120                 125

Asn Lys Arg Ala Pro Tyr Trp Thr Asn Thr Glu Lys Met Glu Lys Arg
        130                 135                 140

Leu His Ala Val Pro Ala Ala Asn Thr Val Lys Phe Arg Cys Pro Ala
145                 150                 155                 160

Gly Gly Asn Pro Met Pro Thr Met Arg Trp Leu Lys Asn Gly Lys Glu
                165                 170                 175

Phe Lys Gln Glu His Arg Ile Gly Gly Tyr Lys Val Arg Asn Gln His
```

```
                180                 185                 190
Trp Ser Leu Ile Met Glu Ser Val Val Pro Ser Asp Lys Gly Asn Tyr
        195                 200                 205

Thr Cys Val Val Glu Asn Glu Tyr Gly Ser Ile Asn His Thr Tyr His
        210                 215                 220

Leu Asp Val Val Glu Arg Ser Pro His Arg Pro Ile Leu Gln Ala Gly
225                 230                 235                 240

Leu Pro Ala Asn Ala Ser Thr Val Gly Gly Asp Val Glu Phe Val
                245                 250                 255

Cys Lys Val Tyr Ser Asp Ala Gln Pro His Ile Gln Trp Ile Lys His
                260                 265                 270

Val Glu Lys Asn Gly Ser Lys Tyr Gly Pro Asp Gly Leu Pro Tyr Leu
        275                 280                 285

Lys Val Leu Lys Ala Ala Gly Val Asn Thr Thr Asp Lys Glu Ile Glu
        290                 295                 300

Val Leu Tyr Ile Arg Asn Val Thr Phe Glu Asp Ala Gly Glu Tyr Thr
305                 310                 315                 320

Cys Leu Ala Gly Asn Ser Ile Gly Ile Ser Phe His Ser Ala Trp Leu
                325                 330                 335

Thr Val Leu Pro Ala Pro Gly Arg Glu Lys Glu Ile Thr Ala Ser Pro
                340                 345                 350

Asp Tyr Leu Glu
        355

<210> SEQ ID NO 28
<211> LENGTH: 27
<212> TYPE: PRT
<213> ORGANISM: Artificial Sequence
<220> FEATURE:
<223> OTHER INFORMATION: Synthetic sequence

<400> SEQUENCE: 28

Asp Ala Ile Ser Ser Gly Asp Asp Glu Asp Asp Thr Asp Gly Ala Glu
1               5                   10                  15

Asp Phe Val Ser Glu Asn Ser Asn Asn Lys Arg
            20                  25

<210> SEQ ID NO 29
<211> LENGTH: 26
<212> TYPE: PRT
<213> ORGANISM: Artificial Sequence
<220> FEATURE:
<223> OTHER INFORMATION: Synthetic sequence

<400> SEQUENCE: 29

Asp Ala Ile Ser Ser Gly Asp Asp Glu Asp Asp Thr Asp Gly Ala Glu
1               5                   10                  15

Asp Phe Val Ser Glu Asn Ser Asn Asn Lys
            20                  25

<210> SEQ ID NO 30
<211> LENGTH: 7
<212> TYPE: PRT
<213> ORGANISM: Artificial Sequence
<220> FEATURE:
<223> OTHER INFORMATION: Synthetic sequence

<400> SEQUENCE: 30

Asp Asp Glu Asp Asp Thr Asp
1               5
```

```
<210> SEQ ID NO 31
<211> LENGTH: 353
<212> TYPE: PRT
<213> ORGANISM: Artificial Sequence
<220> FEATURE:
<223> OTHER INFORMATION: Synthetic sequence

<400> SEQUENCE: 31

Glu Ser Leu Gly Thr Glu Gln Arg Val Gly Arg Ala Ala Glu Val
1               5                   10                  15

Pro Gly Pro Glu Pro Gly Gln Gln Gln Leu Val Phe Gly Ser Gly
                20                  25                  30

Asp Ala Val Glu Leu Ser Cys Pro Pro Gly Gly Gly Pro Met Gly
                35                  40                  45

Pro Thr Val Trp Val Lys Asp Gly Thr Gly Leu Val Pro Ser Glu Arg
        50                  55                  60

Val Leu Val Gly Pro Gln Arg Leu Gln Val Leu Asn Ala Ser His Glu
65                  70                  75                  80

Asp Ser Gly Ala Tyr Ser Cys Arg Gln Arg Leu Thr Gln Arg Val Leu
                85                  90                  95

Cys His Phe Ser Val Arg Val Thr Asp Ala Pro Ser Ser Gly Asp Asp
                100                 105                 110

Glu Asp Gly Glu Asp Glu Ala Glu Asp Thr Gly Val Asp Thr Gly Ala
                115                 120                 125

Pro Tyr Trp Thr Arg Pro Glu Arg Met Asp Lys Lys Leu Leu Ala Val
        130                 135                 140

Pro Ala Ala Asn Thr Val Arg Phe Arg Cys Pro Ala Ala Gly Asn Pro
145                 150                 155                 160

Thr Pro Ser Ile Ser Trp Leu Lys Asn Gly Arg Glu Phe Arg Gly Glu
                165                 170                 175

His Arg Ile Gly Gly Ile Lys Leu Arg His Gln Gln Trp Ser Leu Val
                180                 185                 190

Met Glu Ser Val Val Pro Ser Asp Arg Gly Asn Tyr Thr Cys Val Val
                195                 200                 205

Glu Asn Lys Phe Gly Ser Ile Arg Gln Thr Tyr Thr Leu Asp Val Leu
        210                 215                 220

Glu Arg Ser Pro His Arg Pro Ile Leu Gln Ala Gly Leu Pro Ala Asn
225                 230                 235                 240

Gln Thr Ala Val Leu Gly Ser Asp Val Glu Phe His Cys Lys Val Tyr
                245                 250                 255

Ser Asp Ala Gln Pro His Ile Gln Trp Leu Lys His Val Glu Val Asn
                260                 265                 270

Gly Ser Lys Val Gly Pro Asp Gly Thr Pro Tyr Val Thr Val Leu Lys
                275                 280                 285

Thr Ala Gly Ala Asn Thr Thr Asp Lys Glu Leu Glu Val Leu Ser Leu
        290                 295                 300

His Asn Val Thr Phe Glu Asp Ala Gly Glu Tyr Thr Cys Leu Ala Gly
305                 310                 315                 320

Asn Ser Ile Gly Phe Ser His His Ser Ala Trp Leu Val Val Leu Pro
                325                 330                 335

Ala Glu Glu Glu Leu Val Glu Ala Asp Glu Ala Gly Ser Val Tyr Ala
                340                 345                 350

Gly

<210> SEQ ID NO 32
```

```
<211> LENGTH: 23
<212> TYPE: PRT
<213> ORGANISM: Artificial Sequence
<220> FEATURE:
<223> OTHER INFORMATION: Synthetic sequence

<400> SEQUENCE: 32

Asp Ala Pro Ser Ser Gly Asp Asp Glu Asp Gly Glu Asp Glu Ala Glu
1               5                   10                  15

Asp Thr Gly Val Asp Thr Gly
            20

<210> SEQ ID NO 33
<211> LENGTH: 22
<212> TYPE: PRT
<213> ORGANISM: Artificial Sequence
<220> FEATURE:
<223> OTHER INFORMATION: Synthetic sequence

<400> SEQUENCE: 33

Asp Ala Pro Ser Ser Gly Asp Asp Glu Asp Gly Glu Asp Glu Ala Glu
1               5                   10                  15

Asp Thr Gly Val Asp Thr
            20

<210> SEQ ID NO 34
<211> LENGTH: 6
<212> TYPE: PRT
<213> ORGANISM: Artificial Sequence
<220> FEATURE:
<223> OTHER INFORMATION: Synthetic sequence

<400> SEQUENCE: 34

Asp Asp Glu Asp Gly Glu
1               5

<210> SEQ ID NO 35
<211> LENGTH: 334
<212> TYPE: PRT
<213> ORGANISM: Artificial Sequence
<220> FEATURE:
<223> OTHER INFORMATION: Synthetic sequence

<400> SEQUENCE: 35

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
            20                  25                  30

Arg Leu Cys Cys Gly Arg Ala Glu Arg Gly Gly His Trp Tyr Lys Glu
        35                  40                  45

Gly Ser Arg Leu Ala Pro Ala Gly Arg Val Arg Gly Trp Arg Gly Arg
    50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ala Leu Pro Ser Ser Glu Asp Asp Asp Asp Asp Asp Asp Ser
            100                 105                 110

Ser Ser Glu Glu Lys Glu Thr Asp Asn Thr Lys Pro Asn Pro Val Ala
        115                 120                 125

Pro Tyr Trp Thr His Pro Gln Arg Met Glu Lys Lys Leu His Ala Val
    130                 135                 140
```

```
Pro Ala Gly Asn Thr Val Lys Phe Arg Cys Pro Ala Ala Gly Asn Pro
145                 150                 155                 160

Thr Pro Thr Ile Arg Trp Leu Lys Asp Gly Gln Ala Phe His Gly Glu
            165                 170                 175

Asn Arg Ile Gly Gly Ile Arg Leu Arg His Gln His Trp Ser Leu Val
        180                 185                 190

Met Glu Ser Val Val Pro Ser Asp Arg Gly Thr Tyr Thr Cys Leu Val
    195                 200                 205

Glu Asn Ala Val Gly Ser Ile Arg Tyr Asn Tyr Leu Leu Asp Val Leu
210                 215                 220

Glu Arg Ser Pro His Arg Pro Ile Leu Gln Ala Gly Leu Pro Ala Asn
225                 230                 235                 240

Thr Thr Ala Val Val Gly Ser Asp Val Glu Leu Leu Cys Lys Val Tyr
            245                 250                 255

Ser Asp Ala Gln Pro His Ile Gln Trp Leu Lys His Ile Val Ile Asn
        260                 265                 270

Gly Ser Ser Phe Gly Ala Asp Gly Phe Pro Tyr Val Gln Val Leu Lys
    275                 280                 285

Thr Ala Asp Ile Asn Ser Ser Glu Val Glu Val Leu Tyr Leu Arg Asn
290                 295                 300

Val Ser Ala Glu Asp Ala Gly Glu Tyr Thr Cys Leu Ala Gly Asn Ser
305                 310                 315                 320

Ile Gly Leu Ser Tyr Gln Ser Ala Trp Leu Thr Val Leu Pro
            325                 330

<210> SEQ ID NO 36
<211> LENGTH: 336
<212> TYPE: PRT
<213> ORGANISM: Artificial Sequence
<220> FEATURE:
<223> OTHER INFORMATION: Synthetic sequence

<400> SEQUENCE: 36

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
            20                  25                  30

Arg Leu Cys Cys Gly Arg Ala Glu Arg Gly Gly His Trp Tyr Lys Glu
        35                  40                  45

Gly Ser Arg Leu Ala Pro Ala Gly Arg Val Arg Gly Trp Arg Gly Arg
    50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ala Leu Pro Ser Ser Glu Asp Asp Asp Asp Asp Asp Asp Ser
            100                 105                 110

Ser Ser Glu Glu Lys Glu Thr Asp Asn Thr Lys Pro Asn Arg Met Pro
        115                 120                 125

Val Ala Pro Tyr Trp Thr His Pro Gln Arg Met Glu Lys Lys Leu His
    130                 135                 140

Ala Val Pro Ala Gly Asn Thr Val Lys Phe Arg Cys Pro Ala Ala Gly
145                 150                 155                 160

Asn Pro Thr Pro Thr Ile Arg Trp Leu Lys Asp Gly Gln Ala Phe His
                165                 170                 175

Gly Glu Asn Arg Ile Gly Gly Ile Arg Leu Arg His Gln His Trp Ser
```

```
                            180                 185                 190
Leu Val Met Glu Ser Val Val Pro Ser Asp Arg Gly Thr Tyr Thr Cys
                195                 200                 205
Leu Val Glu Asn Ala Val Gly Ser Ile Arg Tyr Asn Tyr Leu Leu Asp
            210                 215                 220
Val Leu Glu Arg Ser Pro His Arg Pro Ile Leu Gln Ala Gly Leu Pro
225                 230                 235                 240
Ala Asn Thr Thr Ala Val Gly Ser Asp Val Glu Leu Leu Cys Lys
                245                 250                 255
Val Tyr Ser Asp Ala Gln Pro His Ile Gln Trp Leu Lys His Ile Val
                260                 265                 270
Ile Asn Gly Ser Ser Phe Gly Ala Asp Gly Phe Pro Tyr Val Gln Val
                275                 280                 285
Leu Lys Thr Ala Asp Ile Asn Ser Ser Glu Val Glu Val Leu Tyr Leu
            290                 295                 300
Arg Asn Val Ser Ala Glu Asp Ala Gly Glu Tyr Thr Cys Leu Ala Gly
305                 310                 315                 320
Asn Ser Ile Gly Leu Ser Tyr Gln Ser Ala Trp Leu Thr Val Leu Pro
                325                 330                 335

<210> SEQ ID NO 37
<211> LENGTH: 331
<212> TYPE: PRT
<213> ORGANISM: Artificial Sequence
<220> FEATURE:
<223> OTHER INFORMATION: Synthetic sequence

<400> SEQUENCE: 37

Leu Glu Ala Ser Glu Glu Val Glu Leu Glu Pro Cys Leu Ala Pro Ser
1               5                   10                  15
Leu Glu Gln Gln Glu Gln Glu Leu Thr Val Ala Leu Gly Gln Pro Val
                20                  25                  30
Arg Leu Cys Cys Gly Arg Ala Glu Arg Gly Gly His Trp Tyr Lys Glu
            35                  40                  45
Gly Ser Arg Leu Ala Pro Ala Gly Arg Val Arg Gly Trp Arg Gly Arg
        50                  55                  60
Leu Glu Ile Ala Ser Phe Leu Pro Glu Asp Ala Gly Arg Tyr Leu Cys
65                  70                  75                  80
Leu Ala Arg Gly Ser Met Ile Val Leu Gln Asn Leu Thr Leu Ile Thr
                85                  90                  95
Gly Asp Ala Ile Ser Ser Gly Asp Asp Glu Asp Asp Thr Asp Gly Ala
                100                 105                 110
Glu Asp Phe Val Ser Glu Asn Ser Asn Asn Lys Arg Ala Pro Tyr Trp
            115                 120                 125
Thr His Pro Gln Arg Met Glu Lys Lys Leu His Ala Val Pro Ala Gly
        130                 135                 140
Asn Thr Val Lys Phe Arg Cys Pro Ala Ala Gly Asn Pro Thr Pro Thr
145                 150                 155                 160
Ile Arg Trp Leu Lys Asp Gly Gln Ala Phe His Gly Glu Asn Arg Ile
                165                 170                 175
Gly Gly Ile Arg Leu Arg His Gln His Trp Ser Leu Val Met Glu Ser
                180                 185                 190
Val Val Pro Ser Asp Arg Gly Thr Tyr Thr Cys Leu Val Glu Asn Ala
            195                 200                 205
Val Gly Ser Ile Arg Tyr Asn Tyr Leu Leu Asp Val Leu Glu Arg Ser
        210                 215                 220
```

```
Pro His Arg Pro Ile Leu Gln Ala Gly Leu Pro Ala Asn Thr Thr Ala
225                 230                 235                 240

Val Val Gly Ser Asp Val Glu Leu Leu Cys Lys Val Tyr Ser Asp Ala
                245                 250                 255

Gln Pro His Ile Gln Trp Leu Lys His Ile Val Ile Asn Gly Ser Ser
            260                 265                 270

Phe Gly Ala Asp Gly Phe Pro Tyr Val Gln Val Leu Lys Thr Ala Asp
        275                 280                 285

Ile Asn Ser Ser Glu Val Glu Val Leu Tyr Leu Arg Asn Val Ser Ala
    290                 295                 300

Glu Asp Ala Gly Glu Tyr Thr Cys Leu Ala Gly Asn Ser Ile Gly Leu
305                 310                 315                 320

Ser Tyr Gln Ser Ala Trp Leu Thr Val Leu Pro
                325                 330
```

<210> SEQ ID NO 38
<211> LENGTH: 327
<212> TYPE: PRT
<213> ORGANISM: Artificial Sequence
<220> FEATURE:
<223> OTHER INFORMATION: Synthetic sequence

<400> SEQUENCE: 38

```
Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
                20                  25                  30

Arg Leu Cys Cys Gly Arg Ala Glu Arg Gly Gly His Trp Tyr Lys Glu
            35                  40                  45

Gly Ser Arg Leu Ala Pro Ala Gly Arg Val Arg Gly Trp Arg Gly Arg
        50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ala Pro Ser Ser Gly Asp Asp Glu Asp Gly Glu Asp Glu Ala
                100                 105                 110

Glu Asp Thr Gly Val Asp Thr Gly Ala Pro Tyr Trp Thr His Pro Gln
            115                 120                 125

Arg Met Glu Lys Lys Leu His Ala Val Pro Ala Gly Asn Thr Val Lys
        130                 135                 140

Phe Arg Cys Pro Ala Ala Gly Asn Pro Thr Pro Thr Ile Arg Trp Leu
145                 150                 155                 160

Lys Asp Gly Gln Ala Phe His Gly Glu Asn Arg Ile Gly Gly Ile Arg
                165                 170                 175

Leu Arg His Gln His Trp Ser Leu Val Met Glu Ser Val Val Pro Ser
            180                 185                 190

Asp Arg Gly Thr Tyr Thr Cys Leu Val Glu Asn Ala Val Gly Ser Ile
        195                 200                 205

Arg Tyr Asn Tyr Leu Leu Asp Val Leu Glu Arg Ser Pro His Arg Pro
210                 215                 220

Ile Leu Gln Ala Gly Leu Pro Ala Asn Thr Thr Ala Val Val Gly Ser
225                 230                 235                 240

Asp Val Glu Leu Leu Cys Lys Val Tyr Ser Asp Ala Gln Pro His Ile
                245                 250                 255
```

```
Gln Trp Leu Lys His Ile Val Ile Asn Gly Ser Ser Phe Gly Ala Asp
            260                 265                 270

Gly Phe Pro Tyr Val Gln Val Leu Lys Thr Ala Asp Ile Asn Ser Ser
        275                 280                 285

Glu Val Glu Val Leu Tyr Leu Arg Asn Val Ser Ala Glu Asp Ala Gly
    290                 295                 300

Glu Tyr Thr Cys Leu Ala Gly Asn Ser Ile Gly Leu Ser Tyr Gln Ser
305                 310                 315                 320

Ala Trp Leu Thr Val Leu Pro
                325

<210> SEQ ID NO 39
<211> LENGTH: 333
<212> TYPE: PRT
<213> ORGANISM: Artificial Sequence
<220> FEATURE:
<223> OTHER INFORMATION: Synthetic sequence

<400> SEQUENCE: 39

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
            20                  25                  30

Arg Leu Cys Cys Gly Arg Ala Glu Arg Gly Gly His Trp Tyr Lys Glu
        35                  40                  45

Gly Ser Arg Leu Ala Pro Ala Gly Arg Val Arg Gly Trp Arg Gly Arg
    50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ala Leu Pro Ser Ser Glu Asp Asp Asp Asp Asp Asp Asp Ser
            100                 105                 110

Ser Ser Glu Glu Lys Glu Thr Asp Asn Thr Lys Pro Asn Gln Ala Pro
        115                 120                 125

Tyr Trp Thr His Pro Gln Arg Met Glu Lys Lys Leu His Ala Val Pro
    130                 135                 140

Ala Gly Asn Thr Val Lys Phe Arg Cys Pro Ala Ala Gly Asn Pro Thr
145                 150                 155                 160

Pro Thr Ile Arg Trp Leu Lys Asp Gly Gln Ala Phe His Gly Glu Asn
                165                 170                 175

Arg Ile Gly Gly Ile Arg Leu Arg His Gln His Trp Ser Leu Val Met
            180                 185                 190

Glu Ser Val Val Pro Ser Asp Arg Gly Thr Tyr Thr Cys Leu Val Glu
        195                 200                 205

Asn Ala Val Gly Ser Ile Arg Tyr Asn Tyr Leu Leu Asp Val Leu Glu
    210                 215                 220

Arg Ser Pro His Arg Pro Ile Leu Gln Ala Gly Leu Pro Ala Asn Thr
225                 230                 235                 240

Thr Ala Val Val Gly Ser Asp Val Glu Leu Leu Cys Lys Val Tyr Ser
                245                 250                 255

Asp Ala Gln Pro His Ile Gln Trp Leu Lys His Ile Val Ile Asn Gly
            260                 265                 270

Ser Ser Phe Gly Ala Asp Gly Phe Pro Tyr Val Gln Val Leu Lys Thr
        275                 280                 285

Ala Asp Ile Asn Ser Ser Glu Val Glu Val Leu Tyr Leu Arg Asn Val
```

```
                290                 295                 300
Ser Ala Glu Asp Ala Gly Glu Tyr Thr Cys Leu Ala Gly Asn Ser Ile
305                 310                 315                 320

Gly Leu Ser Tyr Gln Ser Ala Trp Leu Thr Val Leu Pro
                325                 330
```

<210> SEQ ID NO 40
<211> LENGTH: 335
<212> TYPE: PRT
<213> ORGANISM: Artificial Sequence
<220> FEATURE:
<223> OTHER INFORMATION: Synthetic sequence

<400> SEQUENCE: 40

```
Leu Glu Ala Ser Glu Glu Val Glu Leu Glu Pro Cys Leu Ala Pro Ser
1               5                   10                  15

Leu Glu Gln Gln Glu Gln Leu Thr Val Ala Leu Gly Gln Pro Val
                20                  25                  30

Arg Leu Cys Cys Gly Arg Ala Glu Arg Gly Gly His Trp Tyr Lys Glu
                35                  40                  45

Gly Ser Arg Leu Ala Pro Ala Gly Arg Val Arg Gly Trp Arg Gly Arg
50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ala Leu Pro Ser Ser Glu Asp Asp Asp Asp Asp Asp Ser
            100                 105                 110

Ser Ser Glu Glu Lys Glu Thr Asp Asn Thr Lys Pro Asn Arg Met Gln
            115                 120                 125

Ala Pro Tyr Trp Thr His Pro Gln Arg Met Glu Lys Lys Leu His Ala
            130                 135                 140

Val Pro Ala Gly Asn Thr Val Lys Phe Arg Cys Pro Ala Ala Gly Asn
145                 150                 155                 160

Pro Thr Pro Thr Ile Arg Trp Leu Lys Asp Gly Gln Ala Phe His Gly
                165                 170                 175

Glu Asn Arg Ile Gly Gly Ile Arg Leu Arg His Gln His Trp Ser Leu
            180                 185                 190

Val Met Glu Ser Val Val Pro Ser Asp Arg Gly Thr Tyr Thr Cys Leu
        195                 200                 205

Val Glu Asn Ala Val Gly Ser Ile Arg Tyr Asn Tyr Leu Leu Asp Val
210                 215                 220

Leu Glu Arg Ser Pro His Arg Pro Ile Leu Gln Ala Gly Leu Pro Ala
225                 230                 235                 240

Asn Thr Thr Ala Val Val Gly Ser Asp Val Glu Leu Leu Cys Lys Val
                245                 250                 255

Tyr Ser Asp Ala Gln Pro His Ile Gln Trp Leu Lys His Ile Val Ile
                260                 265                 270

Asn Gly Ser Ser Phe Gly Ala Asp Gly Phe Pro Tyr Val Gln Val Leu
            275                 280                 285

Lys Thr Ala Asp Ile Asn Ser Ser Glu Val Glu Val Leu Tyr Leu Arg
        290                 295                 300

Asn Val Ser Ala Glu Asp Ala Gly Glu Tyr Thr Cys Leu Ala Gly Asn
305                 310                 315                 320

Ser Ile Gly Leu Ser Tyr Gln Ser Ala Trp Leu Thr Val Leu Pro
                325                 330                 335
```

<210> SEQ ID NO 41
<211> LENGTH: 331
<212> TYPE: PRT
<213> ORGANISM: Artificial Sequence
<220> FEATURE:
<223> OTHER INFORMATION: Synthetic sequence

<400> SEQUENCE: 41

```
Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
            20                  25                  30

Arg Leu Cys Cys Gly Arg Ala Glu Arg Gly Gly His Trp Tyr Lys Glu
        35                  40                  45

Gly Ser Arg Leu Ala Pro Ala Gly Arg Val Arg Gly Trp Arg Gly Arg
    50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ala Ile Ser Ser Gly Asp Asp Glu Asp Asp Thr Asp Gly Ala
            100                 105                 110

Glu Asp Phe Val Ser Glu Asn Ser Asn Asn Lys Gln Ala Pro Tyr Trp
        115                 120                 125

Thr His Pro Gln Arg Met Glu Lys Lys Leu His Ala Val Pro Ala Gly
    130                 135                 140

Asn Thr Val Lys Phe Arg Cys Pro Ala Ala Gly Asn Pro Thr Pro Thr
145                 150                 155                 160

Ile Arg Trp Leu Lys Asp Gly Gln Ala Phe His Gly Glu Asn Arg Ile
                165                 170                 175

Gly Gly Ile Arg Leu Arg His Gln His Trp Ser Leu Val Met Glu Ser
            180                 185                 190

Val Val Pro Ser Asp Arg Gly Thr Tyr Thr Cys Leu Val Glu Asn Ala
        195                 200                 205

Val Gly Ser Ile Arg Tyr Asn Tyr Leu Leu Asp Val Leu Glu Arg Ser
    210                 215                 220

Pro His Arg Pro Ile Leu Gln Ala Gly Leu Pro Ala Asn Thr Thr Ala
225                 230                 235                 240

Val Val Gly Ser Asp Val Glu Leu Leu Cys Lys Val Tyr Ser Asp Ala
                245                 250                 255

Gln Pro His Ile Gln Trp Leu Lys His Ile Val Ile Asn Gly Ser Ser
            260                 265                 270

Phe Gly Ala Asp Gly Phe Pro Tyr Val Gln Val Leu Lys Thr Ala Asp
        275                 280                 285

Ile Asn Ser Ser Glu Val Glu Val Leu Tyr Leu Arg Asn Val Ser Ala
    290                 295                 300

Glu Asp Ala Gly Glu Tyr Thr Cys Leu Ala Gly Asn Ser Ile Gly Leu
305                 310                 315                 320

Ser Tyr Gln Ser Ala Trp Leu Thr Val Leu Pro
                325                 330
```

<210> SEQ ID NO 42
<211> LENGTH: 327
<212> TYPE: PRT
<213> ORGANISM: Artificial Sequence
<220> FEATURE:

<223> OTHER INFORMATION: Synthetic sequence

<400> SEQUENCE: 42

```
Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
            20                  25                  30

Arg Leu Cys Cys Gly Arg Ala Glu Arg Gly Gly His Trp Tyr Lys Glu
        35                  40                  45

Gly Ser Arg Leu Ala Pro Ala Gly Arg Val Arg Gly Trp Arg Gly Arg
    50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ala Pro Ser Ser Gly Asp Asp Glu Asp Gly Glu Asp Glu Ala
            100                 105                 110

Glu Asp Thr Gly Val Asp Thr Gln Ala Pro Tyr Trp Thr His Pro Gln
        115                 120                 125

Arg Met Glu Lys Lys Leu His Ala Val Pro Ala Gly Asn Thr Val Lys
    130                 135                 140

Phe Arg Cys Pro Ala Ala Gly Asn Pro Thr Pro Thr Ile Arg Trp Leu
145                 150                 155                 160

Lys Asp Gly Gln Ala Phe His Gly Glu Asn Arg Ile Gly Gly Ile Arg
                165                 170                 175

Leu Arg His Gln His Trp Ser Leu Val Met Glu Ser Val Val Pro Ser
            180                 185                 190

Asp Arg Gly Thr Tyr Thr Cys Leu Val Glu Asn Ala Val Gly Ser Ile
        195                 200                 205

Arg Tyr Asn Tyr Leu Leu Asp Val Leu Glu Arg Ser Pro His Arg Pro
    210                 215                 220

Ile Leu Gln Ala Gly Leu Pro Ala Asn Thr Thr Ala Val Val Gly Ser
225                 230                 235                 240

Asp Val Glu Leu Leu Cys Lys Val Tyr Ser Asp Ala Gln Pro His Ile
                245                 250                 255

Gln Trp Leu Lys His Ile Val Ile Asn Gly Ser Ser Phe Gly Ala Asp
            260                 265                 270

Gly Phe Pro Tyr Val Gln Val Leu Lys Thr Ala Asp Ile Asn Ser Ser
        275                 280                 285

Glu Val Glu Val Leu Tyr Leu Arg Asn Val Ser Ala Glu Asp Ala Gly
    290                 295                 300

Glu Tyr Thr Cys Leu Ala Gly Asn Ser Ile Gly Leu Ser Tyr Gln Ser
305                 310                 315                 320

Ala Trp Leu Thr Val Leu Pro
                325
```

<210> SEQ ID NO 43
<211> LENGTH: 334
<212> TYPE: PRT
<213> ORGANISM: Artificial Sequence
<220> FEATURE:
<223> OTHER INFORMATION: Synthetic sequence

<400> SEQUENCE: 43

```
Leu Glu Ala Ser Glu Glu Val Glu Leu Glu Pro Cys Leu Ala Pro Ser
1               5                   10                  15
```

```
Leu Glu Gln Gln Glu Gln Glu Leu Thr Val Ala Leu Gly Gln Pro Val
                20                  25                  30

Arg Leu Cys Cys Gly Arg Ala Glu Arg Gly Gly His Trp Tyr Lys Glu
             35                  40                  45

Gly Ser Arg Leu Ala Pro Ala Gly Arg Val Arg Gly Trp Arg Gly Arg
         50                  55                  60

Leu Glu Ile Ala Ser Phe Leu Pro Glu Asp Ala Gly Arg Tyr Leu Cys
 65                  70                  75                  80

Leu Ala Arg Gly Ser Met Ile Val Leu Gln Asn Leu Thr Leu Ile Thr
                 85                  90                  95

Gly Asp Ser Leu Thr Ser Ser Asn Glu Asp Asp Asp Asp Asp Asp Asp
            100                 105                 110

Ser Ser Ser Glu Asp Pro Ser Asn Arg His Ser Tyr Pro Gln Gln Ala
            115                 120                 125

Pro Tyr Trp Thr His Pro Gln Arg Met Glu Lys Lys Leu His Ala Val
            130                 135                 140

Pro Ala Gly Asn Thr Val Lys Phe Arg Cys Pro Ala Ala Gly Asn Pro
145                 150                 155                 160

Thr Pro Thr Ile Arg Trp Leu Lys Asp Gly Gln Ala Phe His Gly Glu
                165                 170                 175

Asn Arg Ile Gly Gly Ile Arg Leu Arg His Gln His Trp Ser Leu Val
                180                 185                 190

Met Glu Ser Val Val Pro Ser Asp Arg Gly Thr Tyr Thr Cys Leu Val
            195                 200                 205

Glu Asn Ala Val Gly Ser Ile Arg Tyr Asn Tyr Leu Leu Asp Val Leu
        210                 215                 220

Glu Arg Ser Pro His Arg Pro Ile Leu Gln Ala Gly Leu Pro Ala Asn
225                 230                 235                 240

Thr Thr Ala Val Val Gly Ser Asp Val Glu Leu Leu Cys Lys Val Tyr
                245                 250                 255

Ser Asp Ala Gln Pro His Ile Gln Trp Leu Lys His Ile Val Ile Asn
            260                 265                 270

Gly Ser Ser Phe Gly Ala Asp Gly Phe Pro Tyr Val Gln Val Leu Lys
        275                 280                 285

Thr Ala Asp Ile Asn Ser Ser Glu Val Glu Val Leu Tyr Leu Arg Asn
    290                 295                 300

Val Ser Ala Glu Asp Ala Gly Glu Tyr Thr Cys Leu Ala Gly Asn Ser
305                 310                 315                 320

Ile Gly Leu Ser Tyr Gln Ser Ala Trp Leu Thr Val Leu Pro
                325                 330

<210> SEQ ID NO 44
<211> LENGTH: 329
<212> TYPE: PRT
<213> ORGANISM: Artificial Sequence
<220> FEATURE:
<223> OTHER INFORMATION: Synthetic sequence

<400> SEQUENCE: 44

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
                20                  25                  30

Arg Leu Cys Cys Gly Arg Ala Glu Arg Gly Gly His Trp Tyr Lys Glu
             35                  40                  45

Gly Ser Arg Leu Ala Pro Ala Gly Arg Val Arg Gly Trp Arg Gly Arg
```

-continued

```
                    50                  55                  60
Leu Glu Ile Ala Ser Phe Leu Pro Glu Asp Ala Gly Arg Tyr Leu Cys
 65                  70                  75                  80

Leu Ala Arg Gly Ser Met Ile Val Leu Gln Asn Leu Thr Leu Ile Thr
                 85                  90                  95

Gly Asp Ser Leu Thr Ser Ser Asn Asp Glu Asp Thr Asp Asp
                100                 105                 110

Pro Ser Asn Arg His Ser Tyr Pro Gln Gln Ala Pro Tyr Trp Thr His
                115                 120                 125

Pro Gln Arg Met Glu Lys Lys Leu His Ala Val Pro Ala Gly Asn Thr
130                 135                 140

Val Lys Phe Arg Cys Pro Ala Ala Gly Asn Pro Thr Pro Thr Ile Arg
145                 150                 155                 160

Trp Leu Lys Asp Gly Gln Ala Phe His Gly Glu Asn Arg Ile Gly Gly
                165                 170                 175

Ile Arg Leu Arg His Gln His Trp Ser Leu Val Met Glu Ser Val Val
                180                 185                 190

Pro Ser Asp Arg Gly Thr Tyr Thr Cys Leu Val Glu Asn Ala Val Gly
                195                 200                 205

Ser Ile Arg Tyr Asn Tyr Leu Leu Asp Val Leu Glu Arg Ser Pro His
210                 215                 220

Arg Pro Ile Leu Gln Ala Gly Leu Pro Ala Asn Thr Thr Ala Val Val
225                 230                 235                 240

Gly Ser Asp Val Glu Leu Leu Cys Lys Val Tyr Ser Asp Ala Gln Pro
                245                 250                 255

His Ile Gln Trp Leu Lys His Ile Val Ile Asn Gly Ser Ser Phe Gly
                260                 265                 270

Ala Asp Gly Phe Pro Tyr Val Gln Val Leu Lys Thr Ala Asp Ile Asn
                275                 280                 285

Ser Ser Glu Val Glu Val Leu Tyr Leu Arg Asn Val Ser Ala Glu Asp
290                 295                 300

Ala Gly Glu Tyr Thr Cys Leu Ala Gly Asn Ser Ile Gly Leu Ser Tyr
305                 310                 315                 320

Gln Ser Ala Trp Leu Thr Val Leu Pro
                325

<210> SEQ ID NO 45
<211> LENGTH: 328
<212> TYPE: PRT
<213> ORGANISM: Artificial Sequence
<220> FEATURE:
<223> OTHER INFORMATION: Synthetic sequence

<400> SEQUENCE: 45

Leu Glu Ala Ser Glu Glu Val Glu Leu Glu Pro Cys Leu Ala Pro Ser
 1               5                  10                  15

Leu Glu Gln Gln Glu Gln Glu Leu Thr Val Ala Leu Gly Gln Pro Val
                20                  25                  30

Arg Leu Cys Cys Gly Arg Ala Glu Arg Gly Gly His Trp Tyr Lys Glu
            35                  40                  45

Gly Ser Arg Leu Ala Pro Ala Gly Arg Val Arg Gly Trp Arg Gly Arg
            50                  55                  60

Leu Glu Ile Ala Ser Phe Leu Pro Glu Asp Ala Gly Arg Tyr Leu Cys
 65                  70                  75                  80

Leu Ala Arg Gly Ser Met Ile Val Leu Gln Asn Leu Thr Leu Ile Thr
                 85                  90                  95
```

```
Gly Asp Ser Leu Thr Ser Ser Asn Asp Asp Glu Asp Gly Glu Asp Pro
            100                 105                 110

Ser Asn Arg His Ser Tyr Pro Gln Gln Ala Pro Tyr Trp Thr His Pro
        115                 120                 125

Gln Arg Met Glu Lys Lys Leu His Ala Val Pro Ala Gly Asn Thr Val
    130                 135                 140

Lys Phe Arg Cys Pro Ala Ala Gly Asn Pro Thr Pro Thr Ile Arg Trp
145                 150                 155                 160

Leu Lys Asp Gly Gln Ala Phe His Gly Glu Asn Arg Ile Gly Gly Ile
                165                 170                 175

Arg Leu Arg His Gln His Trp Ser Leu Val Met Glu Ser Val Val Pro
            180                 185                 190

Ser Asp Arg Gly Thr Tyr Thr Cys Leu Val Glu Asn Ala Val Gly Ser
        195                 200                 205

Ile Arg Tyr Asn Tyr Leu Leu Asp Val Leu Glu Arg Ser Pro His Arg
    210                 215                 220

Pro Ile Leu Gln Ala Gly Leu Pro Ala Asn Thr Thr Ala Val Val Gly
225                 230                 235                 240

Ser Asp Val Glu Leu Leu Cys Lys Val Tyr Ser Asp Ala Gln Pro His
                245                 250                 255

Ile Gln Trp Leu Lys His Ile Val Ile Asn Gly Ser Ser Phe Gly Ala
            260                 265                 270

Asp Gly Phe Pro Tyr Val Gln Val Leu Lys Thr Ala Asp Ile Asn Ser
        275                 280                 285

Ser Glu Val Glu Val Leu Tyr Leu Arg Asn Val Ser Ala Glu Asp Ala
    290                 295                 300

Gly Glu Tyr Thr Cys Leu Ala Gly Asn Ser Ile Gly Leu Ser Tyr Gln
305                 310                 315                 320

Ser Ala Trp Leu Thr Val Leu Pro
                325

<210> SEQ ID NO 46
<211> LENGTH: 10
<212> TYPE: PRT
<213> ORGANISM: Artificial Sequence
<220> FEATURE:
<223> OTHER INFORMATION: Synthetic sequence

<400> SEQUENCE: 46

Asp Asp Glu Asp Pro Lys Ser His Arg Asp
1               5                   10

<210> SEQ ID NO 47
<211> LENGTH: 11
<212> TYPE: PRT
<213> ORGANISM: Artificial Sequence
<220> FEATURE:
<223> OTHER INFORMATION: Synthetic sequence

<400> SEQUENCE: 47

Asp Asp Glu Asp Pro Lys Ser His Arg Asp Pro
1               5                   10

<210> SEQ ID NO 48
<211> LENGTH: 12
<212> TYPE: PRT
<213> ORGANISM: Artificial Sequence
<220> FEATURE:
<223> OTHER INFORMATION: Synthetic sequence
```

<400> SEQUENCE: 48

Asp Asp Glu Asp Pro Lys Ser His Arg Asp Pro Ser
1               5                   10

<210> SEQ ID NO 49
<211> LENGTH: 13
<212> TYPE: PRT
<213> ORGANISM: Artificial Sequence
<220> FEATURE:
<223> OTHER INFORMATION: Synthetic sequence

<400> SEQUENCE: 49

Asp Asp Glu Asp Pro Lys Ser His Arg Asp Pro Ser Asn
1               5                   10

<210> SEQ ID NO 50
<211> LENGTH: 14
<212> TYPE: PRT
<213> ORGANISM: Artificial Sequence
<220> FEATURE:
<223> OTHER INFORMATION: Synthetic sequence

<400> SEQUENCE: 50

Asp Asp Glu Asp Pro Lys Ser His Arg Asp Pro Ser Asn Arg
1               5                   10

<210> SEQ ID NO 51
<211> LENGTH: 11
<212> TYPE: PRT
<213> ORGANISM: Artificial Sequence
<220> FEATURE:
<223> OTHER INFORMATION: Synthetic sequence

<400> SEQUENCE: 51

Asn Asp Asp Glu Asp Pro Lys Ser His Arg Asp
1               5                   10

<210> SEQ ID NO 52
<211> LENGTH: 12
<212> TYPE: PRT
<213> ORGANISM: Artificial Sequence
<220> FEATURE:
<223> OTHER INFORMATION: Synthetic sequence

<400> SEQUENCE: 52

Asn Asp Asp Glu Asp Pro Lys Ser His Arg Asp Pro
1               5                   10

<210> SEQ ID NO 53
<211> LENGTH: 13
<212> TYPE: PRT
<213> ORGANISM: Artificial Sequence
<220> FEATURE:
<223> OTHER INFORMATION: Synthetic sequence

<400> SEQUENCE: 53

Asn Asp Asp Glu Asp Pro Lys Ser His Arg Asp Pro Ser
1               5                   10

<210> SEQ ID NO 54
<211> LENGTH: 14
<212> TYPE: PRT
<213> ORGANISM: Artificial Sequence
<220> FEATURE:
<223> OTHER INFORMATION: Synthetic sequence

<400> SEQUENCE: 54

```
Asn Asp Asp Glu Asp Pro Lys Ser His Arg Asp Pro Ser Asn
1               5                   10
```

<210> SEQ ID NO 55
<211> LENGTH: 15
<212> TYPE: PRT
<213> ORGANISM: Artificial Sequence
<220> FEATURE:
<223> OTHER INFORMATION: Synthetic sequence

<400> SEQUENCE: 55

```
Asn Asp Asp Glu Asp Pro Lys Ser His Arg Asp Pro Ser Asn Arg
1               5                   10                  15
```

<210> SEQ ID NO 56
<211> LENGTH: 13
<212> TYPE: PRT
<213> ORGANISM: Artificial Sequence
<220> FEATURE:
<223> OTHER INFORMATION: Synthetic sequence

<400> SEQUENCE: 56

```
Glu Asp Asp Asp Asp Asp Asp Asp Ser Ser Ser Glu Glu
1               5                   10
```

<210> SEQ ID NO 57
<211> LENGTH: 15
<212> TYPE: PRT
<213> ORGANISM: Artificial Sequence
<220> FEATURE:
<223> OTHER INFORMATION: Synthetic sequence

<400> SEQUENCE: 57

```
Glu Asp Asp Asp Asp Asp Asp Asp Ser Ser Ser Glu Glu Lys Glu
1               5                   10                  15
```

<210> SEQ ID NO 58
<211> LENGTH: 17
<212> TYPE: PRT
<213> ORGANISM: Artificial Sequence
<220> FEATURE:
<223> OTHER INFORMATION: Synthetic sequence

<400> SEQUENCE: 58

```
Glu Asp Asp Asp Asp Asp Asp Asp Ser Ser Ser Glu Glu Lys Glu Thr
1               5                   10                  15

Asp
```

<210> SEQ ID NO 59
<211> LENGTH: 10
<212> TYPE: PRT
<213> ORGANISM: Artificial Sequence
<220> FEATURE:
<223> OTHER INFORMATION: Synthetic sequence

<400> SEQUENCE: 59

```
Asp Asp Glu Asp Asp Thr Asp Gly Ala Glu
1               5                   10
```

<210> SEQ ID NO 60
<211> LENGTH: 11
<212> TYPE: PRT
<213> ORGANISM: Artificial Sequence
<220> FEATURE:
<223> OTHER INFORMATION: Synthetic sequence

<400> SEQUENCE: 60

```
Asp Asp Glu Asp Asp Thr Asp Gly Ala Glu Asp
1               5                   10

<210> SEQ ID NO 61
<211> LENGTH: 15
<212> TYPE: PRT
<213> ORGANISM: Artificial Sequence
<220> FEATURE:
<223> OTHER INFORMATION: Synthetic sequence

<400> SEQUENCE: 61

Asp Asp Glu Asp Asp Thr Asp Gly Ala Glu Asp Phe Val Ser Glu
1               5                   10                  15

<210> SEQ ID NO 62
<211> LENGTH: 7
<212> TYPE: PRT
<213> ORGANISM: Artificial Sequence
<220> FEATURE:
<223> OTHER INFORMATION: Synthetic sequence

<400> SEQUENCE: 62

Asp Asp Glu Asp Gly Glu Asp
1               5

<210> SEQ ID NO 63
<211> LENGTH: 8
<212> TYPE: PRT
<213> ORGANISM: Artificial Sequence
<220> FEATURE:
<223> OTHER INFORMATION: Synthetic sequence

<400> SEQUENCE: 63

Asp Asp Glu Asp Gly Glu Asp Glu
1               5

<210> SEQ ID NO 64
<211> LENGTH: 10
<212> TYPE: PRT
<213> ORGANISM: Artificial Sequence
<220> FEATURE:
<223> OTHER INFORMATION: Synthetic sequence

<400> SEQUENCE: 64

Asp Asp Glu Asp Gly Glu Asp Glu Ala Glu
1               5                   10

<210> SEQ ID NO 65
<211> LENGTH: 11
<212> TYPE: PRT
<213> ORGANISM: Artificial Sequence
<220> FEATURE:
<223> OTHER INFORMATION: Synthetic sequence

<400> SEQUENCE: 65

Asp Asp Glu Asp Gly Glu Asp Glu Ala Glu Asp
1               5                   10

<210> SEQ ID NO 66
<211> LENGTH: 21
<212> TYPE: PRT
<213> ORGANISM: Artificial Sequence
<220> FEATURE:
<223> OTHER INFORMATION: Synthetic sequence

<400> SEQUENCE: 66

Met Trp Ser Trp Lys Cys Leu Leu Phe Trp Ala Val Leu Val Thr Ala
1               5                   10                  15
```

```
Thr Leu Cys Thr Ala
        20

<210> SEQ ID NO 67
<211> LENGTH: 21
<212> TYPE: PRT
<213> ORGANISM: Artificial Sequence
<220> FEATURE:
<223> OTHER INFORMATION: Synthetic sequence

<400> SEQUENCE: 67

Met Val Ser Trp Gly Arg Phe Ile Cys Leu Val Val Val Thr Met Ala
1               5                   10                  15

Thr Leu Ser Leu Ala
        20

<210> SEQ ID NO 68
<211> LENGTH: 22
<212> TYPE: PRT
<213> ORGANISM: Artificial Sequence
<220> FEATURE:
<223> OTHER INFORMATION: Synthetic sequence

<400> SEQUENCE: 68

Met Gly Ala Pro Ala Cys Ala Leu Ala Leu Cys Val Ala Val Ala Ile
1               5                   10                  15

Val Ala Gly Ala Ser Ser
        20

<210> SEQ ID NO 69
<211> LENGTH: 21
<212> TYPE: PRT
<213> ORGANISM: Artificial Sequence
<220> FEATURE:
<223> OTHER INFORMATION: Synthetic sequence

<400> SEQUENCE: 69

Met Arg Leu Leu Leu Ala Leu Leu Gly Ile Leu Leu Ser Val Pro Gly
1               5                   10                  15

Pro Pro Val Leu Ser
        20

<210> SEQ ID NO 70
<211> LENGTH: 8
<212> TYPE: PRT
<213> ORGANISM: Artificial Sequence
<220> FEATURE:
<223> OTHER INFORMATION: Synthetic sequence

<400> SEQUENCE: 70

Leu Glu Ala Ser Glu Glu Val Glu
1               5

<210> SEQ ID NO 71
<211> LENGTH: 19
<212> TYPE: PRT
<213> ORGANISM: Artificial Sequence
<220> FEATURE:
<223> OTHER INFORMATION: Synthetic sequence

<400> SEQUENCE: 71

Leu Pro Glu Glu Asp Pro Thr Trp Thr Ala Ala Ala Pro Glu Ala Arg
1               5                   10                  15

Tyr Thr Asp
```

```
<210> SEQ ID NO 72
<211> LENGTH: 232
<212> TYPE: PRT
<213> ORGANISM: Artificial Sequence
<220> FEATURE:
<223> OTHER INFORMATION: Synthetic sequence

<400> SEQUENCE: 72

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 73
<211> LENGTH: 228
<212> TYPE: PRT
<213> ORGANISM: Artificial Sequence
<220> FEATURE:
<223> OTHER INFORMATION: Synthetic sequence

<400> SEQUENCE: 73

Glu Arg Lys Cys Cys Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80
```

```
Phe Arg Val Val Ser Val Leu Thr Val Val His Gln Asp Trp Leu Asn
                85                  90                  95

Gly Lys Glu Tyr Lys Cys Lys Val Ser Asn Lys Gly Leu Pro Ala Pro
            100                 105                 110

Ile Glu Lys Thr Ile Ser Lys Thr Lys Gly Gln Pro Arg Glu Pro Gln
        115                 120                 125

Val Tyr Thr Leu Pro Pro Ser Arg Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys
225

<210> SEQ ID NO 74
<211> LENGTH: 229
<212> TYPE: PRT
<213> ORGANISM: Artificial Sequence
<220> FEATURE:
<223> OTHER INFORMATION: Synthetic sequence

<400> SEQUENCE: 74

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
```

```
                        210                 215                 220
Leu Ser Leu Gly Lys
225

<210> SEQ ID NO 75
<211> LENGTH: 21
<212> TYPE: PRT
<213> ORGANISM: Artificial Sequence
<220> FEATURE:
<223> OTHER INFORMATION: Synthetic sequence

<400> SEQUENCE: 75

Met Arg Leu Leu Leu Ala Leu Leu Gly Ile Leu Leu Ser Val Pro Gly
1               5                   10                  15

Pro Pro Val Leu Ser
            20

<210> SEQ ID NO 76
<211> LENGTH: 346
<212> TYPE: PRT
<213> ORGANISM: Artificial Sequence
<220> FEATURE:
<223> OTHER INFORMATION: Synthetic sequence

<400> SEQUENCE: 76

Ala Ser Glu Glu Val Glu Leu Glu Pro Cys Leu Ala Pro Ser Leu Glu
1               5                   10                  15

Gln Gln Glu Gln Glu Leu Thr Val Ala Leu Gly Gln Pro Val Arg Leu
                20                  25                  30

Cys Cys Gly Arg Ala Glu Arg Gly Gly His Trp Tyr Lys Glu Gly Ser
            35                  40                  45

Arg Leu Ala Pro Ala Gly Arg Val Arg Gly Trp Arg Gly Arg Leu Glu
        50                  55                  60

Ile Ala Ser Phe Leu Pro Glu Asp Ala Gly Arg Tyr Leu Cys Leu Ala
65                  70                  75                  80

Arg Gly Ser Met Ile Val Leu Gln Asn Leu Thr Leu Ile Thr Gly Asp
                85                  90                  95

Ser Leu Thr Ser Ser Asn Asp Asp Glu Asp Pro Lys Ser His Arg Asp
            100                 105                 110

Pro Ser Asn Arg His Ser Tyr Pro Gln Gln Ala Pro Tyr Trp Thr His
        115                 120                 125

Pro Gln Arg Met Glu Lys Lys Leu His Ala Val Pro Ala Gly Asn Thr
130                 135                 140

Val Lys Phe Arg Cys Pro Ala Ala Gly Asn Pro Thr Pro Thr Ile Arg
145                 150                 155                 160

Trp Leu Lys Asp Gly Gln Ala Phe His Gly Glu Asn Arg Ile Gly Gly
                165                 170                 175

Ile Arg Leu Arg His Gln His Trp Ser Leu Val Met Glu Ser Val Val
            180                 185                 190

Pro Ser Asp Arg Gly Thr Tyr Thr Cys Leu Val Glu Asn Ala Val Gly
        195                 200                 205

Ser Ile Arg Tyr Asn Tyr Leu Leu Asp Val Leu Glu Arg Ser Pro His
        210                 215                 220

Arg Pro Ile Leu Gln Ala Gly Leu Pro Ala Asn Thr Thr Ala Val Val
225                 230                 235                 240

Gly Ser Asp Val Glu Leu Leu Cys Lys Val Tyr Ser Asp Ala Gln Pro
                245                 250                 255

His Ile Gln Trp Leu Lys His Ile Val Ile Asn Gly Ser Ser Phe Gly
```

```
                        260                 265                 270
Ala Asp Gly Phe Pro Tyr Val Gln Val Leu Lys Thr Ala Asp Ile Asn
            275                 280                 285

Ser Ser Glu Val Glu Val Leu Tyr Leu Arg Asn Val Ser Ala Glu Asp
        290                 295                 300

Ala Gly Glu Tyr Thr Cys Leu Ala Gly Asn Ser Ile Gly Leu Ser Tyr
305                 310                 315                 320

Gln Ser Ala Trp Leu Thr Val Leu Pro Glu Glu Asp Pro Thr Trp Thr
                325                 330                 335

Ala Ala Ala Pro Glu Ala Arg Tyr Thr Asp
            340                 345

<210> SEQ ID NO 77
<211> LENGTH: 345
<212> TYPE: PRT
<213> ORGANISM: Artificial Sequence
<220> FEATURE:
<223> OTHER INFORMATION: Synthetic sequence

<400> SEQUENCE: 77

Ser Glu Glu Val Glu Leu Glu Pro Cys Leu Ala Pro Ser Leu Glu Gln
1               5                   10                  15

Gln Glu Gln Glu Leu Thr Val Ala Leu Gly Gln Pro Val Arg Leu Cys
            20                  25                  30

Cys Gly Arg Ala Glu Arg Gly Gly His Trp Tyr Lys Glu Gly Ser Arg
        35                  40                  45

Leu Ala Pro Ala Gly Arg Val Arg Gly Trp Arg Gly Arg Leu Glu Ile
    50                  55                  60

Ala Ser Phe Leu Pro Glu Asp Ala Gly Arg Tyr Leu Cys Leu Ala Arg
65                  70                  75                  80

Gly Ser Met Ile Val Leu Gln Asn Leu Thr Leu Ile Thr Gly Asp Ser
                85                  90                  95

Leu Thr Ser Ser Asn Asp Asp Glu Asp Pro Lys Ser His Arg Asp Pro
            100                 105                 110

Ser Asn Arg His Ser Tyr Pro Gln Gln Ala Pro Tyr Trp Thr His Pro
        115                 120                 125

Gln Arg Met Glu Lys Lys Leu His Ala Val Pro Ala Gly Asn Thr Val
    130                 135                 140

Lys Phe Arg Cys Pro Ala Ala Gly Asn Pro Thr Pro Thr Ile Arg Trp
145                 150                 155                 160

Leu Lys Asp Gly Gln Ala Phe His Gly Glu Asn Arg Ile Gly Gly Ile
                165                 170                 175

Arg Leu Arg His Gln His Trp Ser Leu Val Met Glu Ser Val Val Pro
            180                 185                 190

Ser Asp Arg Gly Thr Tyr Thr Cys Leu Val Glu Asn Ala Val Gly Ser
        195                 200                 205

Ile Arg Tyr Asn Tyr Leu Leu Asp Val Leu Glu Arg Ser Pro His Arg
    210                 215                 220

Pro Ile Leu Gln Ala Gly Leu Pro Ala Asn Thr Thr Ala Val Val Gly
225                 230                 235                 240

Ser Asp Val Glu Leu Leu Cys Lys Val Tyr Ser Asp Ala Gln Pro His
                245                 250                 255

Ile Gln Trp Leu Lys His Ile Val Ile Asn Gly Ser Ser Phe Gly Ala
            260                 265                 270

Asp Gly Phe Pro Tyr Val Gln Val Leu Lys Thr Ala Asp Ile Asn Ser
        275                 280                 285
```

Ser Glu Val Glu Val Leu Tyr Leu Arg Asn Val Ser Ala Glu Asp Ala
    290                 295                 300

Gly Glu Tyr Thr Cys Leu Ala Gly Asn Ser Ile Gly Leu Ser Tyr Gln
305                 310                 315                 320

Ser Ala Trp Leu Thr Val Leu Pro Glu Glu Asp Pro Thr Trp Thr Ala
                325                 330                 335

Ala Ala Pro Glu Ala Arg Tyr Thr Asp
            340                 345

<210> SEQ ID NO 78
<211> LENGTH: 343
<212> TYPE: PRT
<213> ORGANISM: Artificial Sequence
<220> FEATURE:
<223> OTHER INFORMATION: Synthetic sequence

<400> SEQUENCE: 78

Glu Val Glu Leu Glu Pro Cys Leu Ala Pro Ser Leu Glu Gln Gln Glu
1               5                   10                  15

Gln Glu Leu Thr Val Ala Leu Gly Gln Pro Val Arg Leu Cys Cys Gly
            20                  25                  30

Arg Ala Glu Arg Gly Gly His Trp Tyr Lys Glu Gly Ser Arg Leu Ala
        35                  40                  45

Pro Ala Gly Arg Val Arg Gly Trp Arg Gly Arg Leu Glu Ile Ala Ser
    50                  55                  60

Phe Leu Pro Glu Asp Ala Gly Arg Tyr Leu Cys Leu Ala Arg Gly Ser
65                  70                  75                  80

Met Ile Val Leu Gln Asn Leu Thr Leu Ile Thr Gly Asp Ser Leu Thr
                85                  90                  95

Ser Ser Asn Asp Asp Glu Asp Pro Lys Ser His Arg Asp Pro Ser Asn
            100                 105                 110

Arg His Ser Tyr Pro Gln Gln Ala Pro Tyr Trp Thr His Pro Gln Arg
        115                 120                 125

Met Glu Lys Lys Leu His Ala Val Pro Ala Gly Asn Thr Val Lys Phe
    130                 135                 140

Arg Cys Pro Ala Ala Gly Asn Pro Thr Pro Thr Ile Arg Trp Leu Lys
145                 150                 155                 160

Asp Gly Gln Ala Phe His Gly Glu Asn Arg Ile Gly Gly Ile Arg Leu
                165                 170                 175

Arg His Gln His Trp Ser Leu Val Met Glu Ser Val Val Pro Ser Asp
            180                 185                 190

Arg Gly Thr Tyr Thr Cys Leu Val Glu Asn Ala Val Gly Ser Ile Arg
        195                 200                 205

Tyr Asn Tyr Leu Leu Asp Val Leu Glu Arg Ser Pro His Arg Pro Ile
    210                 215                 220

Leu Gln Ala Gly Leu Pro Ala Asn Thr Thr Ala Val Val Gly Ser Asp
225                 230                 235                 240

Val Glu Leu Leu Cys Lys Val Tyr Ser Asp Ala Gln Pro His Ile Gln
                245                 250                 255

Trp Leu Lys His Ile Val Ile Asn Gly Ser Ser Phe Gly Ala Asp Gly
            260                 265                 270

Phe Pro Tyr Val Gln Val Leu Lys Thr Ala Asp Ile Asn Ser Ser Glu
        275                 280                 285

Val Glu Val Leu Tyr Leu Arg Asn Val Ser Ala Glu Asp Ala Gly Glu
    290                 295                 300

```
Tyr Thr Cys Leu Ala Gly Asn Ser Ile Gly Leu Ser Tyr Gln Ser Ala
305                 310                 315                 320

Trp Leu Thr Val Leu Pro Glu Glu Asp Pro Thr Trp Thr Ala Ala Ala
            325                 330                 335

Pro Glu Ala Arg Tyr Thr Asp
            340

<210> SEQ ID NO 79
<211> LENGTH: 341
<212> TYPE: PRT
<213> ORGANISM: Artificial Sequence
<220> FEATURE:
<223> OTHER INFORMATION: Synthetic sequence

<400> SEQUENCE: 79

Glu Leu Glu Pro Cys Leu Ala Pro Ser Leu Glu Gln Gln Glu Gln Glu
1               5                   10                  15

Leu Thr Val Ala Leu Gly Gln Pro Val Arg Leu Cys Cys Gly Arg Ala
            20                  25                  30

Glu Arg Gly Gly His Trp Tyr Lys Glu Gly Ser Arg Leu Ala Pro Ala
        35                  40                  45

Gly Arg Val Arg Gly Trp Arg Gly Arg Leu Glu Ile Ala Ser Phe Leu
50                  55                  60

Pro Glu Asp Ala Gly Arg Tyr Leu Cys Leu Ala Arg Gly Ser Met Ile
65                  70                  75                  80

Val Leu Gln Asn Leu Thr Leu Ile Thr Gly Asp Ser Leu Thr Ser Ser
                85                  90                  95

Asn Asp Asp Glu Asp Pro Lys Ser His Arg Asp Pro Ser Asn Arg His
            100                 105                 110

Ser Tyr Pro Gln Gln Ala Pro Tyr Trp Thr His Pro Gln Arg Met Glu
        115                 120                 125

Lys Lys Leu His Ala Val Pro Ala Gly Asn Thr Val Lys Phe Arg Cys
130                 135                 140

Pro Ala Ala Gly Asn Pro Thr Pro Thr Ile Arg Trp Leu Lys Asp Gly
145                 150                 155                 160

Gln Ala Phe His Gly Glu Asn Arg Ile Gly Gly Ile Arg Leu Arg His
                165                 170                 175

Gln His Trp Ser Leu Val Met Glu Ser Val Val Pro Ser Asp Arg Gly
            180                 185                 190

Thr Tyr Thr Cys Leu Val Glu Asn Ala Val Gly Ser Ile Arg Tyr Asn
        195                 200                 205

Tyr Leu Leu Asp Val Leu Glu Arg Ser Pro His Arg Pro Ile Leu Gln
210                 215                 220

Ala Gly Leu Pro Ala Asn Thr Thr Ala Val Val Gly Ser Asp Val Glu
225                 230                 235                 240

Leu Leu Cys Lys Val Tyr Ser Asp Ala Gln Pro His Ile Gln Trp Leu
                245                 250                 255

Lys His Ile Val Ile Asn Gly Ser Ser Phe Gly Ala Asp Gly Phe Pro
            260                 265                 270

Tyr Val Gln Val Leu Lys Thr Ala Asp Ile Asn Ser Ser Glu Val Glu
        275                 280                 285

Val Leu Tyr Leu Arg Asn Val Ser Ala Glu Asp Ala Gly Glu Tyr Thr
290                 295                 300

Cys Leu Ala Gly Asn Ser Ile Gly Leu Ser Tyr Gln Ser Ala Trp Leu
305                 310                 315                 320

Thr Val Leu Pro Glu Glu Asp Pro Thr Trp Thr Ala Ala Ala Pro Glu
```

Ala Arg Tyr Thr Asp
            340

<210> SEQ ID NO 80
<211> LENGTH: 340
<212> TYPE: PRT
<213> ORGANISM: Artificial Sequence
<220> FEATURE:
<223> OTHER INFORMATION: Synthetic sequence

<400> SEQUENCE: 80

Leu Glu Pro Cys Leu Ala Pro Ser Leu Glu Gln Gln Glu Gln Glu Leu
1               5                   10                  15

Thr Val Ala Leu Gly Gln Pro Val Arg Leu Cys Cys Gly Arg Ala Glu
            20                  25                  30

Arg Gly Gly His Trp Tyr Lys Glu Gly Ser Arg Leu Ala Pro Ala Gly
        35                  40                  45

Arg Val Arg Gly Trp Arg Gly Arg Leu Glu Ile Ala Ser Phe Leu Pro
    50                  55                  60

Glu Asp Ala Gly Arg Tyr Leu Cys Leu Ala Arg Gly Ser Met Ile Val
65                  70                  75                  80

Leu Gln Asn Leu Thr Leu Ile Thr Gly Asp Ser Leu Thr Ser Ser Asn
                85                  90                  95

Asp Asp Glu Asp Pro Lys Ser His Arg Asp Pro Ser Asn Arg His Ser
            100                 105                 110

Tyr Pro Gln Gln Ala Pro Tyr Trp Thr His Pro Gln Arg Met Glu Lys
        115                 120                 125

Lys Leu His Ala Val Pro Ala Gly Asn Thr Val Lys Phe Arg Cys Pro
    130                 135                 140

Ala Ala Gly Asn Pro Thr Pro Thr Ile Arg Trp Leu Lys Asp Gly Gln
145                 150                 155                 160

Ala Phe His Gly Glu Asn Arg Ile Gly Gly Ile Arg Leu Arg His Gln
                165                 170                 175

His Trp Ser Leu Val Met Glu Ser Val Val Pro Ser Asp Arg Gly Thr
            180                 185                 190

Tyr Thr Cys Leu Val Glu Asn Ala Val Gly Ser Ile Arg Tyr Asn Tyr
        195                 200                 205

Leu Leu Asp Val Leu Glu Arg Ser Pro His Arg Pro Ile Leu Gln Ala
    210                 215                 220

Gly Leu Pro Ala Asn Thr Thr Ala Val Val Gly Ser Asp Val Glu Leu
225                 230                 235                 240

Leu Cys Lys Val Tyr Ser Asp Ala Gln Pro His Ile Gln Trp Leu Lys
                245                 250                 255

His Ile Val Ile Asn Gly Ser Ser Phe Gly Ala Asp Gly Phe Pro Tyr
            260                 265                 270

Val Gln Val Leu Lys Thr Ala Asp Ile Asn Ser Ser Glu Val Glu Val
        275                 280                 285

Leu Tyr Leu Arg Asn Val Ser Ala Glu Asp Ala Gly Tyr Thr Cys
    290                 295                 300

Leu Ala Gly Asn Ser Ile Gly Leu Ser Tyr Gln Ser Ala Trp Leu Thr
305                 310                 315                 320

Val Leu Pro Glu Glu Asp Pro Thr Trp Thr Ala Ala Pro Glu Ala
                325                 330                 335

Arg Tyr Thr Asp
            340

<210> SEQ ID NO 81
<211> LENGTH: 323
<212> TYPE: PRT
<213> ORGANISM: Artificial Sequence
<220> FEATURE:
<223> OTHER INFORMATION: Synthetic sequence

<400> SEQUENCE: 81

```
Leu Glu Pro Cys Leu Ala Pro Ser Leu Glu Gln Gln Glu Gln Glu Leu
1               5                   10                  15

Thr Val Ala Leu Gly Gln Pro Val Arg Leu Cys Cys Gly Arg Ala Glu
            20                  25                  30

Arg Gly Gly His Trp Tyr Lys Glu Gly Ser Arg Leu Ala Pro Ala Gly
        35                  40                  45

Arg Val Arg Gly Trp Arg Gly Arg Leu Glu Ile Ala Ser Phe Leu Pro
    50                  55                  60

Glu Asp Ala Gly Arg Tyr Leu Cys Leu Ala Arg Gly Ser Met Ile Val
65                  70                  75                  80

Leu Gln Asn Leu Thr Leu Ile Thr Gly Asp Ser Leu Thr Ser Ser Asn
                85                  90                  95

Asp Asp Glu Asp Pro Lys Ser His Arg Asp Pro Ser Asn Arg His Ser
            100                 105                 110

Tyr Pro Gln Gln Ala Pro Tyr Trp Thr His Pro Gln Arg Met Glu Lys
        115                 120                 125

Lys Leu His Ala Val Pro Ala Gly Asn Thr Val Lys Phe Arg Cys Pro
    130                 135                 140

Ala Ala Gly Asn Pro Thr Pro Thr Ile Arg Trp Leu Lys Asp Gly Gln
145                 150                 155                 160

Ala Phe His Gly Glu Asn Arg Ile Gly Gly Ile Arg Leu Arg His Gln
                165                 170                 175

His Trp Ser Leu Val Met Glu Ser Val Val Pro Ser Asp Arg Gly Thr
            180                 185                 190

Tyr Thr Cys Leu Val Glu Asn Ala Val Gly Ser Ile Arg Tyr Asn Tyr
        195                 200                 205

Leu Leu Asp Val Leu Glu Arg Ser Pro His Arg Pro Ile Leu Gln Ala
    210                 215                 220

Gly Leu Pro Ala Asn Thr Thr Ala Val Val Gly Ser Asp Val Glu Leu
225                 230                 235                 240

Leu Cys Lys Val Tyr Ser Asp Ala Gln Pro His Ile Gln Trp Leu Lys
                245                 250                 255

His Ile Val Ile Asn Gly Ser Ser Phe Gly Ala Asp Gly Phe Pro Tyr
            260                 265                 270

Val Gln Val Leu Lys Thr Ala Asp Ile Asn Ser Ser Glu Val Glu Val
        275                 280                 285

Leu Tyr Leu Arg Asn Val Ser Ala Glu Asp Ala Gly Tyr Thr Cys
    290                 295                 300

Leu Ala Gly Asn Ser Ile Gly Leu Ser Tyr Gln Ser Ala Trp Leu Thr
305                 310                 315                 320

Val Leu Pro
```

<210> SEQ ID NO 82
<211> LENGTH: 369
<212> TYPE: PRT
<213> ORGANISM: Artificial Sequence
<220> FEATURE:
<223> OTHER INFORMATION: Synthetic sequence

```
<400> SEQUENCE: 82

Met Arg Leu Leu Leu Ala Leu Leu Gly Ile Leu Leu Ser Val Pro Gly
1               5                   10                  15

Pro Pro Val Leu Ser Leu Glu Ala Ser Glu Glu Val Glu Leu Glu Pro
            20                  25                  30

Cys Leu Ala Pro Ser Leu Glu Gln Gln Glu Gln Glu Leu Thr Val Ala
        35                  40                  45

Leu Gly Gln Pro Val Arg Leu Cys Cys Gly Arg Ala Glu Arg Gly Gly
    50                  55                  60

His Trp Tyr Lys Glu Gly Ser Arg Leu Ala Pro Ala Gly Arg Val Arg
65                  70                  75                  80

Gly Trp Arg Gly Arg Leu Glu Ile Ala Ser Phe Leu Pro Glu Asp Ala
                85                  90                  95

Gly Arg Tyr Leu Cys Leu Ala Arg Gly Ser Met Ile Val Leu Gln Asn
            100                 105                 110

Leu Thr Leu Ile Thr Gly Asp Ser Leu Thr Ser Ser Asn Asp Asp Glu
        115                 120                 125

Asp Pro Lys Ser His Arg Asp Pro Ser Asn Arg His Ser Tyr Pro Gln
    130                 135                 140

Gln Ala Pro Tyr Trp Thr His Pro Gln Arg Met Glu Lys Lys Leu His
145                 150                 155                 160

Ala Val Pro Ala Gly Asn Thr Val Lys Phe Arg Cys Pro Ala Ala Gly
                165                 170                 175

Asn Pro Thr Pro Thr Ile Arg Trp Leu Lys Asp Gly Gln Ala Phe His
            180                 185                 190

Gly Glu Asn Arg Ile Gly Gly Ile Arg Leu Arg His Gln His Trp Ser
        195                 200                 205

Leu Val Met Glu Ser Val Val Pro Ser Asp Arg Gly Thr Tyr Thr Cys
    210                 215                 220

Leu Val Glu Asn Ala Val Gly Ser Ile Arg Tyr Asn Tyr Leu Leu Asp
225                 230                 235                 240

Val Leu Glu Arg Ser Pro His Arg Pro Ile Leu Gln Ala Gly Leu Pro
                245                 250                 255

Ala Asn Thr Thr Ala Val Val Gly Ser Asp Val Glu Leu Leu Cys Lys
            260                 265                 270

Val Tyr Ser Asp Ala Gln Pro His Ile Gln Trp Leu Lys His Ile Val
        275                 280                 285

Ile Asn Gly Ser Ser Phe Gly Ala Asp Gly Phe Pro Tyr Val Gln Val
    290                 295                 300

Leu Lys Thr Ala Asp Ile Asn Ser Ser Glu Val Glu Val Leu Tyr Leu
305                 310                 315                 320

Arg Asn Val Ser Ala Glu Asp Ala Gly Glu Tyr Thr Cys Leu Ala Gly
                325                 330                 335

Asn Ser Ile Gly Leu Ser Tyr Gln Ser Ala Trp Leu Thr Val Leu Pro
            340                 345                 350

Glu Glu Asp Pro Thr Trp Thr Ala Ala Pro Glu Ala Arg Tyr Thr
        355                 360                 365

Asp

<210> SEQ ID NO 83
<211> LENGTH: 376
<212> TYPE: PRT
<213> ORGANISM: Artificial Sequence
<220> FEATURE:
```

<223> OTHER INFORMATION: Synthetic sequence

<400> SEQUENCE: 83

```
Met Trp Ser Trp Lys Cys Leu Leu Phe Trp Ala Val Leu Val Thr Ala
1               5                   10                  15
Thr Leu Cys Thr Ala Arg Pro Ser Pro Thr Leu Pro Glu Gln Ala Gln
            20                  25                  30
Pro Trp Gly Ala Pro Val Glu Val Glu Ser Phe Leu Val His Pro Gly
        35                  40                  45
Asp Leu Leu Gln Leu Arg Cys Arg Leu Arg Asp Asp Val Gln Ser Ile
    50                  55                  60
Asn Trp Leu Arg Asp Gly Val Gln Leu Ala Glu Ser Asn Arg Thr Arg
65                  70                  75                  80
Ile Thr Gly Glu Glu Val Glu Val Gln Asp Ser Val Pro Ala Asp Ser
                85                  90                  95
Gly Leu Tyr Ala Cys Val Thr Ser Ser Pro Ser Gly Ser Asp Thr Thr
            100                 105                 110
Tyr Phe Ser Val Asn Val Ser Asp Ala Leu Pro Ser Ser Glu Asp Asp
        115                 120                 125
Asp Asp Asp Asp Ser Ser Ser Glu Glu Lys Glu Thr Asp Asn Thr
    130                 135                 140
Lys Pro Asn Arg Met Pro Val Ala Pro Tyr Trp Thr Ser Pro Glu Lys
145                 150                 155                 160
Met Glu Lys Lys Leu His Ala Val Pro Ala Ala Lys Thr Val Lys Phe
                165                 170                 175
Lys Cys Pro Ser Ser Gly Thr Pro Asn Pro Thr Leu Arg Trp Leu Lys
            180                 185                 190
Asn Gly Lys Glu Phe Lys Pro Asp His Arg Ile Gly Gly Tyr Lys Val
        195                 200                 205
Arg Tyr Ala Thr Trp Ser Ile Ile Met Asp Ser Val Val Pro Ser Asp
    210                 215                 220
Lys Gly Asn Tyr Thr Cys Ile Val Glu Asn Glu Tyr Gly Ser Ile Asn
225                 230                 235                 240
His Thr Tyr Gln Leu Asp Val Val Glu Arg Ser Pro His Arg Pro Ile
                245                 250                 255
Leu Gln Ala Gly Leu Pro Ala Asn Lys Thr Val Ala Leu Gly Ser Asn
            260                 265                 270
Val Glu Phe Met Cys Lys Val Tyr Ser Asp Pro Gln Pro His Ile Gln
        275                 280                 285
Trp Leu Lys His Ile Glu Val Asn Gly Ser Lys Ile Gly Pro Asp Asn
    290                 295                 300
Leu Pro Tyr Val Gln Ile Leu Lys Thr Ala Gly Val Asn Thr Thr Asp
305                 310                 315                 320
Lys Glu Met Glu Val Leu His Leu Arg Asn Val Ser Phe Glu Asp Ala
                325                 330                 335
Gly Glu Tyr Thr Cys Leu Ala Gly Asn Ser Ile Gly Leu Ser His His
            340                 345                 350
Ser Ala Trp Leu Thr Val Leu Glu Ala Leu Glu Glu Arg Pro Ala Val
        355                 360                 365
Met Thr Ser Pro Leu Tyr Leu Glu
    370                 375
```

<210> SEQ ID NO 84
<211> LENGTH: 377
<212> TYPE: PRT

<213> ORGANISM: Artificial Sequence
<220> FEATURE:
<223> OTHER INFORMATION: Synthetic sequence

<400> SEQUENCE: 84

```
Met Val Ser Trp Gly Arg Phe Ile Cys Leu Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Glu Pro Pro Thr Lys Tyr Gln Ile Ser Gln Pro Glu
        35                  40                  45

Val Tyr Val Ala Ala Pro Gly Glu Ser Leu Glu Val Arg Cys Leu Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
        115                 120                 125

Ser Ser Gly Asp Asp Glu Asp Asp Thr Asp Gly Ala Glu Asp Phe Val
130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
        195                 200                 205

Val Arg Asn Gln His Trp Ser Leu Ile Met Glu Ser Val Val Pro Ser
    210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Pro His Arg Pro
                245                 250                 255

Ile Leu Gln Ala Gly Leu Pro Ala Asn Ala Ser Thr Val Val Gly Gly
            260                 265                 270

Asp Val Glu Phe Val Cys Lys Val Tyr Ser Asp Ala Gln Pro His Ile
        275                 280                 285

Gln Trp Ile Lys His Val Glu Lys Asn Gly Ser Lys Tyr Gly Pro Asp
    290                 295                 300

Gly Leu Pro Tyr Leu Lys Val Leu Lys Ala Ala Gly Val Asn Thr Thr
305                 310                 315                 320

Asp Lys Glu Ile Glu Val Leu Tyr Ile Arg Asn Val Thr Phe Glu Asp
                325                 330                 335

Ala Gly Glu Tyr Thr Cys Leu Ala Gly Asn Ser Ile Gly Ile Ser Phe
            340                 345                 350

His Ser Ala Trp Leu Thr Val Leu Pro Ala Pro Gly Arg Glu Lys Glu
        355                 360                 365

Ile Thr Ala Ser Pro Asp Tyr Leu Glu
    370                 375
```

<210> SEQ ID NO 85

<211> LENGTH: 375
<212> TYPE: PRT
<213> ORGANISM: Artificial Sequence
<220> FEATURE:
<223> OTHER INFORMATION: Synthetic sequence

<400> SEQUENCE: 85

Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
            20                  25                  30

Gly Arg Ala Ala Glu Val Pro Gly Pro Glu Pro Gly Gln Gln Glu Gln
        35                  40                  45

Leu Val Phe Gly Ser Gly Asp Ala Val Glu Leu Ser Cys Pro Pro Pro
    50                  55                  60

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
            100                 105                 110

Leu Thr Gln Arg Val Leu Cys His Phe Ser Val Arg Val Thr Asp Ala
        115                 120                 125

Pro Ser Ser Gly Asp Asp Glu Asp Gly Glu Asp Ala Glu Asp Thr
    130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
            180                 185                 190

Arg Glu Phe Arg Gly Glu His Arg Ile Gly Gly Ile Lys Leu Arg His
        195                 200                 205

Gln Gln Trp Ser Leu Val Met Glu Ser Val Val Pro Ser Asp Arg Gly
    210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
                245                 250                 255

Ala Gly Leu Pro Ala Asn Gln Thr Ala Val Leu Gly Ser Asp Val Glu
            260                 265                 270

Phe His Cys Lys Val Tyr Ser Asp Ala Gln Pro His Ile Gln Trp Leu
        275                 280                 285

Lys His Val Glu Val Asn Gly Ser Lys Val Gly Pro Asp Gly Thr Pro
    290                 295                 300

Tyr Val Thr Val Leu Lys Thr Ala Gly Ala Asn Thr Thr Asp Lys Glu
305                 310                 315                 320

Leu Glu Val Leu Ser Leu His Asn Val Thr Phe Glu Asp Ala Gly Glu
                325                 330                 335

Tyr Thr Cys Leu Ala Gly Asn Ser Ile Gly Phe Ser His His Ser Ala
            340                 345                 350

Trp Leu Val Val Leu Pro Ala Glu Glu Leu Val Glu Ala Asp Glu
        355                 360                 365

Ala Gly Ser Val Tyr Ala Gly
    370                 375

<210> SEQ ID NO 86
<211> LENGTH: 566
<212> TYPE: PRT
<213> ORGANISM: Artificial Sequence
<220> FEATURE:
<223> OTHER INFORMATION: Synthetic sequence

<400> SEQUENCE: 86

```
Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
            20                  25                  30

Arg Leu Cys Cys Gly Arg Ala Glu Arg Gly Gly His Trp Tyr Lys Glu
        35                  40                  45

Gly Ser Arg Leu Ala Pro Ala Gly Arg Val Arg Gly Trp Arg Gly Arg
    50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ala Leu Pro Ser Ser Glu Asp Asp Asp Asp Asp Asp Asp Ser
            100                 105                 110

Ser Ser Glu Glu Lys Glu Thr Asp Asn Thr Lys Pro Asn Pro Val Ala
        115                 120                 125

Pro Tyr Trp Thr His Pro Gln Arg Met Glu Lys Lys Leu His Ala Val
    130                 135                 140

Pro Ala Gly Asn Thr Val Lys Phe Arg Cys Pro Ala Ala Gly Asn Pro
145                 150                 155                 160

Thr Pro Thr Ile Arg Trp Leu Lys Asp Gly Gln Ala Phe His Gly Glu
                165                 170                 175

Asn Arg Ile Gly Gly Ile Arg Leu Arg His Gln His Trp Ser Leu Val
            180                 185                 190

Met Glu Ser Val Val Pro Ser Asp Arg Gly Thr Tyr Thr Cys Leu Val
        195                 200                 205

Glu Asn Ala Val Gly Ser Ile Arg Tyr Asn Tyr Leu Leu Asp Val Leu
    210                 215                 220

Glu Arg Ser Pro His Arg Pro Ile Leu Gln Ala Gly Leu Pro Ala Asn
225                 230                 235                 240

Thr Thr Ala Val Val Gly Ser Asp Val Glu Leu Leu Cys Lys Val Tyr
                245                 250                 255

Ser Asp Ala Gln Pro His Ile Gln Trp Leu Lys His Ile Val Ile Asn
            260                 265                 270

Gly Ser Ser Phe Gly Ala Asp Gly Phe Pro Tyr Val Gln Val Leu Lys
        275                 280                 285

Thr Ala Asp Ile Asn Ser Ser Glu Val Glu Val Leu Tyr Leu Arg Asn
    290                 295                 300

Val Ser Ala Glu Asp Ala Gly Glu Tyr Thr Cys Leu Ala Gly Asn Ser
305                 310                 315                 320

Ile Gly Leu Ser Tyr Gln Ser Ala Trp Leu Thr Val Leu Pro Glu Pro
                325                 330                 335

Lys Ser Ser Asp Lys Thr His Thr Cys Pro Pro Cys Pro Ala Pro Glu
            340                 345                 350

Leu Leu Gly Gly Pro Ser Val Phe Leu Phe Pro Pro Lys Pro Lys Asp
        355                 360                 365

Thr Leu Met Ile Ser Arg Thr Pro Glu Val Thr Cys Val Val Val Asp
```

-continued

```
                    370                 375                 380
Val Ser His Glu Asp Pro Glu Val Lys Phe Asn Trp Tyr Val Asp Gly
385                 390                 395                 400

Val Glu Val His Asn Ala Lys Thr Lys Pro Arg Glu Glu Gln Tyr Asn
                405                 410                 415

Ser Thr Tyr Arg Val Val Ser Val Leu Thr Val Leu His Gln Asp Trp
            420                 425                 430

Leu Asn Gly Lys Glu Tyr Lys Cys Lys Val Ser Asn Lys Ala Leu Pro
        435                 440                 445

Ala Pro Ile Glu Lys Thr Ile Ser Lys Ala Lys Gly Gln Pro Arg Glu
    450                 455                 460

Pro Gln Val Tyr Thr Leu Pro Pro Ser Arg Asp Glu Leu Thr Lys Asn
465                 470                 475                 480

Gln Val Ser Leu Thr Cys Leu Val Lys Gly Phe Tyr Pro Ser Asp Ile
                485                 490                 495

Ala Val Glu Trp Glu Ser Asn Gly Gln Pro Glu Asn Asn Tyr Lys Thr
            500                 505                 510

Thr Pro Pro Val Leu Asp Ser Asp Gly Ser Phe Phe Leu Tyr Ser Lys
        515                 520                 525

Leu Thr Val Asp Lys Ser Arg Trp Gln Gln Gly Asn Val Phe Ser Cys
    530                 535                 540

Ser Val Met His Glu Ala Leu His Asn His Tyr Thr Gln Lys Ser Leu
545                 550                 555                 560

Ser Leu Ser Pro Gly Lys
                565
```

<210> SEQ ID NO 87
<211> LENGTH: 565
<212> TYPE: PRT
<213> ORGANISM: Artificial Sequence
<220> FEATURE:
<223> OTHER INFORMATION: Synthetic sequence

<400> SEQUENCE: 87

```
Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
                20                  25                  30

Arg Leu Cys Cys Gly Arg Ala Glu Arg Gly Gly His Trp Tyr Lys Glu
            35                  40                  45

Gly Ser Arg Leu Ala Pro Ala Gly Arg Val Arg Gly Trp Arg Gly Arg
        50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ala Leu Pro Ser Ser Glu Asp Asp Asp Asp Asp Asp Asp Ser
            100                 105                 110

Ser Ser Glu Glu Lys Glu Thr Asp Asn Thr Lys Pro Asn Gln Ala Pro
        115                 120                 125

Tyr Trp Thr His Pro Gln Arg Met Glu Lys Lys Leu His Ala Val Pro
    130                 135                 140

Ala Gly Asn Thr Val Lys Phe Arg Cys Pro Ala Ala Gly Asn Pro Thr
145                 150                 155                 160

Pro Thr Ile Arg Trp Leu Lys Asp Gly Gln Ala Phe His Gly Glu Asn
                165                 170                 175
```

Arg Ile Gly Gly Ile Arg Leu Arg His Gln His Trp Ser Leu Val Met
            180                 185                 190

Glu Ser Val Val Pro Ser Asp Arg Gly Thr Tyr Thr Cys Leu Val Glu
            195                 200                 205

Asn Ala Val Gly Ser Ile Arg Tyr Asn Tyr Leu Leu Asp Val Leu Glu
210                 215                 220

Arg Ser Pro His Arg Pro Ile Leu Gln Ala Gly Leu Pro Ala Asn Thr
225                 230                 235                 240

Thr Ala Val Val Gly Ser Asp Val Glu Leu Leu Cys Lys Val Tyr Ser
            245                 250                 255

Asp Ala Gln Pro His Ile Gln Trp Leu Lys His Ile Val Ile Asn Gly
            260                 265                 270

Ser Ser Phe Gly Ala Asp Gly Phe Pro Tyr Val Gln Val Leu Lys Thr
            275                 280                 285

Ala Asp Ile Asn Ser Ser Glu Val Glu Val Leu Tyr Leu Arg Asn Val
290                 295                 300

Ser Ala Glu Asp Ala Gly Glu Tyr Thr Cys Leu Ala Gly Asn Ser Ile
305                 310                 315                 320

Gly Leu Ser Tyr Gln Ser Ala Trp Leu Thr Val Leu Pro Glu Pro Lys
            325                 330                 335

Ser Ser Asp Lys Thr His Thr Cys Pro Pro Cys Pro Ala Pro Glu Leu
            340                 345                 350

Leu Gly Gly Pro Ser Val Phe Leu Phe Pro Pro Lys Pro Lys Asp Thr
            355                 360                 365

Leu Met Ile Ser Arg Thr Pro Glu Val Thr Cys Val Val Val Asp Val
370                 375                 380

Ser His Glu Asp Pro Glu Val Lys Phe Asn Trp Tyr Val Asp Gly Val
385                 390                 395                 400

Glu Val His Asn Ala Lys Thr Lys Pro Arg Glu Glu Gln Tyr Asn Ser
            405                 410                 415

Thr Tyr Arg Val Val Ser Val Leu Thr Val Leu His Gln Asp Trp Leu
            420                 425                 430

Asn Gly Lys Glu Tyr Lys Cys Lys Val Ser Asn Lys Ala Leu Pro Ala
            435                 440                 445

Pro Ile Glu Lys Thr Ile Ser Lys Ala Lys Gly Gln Pro Arg Glu Pro
450                 455                 460

Gln Val Tyr Thr Leu Pro Pro Ser Arg Asp Glu Leu Thr Lys Asn Gln
465                 470                 475                 480

Val Ser Leu Thr Cys Leu Val Lys Gly Phe Tyr Pro Ser Asp Ile Ala
            485                 490                 495

Val Glu Trp Glu Ser Asn Gly Gln Pro Glu Asn Asn Tyr Lys Thr Thr
            500                 505                 510

Pro Pro Val Leu Asp Ser Asp Gly Ser Phe Phe Leu Tyr Ser Lys Leu
            515                 520                 525

Thr Val Asp Lys Ser Arg Trp Gln Gln Gly Asn Val Phe Ser Cys Ser
530                 535                 540

Val Met His Glu Ala Leu His Asn His Tyr Thr Gln Lys Ser Leu Ser
545                 550                 555                 560

Leu Ser Pro Gly Lys
            565

<210> SEQ ID NO 88
<211> LENGTH: 566
<212> TYPE: PRT

<213> ORGANISM: Artificial Sequence
<220> FEATURE:
<223> OTHER INFORMATION: Synthetic sequence

<400> SEQUENCE: 88

```
Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
            20                  25                  30

Arg Leu Cys Cys Gly Arg Ala Glu Arg Gly Gly His Trp Tyr Lys Glu
        35                  40                  45

Gly Ser Arg Leu Ala Pro Ala Gly Arg Val Arg Gly Trp Arg Gly Arg
    50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ser Leu Thr Ser Ser Asn Glu Asp Asp Asp Asp Asp Asp Asp
            100                 105                 110

Ser Ser Ser Glu Asp Pro Ser Asn Arg His Ser Tyr Pro Gln Gln Ala
        115                 120                 125

Pro Tyr Trp Thr His Pro Gln Arg Met Glu Lys Lys Leu His Ala Val
    130                 135                 140

Pro Ala Gly Asn Thr Val Lys Phe Arg Cys Pro Ala Ala Gly Asn Pro
145                 150                 155                 160

Thr Pro Thr Ile Arg Trp Leu Lys Asp Gly Gln Ala Phe His Gly Glu
                165                 170                 175

Asn Arg Ile Gly Gly Ile Arg Leu Arg His Gln His Trp Ser Leu Val
            180                 185                 190

Met Glu Ser Val Val Pro Ser Asp Arg Gly Thr Tyr Thr Cys Leu Val
        195                 200                 205

Glu Asn Ala Val Gly Ser Ile Arg Tyr Asn Tyr Leu Leu Asp Val Leu
    210                 215                 220

Glu Arg Ser Pro His Arg Pro Ile Leu Gln Ala Gly Leu Pro Ala Asn
225                 230                 235                 240

Thr Thr Ala Val Val Gly Ser Asp Val Glu Leu Leu Cys Lys Val Tyr
                245                 250                 255

Ser Asp Ala Gln Pro His Ile Gln Trp Leu Lys His Ile Val Ile Asn
            260                 265                 270

Gly Ser Ser Phe Gly Ala Asp Gly Phe Pro Tyr Val Gln Val Leu Lys
        275                 280                 285

Thr Ala Asp Ile Asn Ser Ser Glu Val Glu Val Leu Tyr Leu Arg Asn
    290                 295                 300

Val Ser Ala Glu Asp Ala Gly Glu Tyr Thr Cys Leu Ala Gly Asn Ser
305                 310                 315                 320

Ile Gly Leu Ser Tyr Gln Ser Ala Trp Leu Thr Val Leu Pro Glu Pro
                325                 330                 335

Lys Ser Ser Asp Lys Thr His Thr Cys Pro Pro Cys Pro Ala Pro Glu
            340                 345                 350

Leu Leu Gly Gly Pro Ser Val Phe Leu Phe Pro Pro Lys Pro Lys Asp
        355                 360                 365

Thr Leu Met Ile Ser Arg Thr Pro Glu Val Thr Cys Val Val Val Asp
    370                 375                 380

Val Ser His Glu Asp Pro Glu Val Lys Phe Asn Trp Tyr Val Asp Gly
385                 390                 395                 400
```

Val Glu Val His Asn Ala Lys Thr Lys Pro Arg Glu Glu Gln Tyr Asn
            405                 410                 415

Ser Thr Tyr Arg Val Val Ser Val Leu Thr Val Leu His Gln Asp Trp
            420                 425                 430

Leu Asn Gly Lys Glu Tyr Lys Cys Lys Val Ser Asn Lys Ala Leu Pro
            435                 440                 445

Ala Pro Ile Glu Lys Thr Ile Ser Lys Ala Lys Gly Gln Pro Arg Glu
450                 455                 460

Pro Gln Val Tyr Thr Leu Pro Pro Ser Arg Asp Glu Leu Thr Lys Asn
465                 470                 475                 480

Gln Val Ser Leu Thr Cys Leu Val Lys Gly Phe Tyr Pro Ser Asp Ile
                485                 490                 495

Ala Val Glu Trp Glu Ser Asn Gly Gln Pro Glu Asn Asn Tyr Lys Thr
            500                 505                 510

Thr Pro Pro Val Leu Asp Ser Asp Gly Ser Phe Phe Leu Tyr Ser Lys
            515                 520                 525

Leu Thr Val Asp Lys Ser Arg Trp Gln Gln Gly Asn Val Phe Ser Cys
            530                 535                 540

Ser Val Met His Glu Ala Leu His Asn His Tyr Thr Gln Lys Ser Leu
545                 550                 555                 560

Ser Leu Ser Pro Gly Lys
            565

<210> SEQ ID NO 89
<211> LENGTH: 495
<212> TYPE: PRT
<213> ORGANISM: Artificial Sequence
<220> FEATURE:
<223> OTHER INFORMATION: Synthetic sequence

<400> SEQUENCE: 89

Leu Glu Ala Ser Glu Glu Val Glu Leu Glu Asp Ser Leu Thr Ser Ser
1               5                   10                  15

Asn Asp Asp Glu Asp Pro Lys Ser His Arg Asp Pro Ser Asn Arg His
            20                  25                  30

Ser Tyr Pro Gln Gln Ala Pro Tyr Trp Thr His Pro Gln Arg Met Glu
            35                  40                  45

Lys Lys Leu His Ala Val Pro Ala Gly Asn Thr Val Lys Phe Arg Cys
50                  55                  60

Pro Ala Ala Gly Asn Pro Thr Pro Thr Ile Arg Trp Leu Lys Asp Gly
65                  70                  75                  80

Gln Ala Phe His Gly Glu Asn Arg Ile Gly Gly Ile Arg Leu Arg His
            85                  90                  95

Gln His Trp Ser Leu Val Met Glu Ser Val Val Pro Ser Asp Arg Gly
            100                 105                 110

Thr Tyr Thr Cys Leu Val Glu Asn Ala Val Gly Ser Ile Arg Tyr Asn
            115                 120                 125

Tyr Leu Leu Asp Val Leu Glu Arg Ser Pro His Arg Pro Ile Leu Gln
130                 135                 140

Ala Gly Leu Pro Ala Asn Thr Thr Ala Val Val Gly Ser Asp Val Glu
145                 150                 155                 160

Leu Leu Cys Lys Val Tyr Ser Asp Ala Gln Pro His Ile Gln Trp Leu
            165                 170                 175

Lys His Ile Val Ile Asn Gly Ser Ser Phe Gly Ala Asp Gly Phe Pro
            180                 185                 190

Tyr Val Gln Val Leu Lys Thr Ala Asp Ile Asn Ser Ser Glu Val Glu
            195                 200                 205

Val Leu Tyr Leu Arg Asn Val Ser Ala Glu Asp Ala Gly Glu Tyr Thr
        210                 215                 220

Cys Leu Ala Gly Asn Ser Ile Gly Leu Ser Tyr Gln Ser Ala Trp Leu
225                 230                 235                 240

Thr Val Leu Pro Glu Glu Asp Pro Thr Trp Thr Ala Ala Pro Glu
                245                 250                 255

Ala Arg Tyr Thr Asp Gly Ser Glu Pro Lys Ser Ser Asp Lys Thr His
                260                 265                 270

Thr Cys Pro Pro Cys Pro Ala Pro Glu Leu Leu Gly Gly Pro Ser Val
            275                 280                 285

Phe Leu Phe Pro Pro Lys Pro Lys Asp Thr Leu Met Ile Ser Arg Thr
        290                 295                 300

Pro Glu Val Thr Cys Val Val Asp Val Ser His Glu Asp Pro Glu
305                 310                 315                 320

Val Lys Phe Asn Trp Tyr Val Asp Gly Val Glu Val His Asn Ala Lys
                325                 330                 335

Thr Lys Pro Arg Glu Glu Gln Tyr Asn Ser Thr Tyr Arg Val Val Ser
            340                 345                 350

Val Leu Thr Val Leu His Gln Asp Trp Leu Asn Gly Lys Glu Tyr Lys
        355                 360                 365

Cys Lys Val Ser Asn Lys Ala Leu Pro Ala Pro Ile Glu Lys Thr Ile
370                 375                 380

Ser Lys Ala Lys Gly Gln Pro Arg Glu Pro Gln Val Tyr Thr Leu Pro
385                 390                 395                 400

Pro Ser Arg Asp Glu Leu Thr Lys Asn Gln Val Ser Leu Thr Cys Leu
                405                 410                 415

Val Lys Gly Phe Tyr Pro Ser Asp Ile Ala Val Glu Trp Glu Ser Asn
            420                 425                 430

Gly Gln Pro Glu Asn Asn Tyr Lys Thr Thr Pro Pro Val Leu Asp Ser
        435                 440                 445

Asp Gly Ser Phe Phe Leu Tyr Ser Lys Leu Thr Val Asp Lys Ser Arg
450                 455                 460

Trp Gln Gln Gly Asn Val Phe Ser Cys Ser Val Met His Glu Ala Leu
465                 470                 475                 480

His Asn His Tyr Thr Gln Lys Ser Leu Ser Leu Ser Pro Gly Lys
                485                 490                 495

<210> SEQ ID NO 90
<211> LENGTH: 468
<212> TYPE: PRT
<213> ORGANISM: Artificial Sequence
<220> FEATURE:
<223> OTHER INFORMATION: Synthetic sequence

<400> SEQUENCE: 90

Leu Glu Ala Ser Glu Glu Val Glu Leu Glu Ala Pro Tyr Trp Thr His
1               5                   10                  15

Pro Gln Arg Met Glu Lys Lys Leu His Ala Val Pro Ala Gly Asn Thr
                20                  25                  30

Val Lys Phe Arg Cys Pro Ala Ala Gly Asn Pro Thr Pro Thr Ile Arg
            35                  40                  45

Trp Leu Lys Asp Gly Gln Ala Phe His Gly Glu Asn Arg Ile Gly Gly
        50                  55                  60

Ile Arg Leu Arg His Gln His Trp Ser Leu Val Met Glu Ser Val Val

```
                65                  70                  75                  80
            Pro Ser Asp Arg Gly Thr Tyr Thr Cys Leu Val Glu Asn Ala Val Gly
                            85                  90                  95

Ser Ile Arg Tyr Asn Tyr Leu Leu Asp Val Leu Glu Arg Ser Pro His
                            100                 105                 110

Arg Pro Ile Leu Gln Ala Gly Leu Pro Ala Asn Thr Ala Val Val
                            115                 120                 125

Gly Ser Asp Val Glu Leu Leu Cys Lys Val Tyr Ser Asp Ala Gln Pro
                            130                 135                 140

His Ile Gln Trp Leu Lys His Ile Val Ile Asn Gly Ser Ser Phe Gly
            145                 150                 155                 160

Ala Asp Gly Phe Pro Tyr Val Gln Val Leu Lys Thr Ala Asp Ile Asn
                            165                 170                 175

Ser Ser Glu Val Glu Val Leu Tyr Leu Arg Asn Val Ser Ala Glu Asp
                            180                 185                 190

Ala Gly Glu Tyr Thr Cys Leu Ala Gly Asn Ser Ile Gly Leu Ser Tyr
                            195                 200                 205

Gln Ser Ala Trp Leu Thr Val Leu Pro Glu Glu Asp Pro Thr Trp Thr
                            210                 215                 220

Ala Ala Ala Pro Glu Ala Arg Tyr Thr Asp Gly Ser Glu Pro Lys Ser
            225                 230                 235                 240

Ser Asp Lys Thr His Thr Cys Pro Pro Cys Pro Ala Pro Glu Leu Leu
                            245                 250                 255

Gly Gly Pro Ser Val Phe Leu Phe Pro Pro Lys Pro Lys Asp Thr Leu
                            260                 265                 270

Met Ile Ser Arg Thr Pro Glu Val Thr Cys Val Val Val Asp Val Ser
                            275                 280                 285

His Glu Asp Pro Glu Val Lys Phe Asn Trp Tyr Val Asp Gly Val Glu
                            290                 295                 300

Val His Asn Ala Lys Thr Lys Pro Arg Glu Glu Gln Tyr Asn Ser Thr
            305                 310                 315                 320

Tyr Arg Val Val Ser Val Leu Thr Val Leu His Gln Asp Trp Leu Asn
                            325                 330                 335

Gly Lys Glu Tyr Lys Cys Lys Val Ser Asn Lys Ala Leu Pro Ala Pro
                            340                 345                 350

Ile Glu Lys Thr Ile Ser Lys Ala Lys Gly Gln Pro Arg Glu Pro Gln
                            355                 360                 365

Val Tyr Thr Leu Pro Pro Ser Arg Asp Glu Leu Thr Lys Asn Gln Val
                            370                 375                 380

Ser Leu Thr Cys Leu Val Lys Gly Phe Tyr Pro Ser Asp Ile Ala Val
            385                 390                 395                 400

Glu Trp Glu Ser Asn Gly Gln Pro Glu Asn Asn Tyr Lys Thr Thr Pro
                            405                 410                 415

Pro Val Leu Asp Ser Asp Gly Ser Phe Phe Leu Tyr Ser Lys Leu Thr
                            420                 425                 430

Val Asp Lys Ser Arg Trp Gln Gln Gly Asn Val Phe Ser Cys Ser Val
                            435                 440                 445

Met His Glu Ala Leu His Asn His Tyr Thr Gln Lys Ser Leu Ser Leu
                            450                 455                 460

Ser Pro Gly Lys
            465

<210> SEQ ID NO 91
<211> LENGTH: 571
```

```
<212> TYPE: PRT
<213> ORGANISM: Artificial Sequence
<220> FEATURE:
<223> OTHER INFORMATION: Synthetic sequence

<400> SEQUENCE: 91

Arg Pro Ser Pro Thr Leu Pro Glu Gln Ala Gln Pro Trp Gly Ala Pro
1               5                   10                  15

Val Glu Val Glu Ser Phe Leu Val His Pro Gly Asp Leu Leu Gln Leu
            20                  25                  30

Arg Cys Arg Leu Arg Asp Asp Val Gln Ser Ile Asn Trp Leu Arg Asp
        35                  40                  45

Gly Val Gln Leu Ala Glu Ser Asn Arg Thr Arg Ile Thr Gly Glu Glu
    50                  55                  60

Val Glu Val Gln Asp Ser Val Pro Ala Asp Ser Gly Leu Tyr Ala Cys
65                  70                  75                  80

Val Thr Ser Ser Pro Ser Gly Ser Asp Thr Thr Tyr Phe Ser Val Asn
                85                  90                  95

Val Ser Asp Ala Leu Pro Ser Ser Glu Asp Asp Asp Asp Asp Asp Asp
            100                 105                 110

Ser Ser Ser Glu Glu Lys Glu Thr Asp Asn Thr Lys Pro Asn Pro Val
        115                 120                 125

Ala Pro Tyr Trp Thr Ser Pro Glu Lys Met Glu Lys Lys Leu His Ala
    130                 135                 140

Val Pro Ala Ala Lys Thr Val Lys Phe Lys Cys Pro Ser Ser Gly Thr
145                 150                 155                 160

Pro Asn Pro Thr Leu Arg Trp Leu Lys Asn Gly Lys Glu Phe Lys Pro
                165                 170                 175

Asp His Arg Ile Gly Gly Tyr Lys Val Arg Tyr Ala Thr Trp Ser Ile
            180                 185                 190

Ile Met Asp Ser Val Val Pro Ser Asp Lys Gly Asn Tyr Thr Cys Ile
        195                 200                 205

Val Glu Asn Glu Tyr Gly Ser Ile Asn His Thr Tyr Gln Leu Asp Val
    210                 215                 220

Val Glu Arg Ser Pro His Arg Pro Ile Leu Gln Ala Gly Leu Pro Ala
225                 230                 235                 240

Asn Lys Thr Val Ala Leu Gly Ser Asn Val Glu Phe Met Cys Lys Val
                245                 250                 255

Tyr Ser Asp Pro Gln Pro His Ile Gln Trp Leu Lys His Ile Glu Val
            260                 265                 270

Asn Gly Ser Lys Ile Gly Pro Asp Asn Leu Pro Tyr Val Gln Ile Leu
        275                 280                 285

Lys Thr Ala Gly Val Asn Thr Thr Asp Lys Glu Met Glu Val Leu His
    290                 295                 300

Leu Arg Asn Val Ser Phe Glu Asp Ala Gly Glu Tyr Thr Cys Leu Ala
305                 310                 315                 320

Gly Asn Ser Ile Gly Leu Ser His His Ser Ala Trp Leu Thr Val Leu
                325                 330                 335

Glu Ala Leu Glu Pro Lys Ser Ser Asp Lys Thr His Thr Cys Pro Pro
            340                 345                 350

Cys Pro Ala Pro Glu Leu Leu Gly Gly Pro Ser Val Phe Leu Phe Pro
        355                 360                 365

Pro Lys Pro Lys Asp Thr Leu Met Ile Ser Arg Thr Pro Glu Val Thr
    370                 375                 380

Cys Val Val Val Asp Val Ser His Glu Asp Pro Glu Val Lys Phe Asn
```

```
                385                 390                 395                 400
Trp Tyr Val Asp Gly Val Glu Val His Asn Ala Lys Thr Lys Pro Arg
                405                 410                 415

Glu Glu Gln Tyr Asn Ser Thr Tyr Arg Val Val Ser Val Leu Thr Val
            420                 425                 430

Leu His Gln Asp Trp Leu Asn Gly Lys Glu Tyr Lys Cys Lys Val Ser
        435                 440                 445

Asn Lys Ala Leu Pro Ala Pro Ile Glu Lys Thr Ile Ser Lys Ala Lys
    450                 455                 460

Gly Gln Pro Arg Glu Pro Gln Val Tyr Thr Leu Pro Pro Ser Arg Asp
465                 470                 475                 480

Glu Leu Thr Lys Asn Gln Val Ser Leu Thr Cys Leu Val Lys Gly Phe
                485                 490                 495

Tyr Pro Ser Asp Ile Ala Val Glu Trp Glu Ser Asn Gly Gln Pro Glu
            500                 505                 510

Asn Asn Tyr Lys Thr Thr Pro Pro Val Leu Asp Ser Asp Gly Ser Phe
        515                 520                 525

Phe Leu Tyr Ser Lys Leu Thr Val Asp Lys Ser Arg Trp Gln Gln Gly
    530                 535                 540

Asn Val Phe Ser Cys Ser Val Met His Glu Ala Leu His Asn His Tyr
545                 550                 555                 560

Thr Gln Lys Ser Leu Ser Leu Ser Pro Gly Lys
                565                 570

<210> SEQ ID NO 92
<211> LENGTH: 30
<212> TYPE: PRT
<213> ORGANISM: Artificial Sequence
<220> FEATURE:
<223> OTHER INFORMATION: Synthetic sequence

<400> SEQUENCE: 92

Asp Ala Leu Pro Ser Ser Glu Asp Asp Asp Asp Asp Asp Asp Ser Ser
1               5                   10                  15

Ser Glu Glu Lys Glu Thr Asp Asn Thr Lys Pro Asn Arg Met
            20                  25                  30

<210> SEQ ID NO 93
<211> LENGTH: 348
<212> TYPE: PRT
<213> ORGANISM: Artificial Sequence
<220> FEATURE:
<223> OTHER INFORMATION: Synthetic sequence

<400> SEQUENCE: 93

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
            20                  25                  30

Arg Leu Cys Cys Gly Arg Ala Glu Arg Gly Gly His Trp Tyr Lys Glu
        35                  40                  45

Gly Ser Arg Leu Ala Pro Ala Gly Arg Val Arg Gly Trp Arg Gly Arg
    50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ser Leu Thr Ser Ser Asn Asp Asp Glu Asp Pro Lys Ser His
```

```
                  100                 105                 110
Arg Asp Pro Ser Asn Arg His Ser Tyr Pro Gln Gln Ala Pro Tyr Trp
            115                 120                 125

Thr His Pro Gln Arg Met Glu Lys Lys Leu His Ala Val Pro Ala Gly
        130                 135                 140

Asn Thr Val Lys Phe Arg Cys Pro Ala Ala Gly Asn Pro Ala Pro Thr
145                 150                 155                 160

Ile Arg Trp Leu Lys Asp Gly Gln Ala Phe His Gly Glu Asn Arg Ile
                165                 170                 175

Gly Gly Ile Arg Leu Arg His Gln His Trp Ser Leu Val Met Glu Ser
            180                 185                 190

Val Val Pro Ser Asp Arg Gly Thr Tyr Thr Cys Leu Val Glu Asn Ala
        195                 200                 205

Val Gly Ser Ile Arg Tyr Asn Tyr Leu Leu Asp Val Leu Glu Arg Ser
210                 215                 220

Pro His Arg Pro Ile Leu Gln Ala Gly Leu Pro Ala Asn Thr Thr Ala
225                 230                 235                 240

Val Val Gly Ser Asp Val Glu Leu Leu Cys Lys Val Tyr Ser Asp Ala
                245                 250                 255

Gln Pro His Ile Gln Trp Leu Lys His Ile Val Ile Asn Gly Ser Ser
            260                 265                 270

Phe Gly Ala Asp Gly Phe Pro Tyr Val Gln Val Leu Lys Thr Ala Asp
        275                 280                 285

Ile Asn Ser Ser Glu Val Glu Val Leu Tyr Leu Arg Asn Val Ser Ala
290                 295                 300

Glu Asp Ala Gly Glu Tyr Thr Cys Leu Ala Gly Asn Ser Ile Gly Leu
305                 310                 315                 320

Ser Tyr Gln Ser Ala Trp Leu Thr Val Leu Pro Glu Glu Asp Pro Thr
                325                 330                 335

Trp Thr Ala Ala Ala Pro Glu Ala Arg Tyr Thr Asp
            340                 345

<210> SEQ ID NO 94
<211> LENGTH: 261
<212> TYPE: PRT
<213> ORGANISM: Artificial Sequence
<220> FEATURE:
<223> OTHER INFORMATION: Synthetic sequence

<400> SEQUENCE: 94

Leu Glu Ala Ser Glu Glu Val Glu Leu Glu Asp Ser Leu Thr Ser Ser
1               5                   10                  15

Asn Asp Asp Glu Asp Pro Lys Ser His Arg Asp Pro Ser Asn Arg His
            20                  25                  30

Ser Tyr Pro Gln Gln Ala Pro Tyr Trp Thr His Pro Gln Arg Met Glu
        35                  40                  45

Lys Lys Leu His Ala Val Pro Ala Gly Asn Thr Val Lys Phe Arg Cys
    50                  55                  60

Pro Ala Ala Gly Asn Pro Thr Pro Thr Ile Arg Trp Leu Lys Asp Gly
65                  70                  75                  80

Gln Ala Phe His Gly Glu Asn Arg Ile Gly Gly Ile Arg Leu Arg His
                85                  90                  95

Gln His Trp Ser Leu Val Met Glu Ser Val Val Pro Ser Asp Arg Gly
            100                 105                 110

Thr Tyr Thr Cys Leu Val Glu Asn Ala Val Gly Ser Ile Arg Tyr Asn
        115                 120                 125
```

Tyr Leu Leu Asp Val Leu Glu Arg Ser Pro His Arg Pro Ile Leu Gln
            130                 135                 140

Ala Gly Leu Pro Ala Asn Thr Thr Ala Val Val Gly Ser Asp Val Glu
145                 150                 155                 160

Leu Leu Cys Lys Val Tyr Ser Asp Ala Gln Pro His Ile Gln Trp Leu
                165                 170                 175

Lys His Ile Val Ile Asn Gly Ser Ser Phe Gly Ala Asp Gly Phe Pro
            180                 185                 190

Tyr Val Gln Val Leu Lys Thr Ala Asp Ile Asn Ser Ser Glu Val Glu
        195                 200                 205

Val Leu Tyr Leu Arg Asn Val Ser Ala Glu Asp Ala Gly Glu Tyr Thr
210                 215                 220

Cys Leu Ala Gly Asn Ser Ile Gly Leu Ser Tyr Gln Ser Ala Trp Leu
225                 230                 235                 240

Thr Val Leu Pro Glu Glu Asp Pro Thr Trp Thr Ala Ala Ala Pro Glu
                245                 250                 255

Ala Arg Tyr Thr Asp
            260

<210> SEQ ID NO 95
<211> LENGTH: 234
<212> TYPE: PRT
<213> ORGANISM: Artificial Sequence
<220> FEATURE:
<223> OTHER INFORMATION: Synthetic sequence

<400> SEQUENCE: 95

Leu Glu Ala Ser Glu Glu Val Glu Leu Glu Ala Pro Tyr Trp Thr His
1               5                   10                  15

Pro Gln Arg Met Glu Lys Lys Leu His Ala Val Pro Ala Gly Asn Thr
            20                  25                  30

Val Lys Phe Arg Cys Pro Ala Ala Gly Asn Pro Thr Pro Thr Ile Arg
        35                  40                  45

Trp Leu Lys Asp Gly Gln Ala Phe His Gly Glu Asn Arg Ile Gly Gly
    50                  55                  60

Ile Arg Leu Arg His Gln His Trp Ser Leu Val Met Glu Ser Val Val
65                  70                  75                  80

Pro Ser Asp Arg Gly Thr Tyr Thr Cys Leu Val Glu Asn Ala Val Gly
                85                  90                  95

Ser Ile Arg Tyr Asn Tyr Leu Leu Asp Val Leu Glu Arg Ser Pro His
            100                 105                 110

Arg Pro Ile Leu Gln Ala Gly Leu Pro Ala Asn Thr Thr Ala Val Val
        115                 120                 125

Gly Ser Asp Val Glu Leu Leu Cys Lys Val Tyr Ser Asp Ala Gln Pro
130                 135                 140

His Ile Gln Trp Leu Lys His Ile Val Ile Asn Gly Ser Ser Phe Gly
145                 150                 155                 160

Ala Asp Gly Phe Pro Tyr Val Gln Val Leu Lys Thr Ala Asp Ile Asn
                165                 170                 175

Ser Ser Glu Val Glu Val Leu Tyr Leu Arg Asn Val Ser Ala Glu Asp
            180                 185                 190

Ala Gly Glu Tyr Thr Cys Leu Ala Gly Asn Ser Ile Gly Leu Ser Tyr
        195                 200                 205

Gln Ser Ala Trp Leu Thr Val Leu Pro Glu Glu Asp Pro Thr Trp Thr
    210                 215                 220

```
Ala Ala Ala Pro Glu Ala Arg Tyr Thr Asp
225                 230
```

<210> SEQ ID NO 96
<211> LENGTH: 15
<212> TYPE: PRT
<213> ORGANISM: Artificial Sequence
<220> FEATURE:
<223> OTHER INFORMATION: Synthetic sequence

<400> SEQUENCE: 96

```
Asn Asp Asp Glu Asp Pro Lys Ser His Arg Asp Pro Ser Asn Arg
1               5                   10                  15
```

<210> SEQ ID NO 97
<211> LENGTH: 15
<212> TYPE: PRT
<213> ORGANISM: Artificial Sequence
<220> FEATURE:
<223> OTHER INFORMATION: Synthetic sequence

<400> SEQUENCE: 97

```
Asn Asp Asp Glu Asp Pro Lys Ser His Arg Asp Leu Ser Asn Arg
1               5                   10                  15
```

<210> SEQ ID NO 98
<211> LENGTH: 17
<212> TYPE: PRT
<213> ORGANISM: Artificial Sequence
<220> FEATURE:
<223> OTHER INFORMATION: Synthetic sequence

<400> SEQUENCE: 98

```
Glu Asp Asp Asp Asp Asp Asp Asp Ser Ser Ser Glu Glu Lys Glu Thr
1               5                   10                  15

Asp
```

<210> SEQ ID NO 99
<211> LENGTH: 15
<212> TYPE: PRT
<213> ORGANISM: Artificial Sequence
<220> FEATURE:
<223> OTHER INFORMATION: Synthetic sequence

<400> SEQUENCE: 99

```
Asp Asp Glu Asp Asp Thr Asp Gly Ala Glu Asp Phe Val Ser Glu
1               5                   10                  15
```

<210> SEQ ID NO 100
<211> LENGTH: 12
<212> TYPE: PRT
<213> ORGANISM: Artificial Sequence
<220> FEATURE:
<223> OTHER INFORMATION: Synthetic sequence

<400> SEQUENCE: 100

```
Gly Asp Asp Glu Asp Gly Glu Asp Glu Ala Glu Asp
1               5                   10
```

<210> SEQ ID NO 101
<211> LENGTH: 4
<212> TYPE: PRT
<213> ORGANISM: Artificial Sequence
<220> FEATURE:
<223> OTHER INFORMATION: Synthetic sequence

<400> SEQUENCE: 101

Asp Asp Glu Asp
1

<210> SEQ ID NO 102
<211> LENGTH: 8
<212> TYPE: PRT
<213> ORGANISM: Artificial Sequence
<220> FEATURE:
<223> OTHER INFORMATION: Synthetic sequence

<400> SEQUENCE: 102

Glu Asp Asp Asp Asp Asp Asp Asp
1               5

<210> SEQ ID NO 103
<211> LENGTH: 5
<212> TYPE: PRT
<213> ORGANISM: Artificial Sequence
<220> FEATURE:
<223> OTHER INFORMATION: Synthetic sequence

<400> SEQUENCE: 103

Asp Asp Glu Asp Asp
1               5

<210> SEQ ID NO 104
<211> LENGTH: 4
<212> TYPE: PRT
<213> ORGANISM: Artificial Sequence
<220> FEATURE:
<223> OTHER INFORMATION: Synthetic sequence

<400> SEQUENCE: 104

Asp Asp Glu Asp
1

<210> SEQ ID NO 105
<211> LENGTH: 333
<212> TYPE: PRT
<213> ORGANISM: Artificial Sequence
<220> FEATURE:
<223> OTHER INFORMATION: Synthetic sequence

<400> SEQUENCE: 105

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
            20                  25                  30

Arg Leu Cys Cys Gly Arg Ala Glu Arg Gly Gly His Trp Tyr Lys Glu
        35                  40                  45

Gly Ser Arg Leu Ala Pro Ala Gly Arg Val Arg Gly Trp Arg Gly Arg
    50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ser Leu Thr Ser Ser Glu Asp Asp Asp Asp Asp Asp Asp Ser
            100                 105                 110

Ser Ser Glu Glu Lys Glu Thr Asp His Ser Tyr Pro Gln Gln Ala Pro
        115                 120                 125

Tyr Trp Thr His Pro Gln Arg Met Glu Lys Lys Leu His Ala Val Pro
    130                 135                 140

Ala Gly Asn Thr Val Lys Phe Arg Cys Pro Ala Ala Gly Asn Pro Thr

```
                145                 150                 155                 160
Pro Thr Ile Arg Trp Leu Lys Asp Gly Gln Ala Phe His Gly Glu Asn
                    165                 170                 175

Arg Ile Gly Gly Ile Arg Leu Arg His Gln His Trp Ser Leu Val Met
                180                 185                 190

Glu Ser Val Val Pro Ser Asp Arg Gly Thr Tyr Thr Cys Leu Val Glu
            195                 200                 205

Asn Ala Val Gly Ser Ile Arg Tyr Asn Tyr Leu Leu Asp Val Leu Glu
        210                 215                 220

Arg Ser Pro His Arg Pro Ile Leu Gln Ala Gly Leu Pro Ala Asn Thr
225                 230                 235                 240

Thr Ala Val Val Gly Ser Asp Val Glu Leu Leu Cys Lys Val Tyr Ser
                245                 250                 255

Asp Ala Gln Pro His Ile Gln Trp Leu Lys His Ile Val Ile Asn Gly
            260                 265                 270

Ser Ser Phe Gly Ala Asp Gly Phe Pro Tyr Val Gln Val Leu Lys Thr
        275                 280                 285

Ala Asp Ile Asn Ser Ser Glu Val Glu Val Leu Tyr Leu Arg Asn Val
290                 295                 300

Ser Ala Glu Asp Ala Gly Glu Tyr Thr Cys Leu Ala Gly Asn Ser Ile
305                 310                 315                 320

Gly Leu Ser Tyr Gln Ser Ala Trp Leu Thr Val Leu Pro
                325                 330

<210> SEQ ID NO 106
<211> LENGTH: 331
<212> TYPE: PRT
<213> ORGANISM: Artificial Sequence
<220> FEATURE:
<223> OTHER INFORMATION: Synthetic sequence

<400> SEQUENCE: 106

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
            20                  25                  30

Arg Leu Cys Cys Gly Arg Ala Glu Arg Gly Gly His Trp Tyr Lys Glu
        35                  40                  45

Gly Ser Arg Leu Ala Pro Ala Gly Arg Val Arg Gly Trp Arg Gly Arg
    50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ser Leu Thr Ser Ser Asp Asp Glu Asp Thr Asp Gly Ala
            100                 105                 110

Glu Asp Phe Val Ser Glu His Ser Tyr Pro Gln Gln Ala Pro Tyr Trp
        115                 120                 125

Thr His Pro Gln Arg Met Glu Lys Lys Leu His Ala Val Pro Ala Gly
    130                 135                 140

Asn Thr Val Lys Phe Arg Cys Pro Ala Ala Gly Asn Pro Thr Pro Thr
145                 150                 155                 160

Ile Arg Trp Leu Lys Asp Gly Gln Ala Phe His Gly Glu Asn Arg Ile
                165                 170                 175

Gly Gly Ile Arg Leu Arg His Gln His Trp Ser Leu Val Met Glu Ser
            180                 185                 190
```

```
Val Val Pro Ser Asp Arg Gly Thr Tyr Thr Cys Leu Val Glu Asn Ala
            195                 200                 205

Val Gly Ser Ile Arg Tyr Asn Tyr Leu Leu Asp Val Leu Glu Arg Ser
        210                 215                 220

Pro His Arg Pro Ile Leu Gln Ala Gly Leu Pro Ala Asn Thr Thr Ala
225                 230                 235                 240

Val Val Gly Ser Asp Val Glu Leu Leu Cys Lys Val Tyr Ser Asp Ala
            245                 250                 255

Gln Pro His Ile Gln Trp Leu Lys His Ile Val Ile Asn Gly Ser Ser
            260                 265                 270

Phe Gly Ala Asp Gly Phe Pro Tyr Val Gln Val Leu Lys Thr Ala Asp
            275                 280                 285

Ile Asn Ser Ser Glu Val Glu Val Leu Tyr Leu Arg Asn Val Ser Ala
            290                 295                 300

Glu Asp Ala Gly Glu Tyr Thr Cys Leu Ala Gly Asn Ser Ile Gly Leu
305                 310                 315                 320

Ser Tyr Gln Ser Ala Trp Leu Thr Val Leu Pro
            325                 330

<210> SEQ ID NO 107
<211> LENGTH: 328
<212> TYPE: PRT
<213> ORGANISM: Artificial Sequence
<220> FEATURE:
<223> OTHER INFORMATION: Synthetic sequence

<400> SEQUENCE: 107

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
            20                  25                  30

Arg Leu Cys Cys Gly Arg Ala Glu Arg Gly Gly His Trp Tyr Lys Glu
        35                  40                  45

Gly Ser Arg Leu Ala Pro Ala Gly Arg Val Arg Gly Trp Arg Gly Arg
    50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ser Leu Thr Ser Ser Gly Asp Asp Glu Asp Gly Glu Asp Glu
            100                 105                 110

Ala Glu Asp His Ser Tyr Pro Gln Gln Ala Pro Tyr Trp Thr His Pro
        115                 120                 125

Gln Arg Met Glu Lys Lys Leu His Ala Val Pro Ala Gly Asn Thr Val
130                 135                 140

Lys Phe Arg Cys Pro Ala Ala Gly Asn Pro Thr Pro Thr Ile Arg Trp
145                 150                 155                 160

Leu Lys Asp Gly Gln Ala Phe His Gly Glu Asn Arg Ile Gly Gly Ile
            165                 170                 175

Arg Leu Arg His Gln His Trp Ser Leu Val Met Glu Ser Val Val Pro
        180                 185                 190

Ser Asp Arg Gly Thr Tyr Thr Cys Leu Val Glu Asn Ala Val Gly Ser
    195                 200                 205

Ile Arg Tyr Asn Tyr Leu Leu Asp Val Leu Glu Arg Ser Pro His Arg
210                 215                 220
```

```
Pro Ile Leu Gln Ala Gly Leu Pro Ala Asn Thr Thr Ala Val Val Gly
225                 230                 235                 240

Ser Asp Val Glu Leu Leu Cys Lys Val Tyr Ser Asp Ala Gln Pro His
                245                 250                 255

Ile Gln Trp Leu Lys His Ile Val Ile Asn Gly Ser Ser Phe Gly Ala
            260                 265                 270

Asp Gly Phe Pro Tyr Val Gln Val Leu Lys Thr Ala Asp Ile Asn Ser
                275                 280                 285

Ser Glu Val Glu Val Leu Tyr Leu Arg Asn Val Ser Ala Glu Asp Ala
290                 295                 300

Gly Glu Tyr Thr Cys Leu Ala Gly Asn Ser Ile Gly Leu Ser Tyr Gln
305                 310                 315                 320

Ser Ala Trp Leu Thr Val Leu Pro
                325
```

<210> SEQ ID NO 108
<211> LENGTH: 335
<212> TYPE: PRT
<213> ORGANISM: Artificial Sequence
<220> FEATURE:
<223> OTHER INFORMATION: Synthetic sequence

<400> SEQUENCE: 108

```
Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
                20                  25                  30

Arg Leu Cys Cys Gly Arg Ala Glu Arg Gly Gly His Trp Tyr Lys Glu
            35                  40                  45

Gly Ser Arg Leu Ala Pro Ala Gly Arg Val Arg Gly Trp Arg Gly Arg
        50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ser Leu Thr Ser Ser Asn Glu Asp Asp Asp Asp Asp Asp Asp
                100                 105                 110

Pro Lys Ser His Arg Asp Pro Ser Asn Arg His Ser Tyr Pro Gln Gln
            115                 120                 125

Ala Pro Tyr Trp Thr His Pro Gln Arg Met Glu Lys Lys Leu His Ala
        130                 135                 140

Val Pro Ala Gly Asn Thr Val Lys Phe Arg Cys Pro Ala Ala Gly Asn
145                 150                 155                 160

Pro Thr Pro Thr Ile Arg Trp Leu Lys Asp Gly Gln Ala Phe His Gly
                165                 170                 175

Glu Asn Arg Ile Gly Gly Ile Arg Leu Arg His Gln His Trp Ser Leu
            180                 185                 190

Val Met Glu Ser Val Val Pro Ser Asp Arg Gly Thr Tyr Thr Cys Leu
        195                 200                 205

Val Glu Asn Ala Val Gly Ser Ile Arg Tyr Asn Tyr Leu Leu Asp Val
    210                 215                 220

Leu Glu Arg Ser Pro His Arg Pro Ile Leu Gln Ala Gly Leu Pro Ala
225                 230                 235                 240

Asn Thr Thr Ala Val Val Gly Ser Asp Val Glu Leu Leu Cys Lys Val
                245                 250                 255

Tyr Ser Asp Ala Gln Pro His Ile Gln Trp Leu Lys His Ile Val Ile
```

-continued

```
                260                 265                 270
Asn Gly Ser Ser Phe Gly Ala Asp Gly Phe Pro Tyr Val Gln Val Leu
            275                 280                 285
Lys Thr Ala Asp Ile Asn Ser Ser Glu Val Glu Val Leu Tyr Leu Arg
        290                 295                 300
Asn Val Ser Ala Glu Asp Ala Gly Glu Tyr Thr Cys Leu Ala Gly Asn
305                 310                 315                 320
Ser Ile Gly Leu Ser Tyr Gln Ser Ala Trp Leu Thr Val Leu Pro
                325                 330                 335

<210> SEQ ID NO 109
<211> LENGTH: 332
<212> TYPE: PRT
<213> ORGANISM: Artificial Sequence
<220> FEATURE:
<223> OTHER INFORMATION: Synthetic sequence

<400> SEQUENCE: 109

Leu Glu Ala Ser Glu Glu Val Glu Leu Glu Pro Cys Leu Ala Pro Ser
1               5                   10                  15
Leu Glu Gln Gln Glu Gln Glu Leu Thr Val Ala Leu Gly Gln Pro Val
            20                  25                  30
Arg Leu Cys Cys Gly Arg Ala Glu Arg Gly Gly His Trp Tyr Lys Glu
        35                  40                  45
Gly Ser Arg Leu Ala Pro Ala Gly Arg Val Arg Gly Trp Arg Gly Arg
    50                  55                  60
Leu Glu Ile Ala Ser Phe Leu Pro Glu Asp Ala Gly Arg Tyr Leu Cys
65                  70                  75                  80
Leu Ala Arg Gly Ser Met Ile Val Leu Gln Asn Leu Thr Leu Ile Thr
                85                  90                  95
Gly Asp Ser Leu Thr Ser Ser Asn Asp Asp Glu Asp Pro Lys Ser
            100                 105                 110
His Arg Asp Pro Ser Asn Arg His Ser Tyr Pro Gln Gln Ala Pro Tyr
        115                 120                 125
Trp Thr His Pro Gln Arg Met Glu Lys Lys Leu His Ala Val Pro Ala
    130                 135                 140
Gly Asn Thr Val Lys Phe Arg Cys Pro Ala Ala Gly Asn Pro Thr Pro
145                 150                 155                 160
Thr Ile Arg Trp Leu Lys Asp Gly Gln Ala Phe His Gly Glu Asn Arg
                165                 170                 175
Ile Gly Gly Ile Arg Leu Arg His Gln His Trp Ser Leu Val Met Glu
            180                 185                 190
Ser Val Val Pro Ser Asp Arg Gly Thr Tyr Thr Cys Leu Val Glu Asn
        195                 200                 205
Ala Val Gly Ser Ile Arg Tyr Asn Tyr Leu Leu Asp Val Leu Glu Arg
    210                 215                 220
Ser Pro His Arg Pro Ile Leu Gln Ala Gly Leu Pro Ala Asn Thr Thr
225                 230                 235                 240
Ala Val Val Gly Ser Asp Val Glu Leu Leu Cys Lys Val Tyr Ser Asp
                245                 250                 255
Ala Gln Pro His Ile Gln Trp Leu Lys His Ile Val Ile Asn Gly Ser
            260                 265                 270
Ser Phe Gly Ala Asp Gly Phe Pro Tyr Val Gln Val Leu Lys Thr Ala
        275                 280                 285
Asp Ile Asn Ser Ser Glu Val Glu Val Leu Tyr Leu Arg Asn Val Ser
    290                 295                 300
```

```
Ala Glu Asp Ala Gly Glu Tyr Thr Cys Leu Ala Gly Asn Ser Ile Gly
305                 310                 315                 320

Leu Ser Tyr Gln Ser Ala Trp Leu Thr Val Leu Pro
            325                 330

<210> SEQ ID NO 110
<211> LENGTH: 331
<212> TYPE: PRT
<213> ORGANISM: Artificial Sequence
<220> FEATURE:
<223> OTHER INFORMATION: Synthetic sequence

<400> SEQUENCE: 110

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
            20                  25                  30

Arg Leu Cys Cys Gly Arg Ala Glu Arg Gly Gly His Trp Tyr Lys Glu
        35                  40                  45

Gly Ser Arg Leu Ala Pro Ala Gly Arg Val Arg Gly Trp Arg Gly Arg
50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ser Leu Thr Ser Ser Asn Asp Asp Glu Asp Pro Lys Ser His
            100                 105                 110

Arg Asp Pro Ser Asn Arg His Ser Tyr Pro Gln Gln Ala Pro Tyr Trp
        115                 120                 125

Thr His Pro Gln Arg Met Glu Lys Lys Leu His Ala Val Pro Ala Gly
130                 135                 140

Asn Thr Val Lys Phe Arg Cys Pro Ala Ala Gly Asn Pro Thr Pro Thr
145                 150                 155                 160

Ile Arg Trp Leu Lys Asp Gly Gln Ala Phe His Gly Glu Asn Arg Ile
                165                 170                 175

Gly Gly Ile Arg Leu Arg His Gln His Trp Ser Leu Val Met Glu Ser
            180                 185                 190

Val Val Pro Ser Asp Arg Gly Thr Tyr Thr Cys Leu Val Glu Asn Ala
        195                 200                 205

Val Gly Ser Ile Arg Tyr Asn Tyr Leu Leu Asp Val Leu Glu Arg Ser
210                 215                 220

Pro His Arg Pro Ile Leu Gln Ala Gly Leu Pro Ala Asn Thr Thr Ala
225                 230                 235                 240

Val Val Gly Ser Asp Val Glu Leu Leu Cys Lys Val Tyr Ser Asp Ala
                245                 250                 255

Gln Pro His Ile Gln Trp Leu Lys His Ile Val Ile Asn Gly Ser Ser
            260                 265                 270

Phe Gly Ala Asp Gly Phe Pro Tyr Val Gln Val Leu Lys Thr Ala Asp
        275                 280                 285

Ile Asn Ser Ser Glu Val Glu Val Leu Tyr Leu Arg Asn Val Ser Ala
290                 295                 300

Glu Asp Ala Gly Glu Tyr Thr Cys Leu Ala Gly Asn Ser Ile Gly Leu
305                 310                 315                 320

Ser Tyr Gln Ser Ala Trp Leu Thr Val Leu Pro
                325                 330
```

<210> SEQ ID NO 111
<211> LENGTH: 331
<212> TYPE: PRT
<213> ORGANISM: Artificial Sequence
<220> FEATURE:
<223> OTHER INFORMATION: Synthetic sequence

<400> SEQUENCE: 111

```
Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
            20                  25                  30

Arg Leu Cys Cys Gly Arg Ala Glu Arg Gly Gly His Trp Tyr Lys Glu
        35                  40                  45

Gly Ser Arg Leu Ala Pro Ala Gly Arg Val Arg Gly Trp Arg Gly Arg
    50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ser Leu Thr Ser Ser Asp Asp Glu Asp Pro Lys Ser His
            100                 105                 110

Arg Asp Pro Ser Asn Arg His Ser Tyr Pro Gln Gln Ala Pro Tyr Trp
        115                 120                 125

Thr His Pro Gln Arg Met Glu Lys Lys Leu His Ala Val Pro Ala Gly
    130                 135                 140

Asn Thr Val Lys Phe Arg Cys Pro Ala Ala Gly Asn Pro Thr Pro Thr
145                 150                 155                 160

Ile Arg Trp Leu Lys Asp Gly Gln Ala Phe His Gly Glu Asn Arg Ile
                165                 170                 175

Gly Gly Ile Arg Leu Arg His Gln His Trp Ser Leu Val Met Glu Ser
            180                 185                 190

Val Val Pro Ser Asp Arg Gly Thr Tyr Thr Cys Leu Val Glu Asn Ala
        195                 200                 205

Val Gly Ser Ile Arg Tyr Asn Tyr Leu Leu Asp Val Leu Glu Arg Ser
    210                 215                 220

Pro His Arg Pro Ile Leu Gln Ala Gly Leu Pro Ala Asn Thr Thr Ala
225                 230                 235                 240

Val Val Gly Ser Asp Val Glu Leu Leu Cys Lys Val Tyr Ser Asp Ala
                245                 250                 255

Gln Pro His Ile Gln Trp Leu Lys His Ile Val Ile Asn Gly Ser Ser
            260                 265                 270

Phe Gly Ala Asp Gly Phe Pro Tyr Val Gln Val Leu Lys Thr Ala Asp
        275                 280                 285

Ile Asn Ser Ser Glu Val Glu Val Leu Tyr Leu Arg Asn Val Ser Ala
    290                 295                 300

Glu Asp Ala Gly Glu Tyr Thr Cys Leu Ala Gly Asn Ser Ile Gly Leu
305                 310                 315                 320

Ser Tyr Gln Ser Ala Trp Leu Thr Val Leu Pro
                325                 330
```

<210> SEQ ID NO 112
<211> LENGTH: 331
<212> TYPE: PRT
<213> ORGANISM: Artificial Sequence
<220> FEATURE:
<223> OTHER INFORMATION: Synthetic sequence

<400> SEQUENCE: 112

```
Leu Glu Ala Ser Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
            20                  25                  30

Arg Leu Cys Cys Gly Arg Ala Glu Arg Gly Gly His Trp Tyr Lys Glu
        35                  40                  45

Gly Ser Arg Leu Ala Pro Ala Gly Arg Val Arg Gly Trp Arg Gly Arg
    50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ser Leu Thr Ser Ser Asn Asp Glu Asp Asp Lys Ser His
            100                 105                 110

Arg Asp Pro Ser Asn Arg His Ser Tyr Pro Gln Gln Ala Pro Tyr Trp
        115                 120                 125

Thr His Pro Gln Arg Met Glu Lys Lys Leu His Ala Val Pro Ala Gly
    130                 135                 140

Asn Thr Val Lys Phe Arg Cys Pro Ala Ala Gly Asn Pro Thr Pro Thr
145                 150                 155                 160

Ile Arg Trp Leu Lys Asp Gly Gln Ala Phe His Gly Glu Asn Arg Ile
                165                 170                 175

Gly Gly Ile Arg Leu Arg His Gln His Trp Ser Leu Val Met Glu Ser
            180                 185                 190

Val Val Pro Ser Asp Arg Gly Thr Tyr Thr Cys Leu Val Glu Asn Ala
        195                 200                 205

Val Gly Ser Ile Arg Tyr Asn Tyr Leu Leu Asp Val Leu Glu Arg Ser
    210                 215                 220

Pro His Arg Pro Ile Leu Gln Ala Gly Leu Pro Ala Asn Thr Thr Ala
225                 230                 235                 240

Val Val Gly Ser Asp Val Glu Leu Leu Cys Lys Val Tyr Ser Asp Ala
                245                 250                 255

Gln Pro His Ile Gln Trp Leu Lys His Ile Val Ile Asn Gly Ser Ser
            260                 265                 270

Phe Gly Ala Asp Gly Phe Pro Tyr Val Gln Val Leu Lys Thr Ala Asp
        275                 280                 285

Ile Asn Ser Ser Glu Val Glu Val Leu Tyr Leu Arg Asn Val Ser Ala
    290                 295                 300

Glu Asp Ala Gly Glu Tyr Thr Cys Leu Ala Gly Asn Ser Ile Gly Leu
305                 310                 315                 320

Ser Tyr Gln Ser Ala Trp Leu Thr Val Leu Pro
                325                 330

<210> SEQ ID NO 113
<211> LENGTH: 331
<212> TYPE: PRT
<213> ORGANISM: Artificial Sequence
<220> FEATURE:
<223> OTHER INFORMATION: Synthetic sequence

<400> SEQUENCE: 113

Leu Glu Ala Ser Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
```

```
                      20                  25                  30
Arg Leu Cys Cys Gly Arg Ala Glu Arg Gly His Trp Tyr Lys Glu
             35                  40                  45

Gly Ser Arg Leu Ala Pro Ala Gly Arg Val Arg Gly Trp Arg Gly Arg
         50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                 85                  90                  95

Gly Asp Ser Leu Thr Ser Ser Asn Asp Asp Glu Asp Pro Lys Ser His
             100                 105                 110

Glu Asp Pro Ser Asn Arg His Ser Tyr Pro Gln Gln Ala Pro Tyr Trp
         115                 120                 125

Thr His Pro Gln Arg Met Glu Lys Lys Leu His Ala Val Pro Ala Gly
         130                 135                 140

Asn Thr Val Lys Phe Arg Cys Pro Ala Ala Gly Asn Pro Thr Pro Thr
145                 150                 155                 160

Ile Arg Trp Leu Lys Asp Gly Gln Ala Phe His Gly Glu Asn Arg Ile
                165                 170                 175

Gly Gly Ile Arg Leu Arg His Gln His Trp Ser Leu Val Met Glu Ser
             180                 185                 190

Val Val Pro Ser Asp Arg Gly Thr Tyr Thr Cys Leu Val Glu Asn Ala
         195                 200                 205

Val Gly Ser Ile Arg Tyr Asn Tyr Leu Leu Asp Val Leu Glu Arg Ser
         210                 215                 220

Pro His Arg Pro Ile Leu Gln Ala Gly Leu Pro Ala Asn Thr Thr Ala
225                 230                 235                 240

Val Val Gly Ser Asp Val Glu Leu Leu Cys Lys Val Tyr Ser Asp Ala
                245                 250                 255

Gln Pro His Ile Gln Trp Leu Lys His Ile Val Ile Asn Gly Ser Ser
             260                 265                 270

Phe Gly Ala Asp Gly Phe Pro Tyr Val Gln Val Leu Lys Thr Ala Asp
         275                 280                 285

Ile Asn Ser Ser Glu Val Glu Val Leu Tyr Leu Arg Asn Val Ser Ala
         290                 295                 300

Glu Asp Ala Gly Glu Tyr Thr Cys Leu Ala Gly Asn Ser Ile Gly Leu
305                 310                 315                 320

Ser Tyr Gln Ser Ala Trp Leu Thr Val Leu Pro
                325                 330

<210> SEQ ID NO 114
<211> LENGTH: 331
<212> TYPE: PRT
<213> ORGANISM: Artificial Sequence
<220> FEATURE:
<223> OTHER INFORMATION: Synthetic sequence

<400> SEQUENCE: 114

Leu Glu Ala Ser Glu Glu Val Glu Leu Glu Pro Cys Leu Ala Pro Ser
1               5                  10                  15

Leu Glu Gln Gln Glu Gln Glu Leu Thr Val Ala Leu Gly Gln Pro Val
            20                  25                  30

Arg Leu Cys Cys Gly Arg Ala Glu Arg Gly Gly His Trp Tyr Lys Glu
         35                  40                  45

Gly Ser Arg Leu Ala Pro Ala Gly Arg Val Arg Gly Trp Arg Gly Arg
     50                  55                  60
```

```
Leu Glu Ile Ala Ser Phe Leu Pro Glu Asp Ala Gly Arg Tyr Leu Cys
 65                  70                  75                  80

Leu Ala Arg Gly Ser Met Ile Val Leu Gln Asn Leu Thr Leu Ile Thr
             85                  90                  95

Gly Asp Ser Leu Thr Ser Ser Asn Asp Asp Glu Asp Pro Lys Ser His
            100                 105                 110

Arg Asp Pro Glu Asn Arg His Ser Tyr Pro Gln Gln Ala Pro Tyr Trp
        115                 120                 125

Thr His Pro Gln Arg Met Glu Lys Lys Leu His Ala Val Pro Ala Gly
        130                 135                 140

Asn Thr Val Lys Phe Arg Cys Pro Ala Ala Gly Asn Pro Thr Pro Thr
145                 150                 155                 160

Ile Arg Trp Leu Lys Asp Gly Gln Ala Phe His Gly Glu Asn Arg Ile
                165                 170                 175

Gly Gly Ile Arg Leu Arg His Gln His Trp Ser Leu Val Met Glu Ser
            180                 185                 190

Val Val Pro Ser Asp Arg Gly Thr Tyr Thr Cys Leu Val Glu Asn Ala
        195                 200                 205

Val Gly Ser Ile Arg Tyr Asn Tyr Leu Leu Asp Val Leu Glu Arg Ser
        210                 215                 220

Pro His Arg Pro Ile Leu Gln Ala Gly Leu Pro Ala Asn Thr Thr Ala
225                 230                 235                 240

Val Val Gly Ser Asp Val Glu Leu Leu Cys Lys Val Tyr Ser Asp Ala
                245                 250                 255

Gln Pro His Ile Gln Trp Leu Lys His Ile Val Ile Asn Gly Ser Ser
            260                 265                 270

Phe Gly Ala Asp Gly Phe Pro Tyr Val Gln Val Leu Lys Thr Ala Asp
        275                 280                 285

Ile Asn Ser Ser Glu Val Glu Val Leu Tyr Leu Arg Asn Val Ser Ala
        290                 295                 300

Glu Asp Ala Gly Glu Tyr Thr Cys Leu Ala Gly Asn Ser Ile Gly Leu
305                 310                 315                 320

Ser Tyr Gln Ser Ala Trp Leu Thr Val Leu Pro
                325                 330

<210> SEQ ID NO 115
<211> LENGTH: 332
<212> TYPE: PRT
<213> ORGANISM: Artificial Sequence
<220> FEATURE:
<223> OTHER INFORMATION: Synthetic sequence

<400> SEQUENCE: 115

Leu Glu Ala Ser Glu Glu Val Glu Leu Glu Pro Cys Leu Ala Pro Ser
 1               5                  10                  15

Leu Glu Gln Gln Glu Gln Glu Leu Thr Val Ala Leu Gly Gln Pro Val
                 20                  25                  30

Arg Leu Cys Cys Gly Arg Ala Glu Arg Gly Gly His Trp Tyr Lys Glu
             35                  40                  45

Gly Ser Arg Leu Ala Pro Ala Gly Arg Val Arg Gly Trp Arg Gly Arg
         50                  55                  60

Leu Glu Ile Ala Ser Phe Leu Pro Glu Asp Ala Gly Arg Tyr Leu Cys
 65                  70                  75                  80

Leu Ala Arg Gly Ser Met Ile Val Leu Gln Asn Leu Thr Leu Ile Thr
                 85                  90                  95
```

```
Gly Asp Ser Leu Thr Ser Ser Asp Asp Asp Asp Asp Ser Ser
            100                 105                 110

Ser Glu Glu Pro Ser Asn Arg His Ser Tyr Pro Gln Gln Ala Pro Tyr
        115                 120                 125

Trp Thr His Pro Gln Arg Met Glu Lys Lys Leu His Ala Val Pro Ala
130                 135                 140

Gly Asn Thr Val Lys Phe Arg Cys Pro Ala Ala Gly Asn Pro Thr Pro
145                 150                 155                 160

Thr Ile Arg Trp Leu Lys Asp Gly Gln Ala Phe His Gly Glu Asn Arg
                165                 170                 175

Ile Gly Gly Ile Arg Leu Arg His Gln His Trp Ser Leu Val Met Glu
                180                 185                 190

Ser Val Val Pro Ser Asp Arg Gly Thr Tyr Thr Cys Leu Val Glu Asn
                195                 200                 205

Ala Val Gly Ser Ile Arg Tyr Asn Tyr Leu Leu Asp Val Leu Glu Arg
210                 215                 220

Ser Pro His Arg Pro Ile Leu Gln Ala Gly Leu Pro Ala Asn Thr Thr
225                 230                 235                 240

Ala Val Val Gly Ser Asp Val Glu Leu Leu Cys Lys Val Tyr Ser Asp
                245                 250                 255

Ala Gln Pro His Ile Gln Trp Leu Lys His Ile Val Ile Asn Gly Ser
                260                 265                 270

Ser Phe Gly Ala Asp Gly Phe Pro Tyr Val Gln Val Leu Lys Thr Ala
        275                 280                 285

Asp Ile Asn Ser Ser Glu Val Glu Val Leu Tyr Leu Arg Asn Val Ser
        290                 295                 300

Ala Glu Asp Ala Gly Glu Tyr Thr Cys Leu Ala Gly Asn Ser Ile Gly
305                 310                 315                 320

Leu Ser Tyr Gln Ser Ala Trp Leu Thr Val Leu Pro
                325                 330

<210> SEQ ID NO 116
<211> LENGTH: 331
<212> TYPE: PRT
<213> ORGANISM: Artificial Sequence
<220> FEATURE:
<223> OTHER INFORMATION: Synthetic sequence

<400> SEQUENCE: 116

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
                20                  25                  30

Arg Leu Cys Cys Gly Arg Ala Glu Arg Gly Gly His Trp Tyr Lys Glu
            35                  40                  45

Gly Ser Arg Leu Ala Pro Ala Gly Arg Val Arg Gly Trp Arg Gly Arg
        50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ser Leu Thr Ser Ser Asp Asp Asp Asp Asp Ser Ser
            100                 105                 110

Glu Glu Pro Ser Asn Arg His Ser Tyr Pro Gln Gln Ala Pro Tyr Trp
        115                 120                 125

Thr His Pro Gln Arg Met Glu Lys Lys Leu His Ala Val Pro Ala Gly
```

```
            130                 135                 140
Asn Thr Val Lys Phe Arg Cys Pro Ala Ala Gly Asn Pro Thr Pro Thr
145                 150                 155                 160

Ile Arg Trp Leu Lys Asp Gly Gln Ala Phe His Gly Glu Asn Arg Ile
                165                 170                 175

Gly Gly Ile Arg Leu Arg His Gln His Trp Ser Leu Val Met Glu Ser
            180                 185                 190

Val Val Pro Ser Asp Arg Gly Thr Tyr Thr Cys Leu Val Glu Asn Ala
                195                 200                 205

Val Gly Ser Ile Arg Tyr Asn Tyr Leu Leu Asp Val Leu Glu Arg Ser
210                 215                 220

Pro His Arg Pro Ile Leu Gln Ala Gly Leu Pro Ala Asn Thr Thr Ala
225                 230                 235                 240

Val Val Gly Ser Asp Val Glu Leu Leu Cys Lys Val Tyr Ser Asp Ala
                245                 250                 255

Gln Pro His Ile Gln Trp Leu Lys His Ile Val Ile Asn Gly Ser Ser
                260                 265                 270

Phe Gly Ala Asp Gly Phe Pro Tyr Val Gln Val Leu Lys Thr Ala Asp
            275                 280                 285

Ile Asn Ser Ser Glu Val Glu Val Leu Tyr Leu Arg Asn Val Ser Ala
            290                 295                 300

Glu Asp Ala Gly Glu Tyr Thr Cys Leu Ala Gly Asn Ser Ile Gly Leu
305                 310                 315                 320

Ser Tyr Gln Ser Ala Trp Leu Thr Val Leu Pro
                325                 330

<210> SEQ ID NO 117
<211> LENGTH: 333
<212> TYPE: PRT
<213> ORGANISM: Artificial Sequence
<220> FEATURE:
<223> OTHER INFORMATION: Synthetic sequence

<400> SEQUENCE: 117

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
                20                  25                  30

Arg Leu Cys Cys Gly Arg Ala Glu Arg Gly Gly His Trp Tyr Lys Glu
            35                  40                  45

Gly Ser Arg Leu Ala Pro Ala Gly Arg Val Arg Gly Trp Arg Gly Arg
50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ser Leu Thr Ser Ser Glu Asp Asp Asp Asp Asp Asp Asp Ser
                100                 105                 110

Ser His Arg Asp Pro Ser Asn Arg His Ser Tyr Pro Gln Gln Ala Pro
            115                 120                 125

Tyr Trp Thr His Pro Gln Arg Met Glu Lys Lys Leu His Ala Val Pro
        130                 135                 140

Ala Gly Asn Thr Val Lys Phe Arg Cys Pro Ala Ala Gly Asn Pro Thr
145                 150                 155                 160

Pro Thr Ile Arg Trp Leu Lys Asp Gly Gln Ala Phe His Gly Glu Asn
                165                 170                 175
```

```
Arg Ile Gly Gly Ile Arg Leu Arg His Gln His Trp Ser Leu Val Met
            180                 185                 190

Glu Ser Val Val Pro Ser Asp Arg Gly Thr Tyr Thr Cys Leu Val Glu
        195                 200                 205

Asn Ala Val Gly Ser Ile Arg Tyr Asn Tyr Leu Leu Asp Val Leu Glu
    210                 215                 220

Arg Ser Pro His Arg Pro Ile Leu Gln Ala Gly Leu Pro Ala Asn Thr
225                 230                 235                 240

Thr Ala Val Val Gly Ser Asp Val Glu Leu Leu Cys Lys Val Tyr Ser
            245                 250                 255

Asp Ala Gln Pro His Ile Gln Trp Leu Lys His Ile Val Ile Asn Gly
        260                 265                 270

Ser Ser Phe Gly Ala Asp Gly Phe Pro Tyr Val Gln Val Leu Lys Thr
    275                 280                 285

Ala Asp Ile Asn Ser Ser Glu Val Glu Val Leu Tyr Leu Arg Asn Val
290                 295                 300

Ser Ala Glu Asp Ala Gly Glu Tyr Thr Cys Leu Ala Gly Asn Ser Ile
305                 310                 315                 320

Gly Leu Ser Tyr Gln Ser Ala Trp Leu Thr Val Leu Pro
            325                 330

<210> SEQ ID NO 118
<211> LENGTH: 331
<212> TYPE: PRT
<213> ORGANISM: Artificial Sequence
<220> FEATURE:
<223> OTHER INFORMATION: Synthetic sequence

<400> SEQUENCE: 118

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
            20                  25                  30

Arg Leu Cys Cys Gly Arg Ala Glu Arg Gly Gly His Trp Tyr Lys Glu
        35                  40                  45

Gly Ser Arg Leu Ala Pro Ala Gly Arg Val Arg Gly Trp Arg Gly Arg
    50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
            85                  90                  95

Gly Asp Ser Leu Thr Ser Ser Asn Asp Asp Glu Asp Pro Lys Ser His
        100                 105                 110

Glu Glu Lys Glu Asn Arg His Ser Tyr Pro Gln Gln Ala Pro Tyr Trp
    115                 120                 125

Thr His Pro Gln Arg Met Glu Lys Lys Leu His Ala Val Pro Ala Gly
130                 135                 140

Asn Thr Val Lys Phe Arg Cys Pro Ala Ala Gly Asn Pro Thr Pro Thr
145                 150                 155                 160

Ile Arg Trp Leu Lys Asp Gly Gln Ala Phe His Gly Glu Asn Arg Ile
            165                 170                 175

Gly Gly Ile Arg Leu Arg His Gln His Trp Ser Leu Val Met Glu Ser
        180                 185                 190

Val Val Pro Ser Asp Arg Gly Thr Tyr Thr Cys Leu Val Glu Asn Ala
    195                 200                 205
```

```
Val Gly Ser Ile Arg Tyr Asn Tyr Leu Leu Asp Val Leu Glu Arg Ser
        210                 215                 220

Pro His Arg Pro Ile Leu Gln Ala Gly Leu Pro Ala Asn Thr Thr Ala
225                 230                 235                 240

Val Val Gly Ser Asp Val Glu Leu Leu Cys Lys Val Tyr Ser Asp Ala
                245                 250                 255

Gln Pro His Ile Gln Trp Leu Lys His Ile Val Ile Asn Gly Ser Ser
                260                 265                 270

Phe Gly Ala Asp Gly Phe Pro Tyr Val Gln Val Leu Lys Thr Ala Asp
            275                 280                 285

Ile Asn Ser Ser Glu Val Glu Val Leu Tyr Leu Arg Asn Val Ser Ala
        290                 295                 300

Glu Asp Ala Gly Glu Tyr Thr Cys Leu Ala Gly Asn Ser Ile Gly Leu
305                 310                 315                 320

Ser Tyr Gln Ser Ala Trp Leu Thr Val Leu Pro
                325                 330

<210> SEQ ID NO 119
<211> LENGTH: 331
<212> TYPE: PRT
<213> ORGANISM: Artificial Sequence
<220> FEATURE:
<223> OTHER INFORMATION: Synthetic sequence

<400> SEQUENCE: 119

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
                20                  25                  30

Arg Leu Cys Cys Gly Arg Ala Glu Arg Gly Gly His Trp Tyr Lys Glu
            35                  40                  45

Gly Ser Arg Leu Ala Pro Ala Gly Arg Val Arg Gly Trp Arg Gly Arg
        50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ser Leu Thr Ser Ser Asn Asp Asp Glu Asp Ser Ser Ser Ser
            100                 105                 110

Glu Asp Pro Ser Asn Arg His Ser Tyr Pro Gln Gln Ala Pro Tyr Trp
        115                 120                 125

Thr His Pro Gln Arg Met Glu Lys Lys Leu His Ala Val Pro Ala Gly
    130                 135                 140

Asn Thr Val Lys Phe Arg Cys Pro Ala Ala Gly Asn Pro Thr Pro Thr
145                 150                 155                 160

Ile Arg Trp Leu Lys Asp Gly Gln Ala Phe His Gly Glu Asn Arg Ile
                165                 170                 175

Gly Gly Ile Arg Leu Arg His Gln His Trp Ser Leu Val Met Glu Ser
            180                 185                 190

Val Val Pro Ser Asp Arg Gly Thr Tyr Thr Cys Leu Val Glu Asn Ala
        195                 200                 205

Val Gly Ser Ile Arg Tyr Asn Tyr Leu Leu Asp Val Leu Glu Arg Ser
    210                 215                 220

Pro His Arg Pro Ile Leu Gln Ala Gly Leu Pro Ala Asn Thr Thr Ala
225                 230                 235                 240

Val Val Gly Ser Asp Val Glu Leu Leu Cys Lys Val Tyr Ser Asp Ala
```

```
                    245                 250                 255
Gln Pro His Ile Gln Trp Leu Lys His Ile Val Ile Asn Gly Ser Ser
                260                 265                 270

Phe Gly Ala Asp Gly Phe Pro Tyr Val Gln Val Leu Lys Thr Ala Asp
            275                 280                 285

Ile Asn Ser Ser Glu Val Glu Val Leu Tyr Leu Arg Asn Val Ser Ala
        290                 295                 300

Glu Asp Ala Gly Glu Tyr Thr Cys Leu Ala Gly Asn Ser Ile Gly Leu
305                 310                 315                 320

Ser Tyr Gln Ser Ala Trp Leu Thr Val Leu Pro
                325                 330

<210> SEQ ID NO 120
<211> LENGTH: 334
<212> TYPE: PRT
<213> ORGANISM: Artificial Sequence
<220> FEATURE:
<223> OTHER INFORMATION: Synthetic sequence

<400> SEQUENCE: 120

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
            20                  25                  30

Arg Leu Cys Cys Gly Arg Ala Glu Arg Gly Gly His Trp Tyr Lys Glu
        35                  40                  45

Gly Ser Arg Leu Ala Pro Ala Gly Arg Val Arg Gly Trp Arg Gly Arg
    50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Ala Leu Thr Leu Ile Thr
                85                  90                  95

Gly Asp Ala Leu Pro Ser Ser Glu Asp Asp Asp Asp Asp Asp Asp Ser
            100                 105                 110

Ser Ser Glu Glu Lys Glu Thr Asp Asn Thr Lys Pro Asn Pro Val Ala
        115                 120                 125

Pro Tyr Trp Thr His Pro Gln Arg Met Glu Lys Lys Leu His Ala Val
    130                 135                 140

Pro Ala Gly Asn Thr Val Lys Phe Arg Cys Pro Ala Ala Gly Asn Pro
145                 150                 155                 160

Thr Pro Thr Ile Arg Trp Leu Lys Asp Gly Gln Ala Phe His Gly Glu
                165                 170                 175

Asn Arg Ile Gly Gly Ile Arg Leu Arg His Gln His Trp Ser Leu Val
            180                 185                 190

Met Glu Ser Val Val Pro Ser Asp Arg Gly Thr Tyr Thr Cys Leu Val
        195                 200                 205

Glu Asn Ala Val Gly Ser Ile Arg Tyr Asn Tyr Leu Leu Asp Val Leu
    210                 215                 220

Glu Arg Ser Pro His Arg Pro Ile Leu Gln Ala Gly Leu Pro Ala Asn
225                 230                 235                 240

Thr Thr Ala Val Val Gly Ser Asp Val Glu Leu Leu Cys Lys Val Tyr
                245                 250                 255

Ser Asp Ala Gln Pro His Ile Gln Trp Leu Lys His Ile Val Ile Asn
            260                 265                 270

Gly Ser Ser Phe Gly Ala Asp Gly Phe Pro Tyr Val Gln Val Leu Lys
        275                 280                 285
```

```
Thr Ala Asp Ile Asn Ser Ser Glu Val Glu Val Leu Tyr Leu Arg Asn
    290                 295                 300

Val Ser Ala Glu Asp Ala Gly Glu Tyr Thr Cys Leu Ala Gly Asn Ser
305                 310                 315                 320

Ile Gly Leu Ser Tyr Gln Ser Ala Trp Leu Thr Val Leu Pro
                325                 330

<210> SEQ ID NO 121
<211> LENGTH: 334
<212> TYPE: PRT
<213> ORGANISM: Artificial Sequence
<220> FEATURE:
<223> OTHER INFORMATION: Synthetic sequence

<400> SEQUENCE: 121

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
                20                  25                  30

Arg Leu Cys Cys Gly Arg Ala Glu Arg Gly Gly His Trp Tyr Lys Glu
            35                  40                  45

Gly Ser Arg Leu Ala Pro Ala Gly Arg Val Arg Gly Trp Arg Gly Arg
    50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ala Leu Pro Ser Ser Glu Asp Asp Asp Asp Asp Asp Asp Ser
            100                 105                 110

Ser Ser Glu Glu Lys Glu Thr Asp Asn Thr Lys Pro Asn Pro Val Ala
    115                 120                 125

Pro Tyr Trp Thr His Pro Gln Arg Met Glu Lys Lys Leu His Ala Val
130                 135                 140

Pro Ala Gly Asn Thr Val Lys Phe Arg Cys Pro Ala Ala Gly Ala Pro
145                 150                 155                 160

Thr Pro Thr Ile Arg Trp Leu Lys Asp Gly Gln Ala Phe His Gly Glu
                165                 170                 175

Asn Arg Ile Gly Gly Ile Arg Leu Arg His Gln His Trp Ser Leu Val
            180                 185                 190

Met Glu Ser Val Val Pro Ser Asp Arg Gly Thr Tyr Thr Cys Leu Val
    195                 200                 205

Glu Asn Ala Val Gly Ser Ile Arg Tyr Asn Tyr Leu Leu Asp Val Leu
210                 215                 220

Glu Arg Ser Pro His Arg Pro Ile Leu Gln Ala Gly Leu Pro Ala Asn
225                 230                 235                 240

Thr Thr Ala Val Val Gly Ser Asp Val Glu Leu Leu Cys Lys Val Tyr
                245                 250                 255

Ser Asp Ala Gln Pro His Ile Gln Trp Leu Lys His Ile Val Ile Asn
            260                 265                 270

Gly Ser Ser Phe Gly Ala Asp Gly Phe Pro Tyr Val Gln Val Leu Lys
    275                 280                 285

Thr Ala Asp Ile Asn Ser Ser Glu Val Glu Val Leu Tyr Leu Arg Asn
    290                 295                 300

Val Ser Ala Glu Asp Ala Gly Glu Tyr Thr Cys Leu Ala Gly Asn Ser
305                 310                 315                 320
```

```
Ile Gly Leu Ser Tyr Gln Ser Ala Trp Leu Thr Val Leu Pro
            325                 330

<210> SEQ ID NO 122
<211> LENGTH: 356
<212> TYPE: PRT
<213> ORGANISM: Artificial Sequence
<220> FEATURE:
<223> OTHER INFORMATION: Synthetic sequence

<400> SEQUENCE: 122

Arg Pro Ser Phe Ser Leu Val Glu Asp Thr Thr Leu Glu Pro Glu Glu
1               5                   10                  15

Pro Pro Thr Lys Tyr Gln Ile Ser Gln Pro Glu Val Tyr Val Ala Ala
            20                  25                  30

Pro Gly Glu Ser Leu Glu Val Arg Cys Leu Leu Lys Asp Ala Ala Val
        35                  40                  45

Ile Ser Trp Thr Lys Asp Gly Val His Leu Gly Pro Asn Asn Arg Thr
50                  55                  60

Val Leu Ile Gly Glu Tyr Leu Gln Ile Lys Gly Ala Thr Pro Arg Asp
65                  70                  75                  80

Ser Gly Leu Tyr Ala Cys Thr Ala Ser Arg Thr Val Asp Ser Glu Thr
                85                  90                  95

Trp Tyr Phe Met Val Asn Val Thr Asp Ala Ile Ser Ser Gly Glu Asp
            100                 105                 110

Asp Asp Asp Asp Asp Ala Glu Asp Phe Val Ser Glu Asn Ser Asn
        115                 120                 125

Asn Lys Arg Ala Pro Tyr Trp Thr Asn Thr Glu Lys Met Glu Lys Arg
130                 135                 140

Leu His Ala Val Pro Ala Ala Asn Thr Val Lys Phe Arg Cys Pro Ala
145                 150                 155                 160

Gly Gly Asn Pro Met Pro Thr Met Arg Trp Leu Lys Asn Gly Lys Glu
                165                 170                 175

Phe Lys Gln Glu His Arg Ile Gly Gly Tyr Lys Val Arg Asn Gln His
            180                 185                 190

Trp Ser Leu Ile Met Glu Ser Val Val Pro Ser Asp Lys Gly Asn Tyr
        195                 200                 205

Thr Cys Val Val Glu Asn Glu Tyr Gly Ser Ile Asn His Thr Tyr His
210                 215                 220

Leu Asp Val Val Glu Arg Ser Pro His Arg Pro Ile Leu Gln Ala Gly
225                 230                 235                 240

Leu Pro Ala Asn Ala Ser Thr Val Val Gly Gly Asp Val Glu Phe Val
                245                 250                 255

Cys Lys Val Tyr Ser Asp Ala Gln Pro His Ile Gln Trp Ile Lys His
            260                 265                 270

Val Glu Lys Asn Gly Ser Lys Tyr Gly Pro Asp Gly Leu Pro Tyr Leu
        275                 280                 285

Lys Val Leu Lys Ala Ala Gly Val Asn Thr Thr Asp Lys Glu Ile Glu
290                 295                 300

Val Leu Tyr Ile Arg Asn Val Thr Phe Glu Asp Ala Gly Glu Tyr Thr
305                 310                 315                 320

Cys Leu Ala Gly Asn Ser Ile Gly Ile Ser Phe His Ser Ala Trp Leu
                325                 330                 335

Thr Val Leu Pro Ala Pro Gly Arg Glu Lys Glu Ile Thr Ala Ser Pro
            340                 345                 350

Asp Tyr Leu Glu
```

<210> SEQ ID NO 123
<211> LENGTH: 353
<212> TYPE: PRT
<213> ORGANISM: Artificial Sequence
<220> FEATURE:
<223> OTHER INFORMATION: Synthetic sequence

<400> SEQUENCE: 123

Glu Ser Leu Gly Thr Glu Gln Arg Val Val Gly Arg Ala Ala Glu Val
1               5                   10                  15

Pro Gly Pro Glu Pro Gly Gln Gln Glu Gln Leu Val Phe Gly Ser Gly
            20                  25                  30

Asp Ala Val Glu Leu Ser Cys Pro Pro Gly Gly Gly Pro Met Gly
        35                  40                  45

Pro Thr Val Trp Val Lys Asp Gly Thr Gly Leu Val Pro Ser Glu Arg
    50                  55                  60

Val Leu Val Gly Pro Gln Arg Leu Gln Val Leu Asn Ala Ser His Glu
65                  70                  75                  80

Asp Ser Gly Ala Tyr Ser Cys Arg Gln Arg Leu Thr Gln Arg Val Leu
                85                  90                  95

Cys His Phe Ser Val Arg Val Thr Asp Ala Pro Ser Ser Glu Asp Asp
            100                 105                 110

Asp Asp Asp Asp Glu Ala Glu Asp Thr Gly Val Asp Thr Gly Ala
        115                 120                 125

Pro Tyr Trp Thr Arg Pro Glu Arg Met Asp Lys Lys Leu Leu Ala Val
    130                 135                 140

Pro Ala Ala Asn Thr Val Arg Phe Arg Cys Pro Ala Ala Gly Asn Pro
145                 150                 155                 160

Thr Pro Ser Ile Ser Trp Leu Lys Asn Gly Arg Glu Phe Arg Gly Glu
                165                 170                 175

His Arg Ile Gly Gly Ile Lys Leu Arg His Gln Gln Trp Ser Leu Val
            180                 185                 190

Met Glu Ser Val Val Pro Ser Asp Arg Gly Asn Tyr Thr Cys Val Val
        195                 200                 205

Glu Asn Lys Phe Gly Ser Ile Arg Gln Thr Tyr Thr Leu Asp Val Leu
    210                 215                 220

Glu Arg Ser Pro His Arg Pro Ile Leu Gln Ala Gly Leu Pro Ala Asn
225                 230                 235                 240

Gln Thr Ala Val Leu Gly Ser Asp Val Glu Phe His Cys Lys Val Tyr
                245                 250                 255

Ser Asp Ala Gln Pro His Ile Gln Trp Leu Lys His Val Glu Val Asn
            260                 265                 270

Gly Ser Lys Val Gly Pro Asp Gly Thr Pro Tyr Val Thr Val Leu Lys
        275                 280                 285

Thr Ala Gly Ala Asn Thr Thr Asp Lys Glu Leu Glu Val Leu Ser Leu
    290                 295                 300

His Asn Val Thr Phe Glu Asp Ala Gly Glu Tyr Thr Cys Leu Ala Gly
305                 310                 315                 320

Asn Ser Ile Gly Phe Ser His His Ser Ala Trp Leu Val Val Leu Pro
                325                 330                 335

Ala Glu Glu Glu Leu Val Glu Ala Asp Glu Ala Gly Ser Val Tyr Ala
            340                 345                 350

Gly

-continued

```
<210> SEQ ID NO 124
<211> LENGTH: 565
<212> TYPE: PRT
<213> ORGANISM: Artificial Sequence
<220> FEATURE:
<223> OTHER INFORMATION: Synthetic sequence

<400> SEQUENCE: 124

Leu Glu Ala Ser Glu Glu Val Glu Leu Glu Pro Cys Leu Ala Pro Ser
1               5                   10                  15

Leu Glu Gln Gln Glu Gln Leu Thr Val Ala Leu Gly Gln Pro Val
            20                  25                  30

Arg Leu Cys Cys Gly Arg Ala Glu Arg Gly Gly His Trp Tyr Lys Glu
        35                  40                  45

Gly Ser Arg Leu Ala Pro Ala Gly Arg Val Arg Gly Trp Arg Gly Arg
    50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ser Leu Thr Ser Ser Glu Asp Asp Asp Asp Asp Asp Ser
            100                 105                 110

Ser Ser Glu Glu Lys Glu Thr Asp His Ser Tyr Pro Gln Gln Ala Pro
        115                 120                 125

Tyr Trp Thr His Pro Gln Arg Met Glu Lys Lys Leu His Ala Val Pro
    130                 135                 140

Ala Gly Asn Thr Val Lys Phe Arg Cys Pro Ala Ala Gly Asn Pro Thr
145                 150                 155                 160

Pro Thr Ile Arg Trp Leu Lys Asp Gly Gln Ala Phe His Gly Glu Asn
                165                 170                 175

Arg Ile Gly Gly Ile Arg Leu Arg His Gln His Trp Ser Leu Val Met
            180                 185                 190

Glu Ser Val Val Pro Ser Asp Arg Gly Thr Tyr Thr Cys Leu Val Glu
        195                 200                 205

Asn Ala Val Gly Ser Ile Arg Tyr Asn Tyr Leu Leu Asp Val Leu Glu
    210                 215                 220

Arg Ser Pro His Arg Pro Ile Leu Gln Ala Gly Leu Pro Ala Asn Thr
225                 230                 235                 240

Thr Ala Val Val Gly Ser Asp Val Glu Leu Leu Cys Lys Val Tyr Ser
                245                 250                 255

Asp Ala Gln Pro His Ile Gln Trp Leu Lys His Ile Val Ile Asn Gly
            260                 265                 270

Ser Ser Phe Gly Ala Asp Gly Phe Pro Tyr Val Gln Val Leu Lys Thr
        275                 280                 285

Ala Asp Ile Asn Ser Ser Glu Val Glu Val Leu Tyr Leu Arg Asn Val
    290                 295                 300

Ser Ala Glu Asp Ala Gly Glu Tyr Thr Cys Leu Ala Gly Asn Ser Ile
305                 310                 315                 320

Gly Leu Ser Tyr Gln Ser Ala Trp Leu Thr Val Leu Pro Glu Pro Lys
                325                 330                 335

Ser Ser Asp Lys Thr His Thr Cys Pro Pro Cys Pro Ala Pro Glu Leu
            340                 345                 350

Leu Gly Gly Pro Ser Val Phe Leu Phe Pro Pro Lys Pro Lys Asp Thr
        355                 360                 365

Leu Met Ile Ser Arg Thr Pro Glu Val Thr Cys Val Val Val Asp Val
```

```
                    370             375             380
Ser His Glu Asp Pro Glu Val Lys Phe Asn Trp Tyr Val Asp Gly Val
385                 390                 395                 400

Glu Val His Asn Ala Lys Thr Lys Pro Arg Glu Glu Gln Tyr Asn Ser
                405                 410                 415

Thr Tyr Arg Val Val Ser Val Leu Thr Val Leu His Gln Asp Trp Leu
            420                 425                 430

Asn Gly Lys Glu Tyr Lys Cys Lys Val Ser Asn Lys Ala Leu Pro Ala
        435                 440                 445

Pro Ile Glu Lys Thr Ile Ser Lys Ala Lys Gly Gln Pro Arg Glu Pro
    450                 455                 460

Gln Val Tyr Thr Leu Pro Pro Ser Arg Asp Glu Leu Thr Lys Asn Gln
465                 470                 475                 480

Val Ser Leu Thr Cys Leu Val Lys Gly Phe Tyr Pro Ser Asp Ile Ala
                485                 490                 495

Val Glu Trp Glu Ser Asn Gly Gln Pro Glu Asn Asn Tyr Lys Thr Thr
                500                 505                 510

Pro Pro Val Leu Asp Ser Asp Gly Ser Phe Phe Leu Tyr Ser Lys Leu
                515                 520                 525

Thr Val Asp Lys Ser Arg Trp Gln Gln Gly Asn Val Phe Ser Cys Ser
            530                 535                 540

Val Met His Glu Ala Leu His Asn His Tyr Thr Gln Lys Ser Leu Ser
545                 550                 555                 560

Leu Ser Pro Gly Lys
                565

<210> SEQ ID NO 125
<211> LENGTH: 563
<212> TYPE: PRT
<213> ORGANISM: Artificial Sequence
<220> FEATURE:
<223> OTHER INFORMATION: Synthetic sequence

<400> SEQUENCE: 125

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
                20                  25                  30

Arg Leu Cys Cys Gly Arg Ala Glu Arg Gly Gly His Trp Tyr Lys Glu
            35                  40                  45

Gly Ser Arg Leu Ala Pro Ala Gly Arg Val Arg Gly Trp Arg Gly Arg
        50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ser Leu Thr Ser Ser Asp Asp Glu Asp Thr Asp Gly Ala
                100                 105                 110

Glu Asp Phe Val Ser Glu His Ser Tyr Pro Gln Gln Ala Pro Tyr Trp
            115                 120                 125

Thr His Pro Gln Arg Met Glu Lys Lys Leu His Ala Val Pro Ala Gly
        130                 135                 140

Asn Thr Val Lys Phe Arg Cys Pro Ala Ala Gly Asn Pro Thr Pro Thr
145                 150                 155                 160

Ile Arg Trp Leu Lys Asp Gly Gln Ala Phe His Gly Glu Asn Arg Ile
                165                 170                 175
```

Gly Gly Ile Arg Leu Arg His Gln His Trp Ser Leu Val Met Glu Ser
            180                 185                 190

Val Val Pro Ser Asp Arg Gly Thr Tyr Thr Cys Leu Val Glu Asn Ala
            195                 200                 205

Val Gly Ser Ile Arg Tyr Asn Tyr Leu Leu Asp Val Leu Glu Arg Ser
            210                 215                 220

Pro His Arg Pro Ile Leu Gln Ala Gly Leu Pro Ala Asn Thr Thr Ala
225                 230                 235                 240

Val Val Gly Ser Asp Val Glu Leu Leu Cys Lys Val Tyr Ser Asp Ala
            245                 250                 255

Gln Pro His Ile Gln Trp Leu Lys His Ile Val Ile Asn Gly Ser Ser
            260                 265                 270

Phe Gly Ala Asp Gly Phe Pro Tyr Val Gln Val Leu Lys Thr Ala Asp
            275                 280                 285

Ile Asn Ser Ser Glu Val Glu Val Leu Tyr Leu Arg Asn Val Ser Ala
            290                 295                 300

Glu Asp Ala Gly Glu Tyr Thr Cys Leu Ala Gly Asn Ser Ile Gly Leu
305                 310                 315                 320

Ser Tyr Gln Ser Ala Trp Leu Thr Val Leu Pro Glu Pro Lys Ser Ser
            325                 330                 335

Asp Lys Thr His Thr Cys Pro Pro Cys Pro Ala Pro Glu Leu Leu Gly
            340                 345                 350

Gly Pro Ser Val Phe Leu Phe Pro Pro Lys Pro Lys Asp Thr Leu Met
            355                 360                 365

Ile Ser Arg Thr Pro Glu Val Thr Cys Val Val Val Asp Val Ser His
            370                 375                 380

Glu Asp Pro Glu Val Lys Phe Asn Trp Tyr Val Asp Gly Val Glu Val
385                 390                 395                 400

His Asn Ala Lys Thr Lys Pro Arg Glu Glu Gln Tyr Asn Ser Thr Tyr
            405                 410                 415

Arg Val Val Ser Val Leu Thr Val Leu His Gln Asp Trp Leu Asn Gly
            420                 425                 430

Lys Glu Tyr Lys Cys Lys Val Ser Asn Lys Ala Leu Pro Ala Pro Ile
            435                 440                 445

Glu Lys Thr Ile Ser Lys Ala Lys Gly Gln Pro Arg Glu Pro Gln Val
            450                 455                 460

Tyr Thr Leu Pro Pro Ser Arg Asp Glu Leu Thr Lys Asn Gln Val Ser
465                 470                 475                 480

Leu Thr Cys Leu Val Lys Gly Phe Tyr Pro Ser Asp Ile Ala Val Glu
            485                 490                 495

Trp Glu Ser Asn Gly Gln Pro Glu Asn Asn Tyr Lys Thr Thr Pro Pro
            500                 505                 510

Val Leu Asp Ser Asp Gly Ser Phe Phe Leu Tyr Ser Lys Leu Thr Val
            515                 520                 525

Asp Lys Ser Arg Trp Gln Gln Gly Asn Val Phe Ser Cys Ser Val Met
            530                 535                 540

His Glu Ala Leu His Asn His Tyr Thr Gln Lys Ser Leu Ser Leu Ser
545                 550                 555                 560

Pro Gly Lys

<210> SEQ ID NO 126
<211> LENGTH: 560
<212> TYPE: PRT
<213> ORGANISM: Artificial Sequence -continued

```
<220> FEATURE:
<223> OTHER INFORMATION: Synthetic sequence

<400> SEQUENCE: 126

Leu Glu Ala Ser Glu Glu Val Glu Leu Glu Pro Cys Leu Ala Pro Ser
1               5                   10                  15

Leu Glu Gln Gln Glu Gln Leu Thr Val Ala Leu Gly Gln Pro Val
            20                  25                  30

Arg Leu Cys Cys Gly Arg Ala Glu Arg Gly Gly His Trp Tyr Lys Glu
        35                  40                  45

Gly Ser Arg Leu Ala Pro Ala Gly Arg Val Arg Gly Trp Arg Gly Arg
    50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ser Leu Thr Ser Ser Gly Asp Asp Glu Asp Gly Glu Asp Glu
            100                 105                 110

Ala Glu Asp His Ser Tyr Pro Gln Gln Ala Pro Tyr Trp Thr His Pro
        115                 120                 125

Gln Arg Met Glu Lys Lys Leu His Ala Val Pro Ala Gly Asn Thr Val
    130                 135                 140

Lys Phe Arg Cys Pro Ala Ala Gly Asn Pro Thr Pro Thr Ile Arg Trp
145                 150                 155                 160

Leu Lys Asp Gly Gln Ala Phe His Gly Glu Asn Arg Ile Gly Gly Ile
                165                 170                 175

Arg Leu Arg His Gln His Trp Ser Leu Val Met Glu Ser Val Val Pro
            180                 185                 190

Ser Asp Arg Gly Thr Tyr Thr Cys Leu Val Glu Asn Ala Val Gly Ser
        195                 200                 205

Ile Arg Tyr Asn Tyr Leu Leu Asp Val Leu Glu Arg Ser Pro His Arg
    210                 215                 220

Pro Ile Leu Gln Ala Gly Leu Pro Ala Asn Thr Thr Ala Val Val Gly
225                 230                 235                 240

Ser Asp Val Glu Leu Leu Cys Lys Val Tyr Ser Asp Ala Gln Pro His
                245                 250                 255

Ile Gln Trp Leu Lys His Ile Val Ile Asn Gly Ser Ser Phe Gly Ala
            260                 265                 270

Asp Gly Phe Pro Tyr Val Gln Val Leu Lys Thr Ala Asp Ile Asn Ser
        275                 280                 285

Ser Glu Val Glu Val Leu Tyr Leu Arg Asn Val Ser Ala Glu Asp Ala
    290                 295                 300

Gly Glu Tyr Thr Cys Leu Ala Gly Asn Ser Ile Gly Leu Ser Tyr Gln
305                 310                 315                 320

Ser Ala Trp Leu Thr Val Leu Pro Glu Pro Lys Ser Ser Asp Lys Thr
                325                 330                 335

His Thr Cys Pro Pro Cys Pro Ala Pro Glu Leu Leu Gly Gly Pro Ser
            340                 345                 350

Val Phe Leu Phe Pro Pro Lys Pro Lys Asp Thr Leu Met Ile Ser Arg
        355                 360                 365

Thr Pro Glu Val Thr Cys Val Val Val Asp Val Ser His Glu Asp Pro
    370                 375                 380

Glu Val Lys Phe Asn Trp Tyr Val Asp Gly Val Glu Val His Asn Ala
385                 390                 395                 400
```

Lys Thr Lys Pro Arg Glu Glu Gln Tyr Asn Ser Thr Tyr Arg Val Val
            405                 410                 415

Ser Val Leu Thr Val Leu His Gln Asp Trp Leu Asn Gly Lys Glu Tyr
        420                 425                 430

Lys Cys Lys Val Ser Asn Lys Ala Leu Pro Ala Pro Ile Glu Lys Thr
    435                 440                 445

Ile Ser Lys Ala Lys Gly Gln Pro Arg Glu Pro Gln Val Tyr Thr Leu
450                 455                 460

Pro Pro Ser Arg Asp Glu Leu Thr Lys Asn Gln Val Ser Leu Thr Cys
465                 470                 475                 480

Leu Val Lys Gly Phe Tyr Pro Ser Asp Ile Ala Val Glu Trp Glu Ser
                485                 490                 495

Asn Gly Gln Pro Glu Asn Asn Tyr Lys Thr Thr Pro Pro Val Leu Asp
            500                 505                 510

Ser Asp Gly Ser Phe Phe Leu Tyr Ser Lys Leu Thr Val Asp Lys Ser
        515                 520                 525

Arg Trp Gln Gln Gly Asn Val Phe Ser Cys Ser Val Met His Glu Ala
    530                 535                 540

Leu His Asn His Tyr Thr Gln Lys Ser Leu Ser Leu Ser Pro Gly Lys
545                 550                 555                 560

<210> SEQ ID NO 127
<211> LENGTH: 335
<212> TYPE: PRT
<213> ORGANISM: Artificial Sequence
<220> FEATURE:
<223> OTHER INFORMATION: Synthetic sequence

<400> SEQUENCE: 127

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
            20                  25                  30

Arg Leu Cys Cys Gly Arg Ala Glu Arg Gly Gly His Trp Tyr Lys Glu
        35                  40                  45

Gly Ser Arg Leu Ala Pro Ala Gly Arg Val Arg Gly Trp Arg Gly Arg
    50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ser Leu Thr Ser Ser Asn Glu Asp Asp Asp Asp Asp Asp Asp
            100                 105                 110

Pro Lys Ser His Arg Asp Pro Ser Asn Arg His Ser Tyr Pro Gln Gln
        115                 120                 125

Ala Pro Tyr Trp Thr His Pro Gln Arg Met Glu Lys Lys Leu His Ala
    130                 135                 140

Val Pro Ala Gly Asn Thr Val Lys Phe Arg Cys Pro Ala Ala Gly Asn
145                 150                 155                 160

Pro Thr Pro Thr Ile Arg Trp Leu Lys Asp Gly Gln Ala Phe His Gly
                165                 170                 175

Glu Asn Arg Ile Gly Gly Ile Arg Leu Arg His Gln His Trp Ser Leu
            180                 185                 190

Val Met Glu Ser Val Val Pro Ser Asp Arg Gly Thr Tyr Thr Cys Leu
        195                 200                 205

Val Glu Asn Ala Val Gly Ser Ile Arg Tyr Asn Tyr Leu Leu Asp Val

-continued

```
             210                 215                 220
Leu Glu Arg Ser Pro His Arg Pro Ile Leu Gln Ala Gly Leu Pro Ala
225                 230                 235                 240

Asn Thr Thr Ala Val Val Gly Ser Asp Val Glu Leu Leu Cys Lys Val
                245                 250                 255

Tyr Ser Asp Ala Gln Pro His Ile Gln Trp Leu Lys His Ile Val Ile
            260                 265                 270

Asn Gly Ser Ser Phe Gly Ala Asp Gly Phe Pro Tyr Val Gln Val Leu
        275                 280                 285

Lys Thr Ala Asp Ile Asn Ser Ser Glu Val Glu Val Leu Tyr Leu Arg
    290                 295                 300

Asn Val Ser Ala Glu Asp Ala Gly Glu Tyr Thr Cys Leu Ala Gly Asn
305                 310                 315                 320

Ser Ile Gly Leu Ser Tyr Gln Ser Ala Trp Leu Thr Val Leu Pro
                325                 330                 335

<210> SEQ ID NO 128
<211> LENGTH: 564
<212> TYPE: PRT
<213> ORGANISM: Artificial Sequence
<220> FEATURE:
<223> OTHER INFORMATION: Synthetic sequence

<400> SEQUENCE: 128

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
                20                  25                  30

Arg Leu Cys Cys Gly Arg Ala Glu Arg Gly Gly His Trp Tyr Lys Glu
            35                  40                  45

Gly Ser Arg Leu Ala Pro Ala Gly Arg Val Arg Gly Trp Arg Gly Arg
        50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ser Leu Thr Ser Ser Asn Asp Asp Glu Asp Pro Lys Ser
            100                 105                 110

His Arg Asp Pro Ser Asn Arg His Ser Tyr Pro Gln Gln Ala Pro Tyr
        115                 120                 125

Trp Thr His Pro Gln Arg Met Glu Lys Lys Leu His Ala Val Pro Ala
130                 135                 140

Gly Asn Thr Val Lys Phe Arg Cys Pro Ala Ala Gly Asn Pro Thr Pro
145                 150                 155                 160

Thr Ile Arg Trp Leu Lys Asp Gly Gln Ala Phe His Gly Glu Asn Arg
                165                 170                 175

Ile Gly Gly Ile Arg Leu Arg His Gln His Trp Ser Leu Val Met Glu
            180                 185                 190

Ser Val Val Pro Ser Asp Arg Gly Thr Tyr Thr Cys Leu Val Glu Asn
        195                 200                 205

Ala Val Gly Ser Ile Arg Tyr Asn Tyr Leu Leu Asp Val Leu Glu Arg
    210                 215                 220

Ser Pro His Arg Pro Ile Leu Gln Ala Gly Leu Pro Ala Asn Thr Thr
225                 230                 235                 240

Ala Val Val Gly Ser Asp Val Glu Leu Leu Cys Lys Val Tyr Ser Asp
                245                 250                 255
```

Ala Gln Pro His Ile Gln Trp Leu Lys His Ile Val Ile Asn Gly Ser
            260                 265                 270

Ser Phe Gly Ala Asp Gly Phe Pro Tyr Val Gln Val Leu Lys Thr Ala
        275                 280                 285

Asp Ile Asn Ser Ser Glu Val Glu Val Leu Tyr Leu Arg Asn Val Ser
    290                 295                 300

Ala Glu Asp Ala Gly Glu Tyr Thr Cys Leu Ala Gly Asn Ser Ile Gly
305                 310                 315                 320

Leu Ser Tyr Gln Ser Ala Trp Leu Thr Val Leu Pro Glu Pro Lys Ser
            325                 330                 335

Ser Asp Lys Thr His Thr Cys Pro Pro Cys Pro Ala Pro Glu Leu Leu
        340                 345                 350

Gly Gly Pro Ser Val Phe Leu Phe Pro Pro Lys Pro Lys Asp Thr Leu
    355                 360                 365

Met Ile Ser Arg Thr Pro Glu Val Thr Cys Val Val Val Asp Val Ser
370                 375                 380

His Glu Asp Pro Glu Val Lys Phe Asn Trp Tyr Val Asp Gly Val Glu
385                 390                 395                 400

Val His Asn Ala Lys Thr Lys Pro Arg Glu Glu Gln Tyr Asn Ser Thr
            405                 410                 415

Tyr Arg Val Val Ser Val Leu Thr Val Leu His Gln Asp Trp Leu Asn
        420                 425                 430

Gly Lys Glu Tyr Lys Cys Lys Val Ser Asn Lys Ala Leu Pro Ala Pro
    435                 440                 445

Ile Glu Lys Thr Ile Ser Lys Ala Lys Gly Gln Pro Arg Glu Pro Gln
450                 455                 460

Val Tyr Thr Leu Pro Pro Ser Arg Asp Glu Leu Thr Lys Asn Gln Val
465                 470                 475                 480

Ser Leu Thr Cys Leu Val Lys Gly Phe Tyr Pro Ser Asp Ile Ala Val
            485                 490                 495

Glu Trp Glu Ser Asn Gly Gln Pro Glu Asn Asn Tyr Lys Thr Thr Pro
        500                 505                 510

Pro Val Leu Asp Ser Asp Gly Ser Phe Phe Leu Tyr Ser Lys Leu Thr
    515                 520                 525

Val Asp Lys Ser Arg Trp Gln Gln Gly Asn Val Phe Ser Cys Ser Val
530                 535                 540

Met His Glu Ala Leu His Asn His Tyr Thr Gln Lys Ser Leu Ser Leu
545                 550                 555                 560

Ser Pro Gly Lys

<210> SEQ ID NO 129
<211> LENGTH: 563
<212> TYPE: PRT
<213> ORGANISM: Artificial Sequence
<220> FEATURE:
<223> OTHER INFORMATION: Synthetic sequence

<400> SEQUENCE: 129

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
            20                  25                  30

Arg Leu Cys Cys Gly Arg Ala Glu Arg Gly Gly His Trp Tyr Lys Glu
        35                  40                  45

Gly Ser Arg Leu Ala Pro Ala Gly Arg Val Arg Gly Trp Arg Gly Arg

```
              50                  55                  60
Leu Glu Ile Ala Ser Phe Leu Pro Glu Asp Ala Gly Arg Tyr Leu Cys
 65                  70                  75                  80

Leu Ala Arg Gly Ser Met Ile Val Leu Gln Asn Leu Thr Leu Ile Thr
                 85                  90                  95

Gly Asp Ser Leu Thr Ser Ser Asn Asp Glu Asp Pro Lys Ser His
                100                 105                 110

Arg Asp Pro Ser Asn Arg His Ser Tyr Pro Gln Gln Ala Pro Tyr Trp
                115                 120                 125

Thr His Pro Gln Arg Met Glu Lys Lys Leu His Ala Val Pro Ala Gly
            130                 135                 140

Asn Thr Val Lys Phe Arg Cys Pro Ala Ala Gly Asn Pro Thr Pro Thr
145                 150                 155                 160

Ile Arg Trp Leu Lys Asp Gly Gln Ala Phe His Gly Glu Asn Arg Ile
                165                 170                 175

Gly Gly Ile Arg Leu Arg His Gln His Trp Ser Leu Val Met Glu Ser
                180                 185                 190

Val Val Pro Ser Asp Arg Gly Thr Tyr Thr Cys Leu Val Glu Asn Ala
                195                 200                 205

Val Gly Ser Ile Arg Tyr Asn Tyr Leu Leu Asp Val Leu Glu Arg Ser
210                 215                 220

Pro His Arg Pro Ile Leu Gln Ala Gly Leu Pro Ala Asn Thr Thr Ala
225                 230                 235                 240

Val Val Gly Ser Asp Val Glu Leu Leu Cys Lys Val Tyr Ser Asp Ala
                245                 250                 255

Gln Pro His Ile Gln Trp Leu Lys His Ile Val Ile Asn Gly Ser Ser
                260                 265                 270

Phe Gly Ala Asp Gly Phe Pro Tyr Val Gln Val Leu Lys Thr Ala Asp
                275                 280                 285

Ile Asn Ser Ser Glu Val Glu Val Leu Tyr Leu Arg Asn Val Ser Ala
                290                 295                 300

Glu Asp Ala Gly Glu Tyr Thr Cys Leu Ala Gly Asn Ser Ile Gly Leu
305                 310                 315                 320

Ser Tyr Gln Ser Ala Trp Leu Thr Val Leu Pro Glu Pro Lys Ser Ser
                325                 330                 335

Asp Lys Thr His Thr Cys Pro Pro Cys Pro Ala Pro Glu Leu Leu Gly
                340                 345                 350

Gly Pro Ser Val Phe Leu Phe Pro Pro Lys Pro Lys Asp Thr Leu Met
                355                 360                 365

Ile Ser Arg Thr Pro Glu Val Thr Cys Val Val Val Asp Val Ser His
                370                 375                 380

Glu Asp Pro Glu Val Lys Phe Asn Trp Tyr Val Asp Gly Val Glu Val
385                 390                 395                 400

His Asn Ala Lys Thr Lys Pro Arg Glu Glu Gln Tyr Asn Ser Thr Tyr
                405                 410                 415

Arg Val Val Ser Val Leu Thr Val Leu His Gln Asp Trp Leu Asn Gly
                420                 425                 430

Lys Glu Tyr Lys Cys Lys Val Ser Asn Lys Ala Leu Pro Ala Pro Ile
                435                 440                 445

Glu Lys Thr Ile Ser Lys Ala Lys Gly Gln Pro Arg Glu Pro Gln Val
                450                 455                 460

Tyr Thr Leu Pro Pro Ser Arg Asp Glu Leu Thr Lys Asn Gln Val Ser
465                 470                 475                 480
```

```
Leu Thr Cys Leu Val Lys Gly Phe Tyr Pro Ser Asp Ile Ala Val Glu
                485                 490                 495

Trp Glu Ser Asn Gly Gln Pro Glu Asn Asn Tyr Lys Thr Thr Pro Pro
            500                 505                 510

Val Leu Asp Ser Asp Gly Ser Phe Phe Leu Tyr Ser Lys Leu Thr Val
            515                 520                 525

Asp Lys Ser Arg Trp Gln Gln Gly Asn Val Phe Ser Cys Ser Val Met
            530                 535                 540

His Glu Ala Leu His Asn His Tyr Thr Gln Lys Ser Leu Ser Leu Ser
545                 550                 555                 560

Pro Gly Lys

<210> SEQ ID NO 130
<211> LENGTH: 563
<212> TYPE: PRT
<213> ORGANISM: Artificial Sequence
<220> FEATURE:
<223> OTHER INFORMATION: Synthetic sequence

<400> SEQUENCE: 130

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
            20                  25                  30

Arg Leu Cys Cys Gly Arg Ala Glu Arg Gly Gly His Trp Tyr Lys Glu
        35                  40                  45

Gly Ser Arg Leu Ala Pro Ala Gly Arg Val Arg Gly Trp Arg Gly Arg
    50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ser Leu Thr Ser Ser Asp Asp Glu Asp Pro Lys Ser His
            100                 105                 110

Arg Asp Pro Ser Asn Arg His Ser Tyr Pro Gln Gln Ala Pro Tyr Trp
            115                 120                 125

Thr His Pro Gln Arg Met Glu Lys Lys Leu His Ala Val Pro Ala Gly
130                 135                 140

Asn Thr Val Lys Phe Arg Cys Pro Ala Ala Gly Asn Pro Thr Pro Thr
145                 150                 155                 160

Ile Arg Trp Leu Lys Asp Gly Gln Ala Phe His Gly Glu Asn Arg Ile
                165                 170                 175

Gly Gly Ile Arg Leu Arg His Gln His Trp Ser Leu Val Met Glu Ser
            180                 185                 190

Val Val Pro Ser Asp Arg Gly Thr Tyr Thr Cys Leu Val Glu Asn Ala
            195                 200                 205

Val Gly Ser Ile Arg Tyr Asn Tyr Leu Leu Asp Val Leu Glu Arg Ser
        210                 215                 220

Pro His Arg Pro Ile Leu Gln Ala Gly Leu Pro Ala Asn Thr Thr Ala
225                 230                 235                 240

Val Val Gly Ser Asp Val Glu Leu Leu Cys Lys Val Tyr Ser Asp Ala
                245                 250                 255

Gln Pro His Ile Gln Trp Leu Lys His Ile Val Ile Asn Gly Ser Ser
            260                 265                 270

Phe Gly Ala Asp Gly Phe Pro Tyr Val Gln Val Leu Lys Thr Ala Asp
            275                 280                 285
```

Ile Asn Ser Ser Glu Val Glu Val Leu Tyr Leu Arg Asn Val Ser Ala
            290                 295                 300

Glu Asp Ala Gly Glu Tyr Thr Cys Leu Ala Gly Asn Ser Ile Gly Leu
305                 310                 315                 320

Ser Tyr Gln Ser Ala Trp Leu Thr Val Leu Pro Glu Pro Lys Ser Ser
                325                 330                 335

Asp Lys Thr His Thr Cys Pro Pro Cys Pro Ala Pro Glu Leu Leu Gly
            340                 345                 350

Gly Pro Ser Val Phe Leu Phe Pro Pro Lys Pro Lys Asp Thr Leu Met
            355                 360                 365

Ile Ser Arg Thr Pro Glu Val Thr Cys Val Val Val Asp Val Ser His
370                 375                 380

Glu Asp Pro Glu Val Lys Phe Asn Trp Tyr Val Asp Gly Val Glu Val
385                 390                 395                 400

His Asn Ala Lys Thr Lys Pro Arg Glu Glu Gln Tyr Asn Ser Thr Tyr
                405                 410                 415

Arg Val Val Ser Val Leu Thr Val Leu His Gln Asp Trp Leu Asn Gly
            420                 425                 430

Lys Glu Tyr Lys Cys Lys Val Ser Asn Lys Ala Leu Pro Ala Pro Ile
            435                 440                 445

Glu Lys Thr Ile Ser Lys Ala Lys Gly Gln Pro Arg Glu Pro Gln Val
450                 455                 460

Tyr Thr Leu Pro Pro Ser Arg Asp Glu Leu Thr Lys Asn Gln Val Ser
465                 470                 475                 480

Leu Thr Cys Leu Val Lys Gly Phe Tyr Pro Ser Asp Ile Ala Val Glu
                485                 490                 495

Trp Glu Ser Asn Gly Gln Pro Glu Asn Asn Tyr Lys Thr Thr Pro Pro
            500                 505                 510

Val Leu Asp Ser Asp Gly Ser Phe Phe Leu Tyr Ser Lys Leu Thr Val
            515                 520                 525

Asp Lys Ser Arg Trp Gln Gln Gly Asn Val Phe Ser Cys Ser Val Met
            530                 535                 540

His Glu Ala Leu His Asn His Tyr Thr Gln Lys Ser Leu Ser Leu Ser
545                 550                 555                 560

Pro Gly Lys

<210> SEQ ID NO 131
<211> LENGTH: 563
<212> TYPE: PRT
<213> ORGANISM: Artificial Sequence
<220> FEATURE:
<223> OTHER INFORMATION: Synthetic sequence

<400> SEQUENCE: 131

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
                20                  25                  30

Arg Leu Cys Cys Gly Arg Ala Glu Arg Gly Gly His Trp Tyr Lys Glu
            35                  40                  45

Gly Ser Arg Leu Ala Pro Ala Gly Arg Val Arg Gly Trp Arg Gly Arg
        50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr

```
                    85                  90                  95
Gly Asp Ser Leu Thr Ser Ser Asn Asp Glu Asp Asp Lys Ser His
                100                 105                 110

Arg Asp Pro Ser Asn Arg His Ser Tyr Pro Gln Gln Ala Pro Tyr Trp
            115                 120                 125

Thr His Pro Gln Arg Met Glu Lys Lys Leu His Ala Val Pro Ala Gly
        130                 135                 140

Asn Thr Val Lys Phe Arg Cys Pro Ala Ala Gly Asn Pro Thr Pro Thr
145                 150                 155                 160

Ile Arg Trp Leu Lys Asp Gly Gln Ala Phe His Gly Glu Asn Arg Ile
                165                 170                 175

Gly Gly Ile Arg Leu Arg His Gln His Trp Ser Leu Val Met Glu Ser
            180                 185                 190

Val Val Pro Ser Asp Arg Gly Thr Tyr Thr Cys Leu Val Glu Asn Ala
        195                 200                 205

Val Gly Ser Ile Arg Tyr Asn Tyr Leu Leu Asp Val Leu Glu Arg Ser
210                 215                 220

Pro His Arg Pro Ile Leu Gln Ala Gly Leu Pro Ala Asn Thr Thr Ala
225                 230                 235                 240

Val Val Gly Ser Asp Val Glu Leu Leu Cys Lys Val Tyr Ser Asp Ala
                245                 250                 255

Gln Pro His Ile Gln Trp Leu Lys His Ile Val Ile Asn Gly Ser Ser
            260                 265                 270

Phe Gly Ala Asp Gly Phe Pro Tyr Val Gln Val Leu Lys Thr Ala Asp
        275                 280                 285

Ile Asn Ser Ser Glu Val Glu Val Leu Tyr Leu Arg Asn Val Ser Ala
    290                 295                 300

Glu Asp Ala Gly Glu Tyr Thr Cys Leu Ala Gly Asn Ser Ile Gly Leu
305                 310                 315                 320

Ser Tyr Gln Ser Ala Trp Leu Thr Val Leu Pro Glu Pro Lys Ser Ser
                325                 330                 335

Asp Lys Thr His Thr Cys Pro Pro Cys Pro Ala Pro Glu Leu Leu Gly
            340                 345                 350

Gly Pro Ser Val Phe Leu Phe Pro Pro Lys Pro Lys Asp Thr Leu Met
        355                 360                 365

Ile Ser Arg Thr Pro Glu Val Thr Cys Val Val Val Asp Val Ser His
    370                 375                 380

Glu Asp Pro Glu Val Lys Phe Asn Trp Tyr Val Asp Gly Val Glu Val
385                 390                 395                 400

His Asn Ala Lys Thr Lys Pro Arg Glu Glu Gln Tyr Asn Ser Thr Tyr
                405                 410                 415

Arg Val Val Ser Val Leu Thr Val Leu His Gln Asp Trp Leu Asn Gly
            420                 425                 430

Lys Glu Tyr Lys Cys Lys Val Ser Asn Lys Ala Leu Pro Ala Pro Ile
        435                 440                 445

Glu Lys Thr Ile Ser Lys Ala Lys Gly Gln Pro Arg Glu Pro Gln Val
    450                 455                 460

Tyr Thr Leu Pro Pro Ser Arg Asp Glu Leu Thr Lys Asn Gln Val Ser
465                 470                 475                 480

Leu Thr Cys Leu Val Lys Gly Phe Tyr Pro Ser Asp Ile Ala Val Glu
                485                 490                 495

Trp Glu Ser Asn Gly Gln Pro Glu Asn Asn Tyr Lys Thr Thr Pro Pro
            500                 505                 510
```

```
Val Leu Asp Ser Asp Gly Ser Phe Phe Leu Tyr Ser Lys Leu Thr Val
        515                 520                 525

Asp Lys Ser Arg Trp Gln Gln Gly Asn Val Phe Ser Cys Ser Val Met
        530                 535                 540

His Glu Ala Leu His Asn His Tyr Thr Gln Lys Ser Leu Ser Leu Ser
545                 550                 555                 560

Pro Gly Lys

<210> SEQ ID NO 132
<211> LENGTH: 563
<212> TYPE: PRT
<213> ORGANISM: Artificial Sequence
<220> FEATURE:
<223> OTHER INFORMATION: Synthetic sequence

<400> SEQUENCE: 132

Leu Glu Ala Ser Glu Glu Val Glu Leu Glu Pro Cys Leu Ala Pro Ser
1               5                   10                  15

Leu Glu Gln Gln Glu Gln Leu Thr Val Ala Leu Gly Gln Pro Val
            20                  25                  30

Arg Leu Cys Cys Gly Arg Ala Glu Arg Gly Gly His Trp Tyr Lys Glu
        35                  40                  45

Gly Ser Arg Leu Ala Pro Ala Gly Arg Val Arg Gly Trp Arg Gly Arg
    50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ser Leu Thr Ser Ser Asn Asp Asp Glu Asp Pro Lys Ser His
            100                 105                 110

Glu Asp Pro Ser Asn Arg His Ser Tyr Pro Gln Gln Ala Pro Tyr Trp
        115                 120                 125

Thr His Pro Gln Arg Met Glu Lys Lys Leu His Ala Val Pro Ala Gly
    130                 135                 140

Asn Thr Val Lys Phe Arg Cys Pro Ala Ala Gly Asn Pro Thr Pro Thr
145                 150                 155                 160

Ile Arg Trp Leu Lys Asp Gly Gln Ala Phe His Gly Glu Asn Arg Ile
                165                 170                 175

Gly Gly Ile Arg Leu Arg His Gln His Trp Ser Leu Val Met Glu Ser
            180                 185                 190

Val Val Pro Ser Asp Arg Gly Thr Tyr Thr Cys Leu Val Glu Asn Ala
        195                 200                 205

Val Gly Ser Ile Arg Tyr Asn Tyr Leu Leu Asp Val Leu Glu Arg Ser
    210                 215                 220

Pro His Arg Pro Ile Leu Gln Ala Gly Leu Pro Ala Asn Thr Thr Ala
225                 230                 235                 240

Val Val Gly Ser Asp Val Glu Leu Leu Cys Lys Val Tyr Ser Asp Ala
                245                 250                 255

Gln Pro His Ile Gln Trp Leu Lys His Ile Val Ile Asn Gly Ser Ser
            260                 265                 270

Phe Gly Ala Asp Gly Phe Pro Tyr Val Gln Val Leu Lys Thr Ala Asp
        275                 280                 285

Ile Asn Ser Ser Glu Val Glu Val Leu Tyr Leu Arg Asn Val Ser Ala
    290                 295                 300

Glu Asp Ala Gly Glu Tyr Thr Cys Leu Ala Gly Asn Ser Ile Gly Leu
305                 310                 315                 320
```

Ser Tyr Gln Ser Ala Trp Leu Thr Val Leu Pro Glu Pro Lys Ser Ser
                        325                    330                  335

Asp Lys Thr His Thr Cys Pro Pro Cys Pro Ala Pro Glu Leu Leu Gly
                340                    345                  350

Gly Pro Ser Val Phe Leu Phe Pro Pro Lys Pro Lys Asp Thr Leu Met
            355                    360                  365

Ile Ser Arg Thr Pro Glu Val Thr Cys Val Val Val Asp Val Ser His
        370                    375                  380

Glu Asp Pro Glu Val Lys Phe Asn Trp Tyr Val Asp Gly Val Glu Val
385                    390                    395                  400

His Asn Ala Lys Thr Lys Pro Arg Glu Glu Gln Tyr Asn Ser Thr Tyr
                405                    410                  415

Arg Val Val Ser Val Leu Thr Val Leu His Gln Asp Trp Leu Asn Gly
            420                    425                  430

Lys Glu Tyr Lys Cys Lys Val Ser Asn Lys Ala Leu Pro Ala Pro Ile
        435                    440                  445

Glu Lys Thr Ile Ser Lys Ala Lys Gly Gln Pro Arg Glu Pro Gln Val
      450                    455                  460

Tyr Thr Leu Pro Pro Ser Arg Asp Glu Leu Thr Lys Asn Gln Val Ser
465                    470                    475                  480

Leu Thr Cys Leu Val Lys Gly Phe Tyr Pro Ser Asp Ile Ala Val Glu
                485                    490                  495

Trp Glu Ser Asn Gly Gln Pro Glu Asn Asn Tyr Lys Thr Thr Pro Pro
            500                    505                  510

Val Leu Asp Ser Asp Gly Ser Phe Phe Leu Tyr Ser Lys Leu Thr Val
        515                    520                  525

Asp Lys Ser Arg Trp Gln Gln Gly Asn Val Phe Ser Cys Ser Val Met
      530                    535                  540

His Glu Ala Leu His Asn His Tyr Thr Gln Lys Ser Leu Ser Leu Ser
545                    550                    555                  560

Pro Gly Lys

```
<210> SEQ ID NO 133
<211> LENGTH: 563
<212> TYPE: PRT
<213> ORGANISM: Artificial Sequence
<220> FEATURE:
<223> OTHER INFORMATION: Synthetic sequence

<400> SEQUENCE: 133
```

Leu Glu Ala Ser Glu Glu Val Glu Leu Glu Pro Cys Leu Ala Pro Ser
1                  5                    10                  15

Leu Glu Gln Gln Glu Gln Glu Leu Thr Val Ala Leu Gly Gln Pro Val
                20                    25                  30

Arg Leu Cys Cys Gly Arg Ala Glu Arg Gly Gly His Trp Tyr Lys Glu
        35                    40                  45

Gly Ser Arg Leu Ala Pro Ala Gly Arg Val Arg Gly Trp Arg Gly Arg
      50                    55                  60

Leu Glu Ile Ala Ser Phe Leu Pro Glu Asp Ala Gly Arg Tyr Leu Cys
65                    70                    75                  80

Leu Ala Arg Gly Ser Met Ile Val Leu Gln Asn Leu Thr Leu Ile Thr
                85                    90                  95

Gly Asp Ser Leu Thr Ser Ser Asn Asp Asp Glu Asp Pro Lys Ser His
            100                    105                  110

Arg Asp Pro Glu Asn Arg His Ser Tyr Pro Gln Gln Ala Pro Tyr Trp

```
            115                 120                 125
Thr His Pro Gln Arg Met Glu Lys Leu His Ala Val Pro Ala Gly
130                 135                 140

Asn Thr Val Lys Phe Arg Cys Pro Ala Ala Gly Asn Pro Thr Pro Thr
145                 150                 155                 160

Ile Arg Trp Leu Lys Asp Gly Gln Ala Phe His Gly Glu Asn Arg Ile
                165                 170                 175

Gly Gly Ile Arg Leu Arg His Gln His Trp Ser Leu Val Met Glu Ser
            180                 185                 190

Val Val Pro Ser Asp Arg Gly Thr Tyr Thr Cys Leu Val Glu Asn Ala
        195                 200                 205

Val Gly Ser Ile Arg Tyr Asn Tyr Leu Leu Asp Val Leu Glu Arg Ser
    210                 215                 220

Pro His Arg Pro Ile Leu Gln Ala Gly Leu Pro Ala Asn Thr Thr Ala
225                 230                 235                 240

Val Val Gly Ser Asp Val Glu Leu Leu Cys Lys Val Tyr Ser Asp Ala
                245                 250                 255

Gln Pro His Ile Gln Trp Leu Lys His Ile Val Ile Asn Gly Ser Ser
                260                 265                 270

Phe Gly Ala Asp Gly Phe Pro Tyr Val Gln Val Leu Lys Thr Ala Asp
            275                 280                 285

Ile Asn Ser Ser Glu Val Glu Val Leu Tyr Leu Arg Asn Val Ser Ala
        290                 295                 300

Glu Asp Ala Gly Glu Tyr Thr Cys Leu Ala Gly Asn Ser Ile Gly Leu
305                 310                 315                 320

Ser Tyr Gln Ser Ala Trp Leu Thr Val Leu Pro Glu Pro Lys Ser Ser
                325                 330                 335

Asp Lys Thr His Thr Cys Pro Pro Cys Pro Ala Pro Glu Leu Leu Gly
                340                 345                 350

Gly Pro Ser Val Phe Leu Phe Pro Pro Lys Pro Lys Asp Thr Leu Met
            355                 360                 365

Ile Ser Arg Thr Pro Glu Val Thr Cys Val Val Val Asp Val Ser His
        370                 375                 380

Glu Asp Pro Glu Val Lys Phe Asn Trp Tyr Val Asp Gly Val Glu Val
385                 390                 395                 400

His Asn Ala Lys Thr Lys Pro Arg Glu Glu Gln Tyr Asn Ser Thr Tyr
                405                 410                 415

Arg Val Val Ser Val Leu Thr Val Leu His Gln Asp Trp Leu Asn Gly
                420                 425                 430

Lys Glu Tyr Lys Cys Lys Val Ser Asn Lys Ala Leu Pro Ala Pro Ile
            435                 440                 445

Glu Lys Thr Ile Ser Lys Ala Lys Gly Gln Pro Arg Glu Pro Gln Val
        450                 455                 460

Tyr Thr Leu Pro Pro Ser Arg Asp Glu Leu Thr Lys Asn Gln Val Ser
465                 470                 475                 480

Leu Thr Cys Leu Val Lys Gly Phe Tyr Pro Ser Asp Ile Ala Val Glu
                485                 490                 495

Trp Glu Ser Asn Gly Gln Pro Glu Asn Asn Tyr Lys Thr Thr Pro Pro
                500                 505                 510

Val Leu Asp Ser Asp Gly Ser Phe Phe Leu Tyr Ser Lys Leu Thr Val
            515                 520                 525

Asp Lys Ser Arg Trp Gln Gln Gly Asn Val Phe Ser Cys Ser Val Met
        530                 535                 540
```

His Glu Ala Leu His Asn His Tyr Thr Gln Lys Ser Leu Ser Leu Ser
545                 550                 555                 560

Pro Gly Lys

<210> SEQ ID NO 134
<211> LENGTH: 564
<212> TYPE: PRT
<213> ORGANISM: Artificial Sequence
<220> FEATURE:
<223> OTHER INFORMATION: Synthetic sequence

<400> SEQUENCE: 134

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
            20                  25                  30

Arg Leu Cys Cys Gly Arg Ala Glu Arg Gly Gly His Trp Tyr Lys Glu
        35                  40                  45

Gly Ser Arg Leu Ala Pro Ala Gly Arg Val Arg Gly Trp Arg Gly Arg
    50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ser Leu Thr Ser Ser Asp Asp Asp Asp Asp Asp Asp Ser Ser
            100                 105                 110

Ser Glu Glu Pro Ser Asn Arg His Ser Tyr Pro Gln Gln Ala Pro Tyr
        115                 120                 125

Trp Thr His Pro Gln Arg Met Glu Lys Lys Leu His Ala Val Pro Ala
    130                 135                 140

Gly Asn Thr Val Lys Phe Arg Cys Pro Ala Ala Gly Asn Pro Thr Pro
145                 150                 155                 160

Thr Ile Arg Trp Leu Lys Asp Gly Gln Ala Phe His Gly Glu Asn Arg
                165                 170                 175

Ile Gly Gly Ile Arg Leu Arg His Gln His Trp Ser Leu Val Met Glu
            180                 185                 190

Ser Val Val Pro Ser Asp Arg Gly Thr Tyr Thr Cys Leu Val Glu Asn
        195                 200                 205

Ala Val Gly Ser Ile Arg Tyr Asn Tyr Leu Leu Asp Val Leu Glu Arg
    210                 215                 220

Ser Pro His Arg Pro Ile Leu Gln Ala Gly Leu Pro Ala Asn Thr Thr
225                 230                 235                 240

Ala Val Val Gly Ser Asp Val Glu Leu Leu Cys Lys Val Tyr Ser Asp
                245                 250                 255

Ala Gln Pro His Ile Gln Trp Leu Lys His Ile Val Ile Asn Gly Ser
            260                 265                 270

Ser Phe Gly Ala Asp Gly Phe Pro Tyr Val Gln Val Leu Lys Thr Ala
        275                 280                 285

Asp Ile Asn Ser Ser Glu Val Glu Val Leu Tyr Leu Arg Asn Val Ser
    290                 295                 300

Ala Glu Asp Ala Gly Glu Tyr Thr Cys Leu Ala Gly Asn Ser Ile Gly
305                 310                 315                 320

Leu Ser Tyr Gln Ser Ala Trp Leu Thr Val Leu Pro Glu Pro Lys Ser
                325                 330                 335

Ser Asp Lys Thr His Thr Cys Pro Pro Cys Pro Ala Pro Glu Leu Leu
            340                 345                 350

Gly Gly Pro Ser Val Phe Leu Phe Pro Pro Lys Pro Lys Asp Thr Leu
            355                 360                 365

Met Ile Ser Arg Thr Pro Glu Val Thr Cys Val Val Val Asp Val Ser
    370                 375                 380

His Glu Asp Pro Glu Val Lys Phe Asn Trp Tyr Val Asp Gly Val Glu
385                 390                 395                 400

Val His Asn Ala Lys Thr Lys Pro Arg Glu Glu Gln Tyr Asn Ser Thr
                405                 410                 415

Tyr Arg Val Val Ser Val Leu Thr Val Leu His Gln Asp Trp Leu Asn
            420                 425                 430

Gly Lys Glu Tyr Lys Cys Lys Val Ser Asn Lys Ala Leu Pro Ala Pro
        435                 440                 445

Ile Glu Lys Thr Ile Ser Lys Ala Lys Gly Gln Pro Arg Glu Pro Gln
    450                 455                 460

Val Tyr Thr Leu Pro Pro Ser Arg Asp Glu Leu Thr Lys Asn Gln Val
465                 470                 475                 480

Ser Leu Thr Cys Leu Val Lys Gly Phe Tyr Pro Ser Asp Ile Ala Val
                485                 490                 495

Glu Trp Glu Ser Asn Gly Gln Pro Glu Asn Asn Tyr Lys Thr Thr Pro
            500                 505                 510

Pro Val Leu Asp Ser Asp Gly Ser Phe Phe Leu Tyr Ser Lys Leu Thr
        515                 520                 525

Val Asp Lys Ser Arg Trp Gln Gln Gly Asn Val Phe Ser Cys Ser Val
    530                 535                 540

Met His Glu Ala Leu His Asn His Tyr Thr Gln Lys Ser Leu Ser Leu
545                 550                 555                 560

Ser Pro Gly Lys

<210> SEQ ID NO 135
<211> LENGTH: 563
<212> TYPE: PRT
<213> ORGANISM: Artificial Sequence
<220> FEATURE:
<223> OTHER INFORMATION: Synthetic sequence

<400> SEQUENCE: 135

Leu Glu Ala Ser Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
                20                  25                  30

Arg Leu Cys Cys Gly Arg Ala Glu Arg Gly Gly His Trp Tyr Lys Glu
            35                  40                  45

Gly Ser Arg Leu Ala Pro Ala Gly Arg Val Arg Gly Trp Arg Gly Arg
        50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ser Leu Thr Ser Ser Asp Asp Asp Asp Asp Ser Ser Ser
            100                 105                 110

Glu Glu Pro Ser Asn Arg His Ser Tyr Pro Gln Gln Ala Pro Tyr Trp
        115                 120                 125

Thr His Pro Gln Arg Met Glu Lys Lys Leu His Ala Val Pro Ala Gly
    130                 135                 140

Asn Thr Val Lys Phe Arg Cys Pro Ala Ala Gly Asn Pro Thr Pro Thr

```
            145                 150                 155                 160
Ile Arg Trp Leu Lys Asp Gly Gln Ala Phe His Gly Glu Asn Arg Ile
                165                 170                 175
Gly Gly Ile Arg Leu Arg His Gln His Trp Ser Leu Val Met Glu Ser
                180                 185                 190
Val Val Pro Ser Asp Arg Gly Thr Tyr Thr Cys Leu Val Glu Asn Ala
                195                 200                 205
Val Gly Ser Ile Arg Tyr Asn Tyr Leu Leu Asp Val Leu Glu Arg Ser
                210                 215                 220
Pro His Arg Pro Ile Leu Gln Ala Gly Leu Pro Ala Asn Thr Thr Ala
225                 230                 235                 240
Val Val Gly Ser Asp Val Glu Leu Leu Cys Lys Val Tyr Ser Asp Ala
                245                 250                 255
Gln Pro His Ile Gln Trp Leu Lys His Ile Val Ile Asn Gly Ser Ser
                260                 265                 270
Phe Gly Ala Asp Gly Phe Pro Tyr Val Gln Val Leu Lys Thr Ala Asp
                275                 280                 285
Ile Asn Ser Ser Glu Val Glu Val Leu Tyr Leu Arg Asn Val Ser Ala
                290                 295                 300
Glu Asp Ala Gly Glu Tyr Thr Cys Leu Ala Gly Asn Ser Ile Gly Leu
305                 310                 315                 320
Ser Tyr Gln Ser Ala Trp Leu Thr Val Leu Pro Glu Pro Lys Ser Ser
                325                 330                 335
Asp Lys Thr His Thr Cys Pro Pro Cys Pro Ala Pro Glu Leu Leu Gly
                340                 345                 350
Gly Pro Ser Val Phe Leu Phe Pro Pro Lys Pro Lys Asp Thr Leu Met
                355                 360                 365
Ile Ser Arg Thr Pro Glu Val Thr Cys Val Val Val Asp Val Ser His
                370                 375                 380
Glu Asp Pro Glu Val Lys Phe Asn Trp Tyr Val Asp Gly Val Glu Val
385                 390                 395                 400
His Asn Ala Lys Thr Lys Pro Arg Glu Glu Gln Tyr Asn Ser Thr Tyr
                405                 410                 415
Arg Val Val Ser Val Leu Thr Val Leu His Gln Asp Trp Leu Asn Gly
                420                 425                 430
Lys Glu Tyr Lys Cys Lys Val Ser Asn Lys Ala Leu Pro Ala Pro Ile
                435                 440                 445
Glu Lys Thr Ile Ser Lys Ala Lys Gly Gln Pro Arg Glu Pro Gln Val
                450                 455                 460
Tyr Thr Leu Pro Pro Ser Arg Asp Glu Leu Thr Lys Asn Gln Val Ser
465                 470                 475                 480
Leu Thr Cys Leu Val Lys Gly Phe Tyr Pro Ser Asp Ile Ala Val Glu
                485                 490                 495
Trp Glu Ser Asn Gly Gln Pro Glu Asn Asn Tyr Lys Thr Thr Pro Pro
                500                 505                 510
Val Leu Asp Ser Asp Gly Ser Phe Phe Leu Tyr Ser Lys Leu Thr Val
                515                 520                 525
Asp Lys Ser Arg Trp Gln Gln Gly Asn Val Phe Ser Cys Ser Val Met
                530                 535                 540
His Glu Ala Leu His Asn His Tyr Thr Gln Lys Ser Leu Ser Leu Ser
545                 550                 555                 560
Pro Gly Lys
```

```
<210> SEQ ID NO 136
<211> LENGTH: 565
<212> TYPE: PRT
<213> ORGANISM: Artificial Sequence
<220> FEATURE:
<223> OTHER INFORMATION: Synthetic sequence

<400> SEQUENCE: 136

Leu Glu Ala Ser Glu Glu Val Glu Leu Glu Pro Cys Leu Ala Pro Ser
1               5                   10                  15

Leu Glu Gln Gln Glu Gln Leu Thr Val Ala Leu Gly Gln Pro Val
            20                  25                  30

Arg Leu Cys Cys Gly Arg Ala Glu Arg Gly Gly His Trp Tyr Lys Glu
        35                  40                  45

Gly Ser Arg Leu Ala Pro Ala Gly Arg Val Arg Gly Trp Arg Gly Arg
    50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ser Leu Thr Ser Ser Glu Asp Asp Asp Asp Asp Asp Ser
            100                 105                 110

Ser His Arg Asp Pro Ser Asn Arg His Ser Tyr Pro Gln Gln Ala Pro
        115                 120                 125

Tyr Trp Thr His Pro Gln Arg Met Glu Lys Lys Leu His Ala Val Pro
    130                 135                 140

Ala Gly Asn Thr Val Lys Phe Arg Cys Pro Ala Ala Gly Asn Pro Thr
145                 150                 155                 160

Pro Thr Ile Arg Trp Leu Lys Asp Gly Gln Ala Phe His Gly Glu Asn
                165                 170                 175

Arg Ile Gly Gly Ile Arg Leu Arg His Gln His Trp Ser Leu Val Met
            180                 185                 190

Glu Ser Val Val Pro Ser Asp Arg Gly Thr Tyr Thr Cys Leu Val Glu
        195                 200                 205

Asn Ala Val Gly Ser Ile Arg Tyr Asn Tyr Leu Leu Asp Val Leu Glu
    210                 215                 220

Arg Ser Pro His Arg Pro Ile Leu Gln Ala Gly Leu Pro Ala Asn Thr
225                 230                 235                 240

Thr Ala Val Val Gly Ser Asp Val Glu Leu Leu Cys Lys Val Tyr Ser
                245                 250                 255

Asp Ala Gln Pro His Ile Gln Trp Leu Lys His Ile Val Ile Asn Gly
            260                 265                 270

Ser Ser Phe Gly Ala Asp Gly Phe Pro Tyr Val Gln Val Leu Lys Thr
        275                 280                 285

Ala Asp Ile Asn Ser Ser Glu Val Glu Val Leu Tyr Leu Arg Asn Val
    290                 295                 300

Ser Ala Glu Asp Ala Gly Glu Tyr Thr Cys Leu Ala Gly Asn Ser Ile
305                 310                 315                 320

Gly Leu Ser Tyr Gln Ser Ala Trp Leu Thr Val Leu Pro Glu Pro Lys
                325                 330                 335

Ser Ser Asp Lys Thr His Thr Cys Pro Pro Cys Pro Ala Pro Glu Leu
            340                 345                 350

Leu Gly Gly Pro Ser Val Phe Leu Phe Pro Pro Lys Pro Lys Asp Thr
        355                 360                 365

Leu Met Ile Ser Arg Thr Pro Glu Val Thr Cys Val Val Val Asp Val
    370                 375                 380
```

```
Ser His Glu Asp Pro Glu Val Lys Phe Asn Trp Tyr Val Asp Gly Val
385                 390                 395                 400

Glu Val His Asn Ala Lys Thr Lys Pro Arg Glu Glu Gln Tyr Asn Ser
            405                 410                 415

Thr Tyr Arg Val Val Ser Val Leu Thr Val Leu His Gln Asp Trp Leu
        420                 425                 430

Asn Gly Lys Glu Tyr Lys Cys Lys Val Ser Asn Lys Ala Leu Pro Ala
            435                 440                 445

Pro Ile Glu Lys Thr Ile Ser Lys Ala Lys Gly Gln Pro Arg Glu Pro
        450                 455                 460

Gln Val Tyr Thr Leu Pro Pro Ser Arg Asp Glu Leu Thr Lys Asn Gln
465                 470                 475                 480

Val Ser Leu Thr Cys Leu Val Lys Gly Phe Tyr Pro Ser Asp Ile Ala
            485                 490                 495

Val Glu Trp Glu Ser Asn Gly Gln Pro Glu Asn Asn Tyr Lys Thr Thr
            500                 505                 510

Pro Pro Val Leu Asp Ser Asp Gly Ser Phe Phe Leu Tyr Ser Lys Leu
            515                 520                 525

Thr Val Asp Lys Ser Arg Trp Gln Gln Gly Asn Val Phe Ser Cys Ser
            530                 535                 540

Val Met His Glu Ala Leu His Asn His Tyr Thr Gln Lys Ser Leu Ser
545                 550                 555                 560

Leu Ser Pro Gly Lys
            565

<210> SEQ ID NO 137
<211> LENGTH: 563
<212> TYPE: PRT
<213> ORGANISM: Artificial Sequence
<220> FEATURE:
<223> OTHER INFORMATION: Synthetic sequence

<400> SEQUENCE: 137

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
            20                  25                  30

Arg Leu Cys Cys Gly Arg Ala Glu Arg Gly Gly His Trp Tyr Lys Glu
        35                  40                  45

Gly Ser Arg Leu Ala Pro Ala Gly Arg Val Arg Gly Trp Arg Gly Arg
    50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
            85                  90                  95

Gly Asp Ser Leu Thr Ser Ser Asn Asp Asp Glu Asp Pro Lys Ser His
            100                 105                 110

Glu Glu Lys Glu Asn Arg His Ser Tyr Pro Gln Gln Ala Pro Tyr Trp
        115                 120                 125

Thr His Pro Gln Arg Met Glu Lys Lys Leu His Ala Val Pro Ala Gly
    130                 135                 140

Asn Thr Val Lys Phe Arg Cys Pro Ala Ala Gly Asn Pro Thr Pro Thr
145                 150                 155                 160

Ile Arg Trp Leu Lys Asp Gly Gln Ala Phe His Gly Glu Asn Arg Ile
            165                 170                 175
```

```
Gly Gly Ile Arg Leu Arg His Gln His Trp Ser Leu Val Met Glu Ser
            180                 185                 190

Val Val Pro Ser Asp Arg Gly Thr Tyr Thr Cys Leu Val Glu Asn Ala
        195                 200                 205

Val Gly Ser Ile Arg Tyr Asn Tyr Leu Leu Asp Val Leu Glu Arg Ser
    210                 215                 220

Pro His Arg Pro Ile Leu Gln Ala Gly Leu Pro Ala Asn Thr Thr Ala
225                 230                 235                 240

Val Val Gly Ser Asp Val Glu Leu Leu Cys Lys Val Tyr Ser Asp Ala
                245                 250                 255

Gln Pro His Ile Gln Trp Leu Lys His Ile Val Ile Asn Gly Ser Ser
            260                 265                 270

Phe Gly Ala Asp Gly Phe Pro Tyr Val Gln Val Leu Lys Thr Ala Asp
        275                 280                 285

Ile Asn Ser Ser Glu Val Glu Val Leu Tyr Leu Arg Asn Val Ser Ala
    290                 295                 300

Glu Asp Ala Gly Glu Tyr Thr Cys Leu Ala Gly Asn Ser Ile Gly Leu
305                 310                 315                 320

Ser Tyr Gln Ser Ala Trp Leu Thr Val Leu Pro Glu Pro Lys Ser Ser
                325                 330                 335

Asp Lys Thr His Thr Cys Pro Pro Cys Pro Ala Pro Glu Leu Leu Gly
            340                 345                 350

Gly Pro Ser Val Phe Leu Phe Pro Pro Lys Pro Lys Asp Thr Leu Met
        355                 360                 365

Ile Ser Arg Thr Pro Glu Val Thr Cys Val Val Val Asp Val Ser His
    370                 375                 380

Glu Asp Pro Glu Val Lys Phe Asn Trp Tyr Val Asp Gly Val Glu Val
385                 390                 395                 400

His Asn Ala Lys Thr Lys Pro Arg Glu Glu Gln Tyr Asn Ser Thr Tyr
                405                 410                 415

Arg Val Val Ser Val Leu Thr Val Leu His Gln Asp Trp Leu Asn Gly
            420                 425                 430

Lys Glu Tyr Lys Cys Lys Val Ser Asn Lys Ala Leu Pro Ala Pro Ile
        435                 440                 445

Glu Lys Thr Ile Ser Lys Ala Lys Gly Gln Pro Arg Glu Pro Gln Val
    450                 455                 460

Tyr Thr Leu Pro Pro Ser Arg Asp Glu Leu Thr Lys Asn Gln Val Ser
465                 470                 475                 480

Leu Thr Cys Leu Val Lys Gly Phe Tyr Pro Ser Asp Ile Ala Val Glu
                485                 490                 495

Trp Glu Ser Asn Gly Gln Pro Glu Asn Asn Tyr Lys Thr Thr Pro Pro
            500                 505                 510

Val Leu Asp Ser Asp Gly Ser Phe Phe Leu Tyr Ser Lys Leu Thr Val
        515                 520                 525

Asp Lys Ser Arg Trp Gln Gln Gly Asn Val Phe Ser Cys Ser Val Met
    530                 535                 540

His Glu Ala Leu His Asn His Tyr Thr Gln Lys Ser Leu Ser Leu Ser
545                 550                 555                 560

Pro Gly Lys

<210> SEQ ID NO 138
<211> LENGTH: 563
<212> TYPE: PRT
<213> ORGANISM: Artificial Sequence
<220> FEATURE:
```

-continued

<223> OTHER INFORMATION: Synthetic sequence

<400> SEQUENCE: 138

```
Leu Glu Ala Ser Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
            20                  25                  30

Arg Leu Cys Cys Gly Arg Ala Glu Arg Gly Gly His Trp Tyr Lys Glu
            35                  40                  45

Gly Ser Arg Leu Ala Pro Ala Gly Arg Val Arg Gly Trp Arg Gly Arg
        50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ser Leu Thr Ser Ser Asn Asp Glu Asp Ser Ser Ser
            100                 105                 110

Glu Asp Pro Ser Asn Arg His Ser Tyr Pro Gln Gln Ala Pro Tyr Trp
            115                 120                 125

Thr His Pro Gln Arg Met Glu Lys Lys Leu His Ala Val Pro Ala Gly
            130                 135                 140

Asn Thr Val Lys Phe Arg Cys Pro Ala Ala Gly Asn Pro Thr Pro Thr
145                 150                 155                 160

Ile Arg Trp Leu Lys Asp Gly Gln Ala Phe His Gly Glu Asn Arg Ile
                165                 170                 175

Gly Gly Ile Arg Leu Arg His Gln His Trp Ser Leu Val Met Glu Ser
            180                 185                 190

Val Val Pro Ser Asp Arg Gly Thr Tyr Thr Cys Leu Val Glu Asn Ala
            195                 200                 205

Val Gly Ser Ile Arg Tyr Asn Tyr Leu Leu Asp Val Leu Glu Arg Ser
            210                 215                 220

Pro His Arg Pro Ile Leu Gln Ala Gly Leu Pro Ala Asn Thr Thr Ala
225                 230                 235                 240

Val Val Gly Ser Asp Val Glu Leu Leu Cys Lys Val Tyr Ser Asp Ala
                245                 250                 255

Gln Pro His Ile Gln Trp Leu Lys His Ile Val Ile Asn Gly Ser Ser
            260                 265                 270

Phe Gly Ala Asp Gly Phe Pro Tyr Val Gln Val Leu Lys Thr Ala Asp
            275                 280                 285

Ile Asn Ser Ser Glu Val Glu Val Leu Tyr Leu Arg Asn Val Ser Ala
            290                 295                 300

Glu Asp Ala Gly Glu Tyr Thr Cys Leu Ala Gly Asn Ser Ile Gly Leu
305                 310                 315                 320

Ser Tyr Gln Ser Ala Trp Leu Thr Val Leu Pro Glu Pro Lys Ser Ser
                325                 330                 335

Asp Lys Thr His Thr Cys Pro Pro Cys Pro Ala Pro Glu Leu Leu Gly
            340                 345                 350

Gly Pro Ser Val Phe Leu Phe Pro Pro Lys Pro Lys Asp Thr Leu Met
            355                 360                 365

Ile Ser Arg Thr Pro Glu Val Thr Cys Val Val Val Asp Val Ser His
            370                 375                 380

Glu Asp Pro Glu Val Lys Phe Asn Trp Tyr Val Asp Gly Val Glu Val
385                 390                 395                 400

His Asn Ala Lys Thr Lys Pro Arg Glu Glu Gln Tyr Asn Ser Thr Tyr
```

```
                    405                 410                 415
Arg Val Val Ser Val Leu Thr Val Leu His Gln Asp Trp Leu Asn Gly
            420                 425                 430

Lys Glu Tyr Lys Cys Lys Val Ser Asn Lys Ala Leu Pro Ala Pro Ile
            435                 440                 445

Glu Lys Thr Ile Ser Lys Ala Lys Gly Gln Pro Arg Glu Pro Gln Val
        450                 455                 460

Tyr Thr Leu Pro Pro Ser Arg Asp Glu Leu Thr Lys Asn Gln Val Ser
465                 470                 475                 480

Leu Thr Cys Leu Val Lys Gly Phe Tyr Pro Ser Asp Ile Ala Val Glu
            485                 490                 495

Trp Glu Ser Asn Gly Gln Pro Glu Asn Asn Tyr Lys Thr Thr Pro Pro
            500                 505                 510

Val Leu Asp Ser Asp Gly Ser Phe Phe Leu Tyr Ser Lys Leu Thr Val
            515                 520                 525

Asp Lys Ser Arg Trp Gln Gln Gly Asn Val Phe Ser Cys Ser Val Met
            530                 535                 540

His Glu Ala Leu His Asn His Tyr Thr Gln Lys Ser Leu Ser Leu Ser
545                 550                 555                 560

Pro Gly Lys

<210> SEQ ID NO 139
<211> LENGTH: 566
<212> TYPE: PRT
<213> ORGANISM: Artificial Sequence
<220> FEATURE:
<223> OTHER INFORMATION: Synthetic sequence

<400> SEQUENCE: 139

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
            20                  25                  30

Arg Leu Cys Cys Gly Arg Ala Glu Arg Gly Gly His Trp Tyr Lys Glu
        35                  40                  45

Gly Ser Arg Leu Ala Pro Ala Gly Arg Val Arg Gly Trp Arg Gly Arg
    50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Ala Leu Thr Leu Ile Thr
                85                  90                  95

Gly Asp Ala Leu Pro Ser Ser Glu Asp Asp Asp Asp Asp Asp Asp Ser
            100                 105                 110

Ser Ser Glu Glu Lys Glu Thr Asp Asn Thr Lys Pro Asn Pro Val Ala
        115                 120                 125

Pro Tyr Trp Thr His Pro Gln Arg Met Glu Lys Lys Leu His Ala Val
    130                 135                 140

Pro Ala Gly Asn Thr Val Lys Phe Arg Cys Pro Ala Ala Gly Asn Pro
145                 150                 155                 160

Thr Pro Thr Ile Arg Trp Leu Lys Asp Gly Gln Ala Phe His Gly Glu
                165                 170                 175

Asn Arg Ile Gly Gly Ile Arg Leu Arg His Gln His Trp Ser Leu Val
            180                 185                 190

Met Glu Ser Val Val Pro Ser Asp Arg Gly Thr Tyr Thr Cys Leu Val
        195                 200                 205
```

```
Glu Asn Ala Val Gly Ser Ile Arg Tyr Asn Tyr Leu Leu Asp Val Leu
    210                 215                 220
Glu Arg Ser Pro His Arg Pro Ile Leu Gln Ala Gly Leu Pro Ala Asn
225                 230                 235                 240
Thr Thr Ala Val Val Gly Ser Asp Val Glu Leu Leu Cys Lys Val Tyr
                245                 250                 255
Ser Asp Ala Gln Pro His Ile Gln Trp Leu Lys His Ile Val Ile Asn
                260                 265                 270
Gly Ser Ser Phe Gly Ala Asp Gly Phe Pro Tyr Val Gln Val Leu Lys
            275                 280                 285
Thr Ala Asp Ile Asn Ser Ser Glu Val Glu Val Leu Tyr Leu Arg Asn
290                 295                 300
Val Ser Ala Glu Asp Ala Gly Glu Tyr Thr Cys Leu Ala Gly Asn Ser
305                 310                 315                 320
Ile Gly Leu Ser Tyr Gln Ser Ala Trp Leu Thr Val Leu Pro Glu Pro
                325                 330                 335
Lys Ser Ser Asp Lys Thr His Thr Cys Pro Pro Cys Pro Ala Pro Glu
                340                 345                 350
Leu Leu Gly Gly Pro Ser Val Phe Leu Phe Pro Pro Lys Pro Lys Asp
            355                 360                 365
Thr Leu Met Ile Ser Arg Thr Pro Glu Val Thr Cys Val Val Val Asp
370                 375                 380
Val Ser His Glu Asp Pro Glu Val Lys Phe Asn Trp Tyr Val Asp Gly
385                 390                 395                 400
Val Glu Val His Asn Ala Lys Thr Lys Pro Arg Glu Glu Gln Tyr Asn
                405                 410                 415
Ser Thr Tyr Arg Val Val Ser Val Leu Thr Val Leu His Gln Asp Trp
                420                 425                 430
Leu Asn Gly Lys Glu Tyr Lys Cys Lys Val Ser Asn Lys Ala Leu Pro
            435                 440                 445
Ala Pro Ile Glu Lys Thr Ile Ser Lys Ala Lys Gly Gln Pro Arg Glu
450                 455                 460
Pro Gln Val Tyr Thr Leu Pro Pro Ser Arg Asp Glu Leu Thr Lys Asn
465                 470                 475                 480
Gln Val Ser Leu Thr Cys Leu Val Lys Gly Phe Tyr Pro Ser Asp Ile
                485                 490                 495
Ala Val Glu Trp Glu Ser Asn Gly Gln Pro Glu Asn Asn Tyr Lys Thr
                500                 505                 510
Thr Pro Pro Val Leu Asp Ser Asp Gly Ser Phe Phe Leu Tyr Ser Lys
            515                 520                 525
Leu Thr Val Asp Lys Ser Arg Trp Gln Gln Gly Asn Val Phe Ser Cys
530                 535                 540
Ser Val Met His Glu Ala Leu His Asn His Tyr Thr Gln Lys Ser Leu
545                 550                 555                 560
Ser Leu Ser Pro Gly Lys
                565

<210> SEQ ID NO 140
<211> LENGTH: 566
<212> TYPE: PRT
<213> ORGANISM: Artificial Sequence
<220> FEATURE:
<223> OTHER INFORMATION: Synthetic sequence

<400> SEQUENCE: 140

Leu Glu Ala Ser Glu Glu Val Glu Leu Glu Pro Cys Leu Ala Pro Ser
```

-continued

```
1               5                   10                  15
Leu Glu Gln Gln Glu Gln Leu Thr Val Ala Leu Gly Gln Pro Val
                20                  25                  30

Arg Leu Cys Cys Gly Arg Ala Glu Arg Gly Gly His Trp Tyr Lys Glu
        35                  40                  45

Gly Ser Arg Leu Ala Pro Ala Gly Arg Val Arg Gly Trp Arg Gly Arg
        50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ala Leu Pro Ser Ser Glu Asp Asp Asp Asp Asp Asp Asp Ser
                100                 105                 110

Ser Ser Glu Glu Lys Glu Thr Asp Asn Thr Lys Pro Asn Pro Val Ala
        115                 120                 125

Pro Tyr Trp Thr His Pro Gln Arg Met Glu Lys Lys Leu His Ala Val
        130                 135                 140

Pro Ala Gly Asn Thr Val Lys Phe Arg Cys Pro Ala Ala Gly Ala Pro
145                 150                 155                 160

Thr Pro Thr Ile Arg Trp Leu Lys Asp Gly Gln Ala Phe His Gly Glu
                165                 170                 175

Asn Arg Ile Gly Gly Ile Arg Leu Arg His Gln His Trp Ser Leu Val
                180                 185                 190

Met Glu Ser Val Val Pro Ser Asp Arg Gly Thr Tyr Thr Cys Leu Val
        195                 200                 205

Glu Asn Ala Val Gly Ser Ile Arg Tyr Asn Tyr Leu Leu Asp Val Leu
        210                 215                 220

Glu Arg Ser Pro His Arg Pro Ile Leu Gln Ala Gly Leu Pro Ala Asn
225                 230                 235                 240

Thr Thr Ala Val Val Gly Ser Asp Val Glu Leu Leu Cys Lys Val Tyr
                245                 250                 255

Ser Asp Ala Gln Pro His Ile Gln Trp Leu Lys His Ile Val Ile Asn
        260                 265                 270

Gly Ser Ser Phe Gly Ala Asp Gly Phe Pro Tyr Val Gln Val Leu Lys
        275                 280                 285

Thr Ala Asp Ile Asn Ser Ser Glu Val Glu Val Leu Tyr Leu Arg Asn
        290                 295                 300

Val Ser Ala Glu Asp Ala Gly Glu Tyr Thr Cys Leu Ala Gly Asn Ser
305                 310                 315                 320

Ile Gly Leu Ser Tyr Gln Ser Ala Trp Leu Thr Val Leu Pro Glu Pro
                325                 330                 335

Lys Ser Ser Asp Lys Thr His Thr Cys Pro Pro Cys Pro Ala Pro Glu
        340                 345                 350

Leu Leu Gly Gly Pro Ser Val Phe Leu Phe Pro Pro Lys Pro Lys Asp
        355                 360                 365

Thr Leu Met Ile Ser Arg Thr Pro Glu Val Thr Cys Val Val Val Asp
        370                 375                 380

Val Ser His Glu Asp Pro Glu Val Lys Phe Asn Trp Tyr Val Asp Gly
385                 390                 395                 400

Val Glu Val His Asn Ala Lys Thr Lys Pro Arg Glu Glu Gln Tyr Asn
                405                 410                 415

Ser Thr Tyr Arg Val Val Ser Val Leu Thr Val Leu His Gln Asp Trp
                420                 425                 430
```

```
Leu Asn Gly Lys Glu Tyr Lys Cys Lys Val Ser Asn Lys Ala Leu Pro
        435                 440                 445

Ala Pro Ile Glu Lys Thr Ile Ser Lys Ala Lys Gly Gln Pro Arg Glu
    450                 455                 460

Pro Gln Val Tyr Thr Leu Pro Pro Ser Arg Asp Glu Leu Thr Lys Asn
465                 470                 475                 480

Gln Val Ser Leu Thr Cys Leu Val Lys Gly Phe Tyr Pro Ser Asp Ile
                485                 490                 495

Ala Val Glu Trp Glu Ser Asn Gly Gln Pro Glu Asn Asn Tyr Lys Thr
            500                 505                 510

Thr Pro Pro Val Leu Asp Ser Asp Gly Ser Phe Phe Leu Tyr Ser Lys
        515                 520                 525

Leu Thr Val Asp Lys Ser Arg Trp Gln Gln Gly Asn Val Phe Ser Cys
    530                 535                 540

Ser Val Met His Glu Ala Leu His Asn His Tyr Thr Gln Lys Ser Leu
545                 550                 555                 560

Ser Leu Ser Pro Gly Lys
                565

<210> SEQ ID NO 141
<211> LENGTH: 588
<212> TYPE: PRT
<213> ORGANISM: Artificial Sequence
<220> FEATURE:
<223> OTHER INFORMATION: Synthetic sequence

<400> SEQUENCE: 141

Arg Pro Ser Phe Ser Leu Val Glu Asp Thr Thr Leu Glu Pro Glu Glu
1               5                   10                  15

Pro Pro Thr Lys Tyr Gln Ile Ser Gln Pro Glu Val Tyr Val Ala Ala
            20                  25                  30

Pro Gly Glu Ser Leu Glu Val Arg Cys Leu Leu Lys Asp Ala Ala Val
        35                  40                  45

Ile Ser Trp Thr Lys Asp Gly Val His Leu Gly Pro Asn Asn Arg Thr
    50                  55                  60

Val Leu Ile Gly Glu Tyr Leu Gln Ile Lys Gly Ala Thr Pro Arg Asp
65                  70                  75                  80

Ser Gly Leu Tyr Ala Cys Thr Ala Ser Arg Thr Val Asp Ser Glu Thr
                85                  90                  95

Trp Tyr Phe Met Val Asn Val Thr Asp Ala Ile Ser Ser Gly Glu Asp
            100                 105                 110

Asp Asp Asp Asp Asp Ala Glu Asp Phe Val Ser Glu Asn Ser Asn
        115                 120                 125

Asn Lys Arg Ala Pro Tyr Trp Thr Asn Thr Glu Lys Met Glu Lys Arg
    130                 135                 140

Leu His Ala Val Pro Ala Ala Asn Thr Val Lys Phe Arg Cys Pro Ala
145                 150                 155                 160

Gly Gly Asn Pro Met Pro Thr Met Arg Trp Leu Lys Asn Gly Lys Glu
                165                 170                 175

Phe Lys Gln Glu His Arg Ile Gly Gly Tyr Lys Val Arg Asn Gln His
            180                 185                 190

Trp Ser Leu Ile Met Glu Ser Val Val Pro Ser Asp Lys Gly Asn Tyr
        195                 200                 205

Thr Cys Val Val Glu Asn Glu Tyr Gly Ser Ile Asn His Thr Tyr His
    210                 215                 220

Leu Asp Val Val Glu Arg Ser Pro His Arg Pro Ile Leu Gln Ala Gly
```

```
              225                 230                 235                 240
Leu Pro Ala Asn Ala Ser Thr Val Val Gly Gly Asp Val Glu Phe Val
                245                 250                 255

Cys Lys Val Tyr Ser Asp Ala Gln Pro His Ile Gln Trp Ile Lys His
                260                 265                 270

Val Glu Lys Asn Gly Ser Lys Tyr Gly Pro Asp Gly Leu Pro Tyr Leu
                275                 280                 285

Lys Val Leu Lys Ala Ala Gly Val Asn Thr Thr Asp Lys Glu Ile Glu
            290                 295                 300

Val Leu Tyr Ile Arg Asn Val Thr Phe Glu Asp Ala Gly Glu Tyr Thr
305                 310                 315                 320

Cys Leu Ala Gly Asn Ser Ile Gly Ile Ser Phe His Ser Ala Trp Leu
                325                 330                 335

Thr Val Leu Pro Ala Pro Gly Arg Glu Lys Glu Ile Thr Ala Ser Pro
                340                 345                 350

Asp Tyr Leu Glu Glu Pro Lys Ser Ser Asp Lys Thr His Thr Cys Pro
                355                 360                 365

Pro Cys Pro Ala Pro Glu Leu Leu Gly Gly Pro Ser Val Phe Leu Phe
            370                 375                 380

Pro Pro Lys Pro Lys Asp Thr Leu Met Ile Ser Arg Thr Pro Glu Val
385                 390                 395                 400

Thr Cys Val Val Val Asp Val Ser His Glu Asp Pro Glu Val Lys Phe
                405                 410                 415

Asn Trp Tyr Val Asp Gly Val Glu Val His Asn Ala Lys Thr Lys Pro
                420                 425                 430

Arg Glu Glu Gln Tyr Asn Ser Thr Tyr Arg Val Val Ser Val Leu Thr
                435                 440                 445

Val Leu His Gln Asp Trp Leu Asn Gly Lys Glu Tyr Lys Cys Lys Val
            450                 455                 460

Ser Asn Lys Ala Leu Pro Ala Pro Ile Glu Lys Thr Ile Ser Lys Ala
465                 470                 475                 480

Lys Gly Gln Pro Arg Glu Pro Gln Val Tyr Thr Leu Pro Pro Ser Arg
                485                 490                 495

Asp Glu Leu Thr Lys Asn Gln Val Ser Leu Thr Cys Leu Val Lys Gly
                500                 505                 510

Phe Tyr Pro Ser Asp Ile Ala Val Glu Trp Glu Ser Asn Gly Gln Pro
                515                 520                 525

Glu Asn Asn Tyr Lys Thr Thr Pro Pro Val Leu Asp Ser Asp Gly Ser
            530                 535                 540

Phe Phe Leu Tyr Ser Lys Leu Thr Val Asp Lys Ser Arg Trp Gln Gln
545                 550                 555                 560

Gly Asn Val Phe Ser Cys Ser Val Met His Glu Ala Leu His Asn His
                565                 570                 575

Tyr Thr Gln Lys Ser Leu Ser Leu Ser Pro Gly Lys
                580                 585

<210> SEQ ID NO 142
<211> LENGTH: 585
<212> TYPE: PRT
<213> ORGANISM: Artificial Sequence
<220> FEATURE:
<223> OTHER INFORMATION: Synthetic sequence

<400> SEQUENCE: 142

Glu Ser Leu Gly Thr Glu Gln Arg Val Val Gly Arg Ala Ala Glu Val
1               5                   10                  15
```

```
Pro Gly Pro Glu Pro Gly Gln Gln Glu Gln Leu Val Phe Gly Ser Gly
            20                  25                  30

Asp Ala Val Glu Leu Ser Cys Pro Pro Gly Gly Gly Pro Met Gly
            35                  40                  45

Pro Thr Val Trp Val Lys Asp Gly Thr Gly Leu Val Pro Ser Glu Arg
 50                  55                  60

Val Leu Val Gly Pro Gln Arg Leu Gln Val Leu Asn Ala Ser His Glu
 65                  70                  75                  80

Asp Ser Gly Ala Tyr Ser Cys Arg Gln Arg Leu Thr Gln Arg Val Leu
                85                  90                  95

Cys His Phe Ser Val Arg Val Thr Asp Ala Pro Ser Ser Glu Asp Asp
                100                 105                 110

Asp Asp Asp Asp Glu Ala Glu Asp Thr Gly Val Asp Thr Gly Ala
            115                 120                 125

Pro Tyr Trp Thr Arg Pro Glu Arg Met Asp Lys Lys Leu Leu Ala Val
            130                 135                 140

Pro Ala Ala Asn Thr Val Arg Phe Arg Cys Pro Ala Ala Gly Asn Pro
145                 150                 155                 160

Thr Pro Ser Ile Ser Trp Leu Lys Asn Gly Arg Glu Phe Arg Gly Glu
                165                 170                 175

His Arg Ile Gly Gly Ile Lys Leu Arg His Gln Gln Trp Ser Leu Val
                180                 185                 190

Met Glu Ser Val Val Pro Ser Asp Arg Gly Asn Tyr Thr Cys Val Val
            195                 200                 205

Glu Asn Lys Phe Gly Ser Ile Arg Gln Thr Tyr Thr Leu Asp Val Leu
            210                 215                 220

Glu Arg Ser Pro His Arg Pro Ile Leu Gln Ala Gly Leu Pro Ala Asn
225                 230                 235                 240

Gln Thr Ala Val Leu Gly Ser Asp Val Glu Phe His Cys Lys Val Tyr
                245                 250                 255

Ser Asp Ala Gln Pro His Ile Gln Trp Leu Lys His Val Glu Val Asn
            260                 265                 270

Gly Ser Lys Val Gly Pro Asp Gly Thr Pro Tyr Val Thr Val Leu Lys
            275                 280                 285

Thr Ala Gly Ala Asn Thr Thr Asp Lys Glu Leu Glu Val Leu Ser Leu
            290                 295                 300

His Asn Val Thr Phe Glu Asp Ala Gly Glu Tyr Thr Cys Leu Ala Gly
305                 310                 315                 320

Asn Ser Ile Gly Phe Ser His His Ser Ala Trp Leu Val Val Leu Pro
                325                 330                 335

Ala Glu Glu Glu Leu Val Glu Ala Asp Glu Ala Gly Ser Val Tyr Ala
            340                 345                 350

Gly Glu Pro Lys Ser Ser Asp Lys Thr His Thr Cys Pro Pro Cys Pro
            355                 360                 365

Ala Pro Glu Leu Leu Gly Gly Pro Ser Val Phe Leu Phe Pro Pro Lys
 370                 375                 380

Pro Lys Asp Thr Leu Met Ile Ser Arg Thr Pro Glu Val Thr Cys Val
385                 390                 395                 400

Val Val Asp Val Ser His Glu Asp Pro Glu Val Lys Phe Asn Trp Tyr
                405                 410                 415

Val Asp Gly Val Glu Val His Asn Ala Lys Thr Lys Pro Arg Glu Glu
            420                 425                 430

Gln Tyr Asn Ser Thr Tyr Arg Val Val Ser Val Leu Thr Val Leu His
```

-continued

```
                435                 440                 445
Gln Asp Trp Leu Asn Gly Lys Glu Tyr Lys Cys Lys Val Ser Asn Lys
450                 455                 460

Ala Leu Pro Ala Pro Ile Glu Lys Thr Ile Ser Lys Ala Lys Gly Gln
465                 470                 475                 480

Pro Arg Glu Pro Gln Val Tyr Thr Leu Pro Pro Ser Arg Asp Glu Leu
                485                 490                 495

Thr Lys Asn Gln Val Ser Leu Thr Cys Leu Val Lys Gly Phe Tyr Pro
                500                 505                 510

Ser Asp Ile Ala Val Glu Trp Glu Ser Asn Gly Gln Pro Glu Asn Asn
                515                 520                 525

Tyr Lys Thr Thr Pro Pro Val Leu Asp Ser Asp Gly Ser Phe Phe Leu
                530                 535                 540

Tyr Ser Lys Leu Thr Val Asp Lys Ser Arg Trp Gln Gln Gly Asn Val
545                 550                 555                 560

Phe Ser Cys Ser Val Met His Glu Ala Leu His Asn His Tyr Thr Gln
                565                 570                 575

Lys Ser Leu Ser Leu Ser Pro Gly Lys
                580                 585

<210> SEQ ID NO 143
<211> LENGTH: 563
<212> TYPE: PRT
<213> ORGANISM: Artificial Sequence
<220> FEATURE:
<223> OTHER INFORMATION: Synthetic sequence

<400> SEQUENCE: 143

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
                20                  25                  30

Arg Leu Cys Cys Gly Arg Ala Glu Arg Gly Gly His Trp Tyr Lys Glu
                35                  40                  45

Gly Ser Arg Leu Ala Pro Ala Gly Arg Val Arg Gly Trp Arg Gly Arg
                50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ala Ile Ser Ser Gly Asp Asp Glu Asp Thr Asp Gly Ala
                100                 105                 110

Glu Asp Phe Val Ser Glu Asn Ser Asn Asn Lys Arg Ala Pro Tyr Trp
                115                 120                 125

Thr His Pro Gln Arg Met Glu Lys Lys Leu His Ala Val Pro Ala Gly
                130                 135                 140

Asn Thr Val Lys Phe Arg Cys Pro Ala Ala Gly Asn Pro Thr Pro Thr
145                 150                 155                 160

Ile Arg Trp Leu Lys Asp Gly Gln Ala Phe His Gly Glu Asn Arg Ile
                165                 170                 175

Gly Gly Ile Arg Leu Arg His Gln His Trp Ser Leu Val Met Glu Ser
                180                 185                 190

Val Val Pro Ser Asp Arg Gly Thr Tyr Thr Cys Leu Val Glu Asn Ala
                195                 200                 205

Val Gly Ser Ile Arg Tyr Asn Tyr Leu Leu Asp Val Leu Glu Arg Ser
                210                 215                 220
```

Pro His Arg Pro Ile Leu Gln Ala Gly Leu Pro Ala Asn Thr Thr Ala
225                 230                 235                 240

Val Val Gly Ser Asp Val Glu Leu Leu Cys Lys Val Tyr Ser Asp Ala
            245                 250                 255

Gln Pro His Ile Gln Trp Leu Lys His Ile Val Ile Asn Gly Ser Ser
        260                 265                 270

Phe Gly Ala Asp Gly Phe Pro Tyr Val Gln Val Leu Lys Thr Ala Asp
    275                 280                 285

Ile Asn Ser Ser Glu Val Glu Val Leu Tyr Leu Arg Asn Val Ser Ala
290                 295                 300

Glu Asp Ala Gly Glu Tyr Thr Cys Leu Ala Gly Asn Ser Ile Gly Leu
305                 310                 315                 320

Ser Tyr Gln Ser Ala Trp Leu Thr Val Leu Pro Glu Pro Lys Ser Ser
            325                 330                 335

Asp Lys Thr His Thr Cys Pro Pro Cys Pro Ala Pro Glu Leu Leu Gly
        340                 345                 350

Gly Pro Ser Val Phe Leu Phe Pro Pro Lys Pro Lys Asp Thr Leu Met
    355                 360                 365

Ile Ser Arg Thr Pro Glu Val Thr Cys Val Val Val Asp Val Ser His
370                 375                 380

Glu Asp Pro Glu Val Lys Phe Asn Trp Tyr Val Asp Gly Val Glu Val
385                 390                 395                 400

His Asn Ala Lys Thr Lys Pro Arg Glu Glu Gln Tyr Asn Ser Thr Tyr
            405                 410                 415

Arg Val Val Ser Val Leu Thr Val Leu His Gln Asp Trp Leu Asn Gly
        420                 425                 430

Lys Glu Tyr Lys Cys Lys Val Ser Asn Lys Ala Leu Pro Ala Pro Ile
    435                 440                 445

Glu Lys Thr Ile Ser Lys Ala Lys Gly Gln Pro Arg Glu Pro Gln Val
450                 455                 460

Tyr Thr Leu Pro Pro Ser Arg Asp Glu Leu Thr Lys Asn Gln Val Ser
465                 470                 475                 480

Leu Thr Cys Leu Val Lys Gly Phe Tyr Pro Ser Asp Ile Ala Val Glu
            485                 490                 495

Trp Glu Ser Asn Gly Gln Pro Glu Asn Asn Tyr Lys Thr Thr Pro Pro
        500                 505                 510

Val Leu Asp Ser Asp Gly Ser Phe Phe Leu Tyr Ser Lys Leu Thr Val
    515                 520                 525

Asp Lys Ser Arg Trp Gln Gln Gly Asn Val Phe Ser Cys Ser Val Met
530                 535                 540

His Glu Ala Leu His Asn His Tyr Thr Gln Lys Ser Leu Ser Leu Ser
545                 550                 555                 560

Pro Gly Lys

<210> SEQ ID NO 144
<211> LENGTH: 559
<212> TYPE: PRT
<213> ORGANISM: Artificial Sequence
<220> FEATURE:
<223> OTHER INFORMATION: Synthetic sequence

<400> SEQUENCE: 144

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val

```
                   20                  25                  30
Arg Leu Cys Cys Gly Arg Ala Glu Arg Gly Gly His Trp Tyr Lys Glu
            35                  40                  45

Gly Ser Arg Leu Ala Pro Ala Gly Arg Val Arg Gly Trp Arg Gly Arg
        50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ala Pro Ser Ser Gly Asp Glu Asp Gly Glu Asp Glu Ala
                100                 105                 110

Glu Asp Thr Gly Val Asp Thr Gly Ala Pro Tyr Trp Thr His Pro Gln
            115                 120                 125

Arg Met Glu Lys Lys Leu His Ala Val Pro Ala Gly Asn Thr Val Lys
        130                 135                 140

Phe Arg Cys Pro Ala Ala Gly Asn Pro Thr Pro Thr Ile Arg Trp Leu
145                 150                 155                 160

Lys Asp Gly Gln Ala Phe His Gly Glu Asn Arg Ile Gly Gly Ile Arg
                165                 170                 175

Leu Arg His Gln His Trp Ser Leu Val Met Glu Ser Val Val Pro Ser
                180                 185                 190

Asp Arg Gly Thr Tyr Thr Cys Leu Val Glu Asn Ala Val Gly Ser Ile
            195                 200                 205

Arg Tyr Asn Tyr Leu Leu Asp Val Leu Glu Arg Ser Pro His Arg Pro
        210                 215                 220

Ile Leu Gln Ala Gly Leu Pro Ala Asn Thr Thr Ala Val Val Gly Ser
225                 230                 235                 240

Asp Val Glu Leu Leu Cys Lys Val Tyr Ser Asp Ala Gln Pro His Ile
                245                 250                 255

Gln Trp Leu Lys His Ile Val Ile Asn Gly Ser Ser Phe Gly Ala Asp
                260                 265                 270

Gly Phe Pro Tyr Val Gln Val Leu Lys Thr Ala Asp Ile Asn Ser Ser
            275                 280                 285

Glu Val Glu Val Leu Tyr Leu Arg Asn Val Ser Ala Glu Asp Ala Gly
        290                 295                 300

Glu Tyr Thr Cys Leu Ala Gly Asn Ser Ile Gly Leu Ser Tyr Gln Ser
305                 310                 315                 320

Ala Trp Leu Thr Val Leu Pro Glu Pro Lys Ser Ser Asp Lys Thr His
                325                 330                 335

Thr Cys Pro Pro Cys Pro Ala Pro Glu Leu Leu Gly Gly Pro Ser Val
                340                 345                 350

Phe Leu Phe Pro Pro Lys Pro Lys Asp Thr Leu Met Ile Ser Arg Thr
            355                 360                 365

Pro Glu Val Thr Cys Val Val Val Asp Val Ser His Glu Asp Pro Glu
        370                 375                 380

Val Lys Phe Asn Trp Tyr Val Asp Gly Val Glu Val His Asn Ala Lys
385                 390                 395                 400

Thr Lys Pro Arg Glu Glu Gln Tyr Asn Ser Thr Tyr Arg Val Val Ser
                405                 410                 415

Val Leu Thr Val Leu His Gln Asp Trp Leu Asn Gly Lys Glu Tyr Lys
            420                 425                 430

Cys Lys Val Ser Asn Lys Ala Leu Pro Ala Pro Ile Glu Lys Thr Ile
        435                 440                 445
```

```
Ser Lys Ala Lys Gly Gln Pro Arg Glu Pro Gln Val Tyr Thr Leu Pro
        450                 455                 460

Pro Ser Arg Asp Glu Leu Thr Lys Asn Gln Val Ser Leu Thr Cys Leu
465                 470                 475                 480

Val Lys Gly Phe Tyr Pro Ser Asp Ile Ala Val Glu Trp Glu Ser Asn
                485                 490                 495

Gly Gln Pro Glu Asn Asn Tyr Lys Thr Thr Pro Pro Val Leu Asp Ser
            500                 505                 510

Asp Gly Ser Phe Phe Leu Tyr Ser Lys Leu Thr Val Asp Lys Ser Arg
        515                 520                 525

Trp Gln Gln Gly Asn Val Phe Ser Cys Ser Val Met His Glu Ala Leu
    530                 535                 540

His Asn His Tyr Thr Gln Lys Ser Leu Ser Leu Ser Pro Gly Lys
545                 550                 555

<210> SEQ ID NO 145
<211> LENGTH: 11
<212> TYPE: PRT
<213> ORGANISM: Artificial Sequence
<220> FEATURE:
<223> OTHER INFORMATION: Synthetic sequence

<400> SEQUENCE: 145

Asn Asp Asp Glu Asp Pro Lys Ser His Arg Asp
1               5                   10

<210> SEQ ID NO 146
<211> LENGTH: 7
<212> TYPE: PRT
<213> ORGANISM: Artificial Sequence
<220> FEATURE:
<223> OTHER INFORMATION: Synthetic sequence

<400> SEQUENCE: 146

Asn Asp Asp Glu Asp Pro Lys
1               5

<210> SEQ ID NO 147
<211> LENGTH: 4
<212> TYPE: PRT
<213> ORGANISM: Artificial Sequence
<220> FEATURE:
<223> OTHER INFORMATION: Synthetic sequence

<400> SEQUENCE: 147

Arg Asp Pro Ser
1

<210> SEQ ID NO 148
<211> LENGTH: 5
<212> TYPE: PRT
<213> ORGANISM: Artificial Sequence
<220> FEATURE:
<223> OTHER INFORMATION: Synthetic sequence

<400> SEQUENCE: 148

Pro Lys Ser His Arg
1               5

<210> SEQ ID NO 149
<211> LENGTH: 12
<212> TYPE: PRT
<213> ORGANISM: Artificial Sequence
<220> FEATURE:
<223> OTHER INFORMATION: Synthetic sequence
```

```
<400> SEQUENCE: 149

Asp Asp Asp Asp Asp Asp Asp Ser Ser Ser Glu Glu
1               5                   10

<210> SEQ ID NO 150
<211> LENGTH: 11
<212> TYPE: PRT
<213> ORGANISM: Artificial Sequence
<220> FEATURE:
<223> OTHER INFORMATION: Synthetic sequence

<400> SEQUENCE: 150

Asp Asp Asp Asp Asp Asp Ser Ser Ser Glu Glu
1               5                   10

<210> SEQ ID NO 151
<211> LENGTH: 9
<212> TYPE: PRT
<213> ORGANISM: Artificial Sequence
<220> FEATURE:
<223> OTHER INFORMATION: Synthetic sequence

<400> SEQUENCE: 151

Glu Asp Asp Asp Asp Asp Asp Asp Ser
1               5

<210> SEQ ID NO 152
<211> LENGTH: 4
<212> TYPE: PRT
<213> ORGANISM: Artificial Sequence
<220> FEATURE:
<223> OTHER INFORMATION: Synthetic sequence

<400> SEQUENCE: 152

Glu Glu Lys Glu
1

<210> SEQ ID NO 153
<211> LENGTH: 5
<212> TYPE: PRT
<213> ORGANISM: Artificial Sequence
<220> FEATURE:
<223> OTHER INFORMATION: Synthetic sequence

<400> SEQUENCE: 153

Asp Ser Ser Ser Glu
1               5

<210> SEQ ID NO 154
<211> LENGTH: 8
<212> TYPE: PRT
<213> ORGANISM: Artificial Sequence
<220> FEATURE:
<223> OTHER INFORMATION: Synthetic sequence

<400> SEQUENCE: 154

Glu Asp Asp Asp Asp Asp Asp Asp
1               5

<210> SEQ ID NO 155
<211> LENGTH: 8
<212> TYPE: PRT
<213> ORGANISM: Artificial Sequence
<220> FEATURE:
<223> OTHER INFORMATION: Synthetic sequence

<400> SEQUENCE: 155
```

```
Asp Asp Glu Asp Asp Thr Asp Gly
1               5

<210> SEQ ID NO 156
<211> LENGTH: 8
<212> TYPE: PRT
<213> ORGANISM: Artificial Sequence
<220> FEATURE:
<223> OTHER INFORMATION: Synthetic sequence

<400> SEQUENCE: 156

Gly Asp Asp Glu Asp Gly Glu Asp
1               5

<210> SEQ ID NO 157
<211> LENGTH: 333
<212> TYPE: PRT
<213> ORGANISM: Artificial Sequence
<220> FEATURE:
<223> OTHER INFORMATION: Synthetic sequence

<400> SEQUENCE: 157

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
            20                  25                  30

Arg Leu Cys Cys Gly Arg Ala Glu Arg Gly Gly His Trp Tyr Lys Glu
        35                  40                  45

Gly Ser Arg Leu Ala Pro Ala Gly Arg Val Arg Gly Trp Arg Gly Arg
    50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ser Leu Thr Ser Ser Glu Asp Asp Asp Asp Asp Asp Asp Ser
            100                 105                 110

Ser Ser Glu Glu Pro Ser Asn Arg His Ser Tyr Pro Gln Gln Ala Pro
        115                 120                 125

Tyr Trp Thr His Pro Gln Arg Met Glu Lys Lys Leu His Ala Val Pro
    130                 135                 140

Ala Gly Asn Thr Val Lys Phe Arg Cys Pro Ala Ala Gly Asn Pro Thr
145                 150                 155                 160

Pro Thr Ile Arg Trp Leu Lys Asp Gly Gln Ala Phe His Gly Glu Asn
                165                 170                 175

Arg Ile Gly Gly Ile Arg Leu Arg His Gln His Trp Ser Leu Val Met
            180                 185                 190

Glu Ser Val Val Pro Ser Asp Arg Gly Thr Tyr Thr Cys Leu Val Glu
        195                 200                 205

Asn Ala Val Gly Ser Ile Arg Tyr Asn Tyr Leu Leu Asp Val Leu Glu
    210                 215                 220

Arg Ser Pro His Arg Pro Ile Leu Gln Ala Gly Leu Pro Ala Asn Thr
225                 230                 235                 240

Thr Ala Val Val Gly Ser Asp Val Glu Leu Leu Cys Lys Val Tyr Ser
                245                 250                 255

Asp Ala Gln Pro His Ile Gln Trp Leu Lys His Ile Val Ile Asn Gly
            260                 265                 270

Ser Ser Phe Gly Ala Asp Gly Phe Pro Tyr Val Gln Val Leu Lys Thr
        275                 280                 285
```

```
Ala Asp Ile Asn Ser Ser Glu Val Glu Val Leu Tyr Leu Arg Asn Val
    290                 295                 300

Ser Ala Glu Asp Ala Gly Glu Tyr Thr Cys Leu Ala Gly Asn Ser Ile
305                 310                 315                 320

Gly Leu Ser Tyr Gln Ser Ala Trp Leu Thr Val Leu Pro
                325                 330

<210> SEQ ID NO 158
<211> LENGTH: 565
<212> TYPE: PRT
<213> ORGANISM: Artificial Sequence
<220> FEATURE:
<223> OTHER INFORMATION: Synthetic sequence

<400> SEQUENCE: 158

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
            20                  25                  30

Arg Leu Cys Cys Gly Arg Ala Glu Arg Gly Gly His Trp Tyr Lys Glu
        35                  40                  45

Gly Ser Arg Leu Ala Pro Ala Gly Arg Val Arg Gly Trp Arg Gly Arg
    50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ser Leu Thr Ser Ser Glu Asp Asp Asp Asp Asp Asp Asp Ser
            100                 105                 110

Ser Ser Glu Glu Pro Ser Asn Arg His Ser Tyr Pro Gln Gln Ala Pro
        115                 120                 125

Tyr Trp Thr His Pro Gln Arg Met Glu Lys Lys Leu His Ala Val Pro
    130                 135                 140

Ala Gly Asn Thr Val Lys Phe Arg Cys Pro Ala Ala Gly Asn Pro Thr
145                 150                 155                 160

Pro Thr Ile Arg Trp Leu Lys Asp Gly Gln Ala Phe His Gly Glu Asn
                165                 170                 175

Arg Ile Gly Gly Ile Arg Leu Arg His Gln His Trp Ser Leu Val Met
            180                 185                 190

Glu Ser Val Val Pro Ser Asp Arg Gly Thr Tyr Thr Cys Leu Val Glu
        195                 200                 205

Asn Ala Val Gly Ser Ile Arg Tyr Asn Tyr Leu Leu Asp Val Leu Glu
    210                 215                 220

Arg Ser Pro His Arg Pro Ile Leu Gln Ala Gly Leu Pro Ala Asn Thr
225                 230                 235                 240

Thr Ala Val Val Gly Ser Asp Val Glu Leu Leu Cys Lys Val Tyr Ser
                245                 250                 255

Asp Ala Gln Pro His Ile Gln Trp Leu Lys His Ile Val Ile Asn Gly
            260                 265                 270

Ser Ser Phe Gly Ala Asp Gly Phe Pro Tyr Val Gln Val Leu Lys Thr
        275                 280                 285

Ala Asp Ile Asn Ser Ser Glu Val Glu Val Leu Tyr Leu Arg Asn Val
    290                 295                 300

Ser Ala Glu Asp Ala Gly Glu Tyr Thr Cys Leu Ala Gly Asn Ser Ile
305                 310                 315                 320
```

-continued

```
Gly Leu Ser Tyr Gln Ser Ala Trp Leu Thr Val Leu Pro Glu Pro Lys
            325                 330                 335

Ser Ser Asp Lys Thr His Thr Cys Pro Pro Cys Pro Ala Pro Glu Leu
        340                 345                 350

Leu Gly Gly Pro Ser Val Phe Leu Phe Pro Pro Lys Pro Lys Asp Thr
    355                 360                 365

Leu Met Ile Ser Arg Thr Pro Glu Val Thr Cys Val Val Val Asp Val
370                 375                 380

Ser His Glu Asp Pro Glu Val Lys Phe Asn Trp Tyr Val Asp Gly Val
385                 390                 395                 400

Glu Val His Asn Ala Lys Thr Lys Pro Arg Glu Glu Gln Tyr Asn Ser
                405                 410                 415

Thr Tyr Arg Val Val Ser Val Leu Thr Val Leu His Gln Asp Trp Leu
            420                 425                 430

Asn Gly Lys Glu Tyr Lys Cys Lys Val Ser Asn Lys Ala Leu Pro Ala
        435                 440                 445

Pro Ile Glu Lys Thr Ile Ser Lys Ala Lys Gly Gln Pro Arg Glu Pro
    450                 455                 460

Gln Val Tyr Thr Leu Pro Pro Ser Arg Asp Glu Leu Thr Lys Asn Gln
465                 470                 475                 480

Val Ser Leu Thr Cys Leu Val Lys Gly Phe Tyr Pro Ser Asp Ile Ala
                485                 490                 495

Val Glu Trp Glu Ser Asn Gly Gln Pro Glu Asn Asn Tyr Lys Thr Thr
            500                 505                 510

Pro Pro Val Leu Asp Ser Asp Gly Ser Phe Phe Leu Tyr Ser Lys Leu
        515                 520                 525

Thr Val Asp Lys Ser Arg Trp Gln Gln Gly Asn Val Phe Ser Cys Ser
    530                 535                 540

Val Met His Glu Ala Leu His Asn His Tyr Thr Gln Lys Ser Leu Ser
545                 550                 555                 560

Leu Ser Pro Gly Lys
                565

<210> SEQ ID NO 159
<211> LENGTH: 13
<212> TYPE: PRT
<213> ORGANISM: Artificial Sequence
<220> FEATURE:
<223> OTHER INFORMATION: Synthetic sequence

<400> SEQUENCE: 159

Glu Asp Asp Asp Asp Asp Asp Ser Ser Ser Glu Glu
1               5                   10

<210> SEQ ID NO 160
<211> LENGTH: 353
<212> TYPE: PRT
<213> ORGANISM: Artificial Sequence
<220> FEATURE:
<223> OTHER INFORMATION: Synthetic sequence

<400> SEQUENCE: 160

Arg Pro Ser Phe Ser Leu Val Glu Asp Thr Thr Leu Glu Pro Glu Glu
1               5                   10                  15

Pro Pro Thr Lys Tyr Gln Ile Ser Gln Pro Glu Val Tyr Val Ala Ala
            20                  25                  30

Pro Gly Glu Ser Leu Glu Val Arg Cys Leu Leu Lys Asp Ala Ala Val
        35                  40                  45
```

```
Ile Ser Trp Thr Lys Asp Gly Val His Leu Gly Pro Asn Asn Arg Thr
 50                  55                  60
Val Leu Ile Gly Glu Tyr Leu Gln Ile Lys Gly Ala Thr Pro Arg Asp
 65                  70                  75                  80
Ser Gly Leu Tyr Ala Cys Thr Ala Ser Arg Thr Val Asp Ser Glu Thr
                 85                  90                  95
Trp Tyr Phe Met Val Asn Val Thr Asp Ala Ile Ser Ser Gly Asp Asp
            100                 105                 110
Glu Asp Asp Thr Asp Gly Ala Glu Asp Phe Val Ser Glu Asn Ser Asn
            115                 120                 125
Asn Lys Arg Ala Pro Tyr Trp Thr Asn Thr Glu Lys Met Glu Lys Arg
    130                 135                 140
Leu His Ala Val Pro Ala Ala Asn Thr Val Lys Phe Arg Cys Pro Ala
145                 150                 155                 160
Gly Gly Asn Pro Met Pro Thr Met Arg Trp Leu Lys Asn Gly Lys Glu
                165                 170                 175
Phe Lys Gln Glu His Arg Ile Gly Gly Tyr Lys Val Arg Asn Gln His
            180                 185                 190
Trp Ser Leu Ile Met Glu Ser Val Val Pro Ser Asp Lys Gly Asn Tyr
    195                 200                 205
Thr Cys Val Val Glu Asn Glu Tyr Gly Ser Ile Asn His Thr Tyr His
    210                 215                 220
Leu Asp Val Val Glu Arg Ser Pro His Arg Pro Ile Leu Gln Ala Gly
225                 230                 235                 240
Leu Pro Ala Asn Ala Ser Thr Val Val Gly Gly Asp Val Glu Phe Val
                245                 250                 255
Cys Lys Val Tyr Ser Asp Ala Gln Pro His Ile Gln Trp Ile Lys His
                260                 265                 270
Val Glu Lys Asn Gly Ser Lys Tyr Gly Pro Asp Gly Leu Pro Tyr Leu
            275                 280                 285
Lys Val Leu Lys Ala Ala Gly Val Asn Thr Thr Asp Lys Glu Ile Glu
    290                 295                 300
Val Leu Tyr Ile Arg Asn Val Thr Phe Glu Asp Ala Gly Glu Tyr Thr
305                 310                 315                 320
Cys Leu Ala Gly Asn Ser Ile Gly Ile Ser Phe His Ser Ala Trp Leu
                325                 330                 335
Thr Val Leu Pro Ala Pro Gly Arg Glu Lys Glu Ile Thr Ala Ser Pro
                340                 345                 350
Asp

<210> SEQ ID NO 161
<211> LENGTH: 350
<212> TYPE: PRT
<213> ORGANISM: Artificial Sequence
<220> FEATURE:
<223> OTHER INFORMATION: Synthetic sequence

<400> SEQUENCE: 161

Glu Ser Leu Gly Thr Glu Gln Arg Val Val Gly Arg Ala Ala Glu Val
1               5                   10                  15
Pro Gly Pro Glu Pro Gly Gln Gln Glu Gln Leu Val Phe Gly Ser Gly
            20                  25                  30
Asp Ala Val Glu Leu Ser Cys Pro Pro Gly Gly Gly Pro Met Gly
            35                  40                  45
Pro Thr Val Trp Val Lys Asp Gly Thr Gly Leu Val Pro Ser Glu Arg
 50                  55                  60
```

Val Leu Val Gly Pro Gln Arg Leu Gln Val Leu Asn Ala Ser His Glu
65                  70                  75                  80

Asp Ser Gly Ala Tyr Ser Cys Arg Gln Arg Leu Thr Gln Arg Val Leu
                85                  90                  95

Cys His Phe Ser Val Arg Val Thr Asp Ala Pro Ser Ser Gly Asp Asp
            100                 105                 110

Glu Asp Gly Glu Asp Glu Ala Glu Asp Thr Gly Val Asp Thr Gly Ala
        115                 120                 125

Pro Tyr Trp Thr Arg Pro Glu Arg Met Asp Lys Lys Leu Leu Ala Val
        130                 135                 140

Pro Ala Ala Asn Thr Val Arg Phe Arg Cys Pro Ala Ala Gly Asn Pro
145                 150                 155                 160

Thr Pro Ser Ile Ser Trp Leu Lys Asn Gly Arg Glu Phe Arg Gly Glu
            165                 170                 175

His Arg Ile Gly Gly Ile Lys Leu Arg His Gln Gln Trp Ser Leu Val
            180                 185                 190

Met Glu Ser Val Val Pro Ser Asp Arg Gly Asn Tyr Thr Cys Val Val
        195                 200                 205

Glu Asn Lys Phe Gly Ser Ile Arg Gln Thr Tyr Thr Leu Asp Val Leu
210                 215                 220

Glu Arg Ser Pro His Arg Pro Ile Leu Gln Ala Gly Leu Pro Ala Asn
225                 230                 235                 240

Gln Thr Ala Val Leu Gly Ser Asp Val Glu Phe His Cys Lys Val Tyr
            245                 250                 255

Ser Asp Ala Gln Pro His Ile Gln Trp Leu Lys His Val Glu Val Asn
            260                 265                 270

Gly Ser Lys Val Gly Pro Asp Gly Thr Pro Tyr Val Thr Val Leu Lys
            275                 280                 285

Thr Ala Gly Ala Asn Thr Thr Asp Lys Glu Leu Glu Val Leu Ser Leu
        290                 295                 300

His Asn Val Thr Phe Glu Asp Ala Gly Glu Tyr Thr Cys Leu Ala Gly
305                 310                 315                 320

Asn Ser Ile Gly Phe Ser His His Ser Ala Trp Leu Val Val Leu Pro
            325                 330                 335

Ala Glu Glu Glu Leu Val Glu Ala Asp Glu Ala Gly Ser Val
        340                 345                 350

<210> SEQ ID NO 162
<211> LENGTH: 587
<212> TYPE: PRT
<213> ORGANISM: Artificial Sequence
<220> FEATURE:
<223> OTHER INFORMATION: Synthetic sequence

<400> SEQUENCE: 162

Arg Pro Ser Phe Ser Leu Val Glu Asp Thr Thr Leu Glu Pro Glu Glu
1               5                   10                  15

Pro Pro Thr Lys Tyr Gln Ile Ser Gln Pro Glu Val Tyr Val Ala Ala
            20                  25                  30

Pro Gly Glu Ser Leu Glu Val Arg Cys Leu Leu Lys Asp Ala Ala Val
        35                  40                  45

Ile Ser Trp Thr Lys Asp Gly Val His Leu Gly Pro Asn Asn Arg Thr
    50                  55                  60

Val Leu Ile Gly Glu Tyr Leu Gln Ile Lys Gly Ala Thr Pro Arg Asp
65                  70                  75                  80

```
Ser Gly Leu Tyr Ala Cys Thr Ala Ser Arg Thr Val Asp Ser Glu Thr
                85                  90                  95

Trp Tyr Phe Met Val Asn Val Thr Asp Ala Ile Ser Ser Gly Asp Asp
            100                 105                 110

Glu Asp Asp Thr Asp Gly Ala Glu Asp Phe Val Ser Glu Asn Ser Asn
        115                 120                 125

Asn Lys Arg Ala Pro Tyr Trp Thr Asn Thr Glu Lys Met Glu Lys Arg
    130                 135                 140

Leu His Ala Val Pro Ala Ala Asn Thr Val Lys Phe Arg Cys Pro Ala
145                 150                 155                 160

Gly Gly Asn Pro Met Pro Thr Met Arg Trp Leu Lys Asn Gly Lys Glu
                165                 170                 175

Phe Lys Gln Glu His Arg Ile Gly Gly Tyr Lys Val Arg Asn Gln His
            180                 185                 190

Trp Ser Leu Ile Met Glu Ser Val Val Pro Ser Asp Lys Gly Asn Tyr
        195                 200                 205

Thr Cys Val Val Glu Asn Glu Tyr Gly Ser Ile Asn His Thr Tyr His
    210                 215                 220

Leu Asp Val Val Glu Arg Ser Pro His Arg Pro Ile Leu Gln Ala Gly
225                 230                 235                 240

Leu Pro Ala Asn Ala Ser Thr Val Val Gly Gly Asp Val Glu Phe Val
                245                 250                 255

Cys Lys Val Tyr Ser Asp Ala Gln Pro His Ile Gln Trp Ile Lys His
            260                 265                 270

Val Glu Lys Asn Gly Ser Lys Tyr Gly Pro Asp Gly Leu Pro Tyr Leu
        275                 280                 285

Lys Val Leu Lys Ala Ala Gly Val Asn Thr Thr Asp Lys Glu Ile Glu
    290                 295                 300

Val Leu Tyr Ile Arg Asn Val Thr Phe Glu Asp Ala Gly Glu Tyr Thr
305                 310                 315                 320

Cys Leu Ala Gly Asn Ser Ile Gly Ile Ser Phe His Ser Ala Trp Leu
                325                 330                 335

Thr Val Leu Pro Ala Pro Gly Arg Glu Lys Glu Ile Thr Ala Ser Pro
            340                 345                 350

Asp Gly Ser Glu Pro Lys Ser Ser Asp Lys Thr His Thr Cys Pro Pro
        355                 360                 365

Cys Pro Ala Pro Glu Leu Leu Gly Gly Pro Ser Val Phe Leu Phe Pro
    370                 375                 380

Pro Lys Pro Lys Asp Thr Leu Met Ile Ser Arg Thr Pro Glu Val Thr
385                 390                 395                 400

Cys Val Val Val Asp Val Ser His Glu Asp Pro Glu Val Lys Phe Asn
                405                 410                 415

Trp Tyr Val Asp Gly Val Glu Val His Asn Ala Lys Thr Lys Pro Arg
            420                 425                 430

Glu Glu Gln Tyr Asn Ser Thr Tyr Arg Val Val Ser Val Leu Thr Val
        435                 440                 445

Leu His Gln Asp Trp Leu Asn Gly Lys Glu Tyr Lys Cys Lys Val Ser
    450                 455                 460

Asn Lys Ala Leu Pro Ala Pro Ile Glu Lys Thr Ile Ser Lys Ala Lys
465                 470                 475                 480

Gly Gln Pro Arg Glu Pro Gln Val Tyr Thr Leu Pro Pro Ser Arg Asp
                485                 490                 495

Glu Leu Thr Lys Asn Gln Val Ser Leu Thr Cys Leu Val Lys Gly Phe
            500                 505                 510
```

Tyr Pro Ser Asp Ile Ala Val Glu Trp Glu Ser Asn Gly Gln Pro Glu
            515                 520                 525

Asn Asn Tyr Lys Thr Thr Pro Pro Val Leu Asp Ser Asp Gly Ser Phe
        530                 535                 540

Phe Leu Tyr Ser Lys Leu Thr Val Asp Lys Ser Arg Trp Gln Gln Gly
545                 550                 555                 560

Asn Val Phe Ser Cys Ser Val Met His Glu Ala Leu His Asn His Tyr
                565                 570                 575

Thr Gln Lys Ser Leu Ser Leu Ser Pro Gly Lys
            580                 585

<210> SEQ ID NO 163
<211> LENGTH: 584
<212> TYPE: PRT
<213> ORGANISM: Artificial Sequence
<220> FEATURE:
<223> OTHER INFORMATION: Synthetic sequence

<400> SEQUENCE: 163

Glu Ser Leu Gly Thr Glu Gln Arg Val Val Gly Arg Ala Ala Glu Val
1               5                   10                  15

Pro Gly Pro Glu Pro Gly Gln Gln Glu Gln Leu Val Phe Gly Ser Gly
            20                  25                  30

Asp Ala Val Glu Leu Ser Cys Pro Pro Pro Gly Gly Pro Met Gly Gly
        35                  40                  45

Pro Thr Val Trp Val Lys Asp Gly Thr Gly Leu Val Pro Ser Glu Arg
    50                  55                  60

Val Leu Val Gly Pro Gln Arg Leu Gln Val Leu Asn Ala Ser His Glu
65                  70                  75                  80

Asp Ser Gly Ala Tyr Ser Cys Arg Gln Arg Leu Thr Gln Arg Val Leu
                85                  90                  95

Cys His Phe Ser Val Arg Val Thr Asp Ala Pro Ser Ser Gly Asp Asp
            100                 105                 110

Glu Asp Gly Glu Asp Glu Ala Glu Asp Thr Gly Val Asp Thr Gly Ala
        115                 120                 125

Pro Tyr Trp Thr Arg Pro Glu Arg Met Asp Lys Lys Leu Leu Ala Val
    130                 135                 140

Pro Ala Ala Asn Thr Val Arg Phe Arg Cys Pro Ala Ala Gly Asn Pro
145                 150                 155                 160

Thr Pro Ser Ile Ser Trp Leu Lys Asn Gly Arg Glu Phe Arg Gly Glu
                165                 170                 175

His Arg Ile Gly Gly Ile Lys Leu Arg His Gln Gln Trp Ser Leu Val
            180                 185                 190

Met Glu Ser Val Val Pro Ser Asp Arg Gly Asn Tyr Thr Cys Val Val
        195                 200                 205

Glu Asn Lys Phe Gly Ser Ile Arg Gln Thr Tyr Thr Leu Asp Val Leu
    210                 215                 220

Glu Arg Ser Pro His Arg Pro Ile Leu Gln Ala Gly Leu Pro Ala Asn
225                 230                 235                 240

Gln Thr Ala Val Leu Gly Ser Asp Val Glu Phe His Cys Lys Val Tyr
                245                 250                 255

Ser Asp Ala Gln Pro His Ile Gln Trp Leu Lys His Val Glu Val Asn
            260                 265                 270

Gly Ser Lys Val Gly Pro Asp Gly Thr Pro Tyr Val Thr Val Leu Lys
        275                 280                 285

```
Thr Ala Gly Ala Asn Thr Thr Asp Lys Glu Leu Glu Val Leu Ser Leu
        290                 295                 300
His Asn Val Thr Phe Glu Asp Ala Gly Glu Tyr Thr Cys Leu Ala Gly
305                 310                 315                 320
Asn Ser Ile Gly Phe Ser His His Ser Ala Trp Leu Val Val Leu Pro
                325                 330                 335
Ala Glu Glu Glu Leu Val Glu Ala Asp Glu Ala Gly Ser Val Gly Ser
            340                 345                 350
Glu Pro Lys Ser Ser Asp Lys Thr His Thr Cys Pro Pro Cys Pro Ala
        355                 360                 365
Pro Glu Leu Leu Gly Gly Pro Ser Val Phe Leu Phe Pro Pro Lys Pro
    370                 375                 380
Lys Asp Thr Leu Met Ile Ser Arg Thr Pro Glu Val Thr Cys Val Val
385                 390                 395                 400
Val Asp Val Ser His Glu Asp Pro Glu Val Lys Phe Asn Trp Tyr Val
                405                 410                 415
Asp Gly Val Glu Val His Asn Ala Lys Thr Lys Pro Arg Glu Glu Gln
            420                 425                 430
Tyr Asn Ser Thr Tyr Arg Val Val Ser Val Leu Thr Val Leu His Gln
        435                 440                 445
Asp Trp Leu Asn Gly Lys Glu Tyr Lys Cys Lys Val Ser Asn Lys Ala
    450                 455                 460
Leu Pro Ala Pro Ile Glu Lys Thr Ile Ser Lys Ala Lys Gly Gln Pro
465                 470                 475                 480
Arg Glu Pro Gln Val Tyr Thr Leu Pro Pro Ser Arg Asp Glu Leu Thr
                485                 490                 495
Lys Asn Gln Val Ser Leu Thr Cys Leu Val Lys Gly Phe Tyr Pro Ser
            500                 505                 510
Asp Ile Ala Val Glu Trp Glu Ser Asn Gly Gln Pro Glu Asn Asn Tyr
        515                 520                 525
Lys Thr Thr Pro Pro Val Leu Asp Ser Asp Gly Ser Phe Phe Leu Tyr
    530                 535                 540
Ser Lys Leu Thr Val Asp Lys Ser Arg Trp Gln Gln Gly Asn Val Phe
545                 550                 555                 560
Ser Cys Ser Val Met His Glu Ala Leu His Asn His Tyr Thr Gln Lys
                565                 570                 575
Ser Leu Ser Leu Ser Pro Gly Lys
            580

<210> SEQ ID NO 164
<211> LENGTH: 353
<212> TYPE: PRT
<213> ORGANISM: Artificial Sequence
<220> FEATURE:
<223> OTHER INFORMATION: Synthetic sequence

<400> SEQUENCE: 164

Arg Pro Ser Phe Ser Leu Val Glu Asp Thr Thr Leu Glu Pro Glu Glu
1               5                   10                  15
Pro Pro Thr Lys Tyr Gln Ile Ser Gln Pro Glu Val Tyr Val Ala Ala
            20                  25                  30
Pro Gly Glu Ser Leu Glu Val Arg Cys Leu Leu Lys Asp Ala Ala Val
        35                  40                  45
Ile Ser Trp Thr Lys Asp Gly Val His Leu Gly Pro Asn Asn Arg Thr
    50                  55                  60
Val Leu Ile Gly Glu Tyr Leu Gln Ile Lys Gly Ala Thr Pro Arg Asp
```

```
                65                  70                  75                  80
Ser Gly Leu Tyr Ala Cys Thr Ala Ser Arg Thr Val Asp Ser Glu Thr
                        85                  90                  95

Trp Tyr Phe Met Val Asn Val Thr Asp Ala Ile Ser Ser Gly Glu Asp
                        100                 105                 110

Asp Asp Asp Asp Asp Ala Glu Asp Phe Val Ser Glu Asn Ser Asn
                        115                 120                 125

Asn Lys Arg Ala Pro Tyr Trp Thr Asn Thr Glu Lys Met Glu Lys Arg
            130                 135                 140

Leu His Ala Val Pro Ala Ala Asn Thr Val Lys Phe Arg Cys Pro Ala
145                 150                 155                 160

Gly Gly Asn Pro Met Pro Thr Met Arg Trp Leu Lys Asn Gly Lys Glu
                        165                 170                 175

Phe Lys Gln Glu His Arg Ile Gly Gly Tyr Lys Val Arg Asn Gln His
                        180                 185                 190

Trp Ser Leu Ile Met Glu Ser Val Val Pro Ser Asp Lys Gly Asn Tyr
            195                 200                 205

Thr Cys Val Val Glu Asn Glu Tyr Gly Ser Ile Asn His Thr Tyr His
        210                 215                 220

Leu Asp Val Val Glu Arg Ser Pro His Arg Pro Ile Leu Gln Ala Gly
225                 230                 235                 240

Leu Pro Ala Asn Ala Ser Thr Val Val Gly Gly Asp Val Glu Phe Val
                        245                 250                 255

Cys Lys Val Tyr Ser Asp Ala Gln Pro His Ile Gln Trp Ile Lys His
                        260                 265                 270

Val Glu Lys Asn Gly Ser Lys Tyr Gly Pro Asp Gly Leu Pro Tyr Leu
            275                 280                 285

Lys Val Leu Lys Ala Ala Gly Val Asn Thr Thr Asp Lys Glu Ile Glu
        290                 295                 300

Val Leu Tyr Ile Arg Asn Val Thr Phe Glu Asp Ala Gly Glu Tyr Thr
305                 310                 315                 320

Cys Leu Ala Gly Asn Ser Ile Gly Ile Ser Phe His Ser Ala Trp Leu
                        325                 330                 335

Thr Val Leu Pro Ala Pro Gly Arg Glu Lys Glu Ile Thr Ala Ser Pro
                        340                 345                 350

Asp

<210> SEQ ID NO 165
<211> LENGTH: 350
<212> TYPE: PRT
<213> ORGANISM: Artificial Sequence
<220> FEATURE:
<223> OTHER INFORMATION: Synthetic sequence

<400> SEQUENCE: 165

Glu Ser Leu Gly Thr Glu Gln Arg Val Val Gly Arg Ala Ala Glu Val
1               5                   10                  15

Pro Gly Pro Glu Pro Gly Gln Gln Glu Gln Leu Val Phe Gly Ser Gly
                20                  25                  30

Asp Ala Val Glu Leu Ser Cys Pro Pro Pro Gly Gly Gly Pro Met Gly
            35                  40                  45

Pro Thr Val Trp Val Lys Asp Gly Thr Gly Leu Val Pro Ser Glu Arg
        50                  55                  60

Val Leu Val Gly Pro Gln Arg Leu Gln Val Leu Asn Ala Ser His Glu
65                  70                  75                  80
```

```
Asp Ser Gly Ala Tyr Ser Cys Arg Gln Arg Leu Thr Gln Arg Val Leu
                85                  90                  95

Cys His Phe Ser Val Arg Val Thr Asp Ala Pro Ser Ser Glu Asp Asp
                100                 105                 110

Asp Asp Asp Asp Glu Ala Glu Asp Thr Gly Val Asp Thr Gly Ala
            115                 120                 125

Pro Tyr Trp Thr Arg Pro Glu Arg Met Asp Lys Lys Leu Leu Ala Val
            130                 135                 140

Pro Ala Ala Asn Thr Val Arg Phe Arg Cys Pro Ala Ala Gly Asn Pro
145                 150                 155                 160

Thr Pro Ser Ile Ser Trp Leu Lys Asn Gly Arg Glu Phe Arg Gly Glu
                165                 170                 175

His Arg Ile Gly Gly Ile Lys Leu Arg His Gln Gln Trp Ser Leu Val
                180                 185                 190

Met Glu Ser Val Val Pro Ser Asp Arg Gly Asn Tyr Thr Cys Val Val
                195                 200                 205

Glu Asn Lys Phe Gly Ser Ile Arg Gln Thr Tyr Thr Leu Asp Val Leu
            210                 215                 220

Glu Arg Ser Pro His Arg Pro Ile Leu Gln Ala Gly Leu Pro Ala Asn
225                 230                 235                 240

Gln Thr Ala Val Leu Gly Ser Asp Val Glu Phe His Cys Lys Val Tyr
                245                 250                 255

Ser Asp Ala Gln Pro His Ile Gln Trp Leu Lys His Val Glu Val Asn
                260                 265                 270

Gly Ser Lys Val Gly Pro Asp Gly Thr Pro Tyr Val Thr Val Leu Lys
            275                 280                 285

Thr Ala Gly Ala Asn Thr Thr Asp Lys Glu Leu Glu Val Leu Ser Leu
290                 295                 300

His Asn Val Thr Phe Glu Asp Ala Gly Glu Tyr Thr Cys Leu Ala Gly
305                 310                 315                 320

Asn Ser Ile Gly Phe Ser His His Ser Ala Trp Leu Val Val Leu Pro
                325                 330                 335

Ala Glu Glu Glu Leu Val Glu Ala Asp Glu Ala Gly Ser Val
            340                 345                 350

<210> SEQ ID NO 166
<211> LENGTH: 587
<212> TYPE: PRT
<213> ORGANISM: Artificial Sequence
<220> FEATURE:
<223> OTHER INFORMATION: Synthetic sequence

<400> SEQUENCE: 166

Arg Pro Ser Phe Ser Leu Val Glu Asp Thr Thr Leu Glu Pro Glu Glu
1               5                   10                  15

Pro Pro Thr Lys Tyr Gln Ile Ser Gln Pro Glu Val Tyr Val Ala Ala
                20                  25                  30

Pro Gly Glu Ser Leu Glu Val Arg Cys Leu Leu Lys Asp Ala Ala Val
            35                  40                  45

Ile Ser Trp Thr Lys Asp Gly Val His Leu Gly Pro Asn Asn Arg Thr
50                  55                  60

Val Leu Ile Gly Glu Tyr Leu Gln Ile Lys Gly Ala Thr Pro Arg Asp
65                  70                  75                  80

Ser Gly Leu Tyr Ala Cys Thr Ala Ser Arg Thr Val Asp Ser Glu Thr
                85                  90                  95

Trp Tyr Phe Met Val Asn Val Thr Asp Ala Ile Ser Ser Gly Glu Asp
```

```
                100                 105                 110
Asp Asp Asp Asp Asp Ala Glu Asp Phe Val Ser Glu Asn Ser Asn
        115                 120                 125
Asn Lys Arg Ala Pro Tyr Trp Thr Asn Thr Glu Lys Met Glu Lys Arg
    130                 135                 140
Leu His Ala Val Pro Ala Asn Thr Val Lys Phe Arg Cys Pro Ala
145                 150                 155                 160
Gly Gly Asn Pro Met Pro Thr Met Arg Trp Leu Lys Asn Gly Lys Glu
                165                 170                 175
Phe Lys Gln Glu His Arg Ile Gly Gly Tyr Lys Val Arg Asn Gln His
            180                 185                 190
Trp Ser Leu Ile Met Glu Ser Val Val Pro Ser Asp Lys Gly Asn Tyr
            195                 200                 205
Thr Cys Val Val Glu Asn Glu Tyr Gly Ser Ile Asn His Thr Tyr His
        210                 215                 220
Leu Asp Val Val Glu Arg Ser Pro His Arg Pro Ile Leu Gln Ala Gly
225                 230                 235                 240
Leu Pro Ala Asn Ala Ser Thr Val Val Gly Gly Asp Val Glu Phe Val
                245                 250                 255
Cys Lys Val Tyr Ser Asp Ala Gln Pro His Ile Gln Trp Ile Lys His
                260                 265                 270
Val Glu Lys Asn Gly Ser Lys Tyr Gly Pro Asp Gly Leu Pro Tyr Leu
            275                 280                 285
Lys Val Leu Lys Ala Ala Gly Val Asn Thr Thr Asp Lys Glu Ile Glu
        290                 295                 300
Val Leu Tyr Ile Arg Asn Val Thr Phe Glu Asp Ala Gly Glu Tyr Thr
305                 310                 315                 320
Cys Leu Ala Gly Asn Ser Ile Gly Ile Ser Phe His Ser Ala Trp Leu
                325                 330                 335
Thr Val Leu Pro Ala Pro Gly Arg Glu Lys Glu Ile Thr Ala Ser Pro
            340                 345                 350
Asp Gly Ser Glu Pro Lys Ser Ser Asp Lys Thr His Thr Cys Pro Pro
        355                 360                 365
Cys Pro Ala Pro Glu Leu Leu Gly Gly Pro Ser Val Phe Leu Phe Pro
    370                 375                 380
Pro Lys Pro Lys Asp Thr Leu Met Ile Ser Arg Thr Pro Glu Val Thr
385                 390                 395                 400
Cys Val Val Val Asp Val Ser His Glu Asp Pro Glu Val Lys Phe Asn
                405                 410                 415
Trp Tyr Val Asp Gly Val Glu Val His Asn Ala Lys Thr Lys Pro Arg
            420                 425                 430
Glu Glu Gln Tyr Asn Ser Thr Tyr Arg Val Val Ser Val Leu Thr Val
        435                 440                 445
Leu His Gln Asp Trp Leu Asn Gly Lys Glu Tyr Lys Cys Lys Val Ser
    450                 455                 460
Asn Lys Ala Leu Pro Ala Pro Ile Glu Lys Thr Ile Ser Lys Ala Lys
465                 470                 475                 480
Gly Gln Pro Arg Glu Pro Gln Val Tyr Thr Leu Pro Pro Ser Arg Asp
                485                 490                 495
Glu Leu Thr Lys Asn Gln Val Ser Leu Thr Cys Leu Val Lys Gly Phe
            500                 505                 510
Tyr Pro Ser Asp Ile Ala Val Glu Trp Glu Ser Asn Gly Gln Pro Glu
        515                 520                 525
```

```
Asn Asn Tyr Lys Thr Thr Pro Pro Val Leu Asp Ser Asp Gly Ser Phe
        530                 535                 540

Phe Leu Tyr Ser Lys Leu Thr Val Asp Lys Ser Arg Trp Gln Gln Gly
545                 550                 555                 560

Asn Val Phe Ser Cys Ser Val Met His Glu Ala Leu His Asn His Tyr
                565                 570                 575

Thr Gln Lys Ser Leu Ser Leu Ser Pro Gly Lys
            580                 585

<210> SEQ ID NO 167
<211> LENGTH: 584
<212> TYPE: PRT
<213> ORGANISM: Artificial Sequence
<220> FEATURE:
<223> OTHER INFORMATION: Synthetic sequence

<400> SEQUENCE: 167

Glu Ser Leu Gly Thr Glu Gln Arg Val Val Gly Arg Ala Ala Glu Val
1               5                   10                  15

Pro Gly Pro Glu Pro Gly Gln Gln Glu Gln Leu Val Phe Gly Ser Gly
            20                  25                  30

Asp Ala Val Glu Leu Ser Cys Pro Pro Gly Gly Pro Met Gly
        35                  40                  45

Pro Thr Val Trp Val Lys Asp Gly Thr Gly Leu Val Pro Ser Glu Arg
    50                  55                  60

Val Leu Val Gly Pro Gln Arg Leu Gln Val Leu Asn Ala Ser His Glu
65                  70                  75                  80

Asp Ser Gly Ala Tyr Ser Cys Arg Gln Arg Leu Thr Gln Arg Val Leu
                85                  90                  95

Cys His Phe Ser Val Arg Val Thr Asp Ala Pro Ser Ser Glu Asp Asp
            100                 105                 110

Asp Asp Asp Asp Asp Glu Ala Glu Asp Thr Gly Val Asp Thr Gly Ala
        115                 120                 125

Pro Tyr Trp Thr Arg Pro Glu Arg Met Asp Lys Lys Leu Leu Ala Val
    130                 135                 140

Pro Ala Ala Asn Thr Val Arg Phe Arg Cys Pro Ala Ala Gly Asn Pro
145                 150                 155                 160

Thr Pro Ser Ile Ser Trp Leu Lys Asn Gly Arg Glu Phe Arg Gly Glu
                165                 170                 175

His Arg Ile Gly Gly Ile Lys Leu Arg His Gln Gln Trp Ser Leu Val
            180                 185                 190

Met Glu Ser Val Val Pro Ser Asp Arg Gly Asn Tyr Thr Cys Val Val
        195                 200                 205

Glu Asn Lys Phe Gly Ser Ile Arg Gln Thr Tyr Thr Leu Asp Val Leu
    210                 215                 220

Glu Arg Ser Pro His Arg Pro Ile Leu Gln Ala Gly Leu Pro Ala Asn
225                 230                 235                 240

Gln Thr Ala Val Leu Gly Ser Asp Val Glu Phe His Cys Lys Val Tyr
                245                 250                 255

Ser Asp Ala Gln Pro His Ile Gln Trp Leu Lys His Val Glu Val Asn
            260                 265                 270

Gly Ser Lys Val Gly Pro Asp Gly Thr Pro Tyr Val Thr Val Leu Lys
        275                 280                 285

Thr Ala Gly Ala Asn Thr Thr Asp Lys Glu Leu Glu Val Leu Ser Leu
    290                 295                 300

His Asn Val Thr Phe Glu Asp Ala Gly Glu Tyr Thr Cys Leu Ala Gly
```

```
                    305                 310                 315                 320

Asn Ser Ile Gly Phe Ser His His Ser Ala Trp Leu Val Val Leu Pro
                325                 330                 335

Ala Glu Glu Leu Val Glu Ala Asp Glu Ala Gly Ser Val Gly Ser
            340                 345                 350

Glu Pro Lys Ser Ser Asp Lys Thr His Thr Cys Pro Pro Cys Pro Ala
                355                 360                 365

Pro Glu Leu Leu Gly Gly Pro Ser Val Phe Leu Phe Pro Pro Lys Pro
            370                 375                 380

Lys Asp Thr Leu Met Ile Ser Arg Thr Pro Glu Val Thr Cys Val Val
385                 390                 395                 400

Val Asp Val Ser His Glu Asp Pro Glu Val Lys Phe Asn Trp Tyr Val
                405                 410                 415

Asp Gly Val Glu Val His Asn Ala Lys Thr Lys Pro Arg Glu Glu Gln
                420                 425                 430

Tyr Asn Ser Thr Tyr Arg Val Val Ser Val Leu Thr Val Leu His Gln
            435                 440                 445

Asp Trp Leu Asn Gly Lys Glu Tyr Lys Cys Lys Val Ser Asn Lys Ala
        450                 455                 460

Leu Pro Ala Pro Ile Glu Lys Thr Ile Ser Lys Ala Lys Gly Gln Pro
465                 470                 475                 480

Arg Glu Pro Gln Val Tyr Thr Leu Pro Pro Ser Arg Asp Glu Leu Thr
                485                 490                 495

Lys Asn Gln Val Ser Leu Thr Cys Leu Val Lys Gly Phe Tyr Pro Ser
            500                 505                 510

Asp Ile Ala Val Glu Trp Glu Ser Asn Gly Gln Pro Glu Asn Asn Tyr
        515                 520                 525

Lys Thr Thr Pro Pro Val Leu Asp Ser Asp Gly Ser Phe Phe Leu Tyr
    530                 535                 540

Ser Lys Leu Thr Val Asp Lys Ser Arg Trp Gln Gln Gly Asn Val Phe
545                 550                 555                 560

Ser Cys Ser Val Met His Glu Ala Leu His Asn His Tyr Thr Gln Lys
                565                 570                 575

Ser Leu Ser Leu Ser Pro Gly Lys
            580

<210> SEQ ID NO 168
<211> LENGTH: 334
<212> TYPE: PRT
<213> ORGANISM: Artificial Sequence
<220> FEATURE:
<223> OTHER INFORMATION: Synthetic sequence

<400> SEQUENCE: 168

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
            20                  25                  30

Arg Leu Cys Cys Gly Arg Ala Glu Arg Gly Gly His Trp Tyr Lys Glu
        35                  40                  45

Gly Ser Arg Leu Ala Pro Ala Gly Arg Val Arg Gly Trp Arg Gly Arg
    50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Ala Leu Thr Leu Ile Thr
                85                  90                  95
```

```
Gly Asp Ala Leu Pro Ser Ser Glu Asp Asp Asp Asp Asp Ser
            100                 105                 110

Ser Ser Glu Glu Lys Glu Thr Asp Asn Thr Lys Pro Asn Pro Val Ala
        115                 120                 125

Pro Tyr Trp Thr His Pro Gln Arg Met Glu Lys Lys Leu His Ala Val
130                 135                 140

Pro Ala Gly Asn Thr Val Lys Phe Arg Cys Pro Ala Ala Gly Ala Pro
145                 150                 155                 160

Thr Pro Thr Ile Arg Trp Leu Lys Asp Gly Gln Ala Phe His Gly Glu
                165                 170                 175

Asn Arg Ile Gly Gly Ile Arg Leu Arg His Gln His Trp Ser Leu Val
            180                 185                 190

Met Glu Ser Val Val Pro Ser Asp Arg Gly Thr Tyr Thr Cys Leu Val
        195                 200                 205

Glu Asn Ala Val Gly Ser Ile Arg Tyr Asn Tyr Leu Leu Asp Val Leu
    210                 215                 220

Glu Arg Ser Pro His Arg Pro Ile Leu Gln Ala Gly Leu Pro Ala Asn
225                 230                 235                 240

Thr Thr Ala Val Val Gly Ser Asp Val Glu Leu Leu Cys Lys Val Tyr
                245                 250                 255

Ser Asp Ala Gln Pro His Ile Gln Trp Leu Lys His Ile Val Ile Asn
            260                 265                 270

Gly Ser Ser Phe Gly Ala Asp Gly Phe Pro Tyr Val Gln Val Leu Lys
        275                 280                 285

Thr Ala Asp Ile Asn Ser Ser Glu Val Glu Val Leu Tyr Leu Arg Asn
    290                 295                 300

Val Ser Ala Glu Asp Ala Gly Tyr Thr Cys Leu Ala Gly Asn Ser
305                 310                 315                 320

Ile Gly Leu Ser Tyr Gln Ser Ala Trp Leu Thr Val Leu Pro
                325                 330
```

<210> SEQ ID NO 169
<211> LENGTH: 566
<212> TYPE: PRT
<213> ORGANISM: Artificial Sequence
<220> FEATURE:
<223> OTHER INFORMATION: Synthetic sequence

<400> SEQUENCE: 169

```
Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
            20                  25                  30

Arg Leu Cys Cys Gly Arg Ala Glu Arg Gly Gly His Trp Tyr Lys Glu
        35                  40                  45

Gly Ser Arg Leu Ala Pro Ala Gly Arg Val Arg Gly Trp Arg Gly Arg
    50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Ala Leu Thr Leu Ile Thr
                85                  90                  95

Gly Asp Ala Leu Pro Ser Ser Glu Asp Asp Asp Asp Asp Ser
            100                 105                 110

Ser Ser Glu Glu Lys Glu Thr Asp Asn Thr Lys Pro Asn Pro Val Ala
        115                 120                 125
```

-continued

```
Pro Tyr Trp Thr His Pro Gln Arg Met Glu Lys Lys Leu His Ala Val
    130                 135                 140
Pro Ala Gly Asn Thr Val Lys Phe Arg Cys Pro Ala Ala Gly Ala Pro
145                 150                 155                 160
Thr Pro Thr Ile Arg Trp Leu Lys Asp Gly Gln Ala Phe His Gly Glu
                165                 170                 175
Asn Arg Ile Gly Gly Ile Arg Leu Arg His Gln His Trp Ser Leu Val
            180                 185                 190
Met Glu Ser Val Val Pro Ser Asp Arg Gly Thr Tyr Thr Cys Leu Val
        195                 200                 205
Glu Asn Ala Val Gly Ser Ile Arg Tyr Asn Tyr Leu Leu Asp Val Leu
    210                 215                 220
Glu Arg Ser Pro His Arg Pro Ile Leu Gln Ala Gly Leu Pro Ala Asn
225                 230                 235                 240
Thr Thr Ala Val Val Gly Ser Asp Val Glu Leu Leu Cys Lys Val Tyr
                245                 250                 255
Ser Asp Ala Gln Pro His Ile Gln Trp Leu Lys His Ile Val Ile Asn
            260                 265                 270
Gly Ser Ser Phe Gly Ala Asp Gly Phe Pro Tyr Val Gln Val Leu Lys
        275                 280                 285
Thr Ala Asp Ile Asn Ser Ser Glu Val Glu Val Leu Tyr Leu Arg Asn
    290                 295                 300
Val Ser Ala Glu Asp Ala Gly Glu Tyr Thr Cys Leu Ala Gly Asn Ser
305                 310                 315                 320
Ile Gly Leu Ser Tyr Gln Ser Ala Trp Leu Thr Val Leu Pro Glu Pro
                325                 330                 335
Lys Ser Ser Asp Lys Thr His Thr Cys Pro Pro Cys Pro Ala Pro Glu
            340                 345                 350
Leu Leu Gly Gly Pro Ser Val Phe Leu Phe Pro Pro Lys Pro Lys Asp
        355                 360                 365
Thr Leu Met Ile Ser Arg Thr Pro Glu Val Thr Cys Val Val Val Asp
    370                 375                 380
Val Ser His Glu Asp Pro Glu Val Lys Phe Asn Trp Tyr Val Asp Gly
385                 390                 395                 400
Val Glu Val His Asn Ala Lys Thr Lys Pro Arg Glu Glu Gln Tyr Asn
                405                 410                 415
Ser Thr Tyr Arg Val Val Ser Val Leu Thr Val Leu His Gln Asp Trp
            420                 425                 430
Leu Asn Gly Lys Glu Tyr Lys Cys Lys Val Ser Asn Lys Ala Leu Pro
        435                 440                 445
Ala Pro Ile Glu Lys Thr Ile Ser Lys Ala Lys Gly Gln Pro Arg Glu
    450                 455                 460
Pro Gln Val Tyr Thr Leu Pro Pro Ser Arg Asp Glu Leu Thr Lys Asn
465                 470                 475                 480
Gln Val Ser Leu Thr Cys Leu Val Lys Gly Phe Tyr Pro Ser Asp Ile
                485                 490                 495
Ala Val Glu Trp Glu Ser Asn Gly Gln Pro Glu Asn Asn Tyr Lys Thr
            500                 505                 510
Thr Pro Pro Val Leu Asp Ser Asp Gly Ser Phe Phe Leu Tyr Ser Lys
        515                 520                 525
Leu Thr Val Asp Lys Ser Arg Trp Gln Gln Gly Asn Val Phe Ser Cys
    530                 535                 540
Ser Val Met His Glu Ala Leu His Asn His Tyr Thr Gln Lys Ser Leu
545                 550                 555                 560
```

```
Ser Leu Ser Pro Gly Lys
            565

<210> SEQ ID NO 170
<211> LENGTH: 229
<212> TYPE: PRT
<213> ORGANISM: Artificial Sequence
<220> FEATURE:
<223> OTHER INFORMATION: Synthetic sequence

<400> SEQUENCE: 170

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 171
<211> LENGTH: 228
<212> TYPE: PRT
<213> ORGANISM: Artificial Sequence
<220> FEATURE:
<223> OTHER INFORMATION: Synthetic sequence

<400> SEQUENCE: 171

Glu Arg Lys Ser Ser Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Gln Phe Asn Trp Tyr Val Asp Gly Val Glu
    50                  55                  60
```

Val His Asn Ala Lys Thr Lys Pro Arg Glu Glu Gln Phe Asn Ser Thr
65                  70                  75                  80

Phe Arg Val Val Ser Val Leu Thr Val Val His Gln Asp Trp Leu Asn
            85                  90                  95

Gly Lys Glu Tyr Lys Cys Lys Val Ser Asn Lys Gly Leu Pro Ala Pro
            100                 105                 110

Ile Glu Lys Thr Ile Ser Lys Thr Lys Gly Gln Pro Arg Glu Pro Gln
            115                 120                 125

Val Tyr Thr Leu Pro Pro Ser Arg Glu Glu Met Thr Lys Asn Gln Val
            130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
            165                 170                 175

Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
            195                 200                 205

Met His Glu Ala Leu His Asn His Tyr Thr Gln Lys Ser Leu Ser Leu
            210                 215                 220

Ser Pro Gly Lys
225

<210> SEQ ID NO 172
<211> LENGTH: 339
<212> TYPE: PRT
<213> ORGANISM: Artificial Sequence
<220> FEATURE:
<223> OTHER INFORMATION: Synthetic sequence

<400> SEQUENCE: 172

Arg Pro Ser Pro Thr Leu Pro Glu Gln Ala Gln Pro Trp Gly Ala Pro
1               5                   10                  15

Val Glu Val Glu Ser Phe Leu Val His Pro Gly Asp Leu Leu Gln Leu
            20                  25                  30

Arg Cys Arg Leu Arg Asp Asp Val Gln Ser Ile Asn Trp Leu Arg Asp
            35                  40                  45

Gly Val Gln Leu Ala Glu Ser Asn Arg Thr Arg Ile Thr Gly Glu Glu
50                  55                  60

Val Glu Val Gln Asp Ser Val Pro Ala Asp Ser Gly Leu Tyr Ala Cys
65                  70                  75                  80

Val Thr Ser Ser Pro Ser Gly Ser Asp Thr Thr Tyr Phe Ser Val Asn
            85                  90                  95

Val Ser Asp Ala Leu Pro Ser Ser Glu Asp Asp Asp Asp Asp Asp Asp
            100                 105                 110

Ser Ser Ser Glu Glu Lys Glu Thr Asp Asn Thr Lys Pro Asn Pro Val
            115                 120                 125

Ala Pro Tyr Trp Thr Ser Pro Glu Lys Met Glu Lys Lys Leu His Ala
            130                 135                 140

Val Pro Ala Ala Lys Thr Val Lys Phe Lys Cys Pro Ser Ser Gly Thr
145                 150                 155                 160

Pro Asn Pro Thr Leu Arg Trp Leu Lys Asn Gly Lys Glu Phe Lys Pro
            165                 170                 175

Asp His Arg Ile Gly Gly Tyr Lys Val Arg Tyr Ala Thr Trp Ser Ile
            180                 185                 190

```
Ile Met Asp Ser Val Val Pro Ser Asp Lys Gly Asn Tyr Thr Cys Ile
        195                 200                 205

Val Glu Asn Glu Tyr Gly Ser Ile Asn His Thr Tyr Gln Leu Asp Val
    210                 215                 220

Val Glu Arg Ser Pro His Arg Pro Ile Leu Gln Ala Gly Leu Pro Ala
225                 230                 235                 240

Asn Lys Thr Val Ala Leu Gly Ser Asn Val Glu Phe Met Cys Lys Val
                245                 250                 255

Tyr Ser Asp Pro Gln Pro His Ile Gln Trp Leu Lys His Ile Glu Val
            260                 265                 270

Asn Gly Ser Lys Ile Gly Pro Asp Asn Leu Pro Tyr Val Gln Ile Leu
        275                 280                 285

Lys Thr Ala Gly Val Asn Thr Thr Asp Lys Glu Met Glu Val Leu His
    290                 295                 300

Leu Arg Asn Val Ser Phe Glu Asp Ala Gly Glu Tyr Thr Cys Leu Ala
305                 310                 315                 320

Gly Asn Ser Ile Gly Leu Ser His His Ser Ala Trp Leu Thr Val Leu
                325                 330                 335

Glu Ala Leu

<210> SEQ ID NO 173
<211> LENGTH: 374
<212> TYPE: PRT
<213> ORGANISM: Artificial Sequence
<220> FEATURE:
<223> OTHER INFORMATION: Synthetic sequence

<400> SEQUENCE: 173

Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Ala Gln
                20                  25                  30

Pro Trp Gly Ala Pro Val Glu Val Glu Ser Phe Leu Val His Pro Gly
            35                  40                  45

Asp Leu Leu Gln Leu Arg Cys Arg Leu Arg Asp Asp Val Gln Ser Ile
    50                  55                  60

Asn Trp Leu Arg Asp Gly Val Gln Leu Ala Glu Ser Asn Arg Thr Arg
65                  70                  75                  80

Ile Thr Gly Glu Glu Val Glu Val Gln Asp Ser Val Pro Ala Asp Ser
                85                  90                  95

Gly Leu Tyr Ala Cys Val Thr Ser Ser Pro Ser Gly Ser Asp Thr Thr
            100                 105                 110

Tyr Phe Ser Val Asn Val Ser Asp Ala Leu Pro Ser Ser Glu Asp Asp
        115                 120                 125

Asp Asp Asp Asp Asp Ser Ser Ser Glu Glu Lys Glu Thr Asp Asn Thr
    130                 135                 140

Lys Pro Asn Pro Val Ala Pro Tyr Trp Thr Ser Pro Glu Lys Met Glu
145                 150                 155                 160

Lys Lys Leu His Ala Val Pro Ala Ala Lys Thr Val Lys Phe Lys Cys
                165                 170                 175

Pro Ser Ser Gly Thr Pro Asn Pro Thr Leu Arg Trp Leu Lys Asn Gly
            180                 185                 190

Lys Glu Phe Lys Pro Asp His Arg Ile Gly Gly Tyr Lys Val Arg Tyr
        195                 200                 205

Ala Thr Trp Ser Ile Ile Met Asp Ser Val Val Pro Ser Asp Lys Gly
    210                 215                 220
```

```
Asn Tyr Thr Cys Ile Val Glu Asn Glu Tyr Gly Ser Ile Asn His Thr
225                 230                 235                 240

Tyr Gln Leu Asp Val Val Glu Arg Ser Pro His Arg Pro Ile Leu Gln
            245                 250                 255

Ala Gly Leu Pro Ala Asn Lys Thr Val Ala Leu Gly Ser Asn Val Glu
        260                 265                 270

Phe Met Cys Lys Val Tyr Ser Asp Pro Gln Pro His Ile Gln Trp Leu
    275                 280                 285

Lys His Ile Glu Val Asn Gly Ser Lys Ile Gly Pro Asp Asn Leu Pro
290                 295                 300

Tyr Val Gln Ile Leu Lys Thr Ala Gly Val Asn Thr Thr Asp Lys Glu
305                 310                 315                 320

Met Glu Val Leu His Leu Arg Asn Val Ser Phe Glu Asp Ala Gly Glu
                325                 330                 335

Tyr Thr Cys Leu Ala Gly Asn Ser Ile Gly Leu Ser His His Ser Ala
            340                 345                 350

Trp Leu Thr Val Leu Glu Ala Leu Glu Glu Arg Pro Ala Val Met Thr
        355                 360                 365

Ser Pro Leu Tyr Leu Glu
    370

<210> SEQ ID NO 174
<211> LENGTH: 352
<212> TYPE: PRT
<213> ORGANISM: Artificial Sequence
<220> FEATURE:
<223> OTHER INFORMATION: Synthetic sequence

<400> SEQUENCE: 174

Met Arg Leu Leu Leu Ala Leu Leu Gly Val Leu Leu Ser Val Pro Gly
1               5                   10                  15

Pro Pro Val Leu Ser Leu Glu Ala Ser Glu Glu Val Glu Leu Glu Pro
            20                  25                  30

Cys Leu Ala Pro Ser Leu Glu Gln Gln Glu Gln Glu Leu Thr Val Ala
        35                  40                  45

Leu Gly Gln Pro Val Arg Leu Cys Cys Gly Arg Ala Glu Arg Gly Gly
    50                  55                  60

His Trp Tyr Lys Glu Gly Ser Arg Leu Ala Pro Ala Gly Arg Val Arg
65                  70                  75                  80

Gly Trp Arg Gly Arg Leu Glu Ile Ala Ser Phe Leu Pro Glu Asp Ala
                85                  90                  95

Gly Arg Tyr Leu Cys Leu Ala Arg Gly Ser Met Ile Val Leu Gln Asn
            100                 105                 110

Leu Thr Leu Ile Thr Gly Asp Ser Leu Thr Ser Ser Asn Asp Asp Glu
        115                 120                 125

Asp Pro Lys Ser His Arg Asp Pro Ser Asn Arg His Ser Tyr Pro Gln
    130                 135                 140

Gln Ala Pro Tyr Trp Thr His Pro Gln Arg Met Glu Lys Lys Leu His
145                 150                 155                 160

Ala Val Pro Ala Gly Asn Thr Val Lys Phe Arg Cys Pro Ala Ala Gly
                165                 170                 175

Asn Pro Thr Pro Thr Ile Arg Trp Leu Lys Asp Gly Gln Ala Phe His
            180                 185                 190

Gly Glu Asn Arg Ile Gly Gly Ile Arg Leu Arg His Gln His Trp Ser
        195                 200                 205
```

-continued

```
Leu Val Met Glu Ser Val Val Pro Ser Asp Arg Gly Thr Tyr Thr Cys
    210             215                 220

Leu Val Glu Asn Ala Val Gly Ser Ile Arg Tyr Asn Tyr Leu Leu Asp
225             230              235                     240

Val Leu Glu Arg Ser Pro His Arg Pro Ile Leu Gln Ala Gly Leu Pro
                245             250                 255

Ala Asn Thr Thr Ala Val Val Gly Ser Asp Val Glu Leu Leu Cys Lys
            260             265             270

Val Tyr Ser Asp Ala Gln Pro His Ile Gln Trp Leu Lys His Ile Val
        275             280             285

Ile Asn Gly Ser Ser Phe Gly Ala Asp Gly Phe Pro Tyr Val Gln Val
    290             295             300

Leu Lys Thr Ala Asp Ile Asn Ser Ser Glu Val Glu Val Leu Tyr Leu
305             310             315                     320

Arg Asn Val Ser Ala Glu Asp Ala Gly Glu Tyr Thr Cys Leu Ala Gly
                325             330                 335

Asn Ser Ile Gly Leu Ser Tyr Gln Ser Ala Trp Leu Thr Val Leu Pro
            340             345             350
```